(12) United States Patent
Berk et al.

(10) Patent No.: US 6,399,619 B1
(45) Date of Patent: Jun. 4, 2002

(54) PYRROLIDINE MODULATORS OF CHEMOKINE RECEPTOR ACTIVITY

(75) Inventors: Scott Berk, Maplewood; Charles G. Caldwell; Kevin T. Chapman, both of Scotch Plains; Jeffrey Hale, Westfield; Christopher Lynch, Scotch Plains; Malcolm MacCoss, Freehold; Sander G. Mills, Scotch Plains; Christopher Willoughby, Clark, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/542,898

(22) Filed: Apr. 4, 2000

Related U.S. Application Data

(60) Provisional application No. 60/128,174, filed on Apr. 6, 1999.

(51) Int. Cl.$^7$ ...................... A61K 31/495; A61K 31/40; C07D 403/00; C07D 401/00; C07D 207/00

(52) U.S. Cl. .................. 514/255.05; 514/340; 514/422; 514/426; 514/429

(58) Field of Search ............................ 514/255.05, 340, 514/422, 426, 429; 544/359, 372; 546/193, 207; 548/517, 518, 566, 570, 577

(56) References Cited

U.S. PATENT DOCUMENTS

| | | | |
|---|---|---|---|
| 5,468,469 A | 11/1995 | Aszalos et al. | 514/150 |
| 5,684,032 A | 11/1997 | Elliott et al. | 514/414 |
| 5,776,954 A | 7/1998 | de Laszlo et al. | 514/340 |

FOREIGN PATENT DOCUMENTS

| | | | |
|---|---|---|---|
| WO | WO 99/09984 | | 3/1999 |
| WO | WO 9909984 | * | 3/1999 |
| WO | 1 013 276 | | 6/2000 |
| WO | WO 00/38680 | | 7/2000 |
| WO | WO 00/39125 | | 7/2000 |

OTHER PUBLICATIONS

C. Dorn et al, "Discovery of Potent Human CCR5 Antagonists for the Treatment of HIV–I Infection", Abstract 117, 219th National Meeting of the American Chemical Society, San Francisco, CA, Mar. 2000.

L. Meurer et al, "Discovery of Potent Human CCR5 Antagonists for the Treatment of HIV–II Infection", Abstract 118, 219th National Meeting of the American Chemical Society, San Francisco, CA, Mar. 2000.

P. Finke et al, "Discovery of Potent Human CCR5 Antagonists for the Treatment of HIV–III Infection", Abstract 119, 219th National Meeting of the American Chemical Society, San Francisco, CA, Mar. 2000.

C. Caldwell et al, "Discovery of Potent Human CCR5 Antagonists for the Treatment of HIV–IV Infection", Abstract 120, 219th National Meeting of the American Chemical Society, San Francisco, CA, Mar. 2000.

J. J. Gomez–Reino et al., "Association of Rheumatoid Arthritis with a Functional Chemokine Receptor, CCR5", Arthritis & Rheumatism, vol. 42, No. 5, May 1999, pp. 989–992.

H. Hotoda, "Small–molecule inhibitors of HIV–1 entry via chemokine receptors", Drugs of the Future, vol. 24, No. 12, 1999, pp. 1355–1362.

T. J. Schall, "Biology of the Rantes/sis Cytokine Family", Cytokine, vol. 3, No. 3, May 1991, pp. 165–183.

P. M. Murphy, "The Molecular Biology of Leukocyte Chenoattractant Receptors", Annual Review of Immunology, vol. 12, 1994, pp. 593–633.

H. Deng et al., "Identification of a major co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.

A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote et al., "Molecular Cloning, Functional Expression, and Signaling Characteristics of C—C Chemokine Receptor", Cell, vol. 72, Feb. 1993, pp. 415–425.

C. Combadiere et al., "Cloning and Functional Expression of a Human Eosinophil CC Chemokine Receptor", J. Biol. Chem., vol. 270, No. 27, Jul. 1995, pp. 16491–16494.

C. A. Power et al., "Molecular Cloning and Functional Expression of a Novel Cc Chemokine Receptor cDNA from a Human Basophilic Line", J. Biol. Chem., vol. 270, No. 33, Aug. 1995, pp. 19495–19500.

M. Samson et al., "Molecular Cloning and Functional Expression of a New Human CC–Chemokine Receptor Gene", Biochemistry, vol. 35, 1996, pp. 3362–3367.

(List continued on next page.)

Primary Examiner—Richard L. Raymond
Assistant Examiner—Sudhaker B. Patel
(74) Attorney, Agent, or Firm—Kenneth R. Walton; J Eric Thies; Melvin Winokur

(57) ABSTRACT

The present invention is directed to pyrrolidine compounds of the formula I:

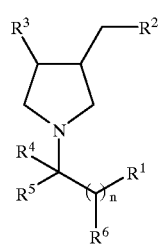

(wherein $R^1$, $R^2$, $R^3$, $R^4$, $R^5$, $R^6$ and n are defined herein) which are useful as modulators of chemokine receptor activity. In particular, these compounds are useful as modulators of the chemokine receptors CCR-5 and/or CCR-3.

28 Claims, No Drawings

OTHER PUBLICATIONS

A. Chaudhuri et al., "Expression of the Duffy Antigen in K562 Cells,", J. Biol. Chem., vol. 269, No. 11, Mar. 1994, p. 7835–7838.

H. Kita et al., "Chemokines Active on Eosinophils: Potential Roles in Allergic Inflammation", J. Exp. Med., vol. 183, Jun. 1996, pp. 2421–2426.

D. Smith et al., "Blocking of HIV–1 Infectivity by a Soluable, Secreted Form of the CD4 Antigen", Science, vol. 238, 1987, pp. 1704–1707.

J. A. Levy, "Infection by Human Immunodeficiency Virus— DC4 is not Enough", N. Eng. J. Med., vol. 335, No. 20, Nov. 1996), pp. 1528–1530.

T. Dragic et al., "HIV–1 entry into CD4+ cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistance to HIV–1 infection in causcasian individuals bearing mutant alleles of the CCR–5 cehmokine receptor gene", Nature, vol. 382, Aug. 1996, pp. 722–725.

C. M. Hill et al., "Natural resistence to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol 383, Oct. 1996, p. 768.

W. S. Blair et al., "HIV–1 entry—an expanding portal for drug discovery", DDT, vol. 5, May 2000, pp. 183–194.

M. Baba et al., "A small–molecule, nonpeptide CCR5 antagonist with highly potent and selective anti–HIV–1 activity", Proc. Natl. Acad. Sci., vol. 96, May 1999, pp. 5698–5703.

R. Horuk et al., "Chemokine Receptor Antagonists", Med. Res. Rev., vol. 20, No. 2, 2000, pp. 155–168.

M. Shiraishi et al., "Discovery of Novel, Potent , and Selective Small–Molecule CCR5 Antagonists as Anti–HIV–1 Agents: Synthesis and Biological Evaluation of Anilide Derivatives with a Quanternary Ammonium Moiety", J. Med. Chem., vol. 43, 2000, pp. 2049–2063.

\* cited by examiner

PYRROLIDINE MODULATORS OF CHEMOKINE RECEPTOR ACTIVITY

This application claims the benefit of U.S. Provisional Application No. 60/128,174, filed Apr. 6, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270, 2212–22128 (1995); Beote, et al, *Cell*, 72, 415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3(or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

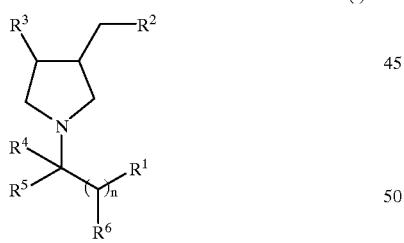

(I)

wherein:
$R^1$ is selected from:
(1) —$CO_2H$,
(2) —$NO_2$,
(3) —tetrazolyl,
(4) —hydroxyisoxazole,
(5) —$SO_2NH$—($C_{0-3}$ alkyl)-$R^9$, wherein $R^9$ is independently selected from: hydrogen, $C_{1-6}$ alkyl, $C_{5-6}$ cyclo alkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
(6) —$SO_2NHCO$—($C_{0-3}$ alkyl)-$R^9$, wherein $R^9$ is independently selected from: hydrogen, $C_{1-6}$ alkyl, $C_{5-6}$ cyclo alkyl, benzyl or phenyl, which is unsubstituted or substituted with 1–14 3 substituents where the substituents are independently selected from: halo, $C_{1-3}$ alkyl, $C_{1-3}$ alkoxy and trifluoromethyl, and
(7) —$P(O)(OH)_2$;
$R^2$ is selected from the group consisting of:

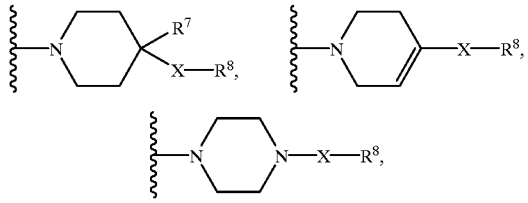

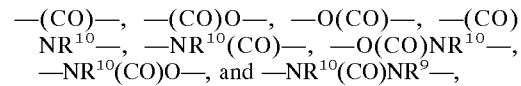

wherein $R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo,
wherein X is —($C_{0-6}$ alkyl)-Y—($C_{0-6}$ alkyl)-,
where the alkyl is unsubstituted or substituted with 1–7 substituents where the substituents are independently selected from:
(a) halo,
(b) hydroxy,
(c) —O—$C_{1-3}$ alkyl, and
(d) trifluoromethyl,
and where Y is selected from:
—(CO)—, —(CO)O—, —O(CO)—, —(CO)$NR^{10}$—, —$NR^{10}$(CO)—, —O(CO)$NR^{10}$—, —$NR^{10}$(CO)O—, and —$NR^{10}$(CO)$NR^9$—,
and where $R^{10}$ is independently selected from: hydrogen, $C_{1-6}$ alkyl, $C_{2-6}$ alkenyl, $C_{2-6}$ alkynyl, benzyl, phenyl, and $C_{1-6}$ alkyl-$C_{3-6}$ cyclo alkyl, which is unsubstituted or substituted with 1–3 substituents where the substituents are independently selected from: halo, $C_{1-3}$ alkyl, $C_{1-3}$ alkoxy and trifluoromethyl,
and wherein $R^8$ is selected from:
phenyl, naphthyl, biphenyl, and heterocycle, which is unsubstituted or substituted with 1–7 of $R^{11}$ where $R^{11}$ is independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), phenyl, trifluoromethyl, and —$NR^9R^{10}$,
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$, (n) —NR⁹—COR¹⁰,
(o) —NR⁹—CO₂R¹⁰,
(p) —CO—NR⁹R¹⁰,
(q) —OCO—NR⁹R¹⁰,
(r) —NR⁹CO—NR⁹R¹⁰,
(s) —S(O)$_m$—R⁹, wherein m is an integer selected from 0, 1 and 2,
(t) —S(O)₂—NR⁹R¹⁰,
(u) —NR⁹S(O)₂—R¹⁰, and
(v) —NR⁹S(O)₂—NR⁹R¹⁰;

R³ is selected from the group consisting of:
  phenyl and heterocycle,
    which is unsubstituted or substituted with 1–7 substituents where the substituents are independently selected from:
    (a) halo,
    (b) trifluoromethyl,
    (c) hydroxy,
    (d) $C_{1-3}$ alkyl,
    (e) —O—$C_{1-3}$ alkyl,
    (f) —CO₂R⁹,
    (g) —NR⁹R¹⁰, and
    (h) —CONR⁹R¹⁰;

R⁴ is selected from:
  $C_{1-10}$ alkyl, $C_{3-8}$ cyclo alkyl, —($C_{1-3}$ alkyl)-$C_{3-8}$ cyclo alkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl,
    which is unsubstituted or substituted with 1–7 of $R^{11}$ where $R^{11}$ is independently as defined above;

R⁵ is selected from:
  hydrogen or $C_{1-6}$ alkyl, wherein the alkyl is unsubstituted or substituted with 1–7 substituents where the substituents are independently selected from:
    (a) halo,
    (b) trifluoromethyl,
    (c) hydroxy,
    (d) $C_{1-3}$ alkyl,
    (e) —O—$C_{1-3}$ alkyl,
    (f) —CO₂R⁹,
    (g) —NR⁹R¹⁰, and
    (h) —CONR⁹R¹⁰,
or where R⁴ and R⁵ may be joined together to form a $C_{3-8}$ cyclo alkyl ring which may be unsubstituted or substituted with 1–7 of $R^{11}$;

R⁶ is independently selected from:
  hydrogen or $C_{1-6}$ alkyl, wherein the alkyl is unsubstituted or substituted with 1–7 substituents where the substituents are independently selected from:
    (a) halo,
    (b) trifluoromethyl,
    (c) hydroxy,
    (d) $C_{1-3}$ alkyl,
    (e) —O—$C_{1-3}$ alkyl,
    (f) —CO₂R⁹,
    (g) —NR⁹R¹⁰, and
    (h) —CONR⁹R¹⁰;

n is an integer selected from 0, 1, 2 and 3;
and pharmaceutically acceptable salts thereof and individual diastereomers thereof.

In one embodiment, the present invention is a compound of formula I, wherein
R¹ is selected from:
(1) —CO₂H,
(2) —NO₂,
(3) —tetrazolyl,
(4) —hydroxyisoxazole,
(5) —SO₂NH—(CO$_{1-3}$ alkyl)—R⁹, wherein R⁹ is independently selected from: hydrogen, $C_{1-6}$ alkyl, $C_{5-6}$ cyclo alkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(6) —P(O)(OH)₂;

R² is selected from the group consisting of:

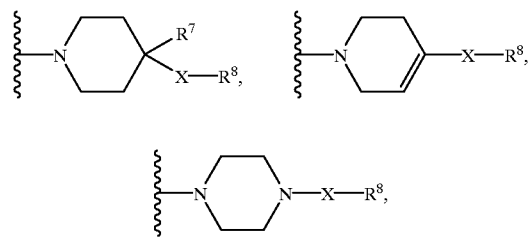

wherein R⁷ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo,
wherein X is —($C_{0-6}$ alkyl)-Y—($C_{0-6}$ alkyl)-,
  where the alkyl is unsubstituted or substituted with 1–7 substituents where the substituents are independently selected from:
    (a) halo,
    (b) hydroxy,
    (c) —O—$C_{1-3}$ alkyl, and
    (d) trifluoromethyl,
  and where Y is selected from:
    —(CO)—, —(CO)O—, —O(CO)—, —(CO)NR¹⁰—, —NR¹⁰(CO)—, —O(CO)NR¹⁰—, —NR¹⁰(CO)O—, and —NR¹⁰(CO)NR⁹—,
  and where $R^{10}$ is independently selected from: hydrogen, $C_{1-6}$ alkyl, $C_{2-6}$ alkenyl, $C_{2-6}$ alkynyl, benzyl, phenyl, and $C_{1-6}$ alkyl-$C_{3-6}$ cyclo alkyl,
    which is unsubstituted or substituted with 1–3 substituents where the substituents are independently selected from: halo, $C_{1-3}$ alkyl, $C_{1-3}$ alkoxy and trifluoromethyl,
and wherein R⁸ is selected from:
  phenyl, naphthyl, biphenyl, and heterocycle,
    which is unsubstituted or substituted with 1–7 of $R^{11}$ where $R^{11}$ is independently selected from:
    (a) halo,
    (b) cyano,
    (c) hydroxy,
    (d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —CO₂H, —CO₂($C_{1-6}$ alkyl), phenyl, trifluoromethyl, and —NR⁹R¹⁰, (e) —O—$C_{1-6}$ alkyl, which is unsubstituted or substituted with 1–5 of $R^{12}$
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$;

$R^3$ is selected from the group consisting of:
phenyl and heterocycle,
which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$ is selected from:
$C_{1-10}$ alkyl, $C_{3-8}$ cyclo alkyl, —($C_{1-3}$ alkyl)-$C_{3-8}$ cyclo alkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl, which is unsubstituted or substituted with 1–7 of $R^{11}$ where $R^{11}$ is independently as defined above;

$R^5$ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$,
or where $R^4$ and $R^5$ may be joined together to form a $C_{3-8}$ cyclo alkyl ring which may be unsubstituted or substituted with 1–7 of $R^{11}$;

$R^6$ is independently selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$, (g) —$NR^9R^{10}$, and
(h) —$CONR^9R^{10}$;

n is an integer selected from 0, 1, 2 and 3;

and pharmaceutically acceptable salts thereof and individual diastereomers thereof.

Preferred compounds of the present invention include those of formula Ia:

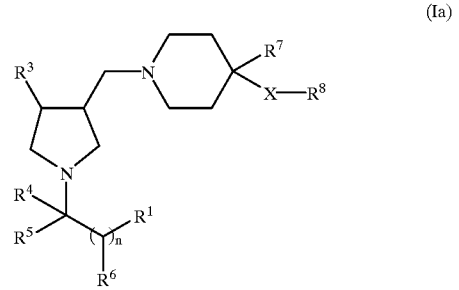

(Ia)

wherein $R^1$, $R^3$, $R^4$, $R^5$, $R^6$, $R^7$, $R^8$, X and n are defined herein;

and pharmaceutically acceptable salts and individual diastereomers thereof.

More preferred compounds of the present invention include those of formula Ic:

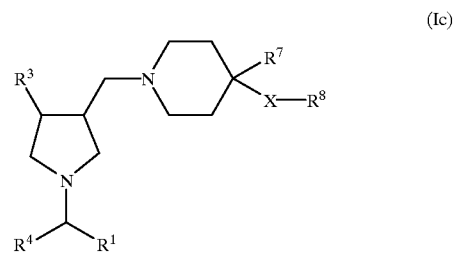

(Ic)

wherein $R^1$, $R^3$, $R^4$, $R^7$, $R^8$ and X are defined herein;

and pharmaceutically acceptable salts and individual diastereomers thereof.

Highly preferred compounds of the present invention include those of formula Id:

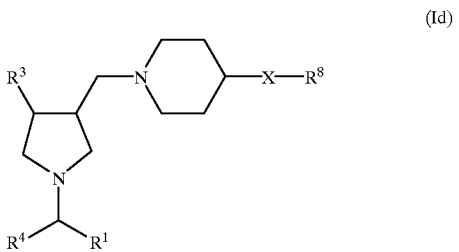

(Id)

wherein $R^1$, $R^3$, $R^4$, $R^8$ and X are defined herein;

and pharmaceutically acceptable salts and individual diastereomers thereof.

More highly preferred compounds of the present invention include those of formula Ie:

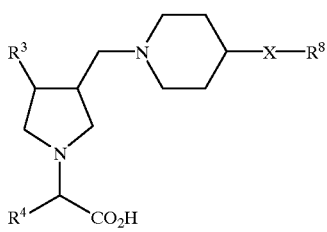

(Ie)

wherein $R^3$, $R^4$, $R^8$ and X are defined herein;
and pharmaceutically acceptable salts and individual diastereomers thereof.

In the present invention it is preferred that $R^1$ is selected from:
(1) —$CO_2H$,
(2) —$P(O)(OH)_2$, and
(3) -tetrazolyl.

In the present invention it is more preferred that $R^1$ is selected from:
(1) —$CO_2H$, and
(2) -tetrazolyl.

In the present invention it is even more preferred that R is —$CO_2H$.

In the present invention it is preferred that $R^2$ is

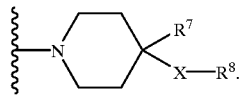

In the present invention it is more preferred that $R^2$ is

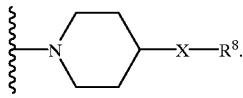

In the present invention it is preferred that $R^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl.

In the present invention it is even more preferred that $R^3$ is selected from the group consisting of:
phenyl, which may be unsubstituted or substituted with 1–5 substituents where the substituents are independently selected from:
(a) fluoro, and
(b) chloro; and
unsubstituted thienyl.

In the present invention it is most preferred that $R^3$ is unsubstituted phenyl, (3-fluoro)phenyl or 3-thienyl.

In the present invention it is preferred that $R^4$ is $C_{1-10}$ alkyl, $C_{3-8}$ cyclo alkyl, or —($C_{1-3}$ alkyl)-$C_{3-8}$ cyclo alkyl, which is unsubstituted or substituted with 1–5 substituents where the substituents are independently selected from:
(a) halo,
(b) hydroxy,
(c) —$C_{1-6}$ alkyl, which is unsubstituted or substituted with halo, cyano, —$CO_2H$, hydroxy or trifluoromethyl,
(d) —O—$C_{1-6}$ alkyl, which is unsubstituted or substituted halo, cyano, —$CO_2H$, hydroxy or trifluoromethyl,
(e) —$CF_3$,
(f) —$CHF_2$,
(g) —$CH_2F$, and
(h) —$CO_2H$.

In the present invention it is more preferred that $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl. In an aspect of this embodiment, in the present invention it is more preferred that $R^4$ is selected from: isopropyl, isobutyl, sec-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl.

In the present invention it is even more preferred that $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl. In an aspect of this embodiment, in the present invention it is more preferred that that $R^4$ is selected from: isopropyl, cyclohexyl, cyclopentyl, cyclobutyl, cyclopropyl, —$CH_2$-cyclobutyl, and —$CH_2$-cyclopropyl.

In the present invention it is most preferred that $R^4$ is selected from: cyclohexyl, isopropyl, sec-butyl, t-butyl, —$CH_2$-cyclobutyl and —$CH_2$-cyclopropyl. In an aspect of this embodiment, in the present invention it is most preferred that $R^4$ is selected from: cyclohexyl, isopropyl, —$CH_2$-cyclobutyl and —$CH_2$-cyclopropyl.

In the present invention it is preferred that $R^5$ is hydrogen.
In the present invention it is preferred that $R^6$ is hydrogen or unsubstituted $C_{1-6}$ alkyl.
In the present invention it is more preferred that $R^6$ is hydrogen.
In the present invention it is preferred that $R^7$ is hydrogen, fluoro, hydroxy or $C_{1-6}$ alkyl.
In the present invention it is more preferred that $R^7$ is hydrogen or fluoro.
In the present invention it is even more preferred that $R^7$ is hydrogen.
In the present invention it is preferred that X is:
—($C_{0-4}$ alkyl)-Y—($C_{0-4}$ alkyl)-,
where the alkyl is unsubstituted or substituted with 1–4 substituents where the substituents are independently selected from:
(a) halo,
(b) hydroxy,
(c) —O—$C_{1-3}$ alkyl, and
(d) trifluoromethyl, and where Y is selected from:
—(CO)NR$^{10}$—, —NR$^{10}$(CO)—, —O(CO)NR$^{10}$—, —NR$^{10}$(CO)O—, and —NR$^{10}$(CO)NR$^9$—,
and where R$^{10}$ is independently selected from: hydrogen, C$_{1-6}$ alkyl, C$_{2-6}$ alkenyl, C$_{2-6}$ alkynyl, benzyl, phenyl, and C$_{1-6}$ alkyl-C$_{3-6}$ cyclo alkyl,
which is unsubstituted or substituted with 1–3 substituents where the substituents are independently selected from: halo, C$_{1-3}$ alkyl, C$_{1-3}$ alkoxy and trifluoromethyl.

In the present invention it is more preferred that X is:
—(C$_{0-2}$ alkyl)-Y—(C$_{0-2}$ alkyl)-,
where the alkyl is unsubstituted or substituted with 1–4 substituents where the substituents are independently selected from:
(a) halo,
(b) hydroxy,
(c) —O—C$_{1-3}$ alkyl, and
(d) trifluoromethyl,
and where Y is selected from:
—(CO)NR$^{10}$—, —NR$^{10}$(CO)—, —O(CO)NR$^{10}$—, —NR$^{10}$(CO)O—, and —NR$^{10}$(CO)NR$^9$—,
where R$^9$ is independently selected from: hydrogen and C$_{1-6}$ alkyl, and
R$^{10}$ is independently selected from: hydrogen, C$_{1-6}$ alkyl, C$_{2-6}$ alkenyl, C$_{2-6}$ alkynyl, benzyl, phenyl, and C$_{1-6}$ alkyl-C$_{3-6}$ cyclo alkyl,
which is unsubstituted or substituted with 1–3 substituents where the substituents are independently selected from: halo, C$_{1-3}$ alkyl, C$_{1-3}$ alkoxy and trifluoromethyl.

In the present invention it is even more preferred that X is selected from:
—(C0$_{-2}$ alkyl)-Y—(C0$_{-2}$ alkyl)-, where the alkyl is unsubstituted,
and where Y is selected from:
—(CO)NR$^{10}$—, —NR$^{10}$(CO)—, —O(CO)NR$^{10}$—, —NR$^{10}$(CO)O—, and —NR$^{10}$(CO)NH—,
where R$^{10}$ is independently selected from: hydrogen, C$_{1-3}$ alkyl, C$_{2-3}$ alkenyl, and C$_{2-3}$ alkynyl.

In the present invention it is most preferred that X is selected from:
(1) —N(C$_{1-4}$ alkyl)(CO)O—CH$_2$—,
(2) —N(allyl)(CO)O—CH$_2$—,
(3) —N(C$_{1-4}$ alkyl)(CO)NH—CH$_2$—,
(4) —N(allyl)(CO)NH—CH$_2$—, and
(5) —N(CH$_2$CH$_3$)(CO)NH—CH$_2$CH$_2$—.

In the present invention it is preferred that R$^8$ is selected from: phenyl, naphthyl, benzoimidazolyl, benzofurazanyl, isoxazolyl, pyrazinyl, pyridazinyl, pyridyl, pyrimidyl, and tetrazolopyridyl,
which is unsubstituted or substituted with 1–7 substituents where the substituents are independently selected from:
(a) halo,
(b) cyano,
(c) hydroxy,
(d) C$_{1-6}$ alkyl, which is unsubstituted or substituted with 1–5 of R$^{12}$ where R$^{12}$ is independently selected from: halo, cyano, hydroxy, C$_{1-6}$ alkoxy, —CO$_2$H, phenyl, —CO$_2$(C$_{1-6}$ alkyl), trifluoromethyl, and —NR$^9$R$^{10}$, wherein R$^9$ and R$^{10}$ are independently selected from: hydrogen, C$_{1-6}$ alkyl, C$_{5-6}$ cyclo alkyl, benzyl or phenyl, which is unsubstituted or substituted with 1–3 substituents where the substituents are independently selected from: halo, C$_{1-3}$ alkyl, C$_{1-3}$ alkoxy and trifluoromethyl;
(e) —O—C$_{1-6}$ alkyl, which is unsubstituted or substituted with 1–5 of R$^{12}$,
(f) —CF$_3$,
(g) —CHF$_2$,
(h) —CH$_2$F,
(i) —NO$_2$,
(j) phenyl,
(k) —CO$_2$R$^9$,
(l) tetrazolyl,
(m) —NR$^9$R$^{10}$,
(n) —NR$^9$—COR$^{10}$,
(o) —NR$^9$—CO$_2$R$^{10}$,
(p) —CO—NR$^9$R$^{10}$,
(q) —OCO—NR$^9$R$^{10}$,
(r) —NR$^9$CO—NR$^9$R$^{10}$,
(s) —S(O)$_m$—R$^9$, wherein m is an integer selected from 0, 1 and 2,
(t) —S(O)$_2$—NR$^9$R$^{10}$,
(u) —NR$^9$S(O)$_2$—R$^{10}$, and
(v) —NR$^9$S(O)$_2$—NR$^9$R$^{10}$.

In the present invention it is more preferred that R$^8$ is selected from: phenyl, benzofurazanyl, benzoimidazolyl, isoxazole, and pyridyl; which is unsubstituted or substituted with 1–5 substituents where the substituents are independently selected from:
(a) halo,
(b) cyano,
(c) —NO$_2$,
(d) —CF$_3$,
(e) —CHF$_2$,
(f) —CH$_2$F,
(g) tetrazolyl,
(h) C$_{1-6}$ alkyl, which is unsubstituted or substituted with phenyl, and
(i) —O—C$_{1-6}$ alkyl.

In the present invention it is even more preferred that R$^8$ is phenyl, which is unsubstituted or substituted with 1–3 substituents where the substituents are independently selected from:
(a) fluoro,
(b) chloro,
(c) cyano,
(d) —NO$_2$, and
(e) —CF$_3$.

In the present invention it is most preferred that R$^8$ is selected from: phenyl, 2-cyanophenyl, 3-cyanophenyl, 4-cyanophenyl, 4-fluorophenyl, 3,4-difluorophenyl, 3,5-difluorophenyl, 2,6-difluorophenyl, 2,4,6-trifluorophenyl, 3-nitrophenyl, 4-nitrophenyl, 4-chlorophenyl, 3-chlorophenyl, 4-trifluoromethylphenyl, and 3,5-bis (trifluoromethyl)phenyl.

In the present invention it is preferred that n is an integer selected from 0 and 1.

In the present invention it is more preferred that n is an integer which is 0.

It is to be understood that embodiments of the present invention include, but are not limited to, compounds of formula I wherein R$^1$, R$^2$, R$^3$, R$^4$, R$^5$, R$^6$, R$^7$, R$^8$, X, and n are defined in accordance with one of the embodiments or aspects thereof as set forth above. Any and all possible combinations of preferred, more preferred, even more preferred, highly preferred, more highly preferred, and/or most preferred definitions of these variables are within the scope of the present invention.

The compounds of the instant invention have at least two asymmetric centers at the ring junction of the substitutents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

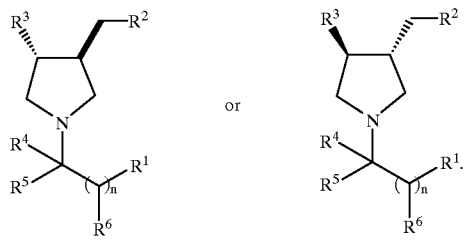

The relative configurations of the most preferred compounds of this invention with respect to the configuration of the substituent on the pyrrolidine nitrogen are of the orientation as depicted:

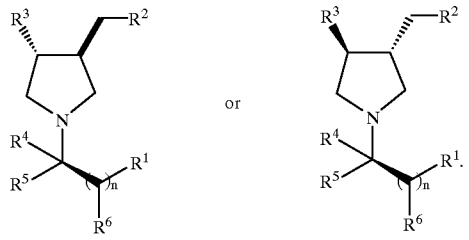

A preferred aspect of the present invention is a compound of Formula (II):

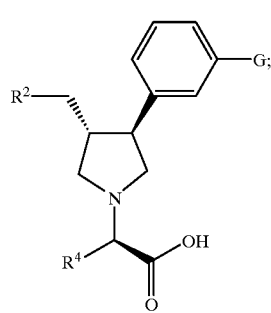

(II)

wherein $R^2$ is selected from the group consisting of

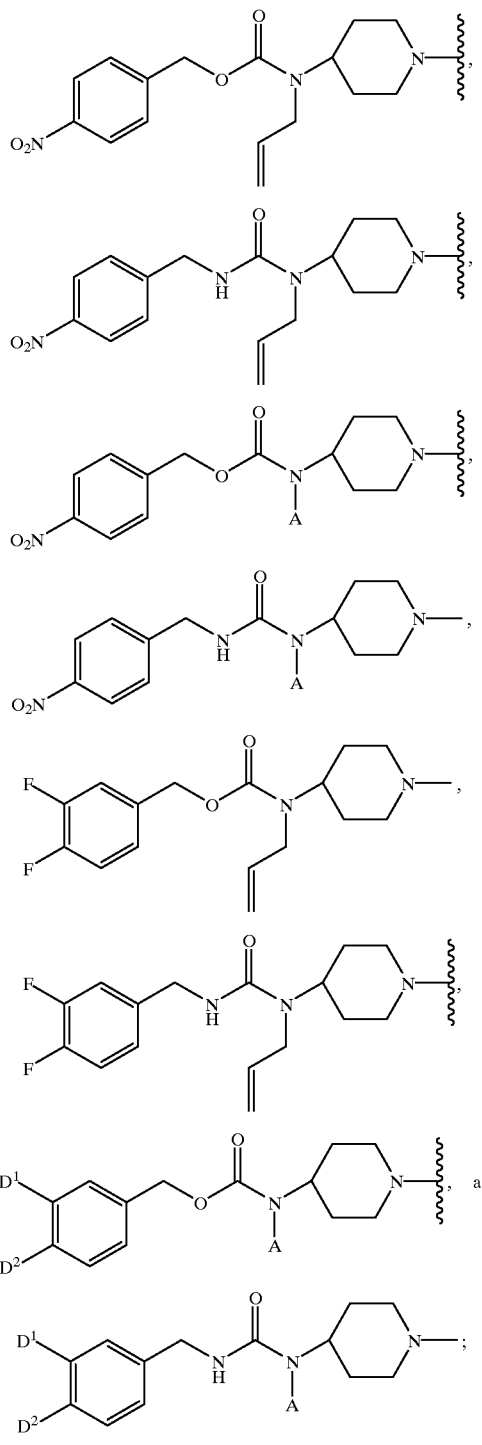

$R^4$ is selected from the group consisting of

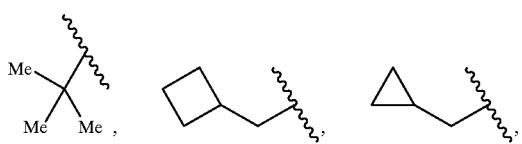

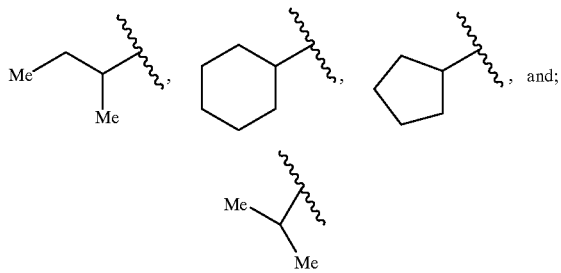

A is methyl, ethyl, propyl, butyl, or cyclopropylmethyl-; and $D^1$ and $D^2$ are both fluoro; or one of $D^1$ and $D^2$ is hydrogen and the other of $D^1$ and $D^2$ is fluoro, chloro, CN, $CF_3$, or $SO_2CH_3$; and G is hydrogen or fluoro;

and pharmaceutically acceptable salts thereof and individual diastereomers thereof.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, Co, as in Co alkyl is defined to identify the presence of a direct covalent bond. As with "$C_{1-8}$ alkyl", the term "$C_{1-6}$ alkyl" means linear or branched chain alkyl groups having from 1 to 6 carbon atoms and includes all of the hexyl alkyl, pentyl alkyl, etc. isomers.

The term "$C_3$–$C_8$ cyclo alkyl" refers to a cyclic ring selected from cyclopropyl, cyclobutyl, cyclopentyl, cyclohexyl, cycloheptyl, and cyclooctyl. The term "$C_3$–$C_6$ cyclo alkyl" refers to a cyclic ring selected from cyclopropyl, cyclobutyl, cyclopentyl, and cyclohexyl. Similar terms (e.g., "$C_4$–$C_6$ cyclo alkyl") have analogous meanings.

The term "$C_{1-6}$ alkoxy" means an —O— alkyl group wherein alkyl is $C_{1-6}$ alkyl as defined above. Suitable alkoxy groups include, but are not limited to, methoxy, ethoxy, n-propoxy, isopropoxy, n-butoxy, isobutoxy, tert-butoxy, and secbutoxy.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothioheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression " . . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cyclo alkyl, benzyl or phenyl, which is unsubstituted or substituted with 1–3 substituents . . . ", encompasses hydrogen, $C_{1-6}$ alkyl, $C_{5-6}$ cyclo alkyl, benzyl, phenyl, mono- and di- and tri-substituted $C_{1-6}$ alkyl, mono- and di- and tri-substituted $C_{5-6}$ cyclo alkyl, mono- and di- and tri-substituted benzyl and mono- and di- and tri-substituted phenyl.

Exemplifying the invention is the use of the compounds disclosed in the Examples and herein.

Specific compounds within the present invention include a compounds which selected from the group consisting of:

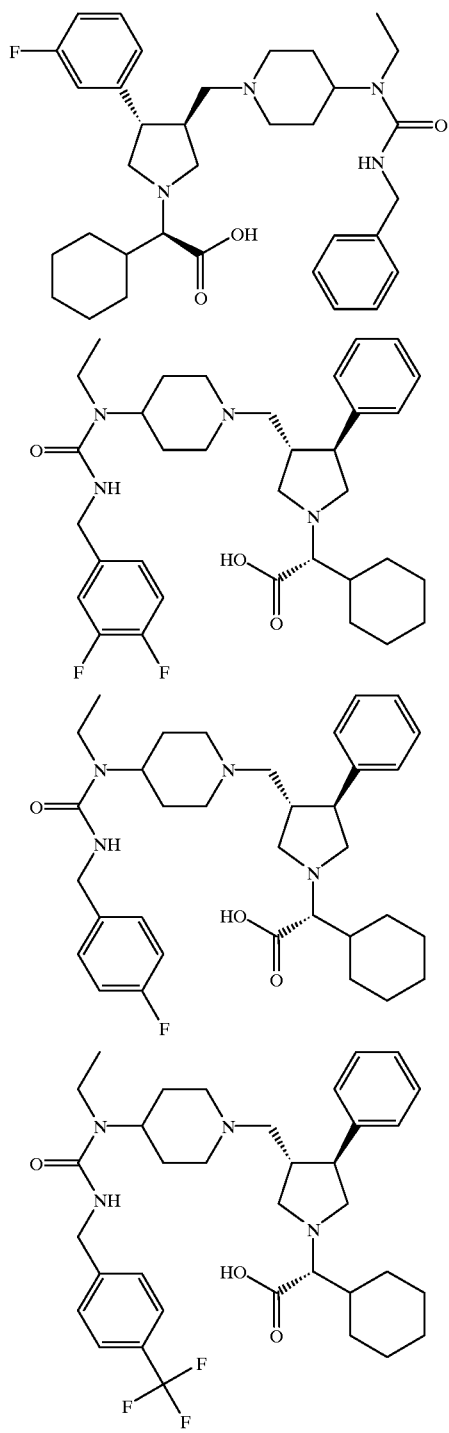

-continued

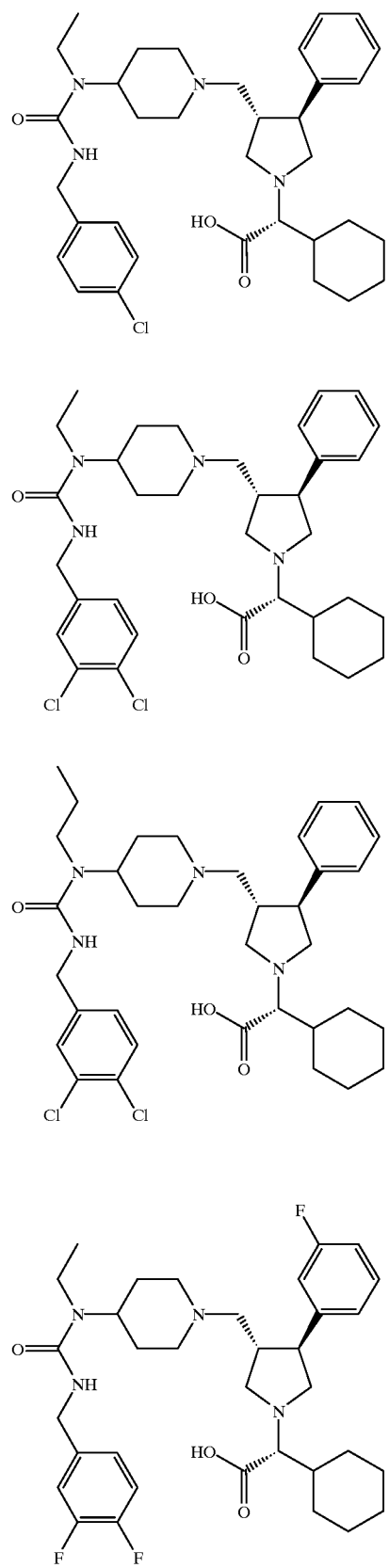

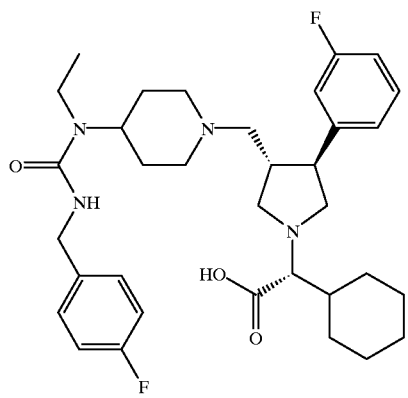
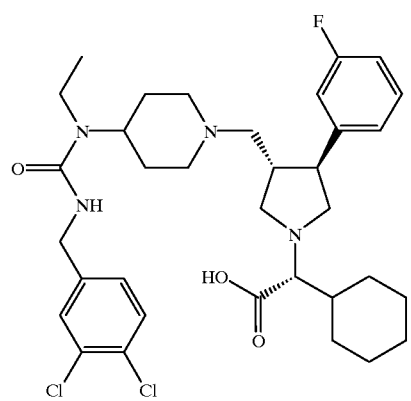
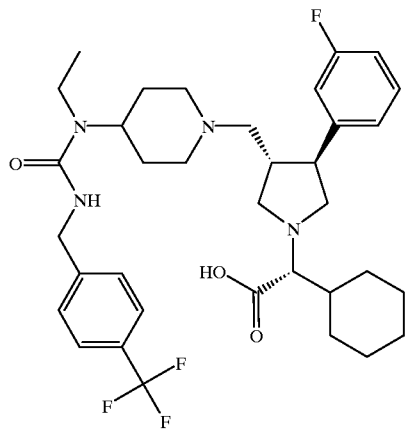
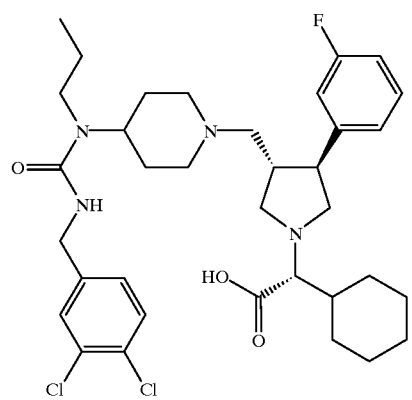
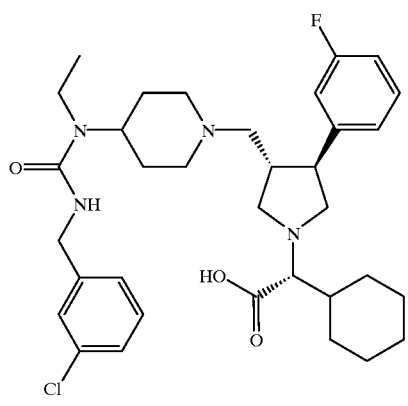
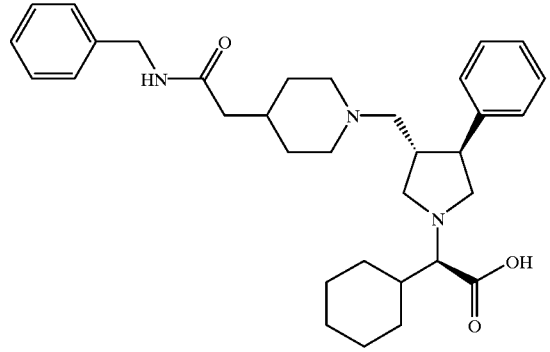
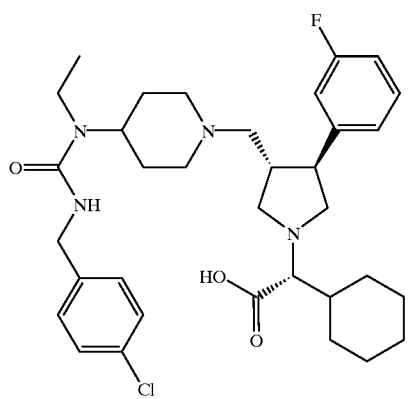
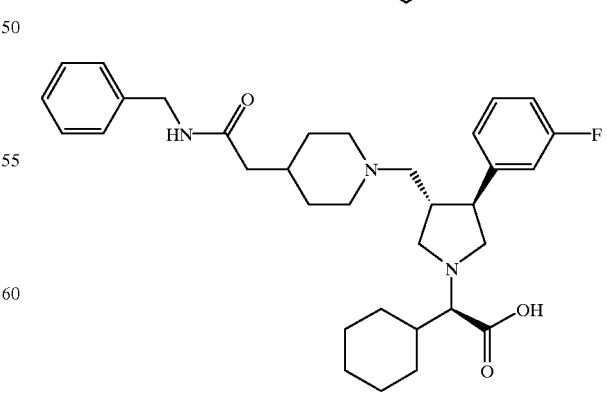

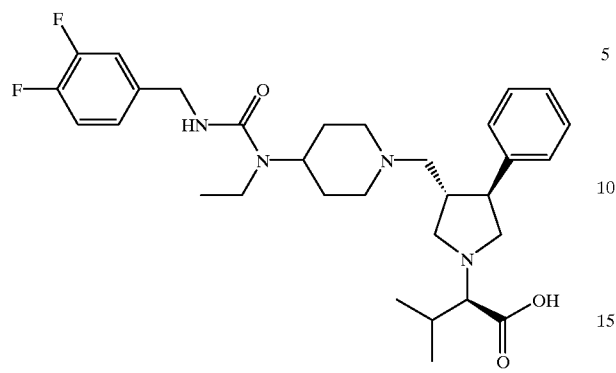
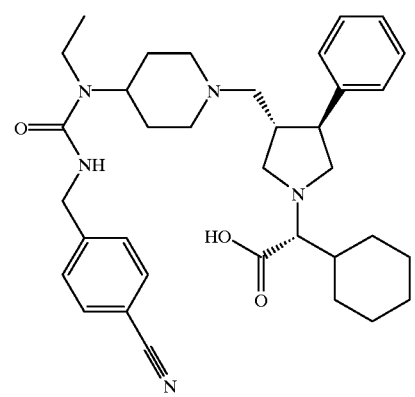
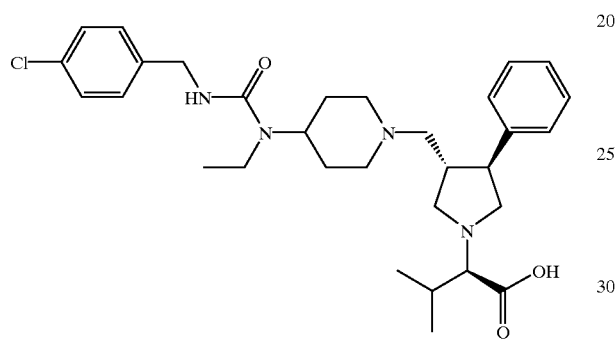
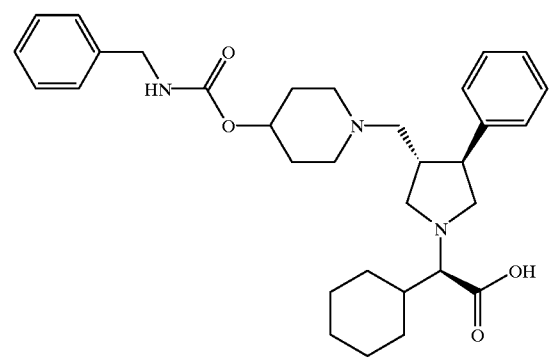
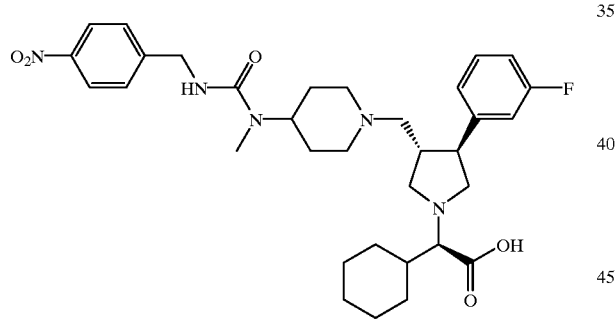
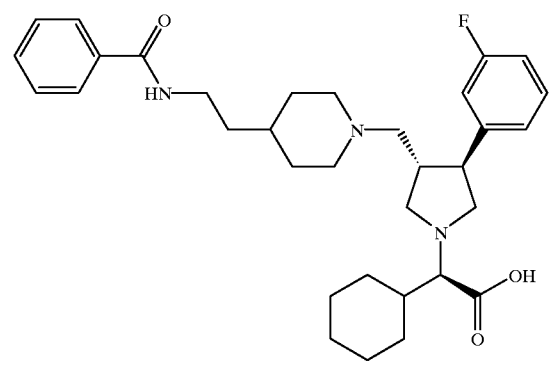
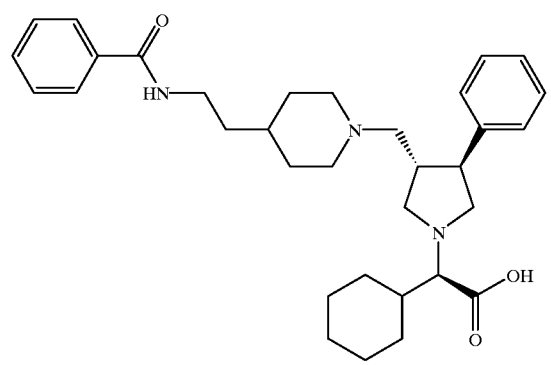
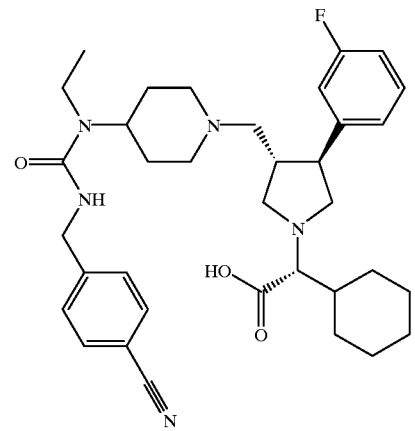

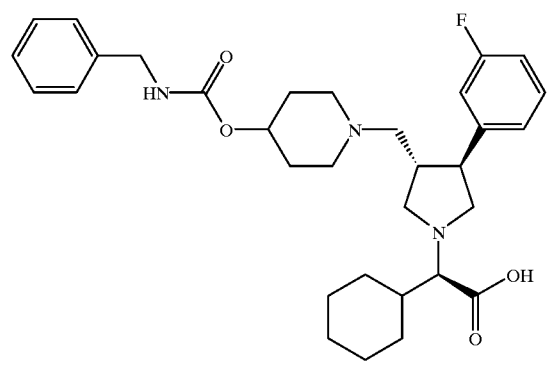
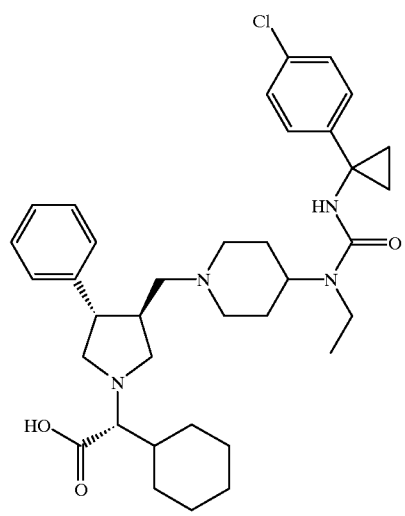
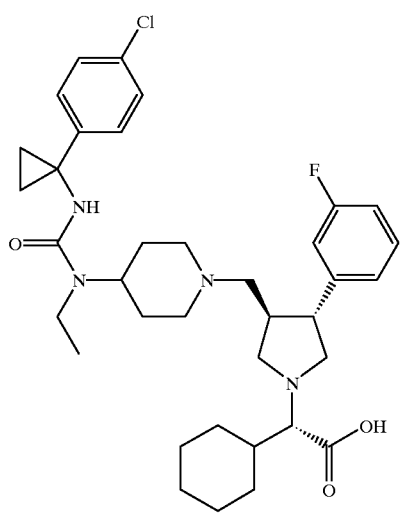
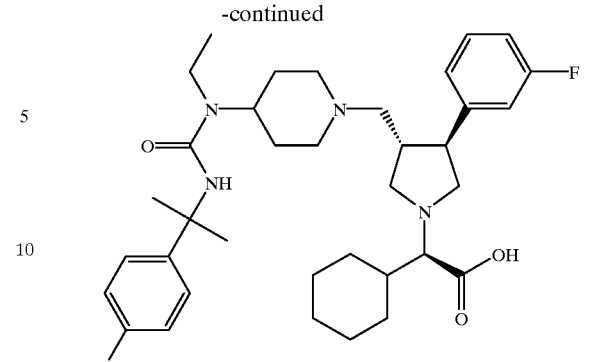
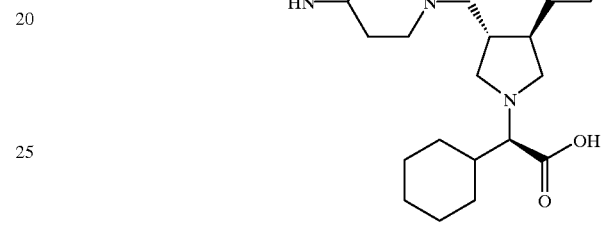
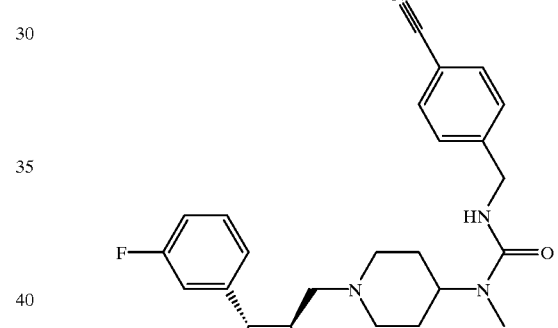
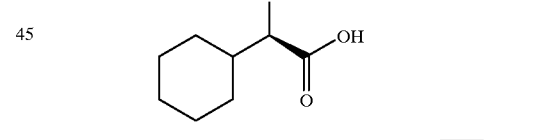
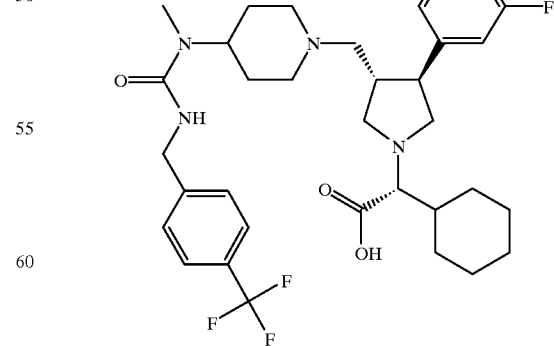

-continued
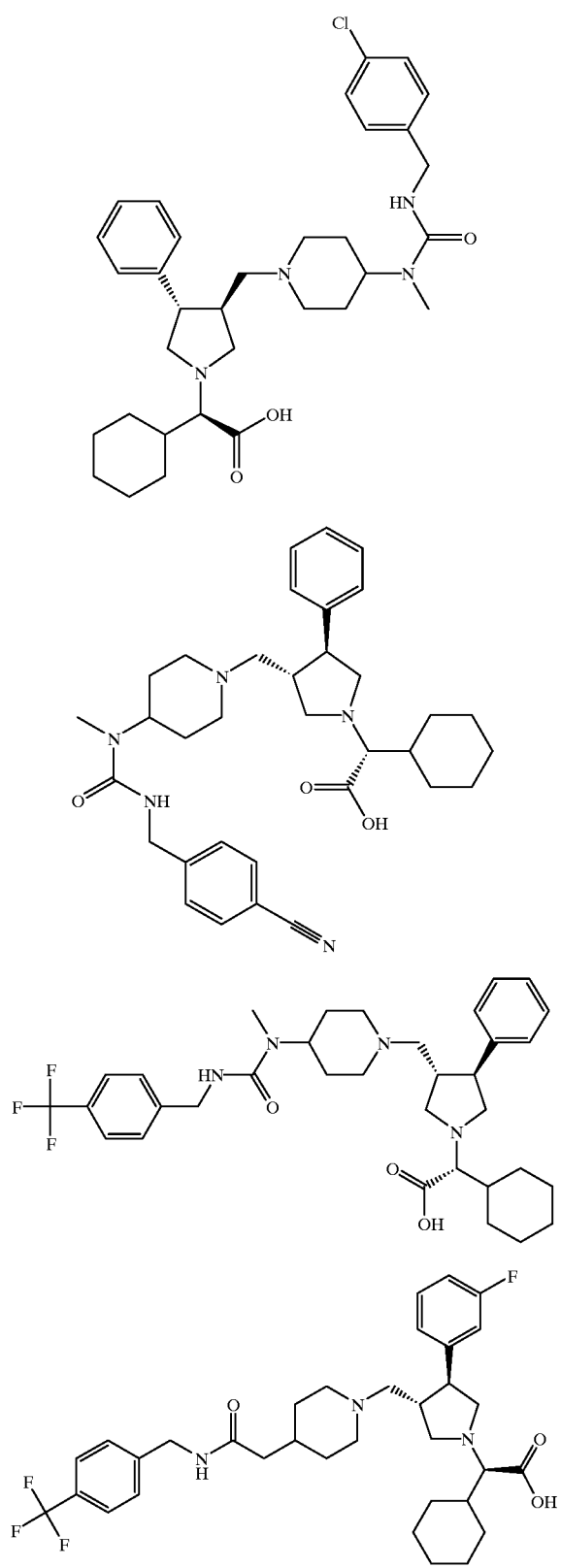
-continued
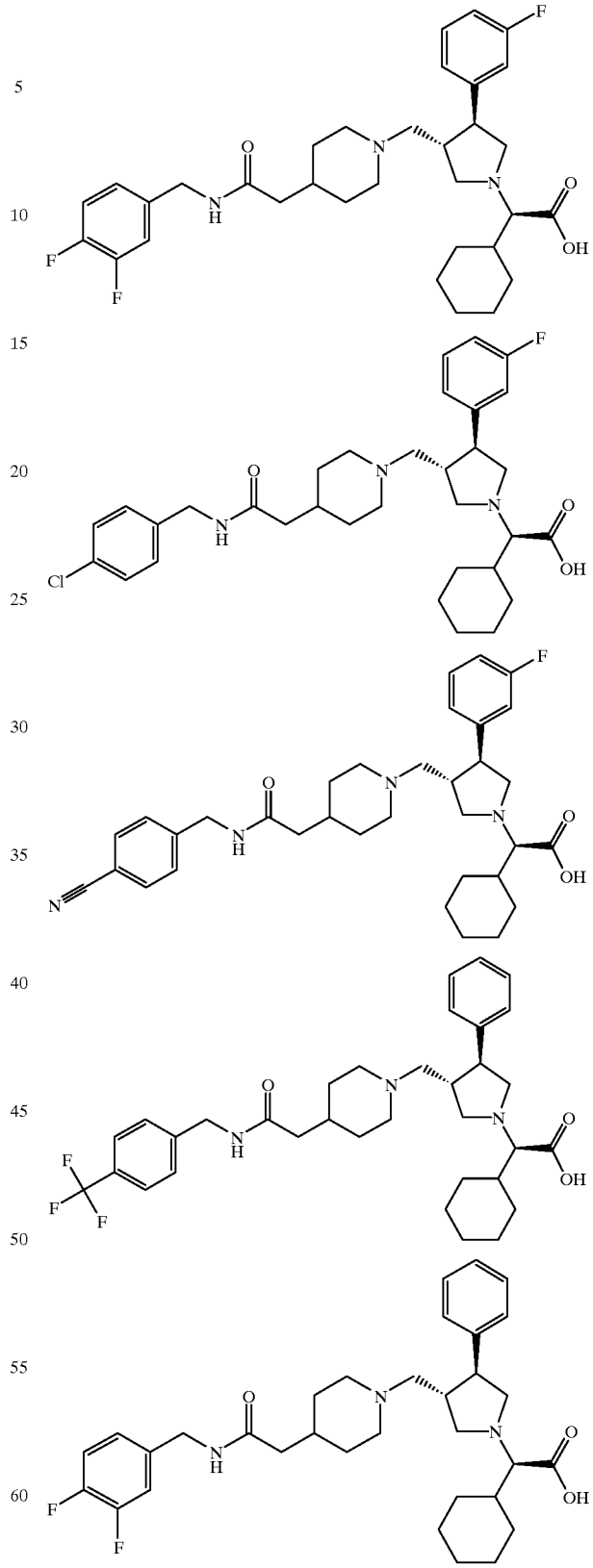

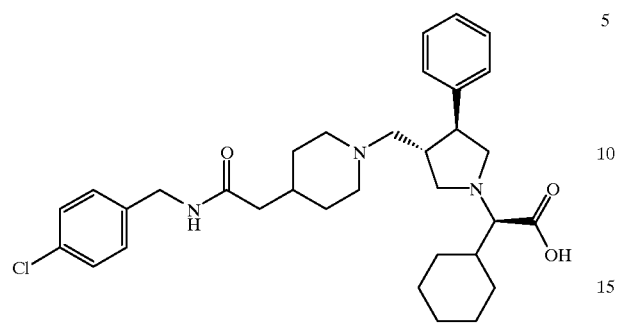
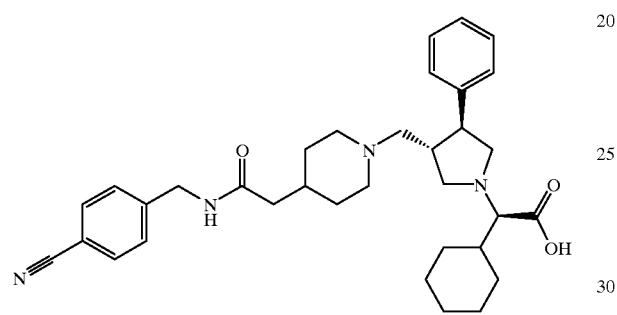
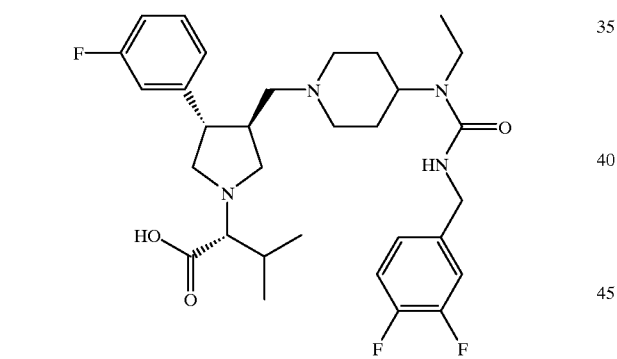
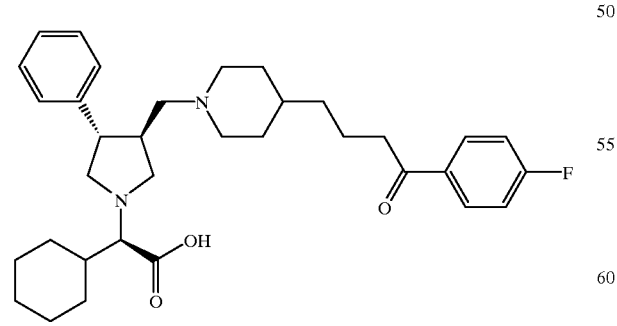
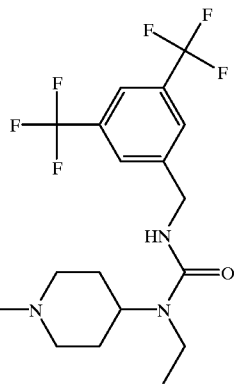
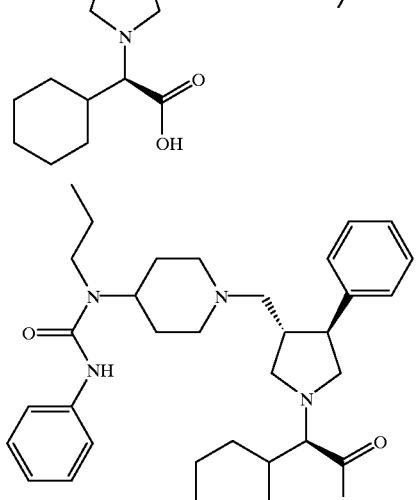
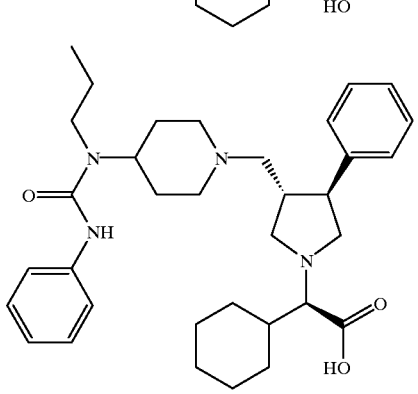
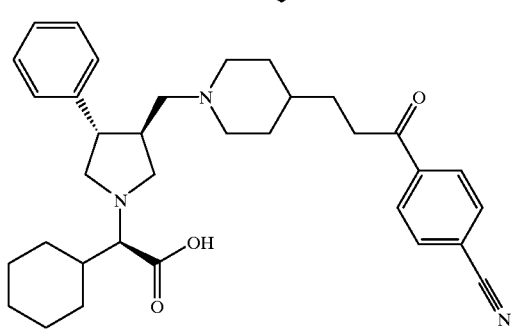

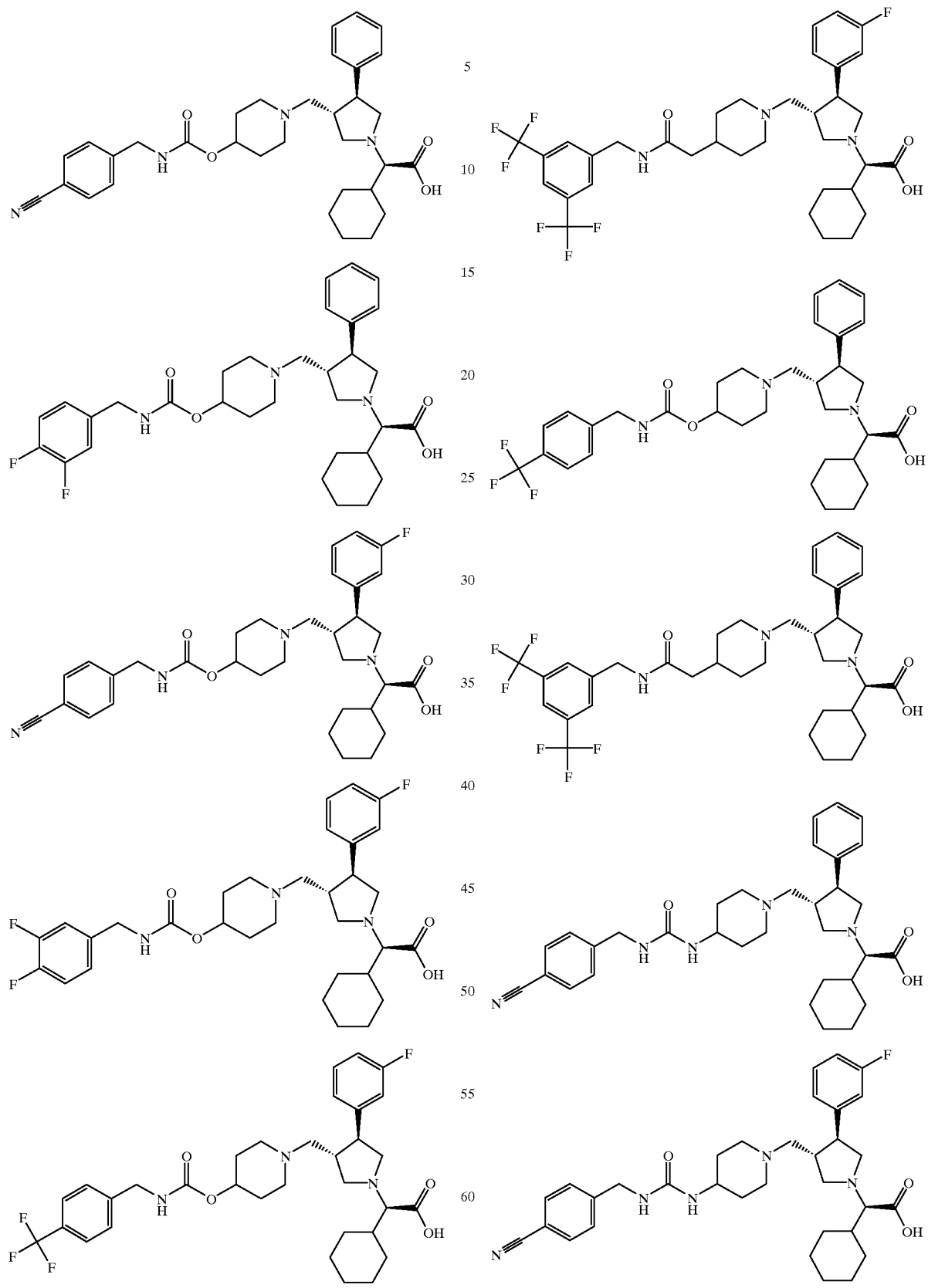

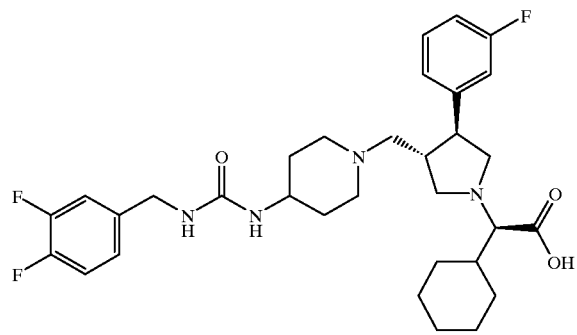
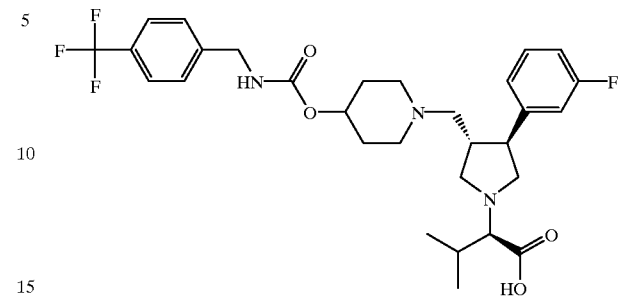
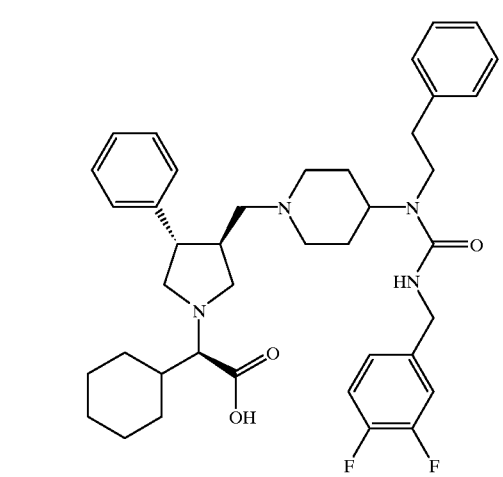
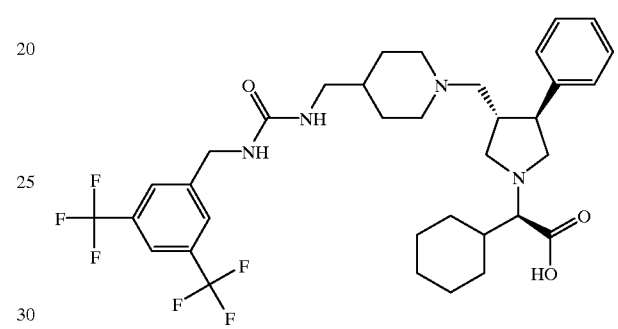
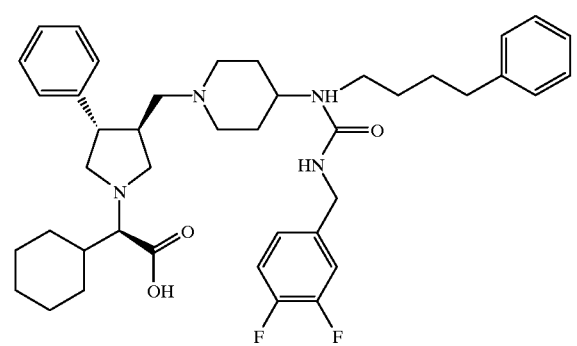
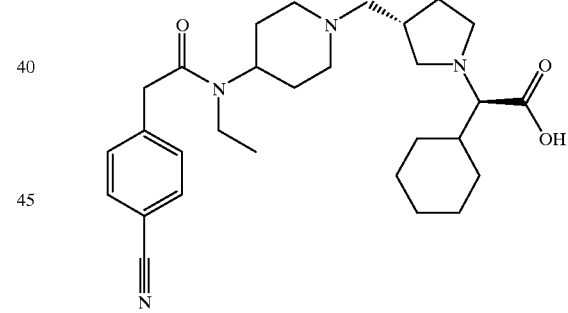
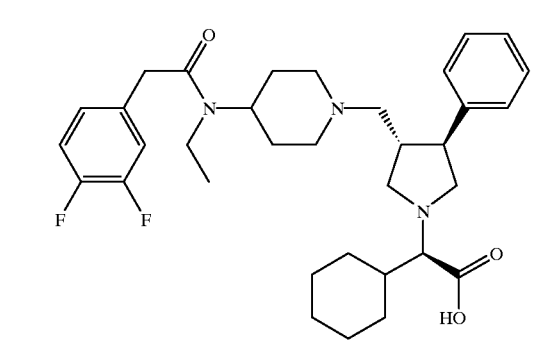
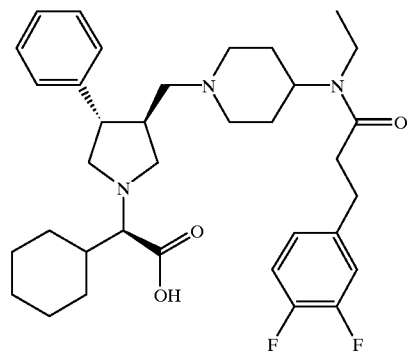

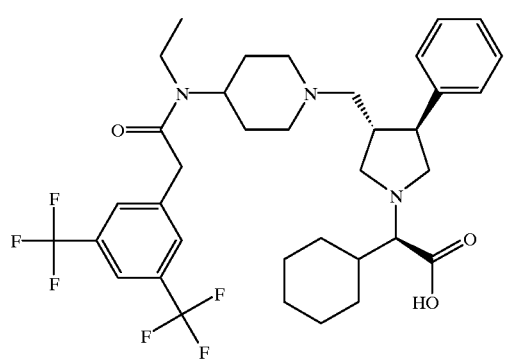
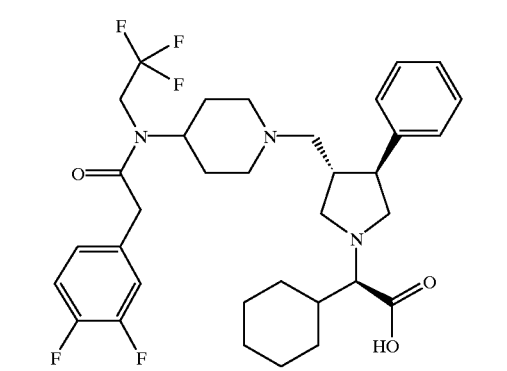
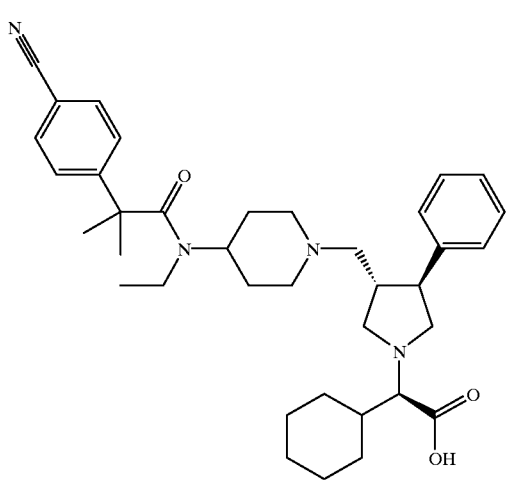
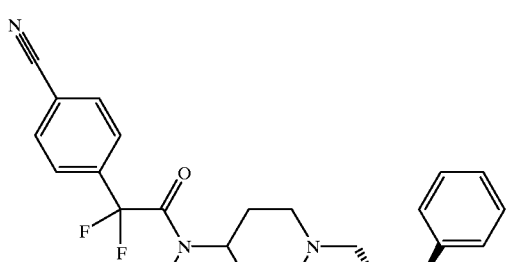
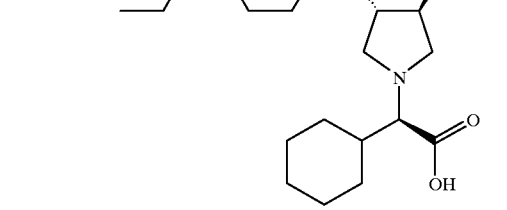
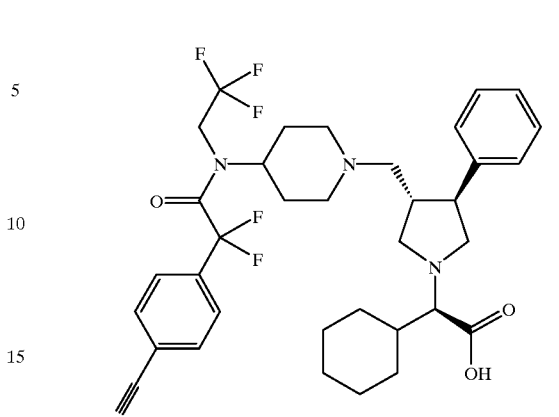
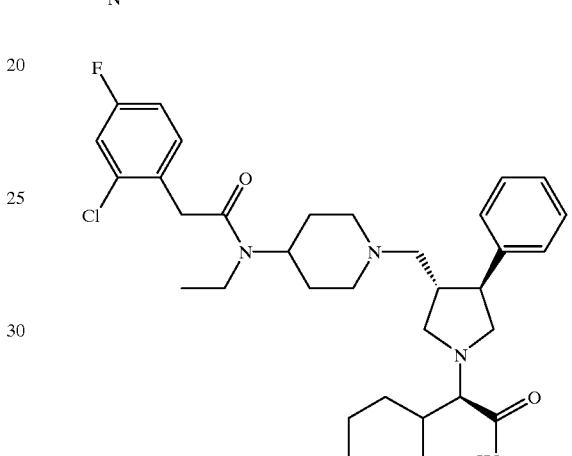
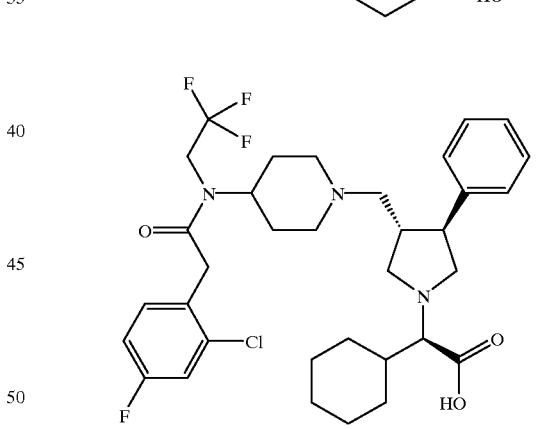
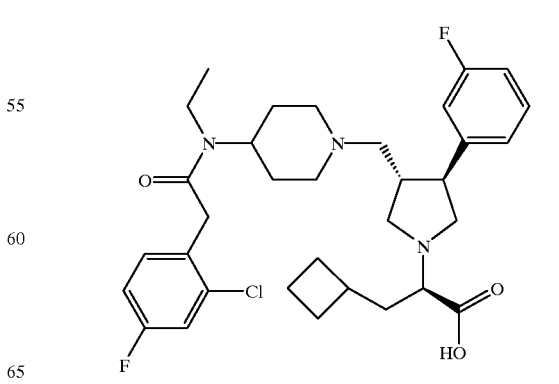

35
-continued
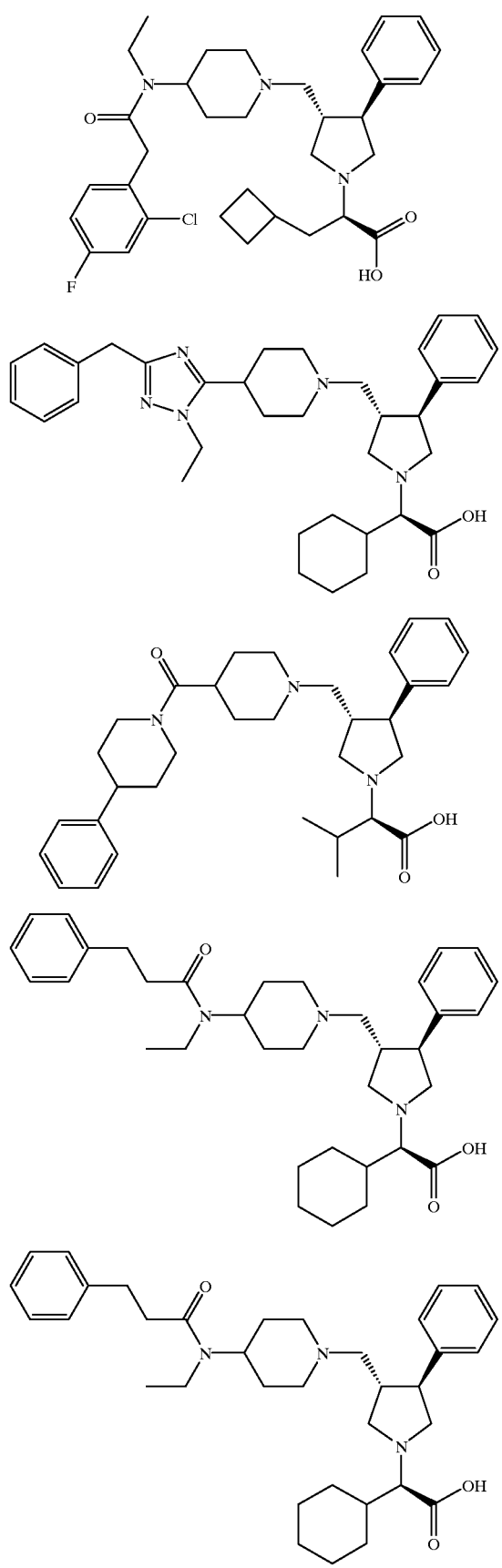
36
-continued
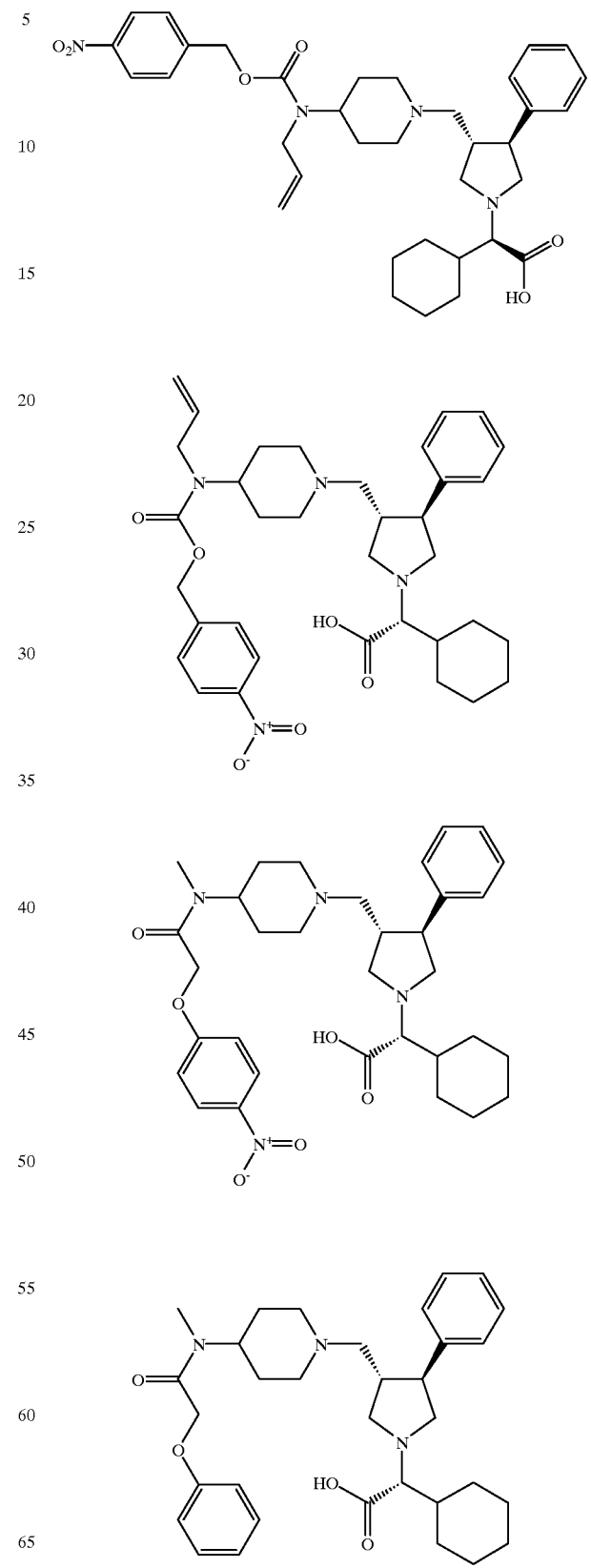

37
-continued
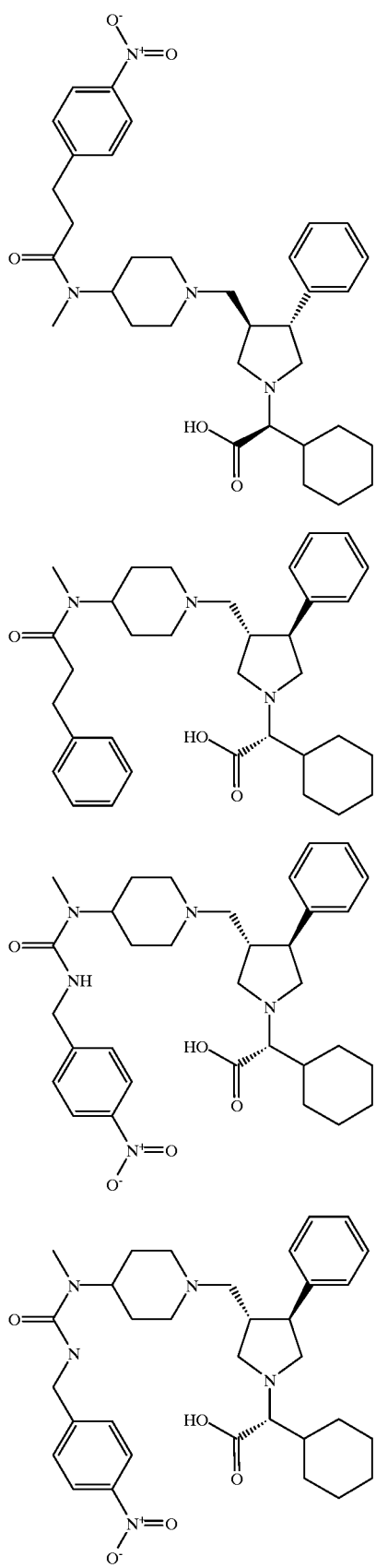
38
-continued
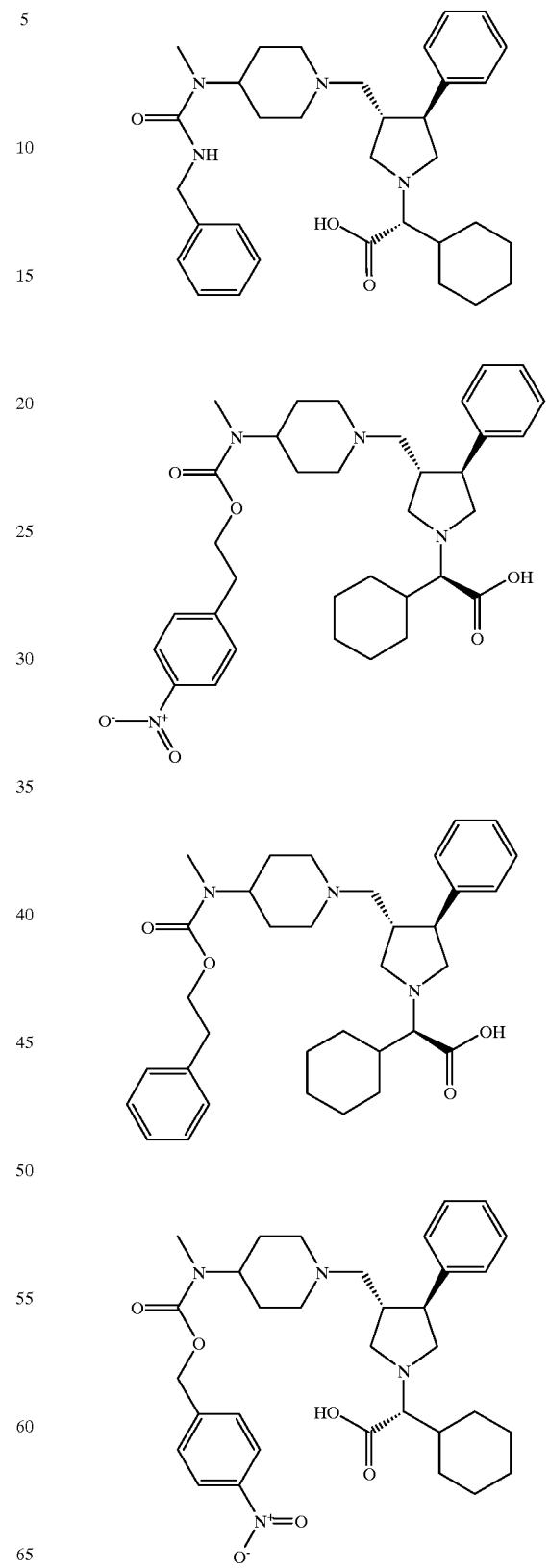

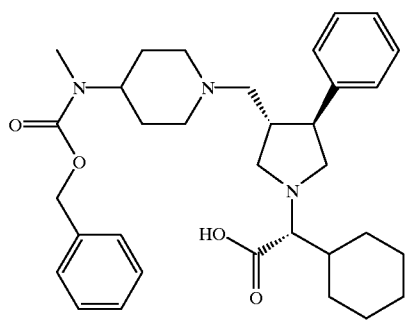
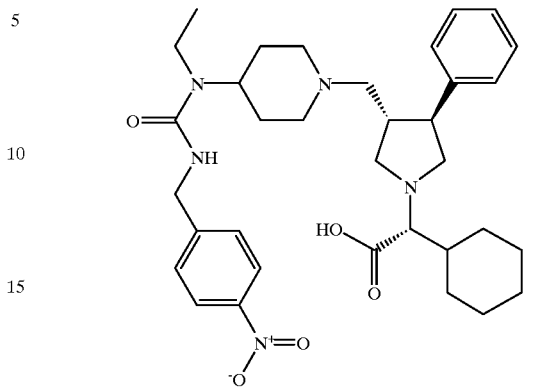
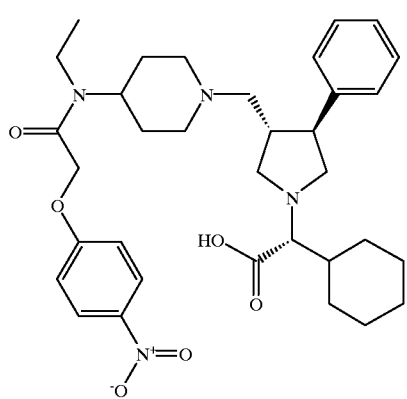
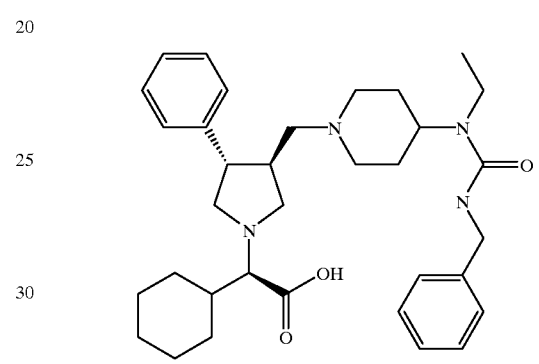
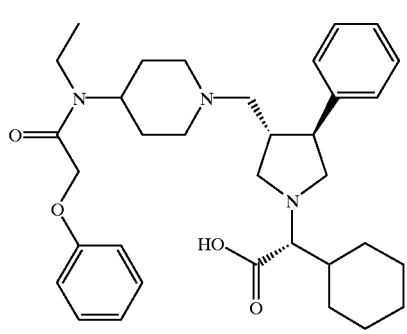
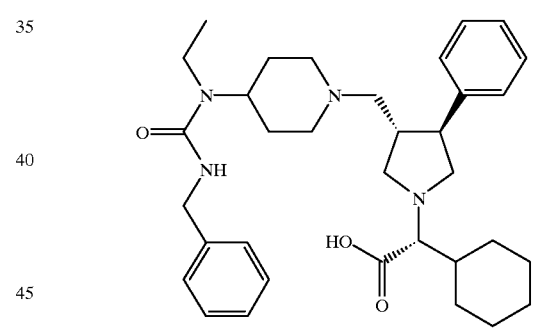
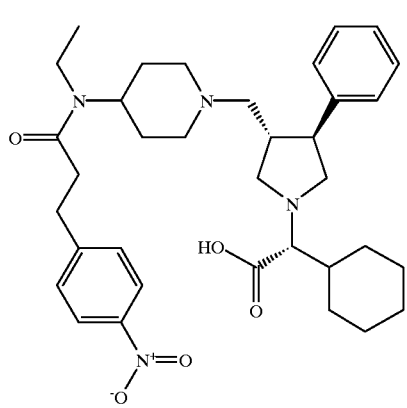
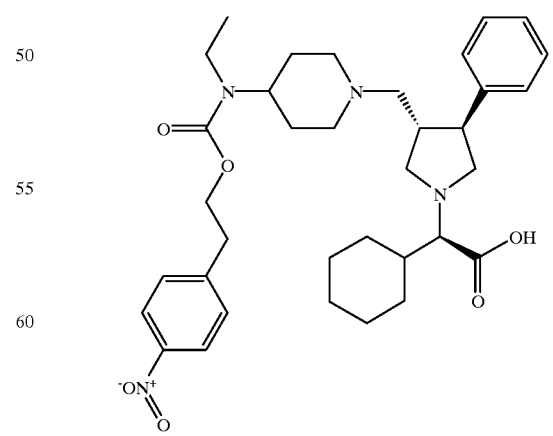

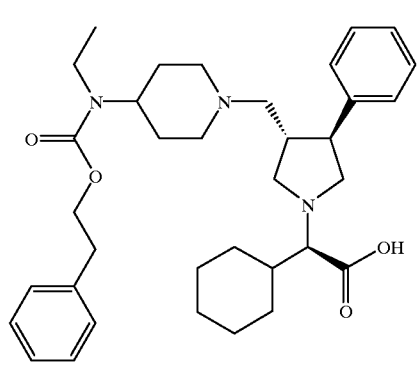
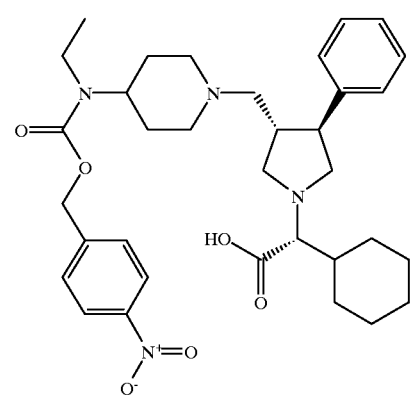
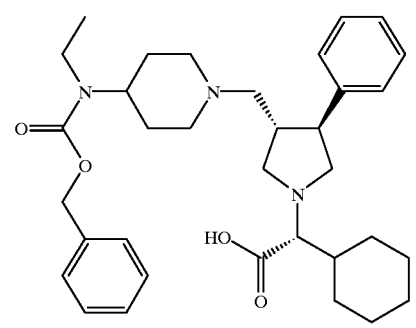
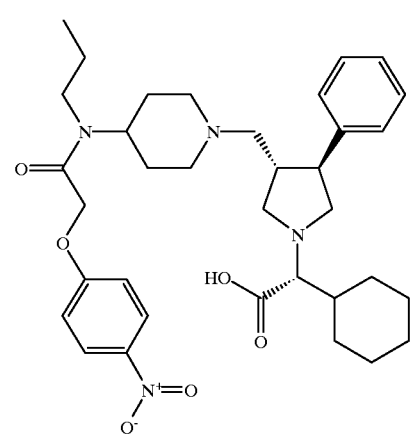
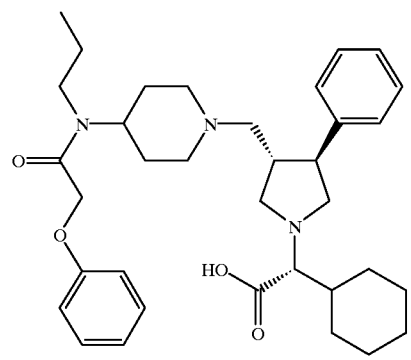
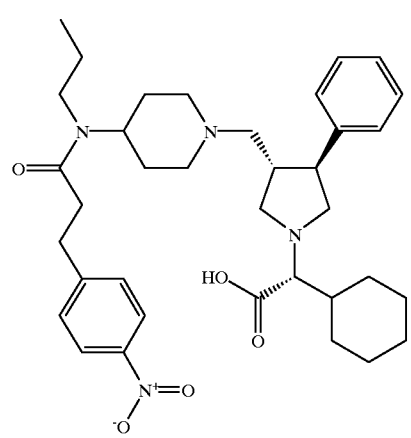
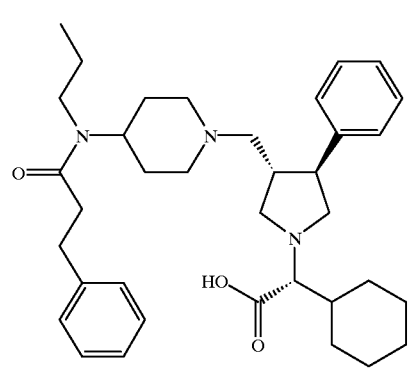
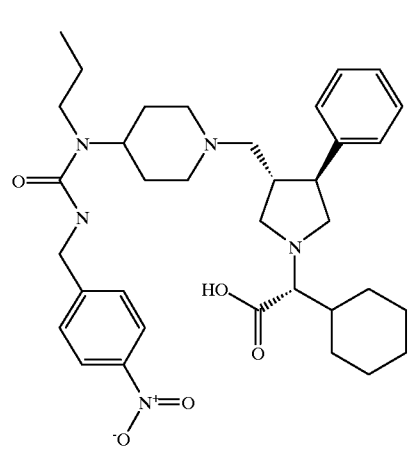

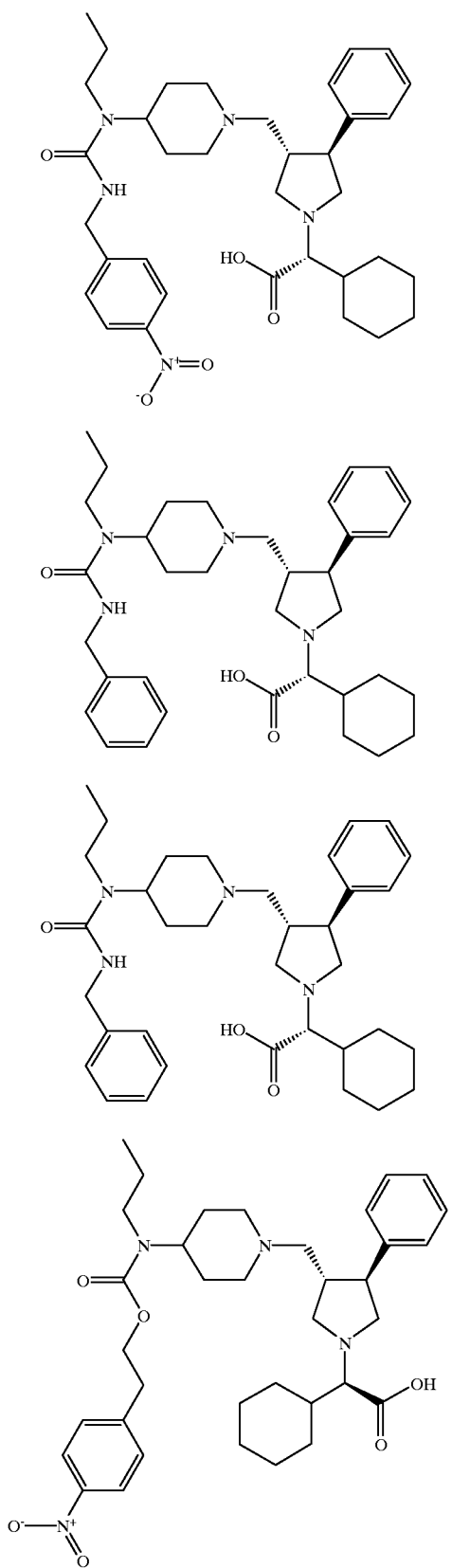
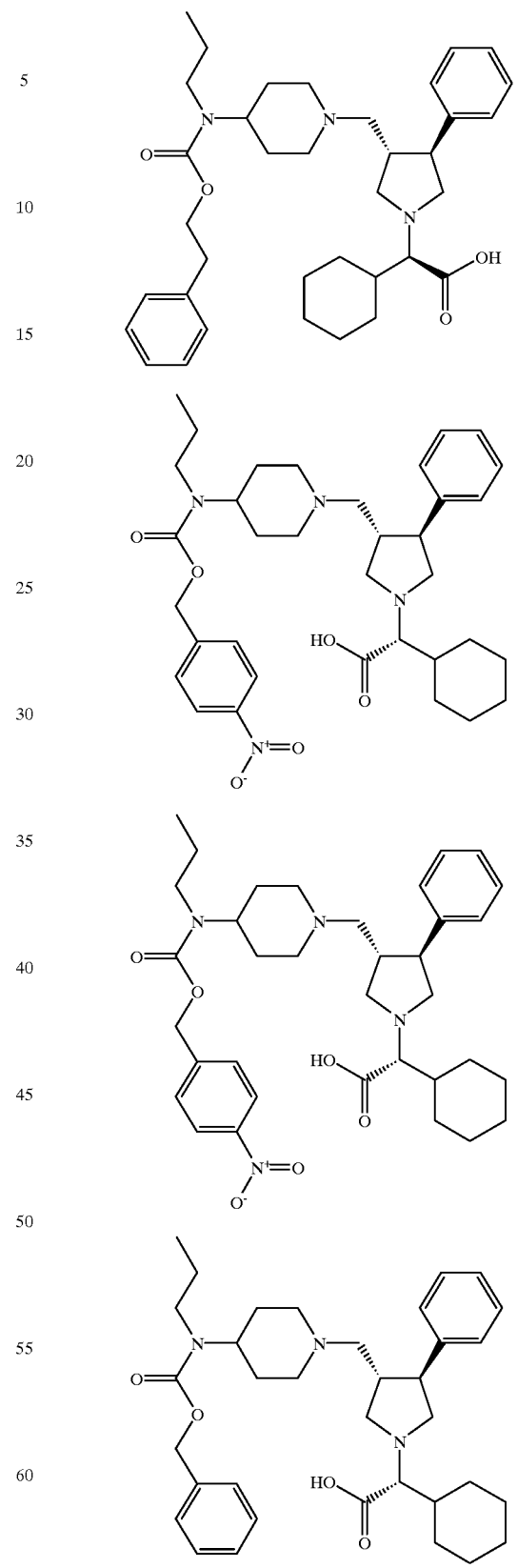

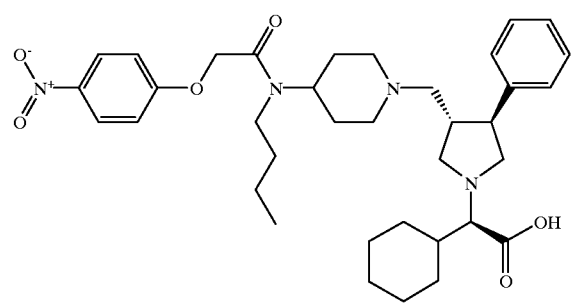
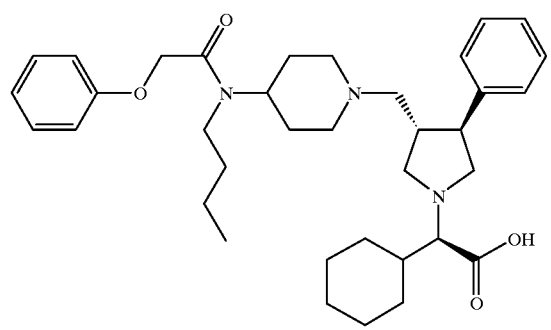
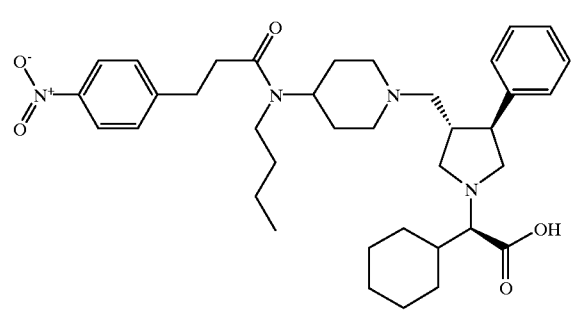
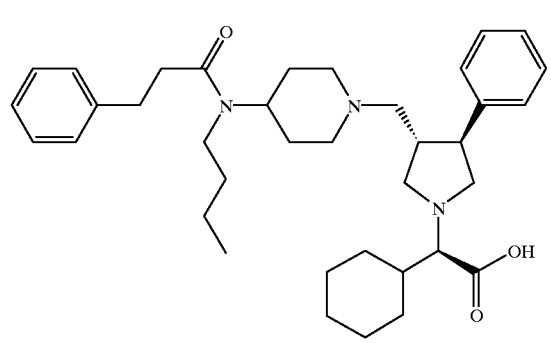
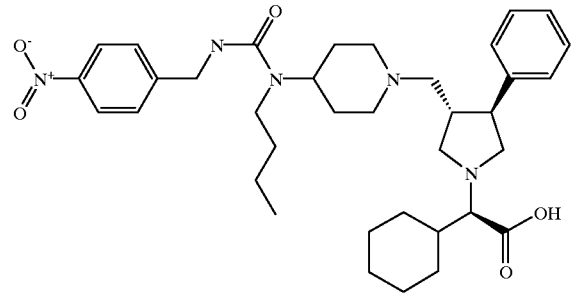
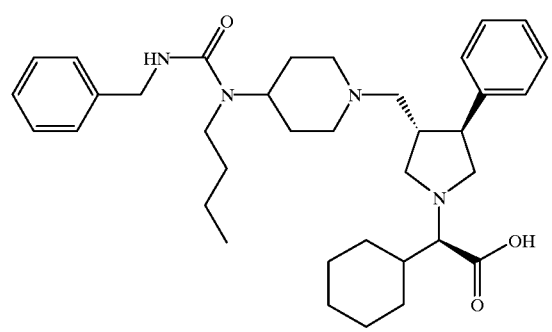

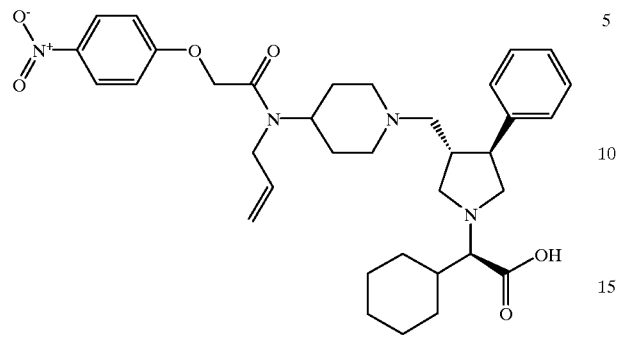
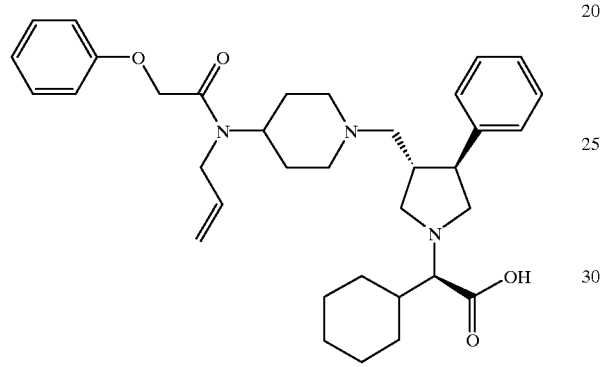
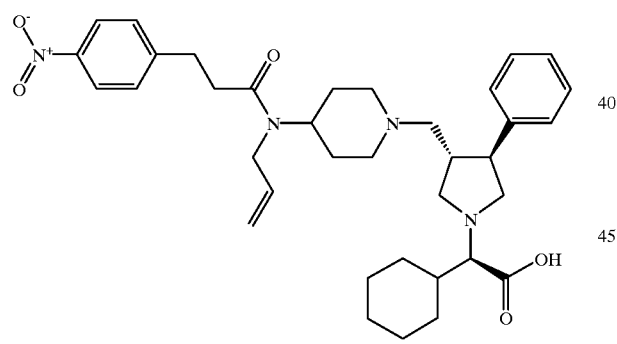
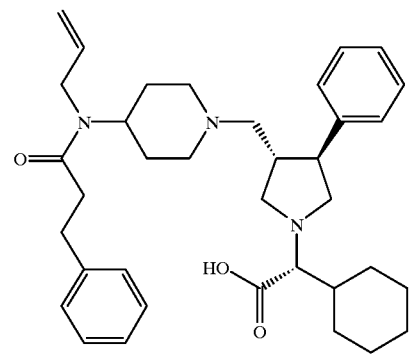
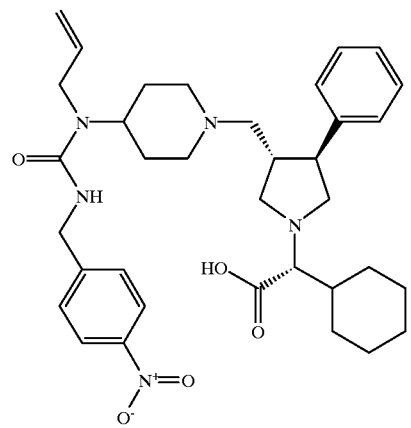
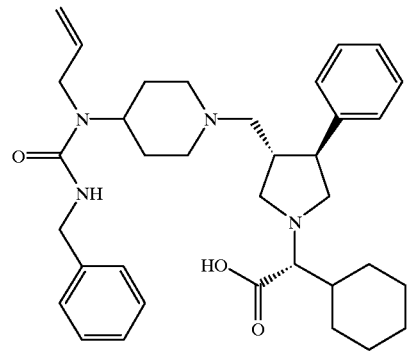
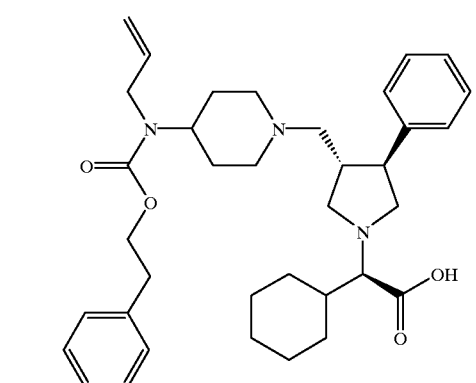
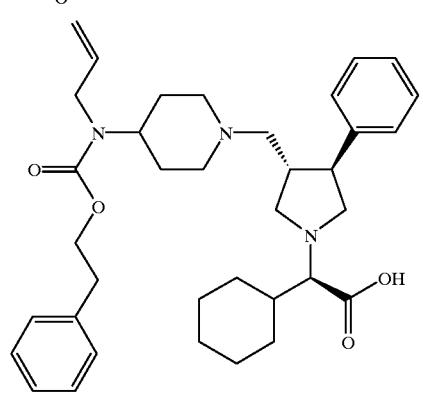

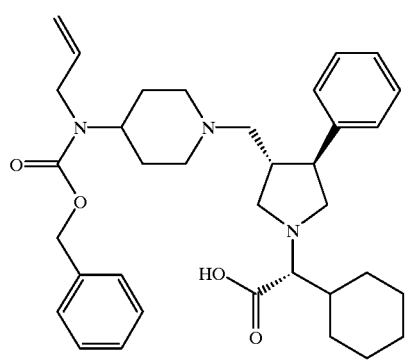
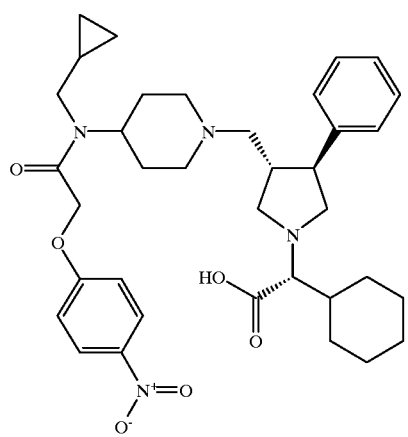
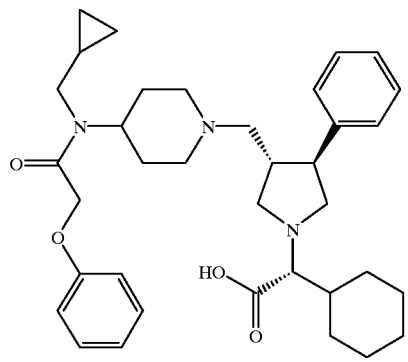
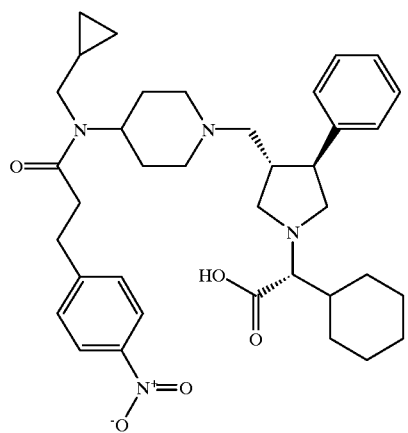
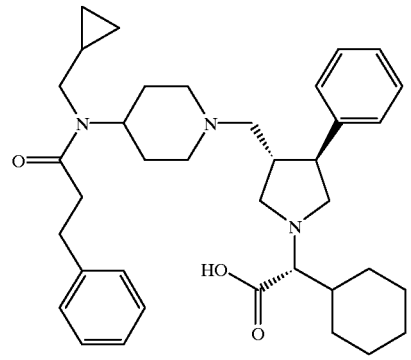
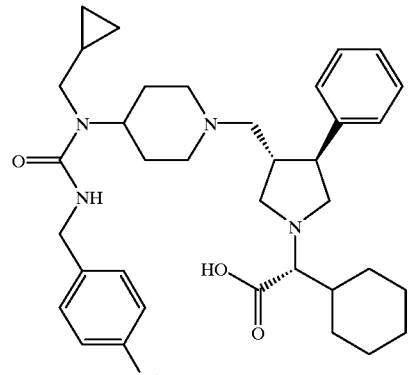
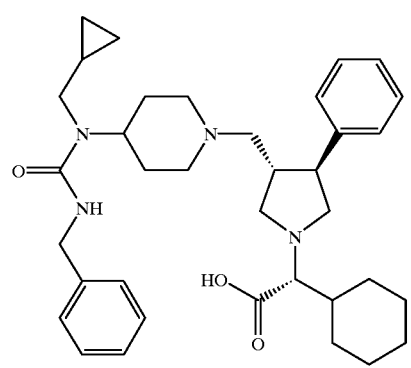
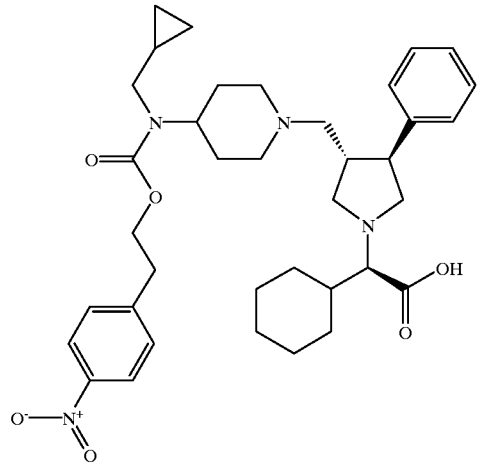

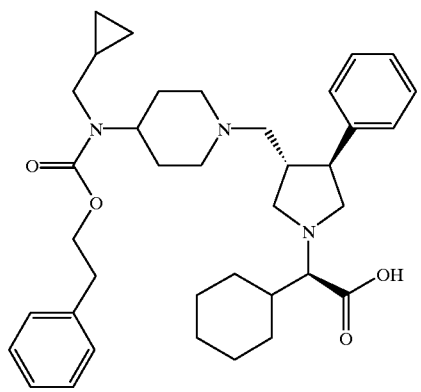
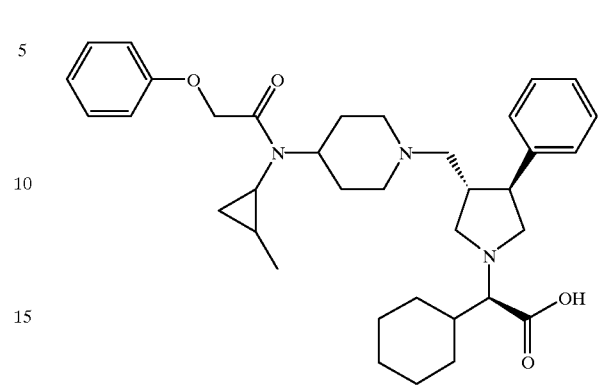
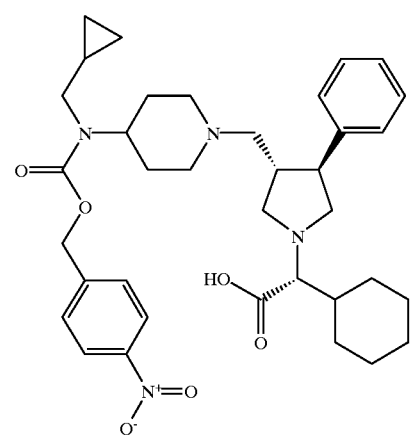
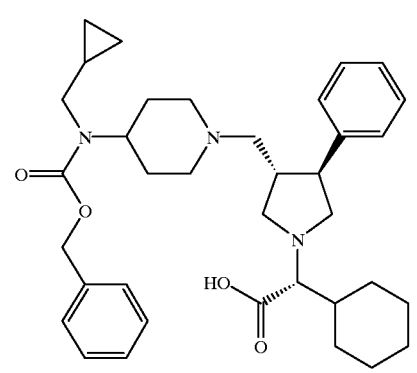
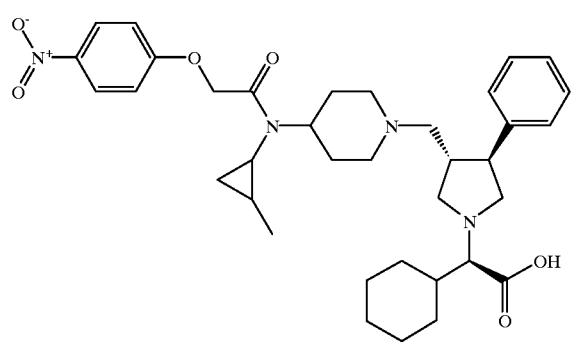
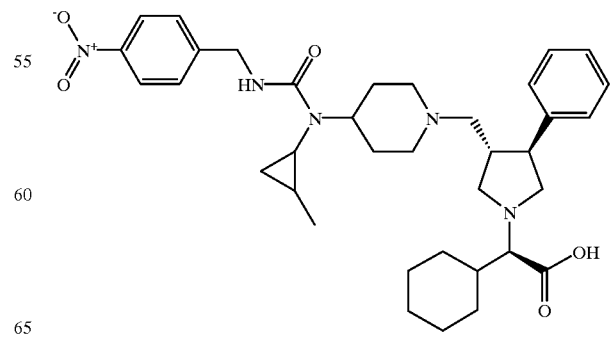

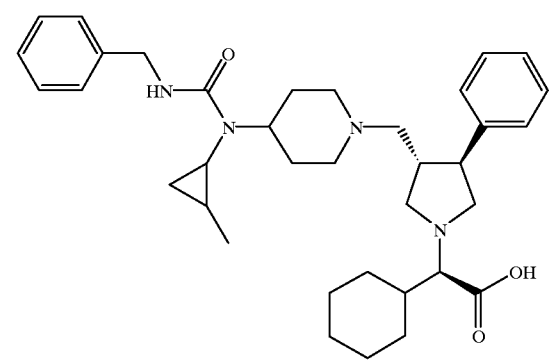
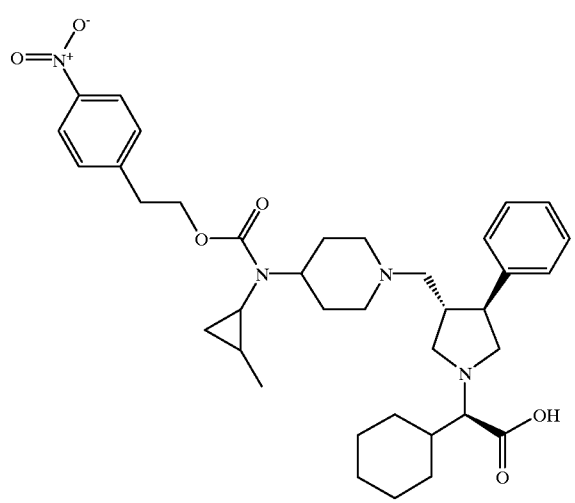
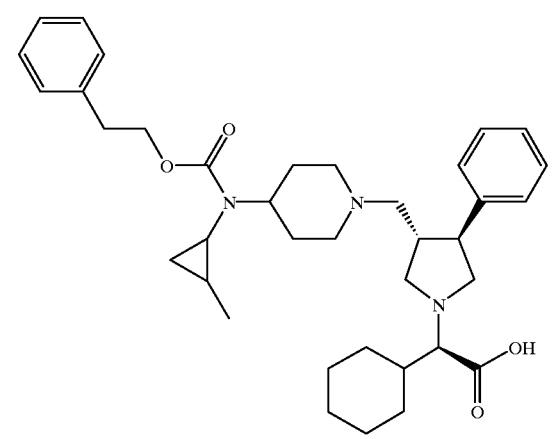
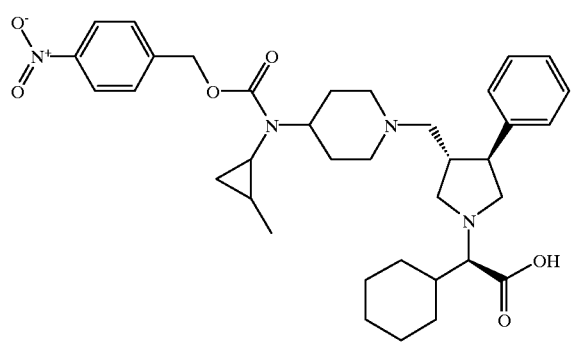
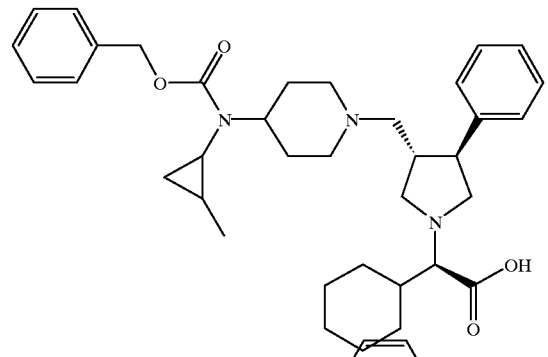
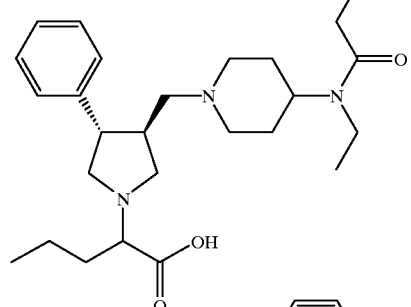
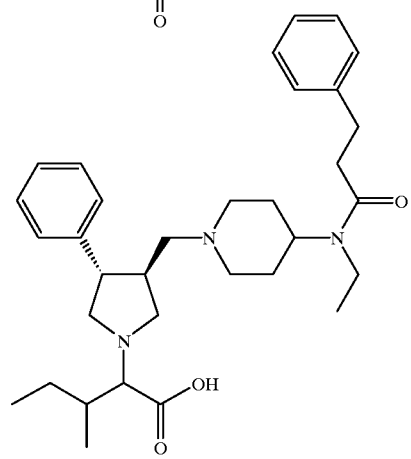
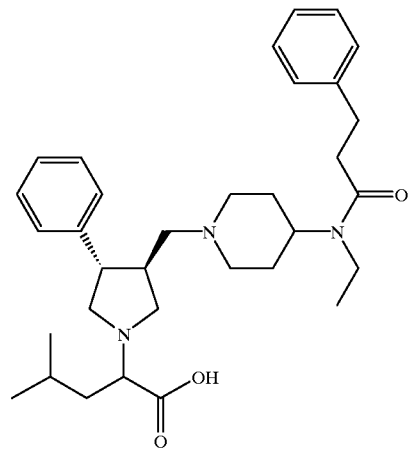

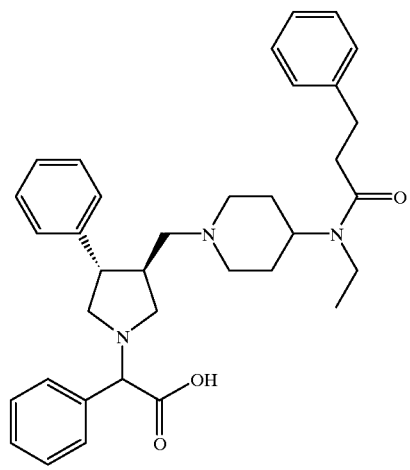
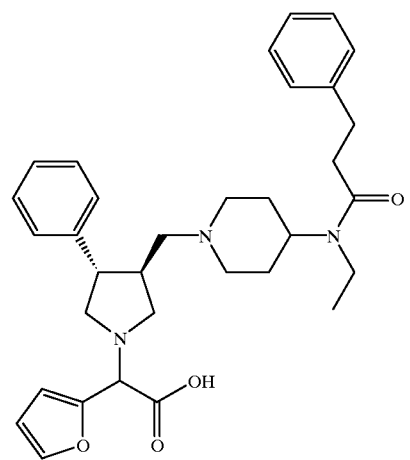
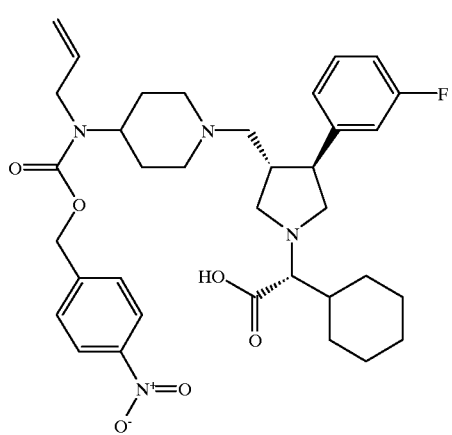
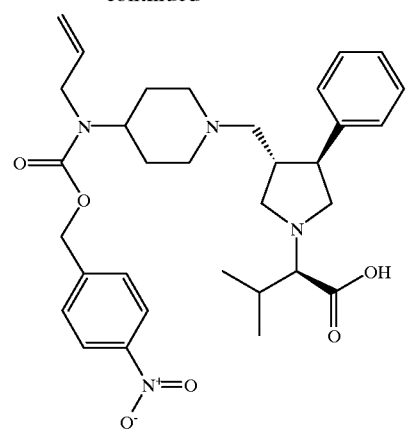
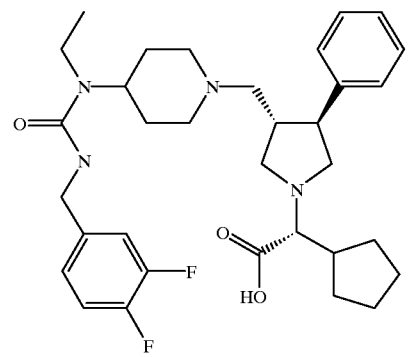
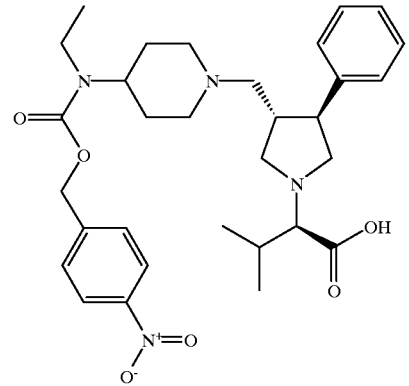
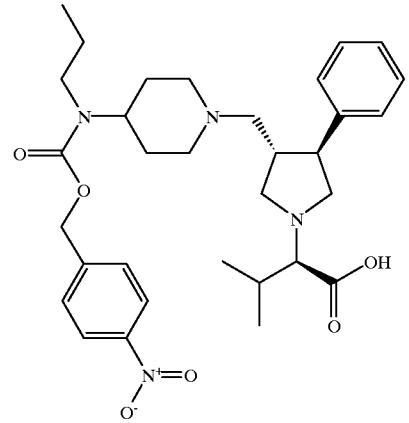

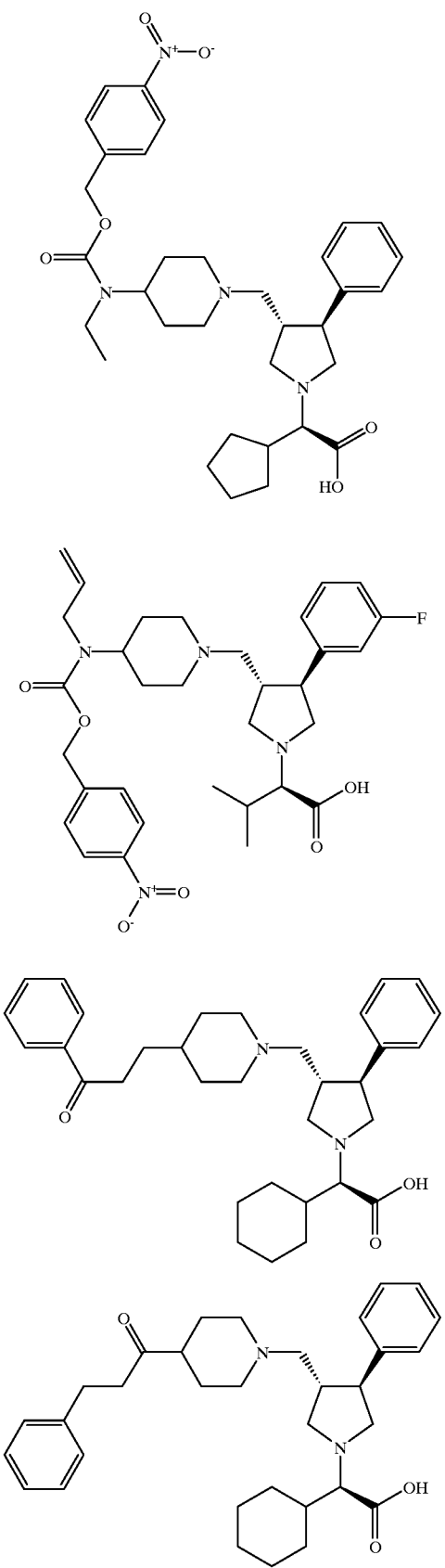
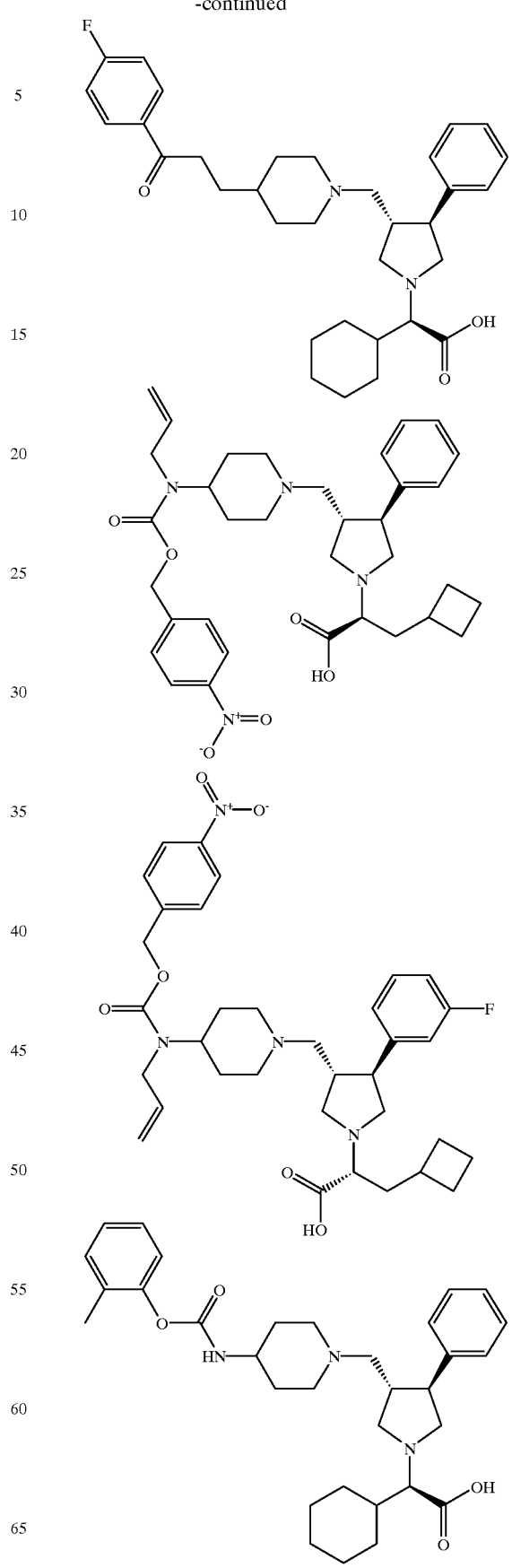

-continued

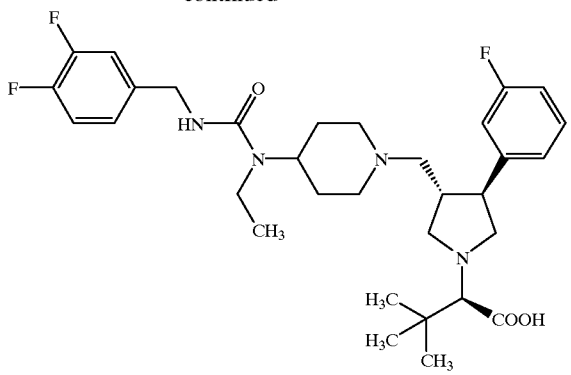

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 488–74892 (1991).

In particular, the compounds of the following examples had activity in binding to the CCR-5 or the CCR-3 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, ADS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases HIV |
| (-) 6-Chloro-4(S)-cyclopropylethynyl-4(S)-trifluoro-methyl-1,4-dihydro-2H-3,1-benzoxazin-2-one | Merck | infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |

-continued

| Drug Name | Manufacturer | Indication |
|---|---|---|
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (-)6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, ADS, ARC (protease inhibitor) |
| Stavudine; d4T Didehydrodeoxy-thymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Sqwbb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |

-continued

| Drug Name | Manufacturer | Indication |
|---|---|---|
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Wanner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1-(S)indanyl)-2(R)-phenylmethyl-4-(S)-hydroxy-5-(1-(4-(3-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4-(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.) The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active. ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

SCHEME 1

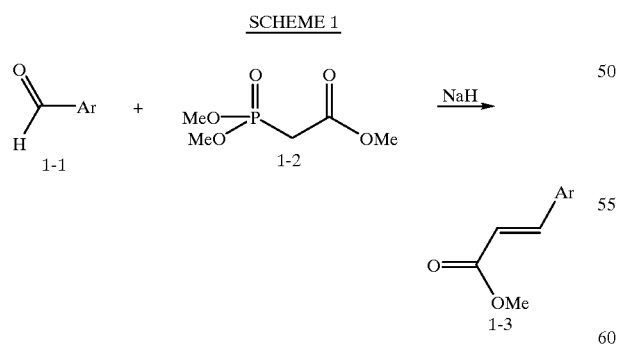

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 or a stabilized Wittig reagent in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

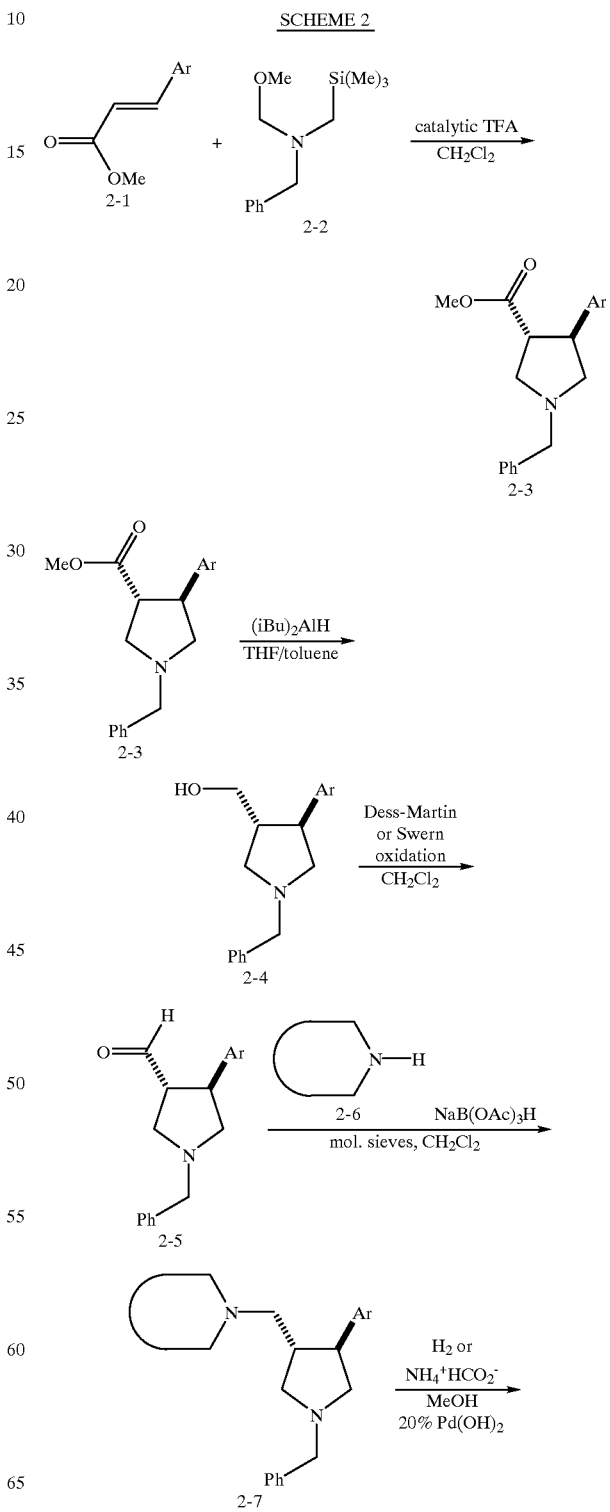

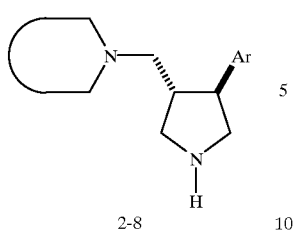

2-8

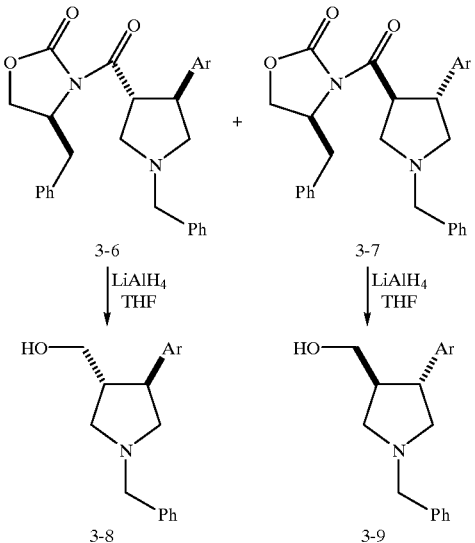

3-6     3-7

↓ LiAlH₄ THF     ↓ LiAlH₄ THF 3-8     3-9

The preparation of compounds within the scope of the instant invention which bear a 1,3,4-trisubstituted pyrrolidine framework is detailed in Scheme 2. Treatment of a trans-cinnamic ester such as 2-1 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride, according to the procedure of Padwa et al (*J. Org. Chem.* 1987, 52, 235) preferentially affords the 3,4-trans pyrrolidine 2-3. Executing this sequence starting from the cis-cinnamic ester results in preferential formation of the 3,4-cis pyrrolidine. Reduction of ester 2-3, for example, with diisobutylaluminum hydride, lithium aluminium hydride, or sodium bis(2-methoxyethoxy)aluminum hydride, provides the primary alcohol 2-4. Oxidation to the aldehyde 2-5 can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine 2-6 then provides diamine 2-7, which can itself be a chemokine receptor modulator. Alternatively, the N-benzyl group is cleaved in a hydrogen atmosphere or with ammonium formate in the presence of 20% palladium hydroxide to provide the secondary amine 2-8.

Scheme 3 shows the preparation of optically pure pyrrolidine intermediates. Hydrolysis of unsaturated ester 3-1 provided acid 3-2, which is converted to diacyl derivative 3-4 by activation of the acid group, for example by formation of a mixed anhydride with pivaloyl chloride, followed by reaction with the lithium salt of 4-(S)-benzyloxazolidin-2-one (3-3). Treatment of 3-4 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride according to the procedure of Padwa et al (*J. Org. Chem.* 1987, 52, 235) affords the diastereomeric pyrrolidines 3-6 and 3-7, which can be separated by flash chromatography, preparative thin layer chromatography, medium pressure liquid chromatography, high pressure liquid chromatography, fractional crystallization, or similar methods known in the art. The separated products are then individually reduced, for example with lithium alumium hydride (LAH) or other strong hydride reducing agents, to provide pyrrolidines 3-8 and 3-9 in optically enriched form.

SCHEME 3

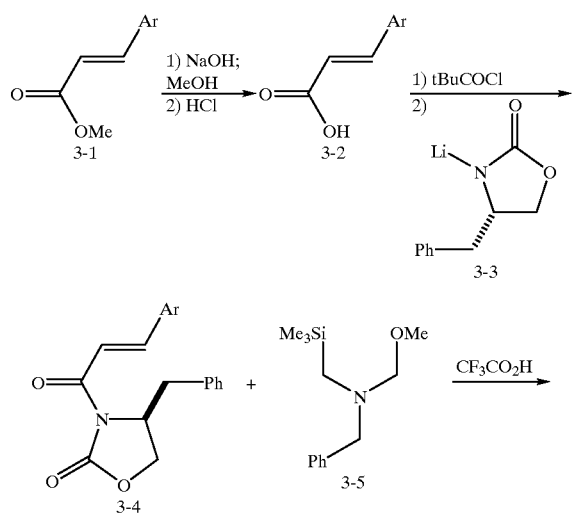

SCHEME 4

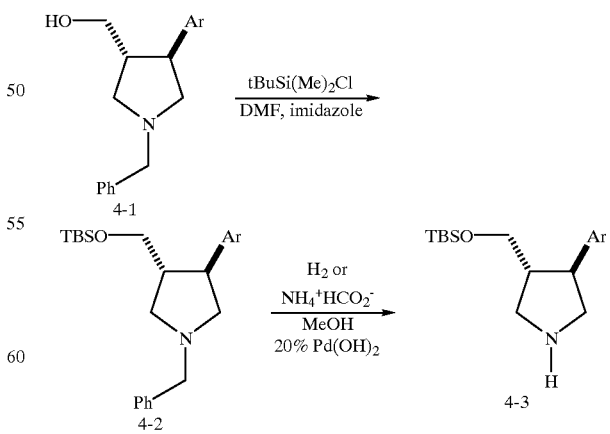

Preparation of a protected pyrrolidine for use as an intermediate in the synthesis of compounds in the instant invention is shown in Scheme 4. The pyrrolidine 4-1 (prepared as shown in Schemes 2 and 3) is protected with a suitable protecting group such as t-butyl-dimethylsilyl to provide silyl ether 4-2. Other silyl groups can also be used in this role, as can other protecting groups for a hydroxy residue (see Greene, T. W.; Wuts, P. G. M. "Protective Groups in Organic Synthesis", 2nd edition, Wiley-Interscience, New York, pp. 10–143 (1991)), subject to the group being stable to conditions used to remove the benzyl group and being removable under conditions that would not adversely affect the remainder of the molecule. Removal of the benzyl group on nitrogen is then carried out by hydrogenolysis, for example by transfer hydrogenation with ammonium formate in the presence of 20% palladium hydroxide or with catalytic hydrogenation with 10% palladium on carbon under one or more atmospheres of hydrogen. Alternatively, compound 4-1 can be debenzylated first under the conditions noted above and then silylated on the hydroxy group, to provide 4-3.

SCHEME 5

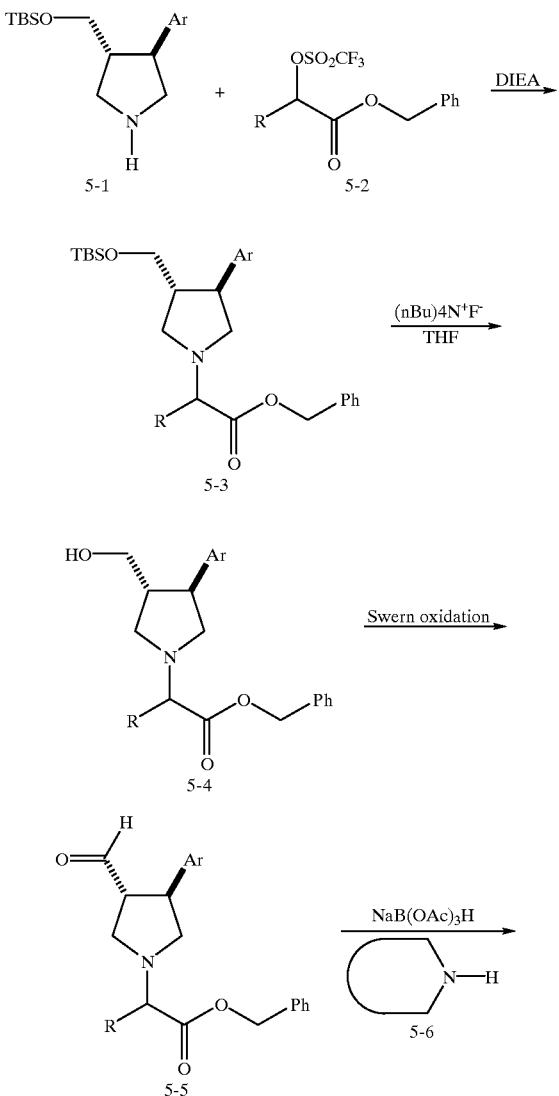

-continued

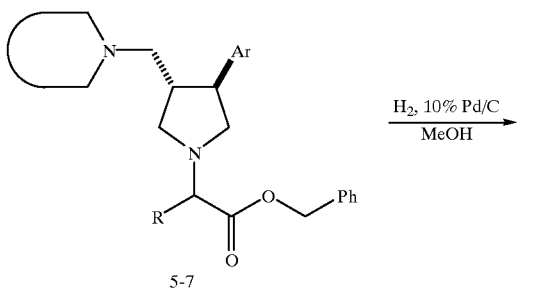

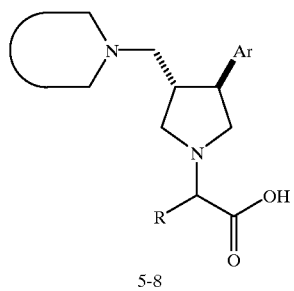

Preparation of some 1,3,4-trisubstituted pyrrolidines within the scope of the instant invention is given in Scheme 5. Alkylation of pyrrolidine 5-1 with the trifluoromethane-sulfonate (triflate) ester of a suitable alpha-hydroxy ester derivative 5-2 in the presence of a hindered base such as DIEA ((N,N-(diisopropyl)ethylamine) or a sparingly soluble base such as potassium carbonate provides the N-substituted product 5-3. Triflate ester 5-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 5-2 instead of a triflate, such as chloride, bromide, iodide, methanesulfonate, ptoluenesulfonate, etc. Deprotection of silyl ether 5-3 is carried out with tetrabutylammonium fluoride in TEF, to afford alcohol 5-4. Alternatively, acidic conditions can be used to remove the silyl group, for example aqueous trifluoroacetic acid, hydrogen fluoride in pyridine, hydrochloric acid, etc. Oxidation of 5-4 to the aldehyde 5-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 5-6 then provides diamine 5-7, which can itself be a chemokine receptor antagonist. Cleavage of the benzyl group with catalytic hydrogenation, for example under an atmosphere of hydrogen in the presence of 10% palladium on carbon as catalyst in methanol or ethanol as solvent, provides acid 5-8. Alternatively, the benzyl ester can be cleaved by treatment with strong aqueous base if the remainder of the molecule is stable to those conditions.

SCHEME 6

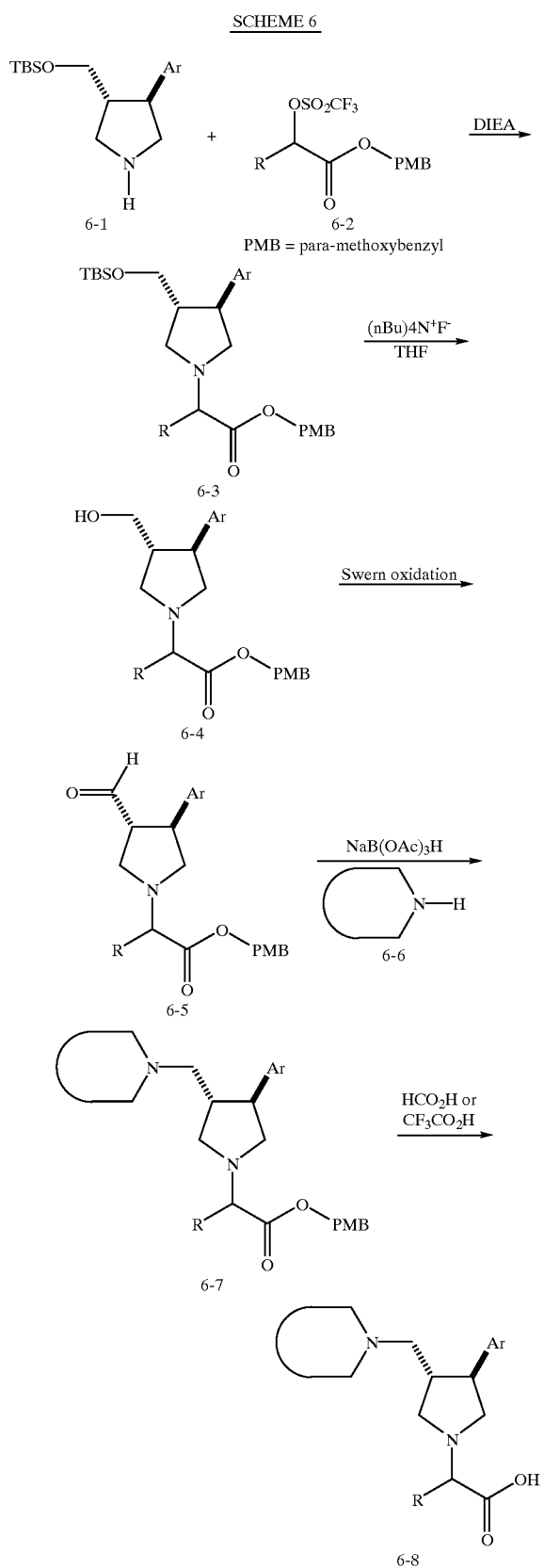

PMB = para-methoxybenzyl protecting group is cleavable under mild acidic conditions is given in Scheme 6. Alkylation of pyrrolidine 6-1 with the triflate ester of a suitable alpha-hydroxy ester derivative 6-2 in the presence of a hindered base such as DIEA or a sparingly soluble base such as potassium carbonate provides the N-substituted product 6-3 (PMB=para-methoxybenzyl). Triflate ester 6-2 is prepared by treating the parent alpha-hydroxy ester with triflic anhydride in the presence of a suitable hindered tertiary amine, such as DIEA, 2,6-lutidine or 2,6-di-tbutyl-4-methylpyridine at or below room temperature in a suitable inert solvent such as dichloromethane or 1,2-dichloroethane. Alternatively, other leaving groups can be employed to activate the alpha-position on ester 6-2 instead of a triflate, such as chloride, bromide, iodide, methanesulfonate, p-toluenesulfonate, etc. Deprotection of silyl ether 6-3 is carried out with tetrabutylammonium fluoride in THF, to afford alcohol 6-4. Alternatively, mildly acidic conditions in some cases can be used to selectively remove the silyl group, for example aqueous trifluoroacetic acid, hydrogen fluoride in pyridine, hydrochloric acid, etc. Oxidation of 6-4 to the aldehyde 6-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 6-6 then provides diamine 6-7, which can itself be a chemokine receptor antagonist. Cleavage of the PMB group with acid, for example with formic acid or trifluoroacetic acid plus anisole, provides acid 6-8. Alternatively, the ester can be cleaved by treatment with strong aqueous base or by catalytic hydrogenation if the remainder of the molecule is stable to those conditions.

SCHEME 7

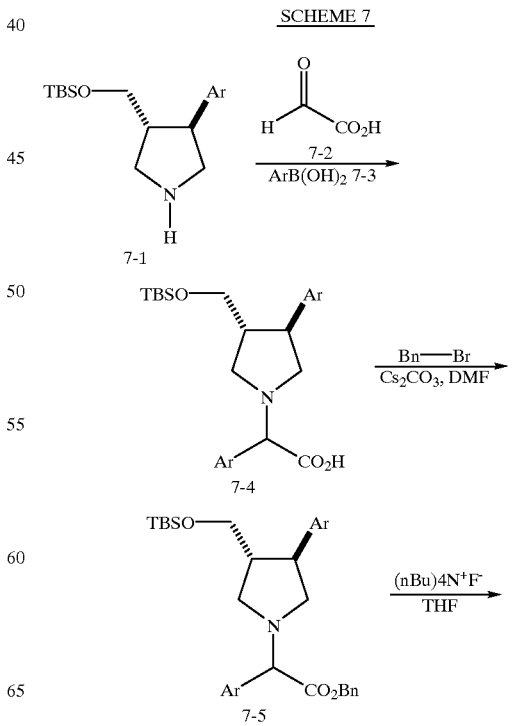

Preparation of 1,3,4-trisubstituted pyrrolidines within the scope of the instant invention wherein the carboxylic acid

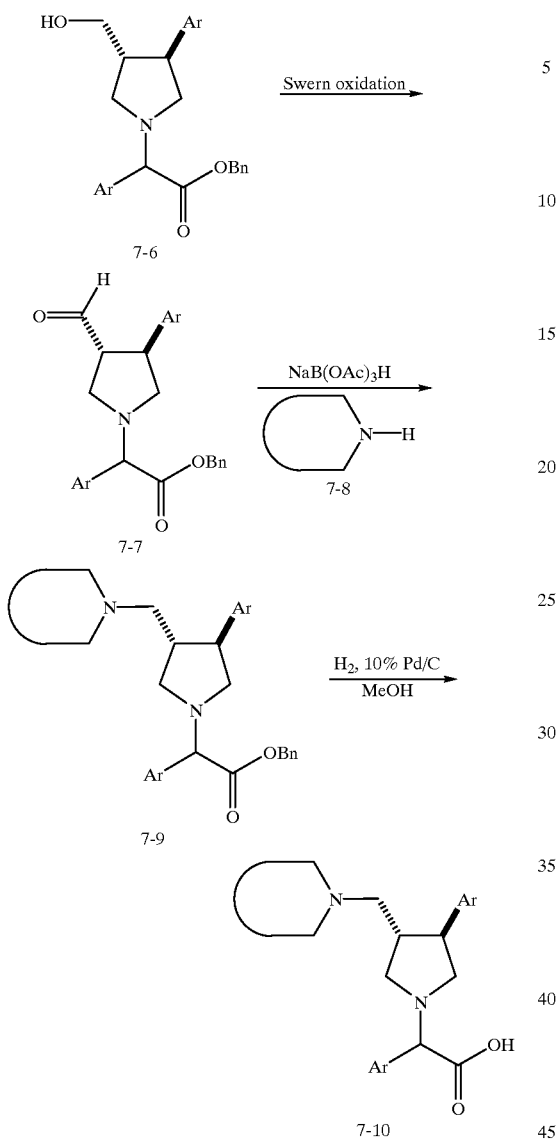

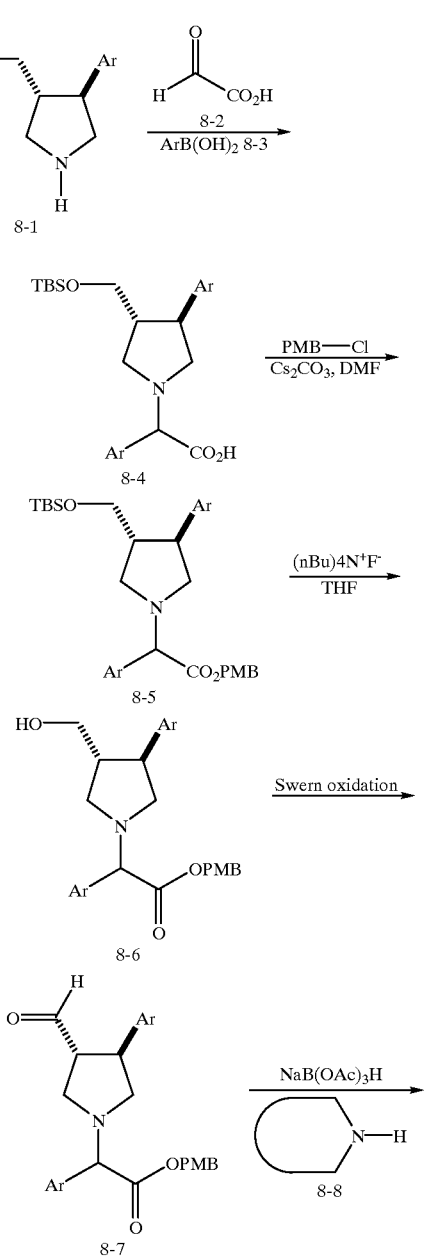

hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 7-8 then provides diamine 7-9, which can itself be a chemokine receptor antagonist. Deprotection of the benzyl ester is carried out with catalytic hydrogenation, for example under an atmosphere of hydrogen in the presence of 10% palladium on carbon as catalyst in methanol or ethanol as solvent, provides acid 7-10. Alternatively, the benzyl ester can be cleaved by treatment with strong aqueous base if the remainder of the molecule is stable to those conditions.

An alternative route for the synthesis of pyrrolidines with a 1-(α-arylacetic acid) substituent is given in Scheme 7. Reaction of the protected pyrrolidine 7-1 with glyoxylic acid in the presence of an aryl boronic acid 7-3 provides the N-aralkylated product 7-4 (see Petasis, N. A.; Goodman, A.; Zavialov, I. A. *Tetrahedron* 1997, 53, 16463–16470; and PCT Int. Appl. WO 9800398). Protection of the acid by alkylation with benzyl bromide in DMF in the presence of cesium carbonate provides ester 7-5. Deprotection of the silyl group with tetrabutylammonium fluoride in THF, or with mild acid such as aqueous trifluoroacetic acid, then provides alcohol 7-6. Alternatively, simultaneous removal of the silyl group of 7-4 and formation of the ester can be carried out by heating 7-4 in an anhydrous solution of the esterifying alcohol in the presence of acid, such as toluenesulfonic acid, triflic acid, hydrochloric acid, and the like. The alcohol 7-6 is oxidized to aldehyde 7-7 using the Swern oxidation conditions. Other methods for oxidizing a primary

81

-continued

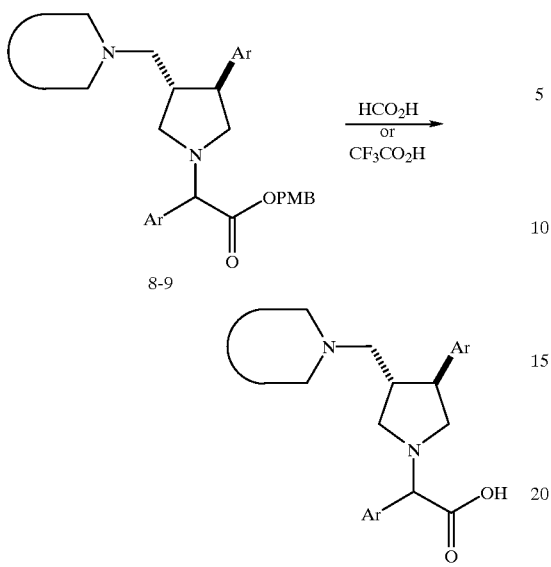

8-9

8-10

An alternative route for the synthesis of pyrrolidines with a 1-(α-arylacetic acid) substituent, wherein the carboxylic acid protecting group can be cleaved in mild acid, is given in Scheme 8. Reaction of the protected pyrrolidine 8-1 with glyoxylic acid in the presence of an arylboronic acid 8-3 provides the Naralkylated product 8-4, according to the procedure of Petasis, N. A.; Goodman, A.; Zavialov, I. A.*Tetrahedron* 1997, 53, 16463–16470 (see also PCT Int. Appl. WO 9800398). Protection of the acid by alkylation with para-methoxybenzyl chloride in DMF in the presence of cesium carbonate provides ester 8-5. Deprotection of the silyl group with tetrabutylammonium fluoride in THF, provides alcohol 8-6. The alcohol 8-6 is oxidized to aldehyde 8-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 8-8 then provides diamine 8-9, which can itself be a chemokine receptor antagonist. Deprotection of the p-methoxybenzyl ester is carried out by treatment with formic acid, trifluoroacetic acid plus anisole, or other moderate acids, at temperatures from 0 degrees C. to 120 degrees C., to provide the chemokine receptor antagonist 8-10.

SCHEME 9

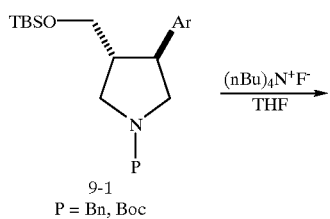

9-1
P = Bn, Boc

82

-continued

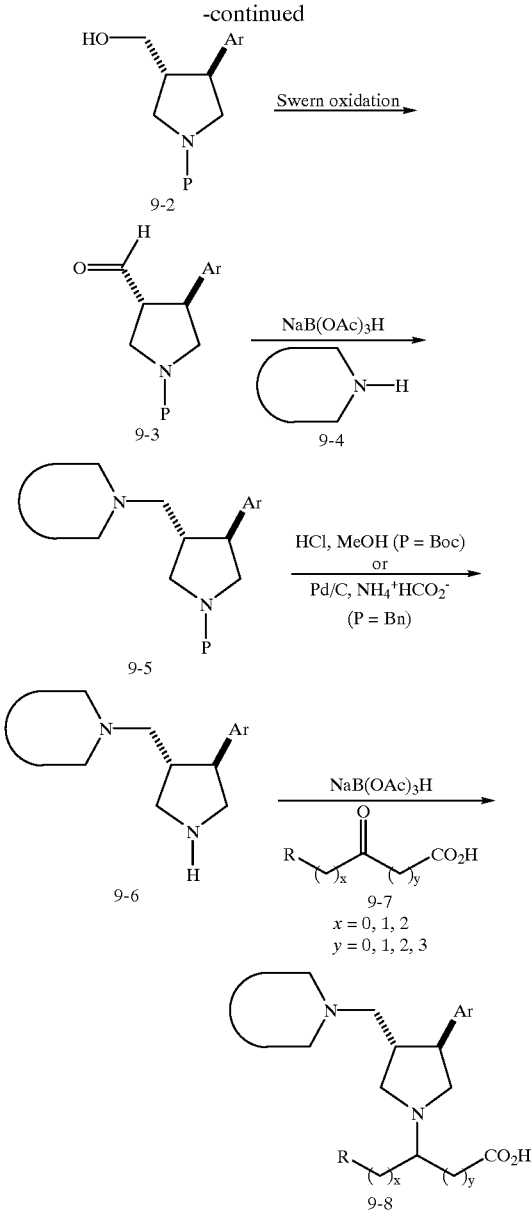

Another method of preparing compounds within the scope of the instant invention is given in Scheme 9. Doubly protected pyrrolidine 9-1 (obtained either as shown in Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 9-2. Oxidation of 9-2 to 9-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 9-4 then provides diamine 9-5, which can itself be a chemokine receptor antagonist. Deprotection of the pyrrolidine nitrogen, when P=Boc, can be carried out with HCl in methanol or with trifluoroacetic acid and anisole in dichloromethane, to give secondary amine 9-6. When P=benzyl, debenzylation is carried out in the presence of palladium on carbon as a catalyst, using either hydrogen gas or ammonium formate to effect transfer hydrogenation. Reductive amination with keto-acid 9-7 then provides pyrrolidine 9-8.

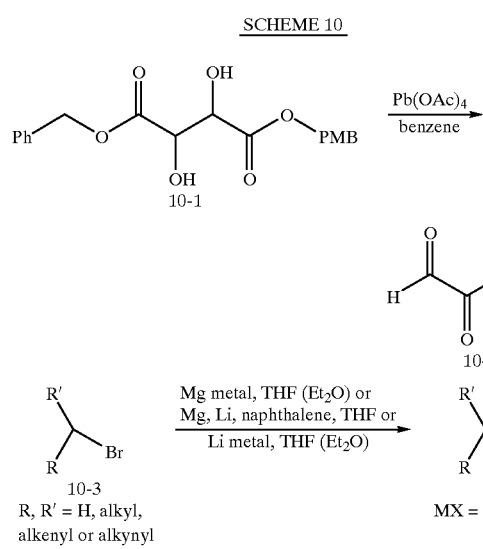

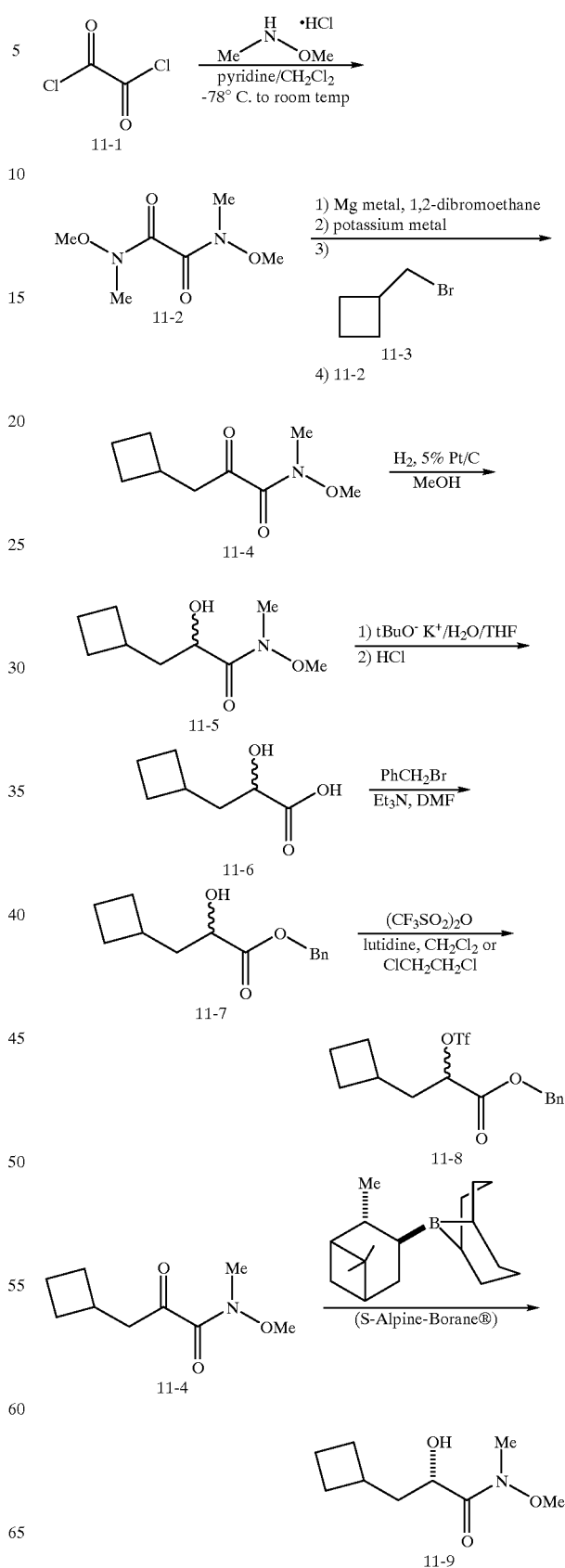

Scheme 10 illustrates preparation of intermediate 2-alkyl-2-trifluoromethanesulfonoxyacetic acid derivatives when the 1-alkyl-1-hydroxyacetic acid is not commerically available. Treatment of the para-methoxybenzyl ester of tartaric acid with lead tetraacetate in benzene provides the glyoxylic ester 10-2. Separately, a commercially available alkyl bromide (such as cyclobutylmethyl bromide) is treated with magnesium metal (in the absence or presence of lithium/naphthalene) or with lithium metal to provide the organometallic intermediate 10-4. Adding 10-4 to the aldehyde 10-2 provides the 2-hydroxy-ester 10-5. Formation of the trifluoromethanesulfonate ester is carried out under standard conditions (for example, with trifluoromethansulfonic anhydride in the presence of a hindered base such as 2,6-lutidine or DIEA in a halogenated solvent at between −78 degrees C. to room temperature, preferably near 0 degrees C., to give 10-6, which is then employed as described above.

Scheme 11 illustrates an alternate preparation of intermediate 2-alkyl-2-trifluoromethanesulfonoxyacetic acid derivatives; in this example, the side chain is exemplified by a cyclobutylmethyl subunit. Treatment of oxalyl chloride (11-1) with N-methyl-N-methoxyamine hydrochloride in the presence of pyridine yields the bis amide 11-2 (also called the bis-Weinreb amide). In a separate vessel, formation of magnesium dibromide in THF, followed by addition of potassium metal, forms a very reactive grade of magnesium metal. Addition of a suitable aliphatic bromide or iodide, for example cyclobutylmethyl bromide (11-3), provides the desired organomagnesium reagent in situ. Addition of bis-amide 11-2, followed by suitable workup, affords the keto-ester 11-4. This compound is reduced by hydrogenation in the presence of 5% platinum on carbon and triethylamine to the racemic alcohol 11-5. Hydrolysis with potassium t-butoxide in THF/water followed by acidification yields the hydroxy acid 11-6. Acid 11-6 is then protected, for example as the benzyl ester, by treatment with benzyl bromide and triethylamine in DMF, to provide 11-7. This ester is then activated with triflic anhydride (or other triflating agents) under the usual conditions. Alternatively, keto-ester 11-4 can be reduced enantioselectively, for example with B-isopinocampheyl-9-borabicyclo[3.3.1]nonane (also known as S-Alpine-borane®) to provide S-hydroxy derivative 11-9, which can be carried through the rest of the sequence as for 11-5.

SCHEME 12

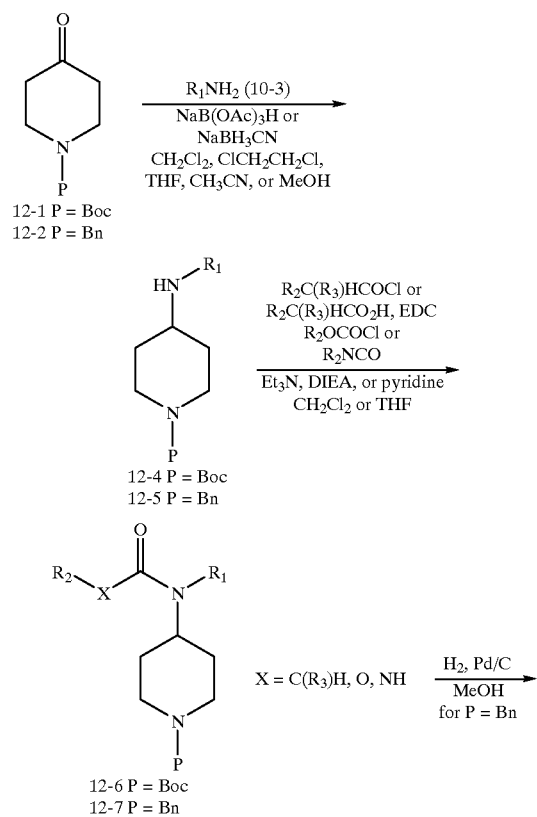

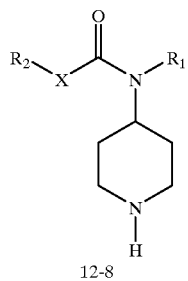

12-8

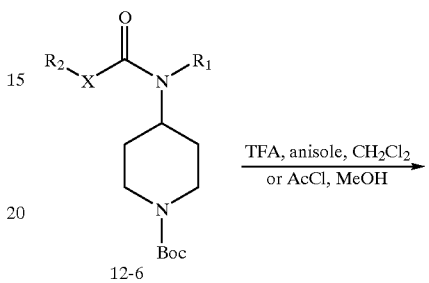

12-6

TFA, anisole, CH$_2$Cl$_2$
or AcCl, MeOH

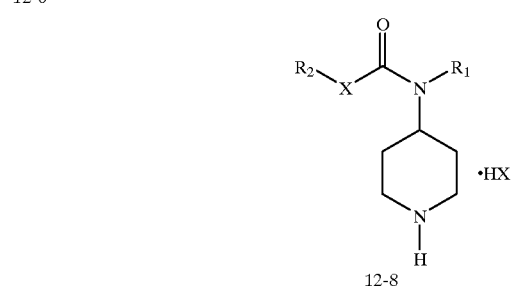

12-8

Synthetic routes for the preparation of piperidines bearing a 4-substituent containing an amide, carbamate or urea functional group are given in Scheme 12. Reductive amination of commercially available 12-1 or 12-2 with primary amine 12-3 in the presence of sodium triacetoxyborohydride or sodium cyanoborohydride in a suitable solvent (for example, methylene chloride, 1,2-dichloroethane, THF, acetonitrile, or methanol) provides amines 12-4 or 12-5. Acylation is then carried out with an acyl chloride (or a carboxylic acid plus an activating agent, such as EDC, DCC, or BOP-Cl) to provide 12-6 or 12-7 as an amide. Alternatively, acylation with achloroformate provides 12-6 or 12-7 as a carbamate. Treatment of 12-4 or 12-5 with an isocyanate affords 12-6 or 12-7 as a urea. For each of these reactions, an amine base is employed, such as triethylamine, DIEA, pyridine, or 2,6-lutidine. In the case of the benzyl-protected derivative 12-7, hydrogenolysis under standard conditions (for example, hydrogen in the presence of palladium on carbon in methanol or ethanol) provided desired intermediate 12-8. For the N-Boc compound 12-6, exposure to suitable anhydrous acidic conditions (for example trifluoroacetic acid and anisole in methylene chloride at temperatures from 0–25 degrees C.) affords the salt of 12-8. This compound is then utilized as the cyclic secondary amine component as shown above in Scheme 2 and in Schemes 5 through 9. Alternatively, if no functionality are present in the alkyl pyrrolidine framework that would be adversely effected by the above mentioned chemistry, then 4-piperidone may be attached directly to the alkylpyrrolidine framework described above, and the chemistry described in this paragraph can be carried out equating the alkylpyrrolidine segment to the group 'P' given in Scheme 12, structures 1 through 7.

SCHEME 13

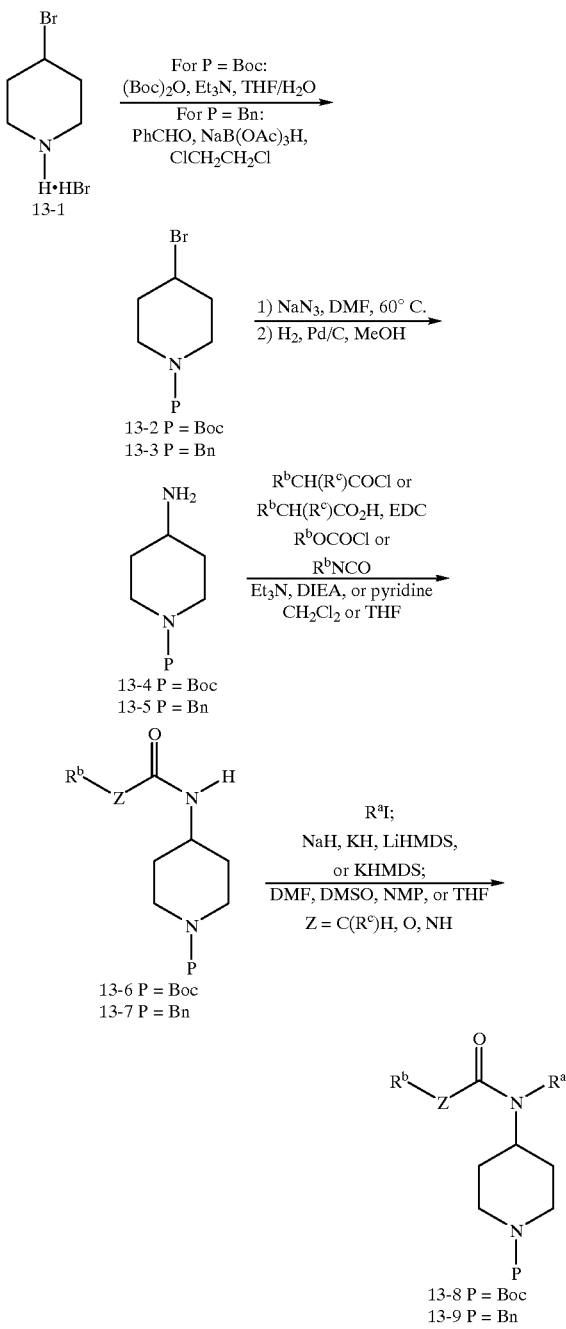

Alternate synthetic routes for the preparation of piperidines bearing a 4-substituent containing an amide, carbamate or urea functional group are given in Scheme 13. Protection of 4-bromopiperidine can be carried out with several proptecting groups for nitrogen. For example, using standard conditions, protection with a Boc group gives 13-2, whereas reductive amination with benzaldehyde yields the N-benzyl derivative 13-3. Displacement of the bromide with sodium azide in 10 warm to hot DMF provides the 4-azidopiperidine derivative, and reduction of the azide with hydrogen in the presence of a palladium catalyst (for the Boc protected intermediate) or with triphenylphosphine followed by hydrolysis (for N-benzyl protected intermediate) provides the aminopiperidine 13-4 or 13-5. Acylation is then carried out with an acyl chloride (or a carboxylic acid plus an activating agent, such as EDC, DCC, or BOP-Cl) to provide 13-6 or 13-7 as an amide. Alternatively, acylation with achloroformate provides 13-6 or 13-7 as a carbamate. Treatment of 13-4 or 13-5 with an isocyanate affords 13-6 or 13-7 as a urea. For each of these reactions, an amine base is employed, such as triethylamine, DIEA, pyridine, or 2,6-lutidine. When X=C(R3)H or O, compounds 13-6 and 13-7 may optionally be alkylated by treatment with a base such as sodium hydride, potassium hydride, LHMDS, KHMDS, or NaHMDS followed by treatment with an alkyl iodide, allyl halide, or propargyl halide. Solvents such as DMF, DMSO, N-methylpyrrolidine or TBF are suitable. These procedures provide carbamate, urea or amide 13-8 and 13-9. Removal of the protecting groups is then carried out as shown in Scheme 12 above, and the resulting 1-unsubstituted piperidines are then utilized as noted in the description for Scheme 12.

In some cases the order of carrying out the foregoing reaction schemes may be varied to facilitate the reaction or to avoid unwanted reaction products. The following examples are provided for the purpose of further illustration only and are not intended to be limitations on the disclosed invention.

General

Concentration of solutions was carried out on a rotary evaporator under reduced pressure. Flash chromatography was carried out on silica gel (230–400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC Conditions

HPLC A. Retention time using the following conditions: Column: YMC ODS A, 5µ, 4.6×50 mm; Gradient Eluant: 10:90 to 90:10 v/v $CH_3CN/H_2O$+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5µ4.6×100 mm column; Gradient Eluant: 10:90 to 90:10 v/v $CH_3CN/H_2O$+0.5% TFA over 10 min, hold 2 min; Detection: PDA,200–400 nm;FlowRate: 2.25 mL/min.

Pyrrolidine 1

3-(R)-(t-Butyldimethylsilyloxymethyl)-4-(S)-phenyl pyrrolidine

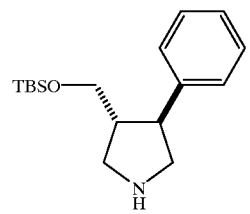

Step A: 3-((E)-Cinnamoyl)-4-(S)-benzyl oxazolidin-2-one

A solution of 222 g (1.5 mol) of trans-cinnamic acid and 250 mL (1.77 mol) of TEA in 3 L of THF at −78° C. was treated with 200 mL of trimethylacetyl chloride maintaining the internal temperature at less than −65° C. The resulting mixture was warmed to 0° C., then cooled to −78° C.

In a separate flask, a solution of 4-(S)-benzyl-oxazolidin-2-one in 2.05 L of THF at −20° C. was treated with 660 mL of 2.5 M n-butyllithium in hexanes over 45 min. The resulting turbid mixture was cooled to −78° C. and then transferred via cannula to the flask containing the mixed anhydride. The resulting mixture was allowed to warm to rt and was stirred for 20 h. The reaction was quenched with 300 mL of sat'd NH$_4$Cl; the resulting mixture was partitioned between EtOAc and H$_2$O and the layers were separated. The organic layer was dried over MgSO$_4$. The aqueous layer was extracted with 2× EtOAc; the extracts were dried and all of the organic extracts were combined. Partial concentration in vacuo caused precipitation of a solid; the mixture was diluted with hexanes and allowed to stand at rt for 1.5 h. The precipitate was filtered and dried to afford 402.2 g (87%) of the title compound: $^1$H NMR (500 MHz) δ2.86 (dd, J=13.5, 9.5, 1H), (3.38, J=13.5, 3.5, 1H), 4.20–4.27 (m, 2H), 4.78–4.83 (m, 1H), 7.24–7.42 (5H), 7.63–7.65 (m, 1H), 7.92 (app d, J=2.5, 1H).

Step B: 3-(1-Benzyl-4-(S)-phenylpyrrolidine-3-(R)-carbonyl)-4-(S)-benzyl oxazolidin-2-one and 3-(1-benzyl-4-(R)-phenyl-pyrrolidine-3-(S)carbonyl)-4-(S)-benzyl oxazolidin-2-one A solution of 402 g (1.3 mol) of 3-((E)-cinnamoyl)-4-(S)-benzyl oxazolidin-2-one (from Step A) and 474 g (2.0 mol) of N-methoxymethyl-N-trimethylsilylmethyl benzyl amine in 4 L of CH$_2$Cl$_2$ at −10° C. was treated with 6 mL of trifluoroacetic acid. The resulting mixture was stirred cold for 4 h and then was treated with an additional 4 mL of trifluoroacetic acid. The reaction mixture was warmed to rt and stirred for 20 h. The reaction was quenched with 2 L of sat'd NaHCO$_3$ and the layers were separated. The organic layer was washed with 1 L of sat'd NaCl and concentrated. Chromatography on 10 kg of silica gel using 4:1 v/v hexanes/EtOAc (24 L), then 7:3 v/v hexanes/EtOAc (36 L), then 3:2 v/v hexanes/EtOAc (32 L) afforded 260.9 g (45%) of 3-(1-benzyl-4-(S)-phenylpyrrolidine-3-(R)-carbonyl)-4-(S)-benzyl oxazolidin-2-one and 247.5 g (43%) of 3-(1-benzyl-4-(R)-phenylpyrrolidine-3-(S)-carbonyl)-4-(S)-benzyl oxazolidin-2 -one. For 3-(1-benzyl-4-(S)-phenylpyrrolidine-3-(R)-carbonyl)-4-(S)-benzyl oxazolidin-2-one: $^1$H NMR (500 MHz) δ2.66 (t, J=8.0, 1H), 2.78 (dd, J=13.0, 9.0, 1H), 2.87 (dd, J=9.0,4.5, 1H), 3.21–3.27 (m, 2H), 3.64 (d, J=11.5, 1H), 3.77 (d, J=11.5, 1H), 4.10–4.15 (m, 2H), 4.61–4.65 (m, 1H), 7.16–7.38 (15H). For 3(1-benzyl-4-(R)-phenylpyrrolidine-3-(S)-carbonyl)-4-(S)-benzyl oxazolidin2-: $^1$H NMR (500 MHz) δ2.69–2.76 (m, 2H), 2.82 (dd, J=9.5, 5.5, 1H), 3.14–3.22 (3H), 3.64 (d, J=13.0, 1H), 3.74 (d, J=13.0, 1H), 4.07 . 4.12 (m, 2H), 4.16 (t, J=9.0, 1H), 4.26–4.30 (m, 1H), 4.65–4.69 (m, 1H), 7.03–7.40 (15H).

Step C: 1-Benzyl-3-(R)-hydroxymethyl-4-(S)-phenylpyrrolidine

A solution of 3-(1-benzyl4-(S)-phenylpyrrolidine-3-(R)-carbonyl)-4(S)-benzyl oxazolidin-2-one (from Step B) in 2.5 L of THF at 10° C. was treated with 1.18 L of 1.0 M lithium aluminum hydride solution in THF over a period of 2 h. The resulting mixture was warmed to rt and stirred for 20 h. The reaction was quenched by adding 40 mL of H$_2$O, then 40 mL of 2.0 N NaOH, then 115 mL of H$_2$O and then was stirred at rt for 1.5 h. The mixture was filtered and the filtrate was concentrated. Chromatography on 4 kg of silica using 4:1 hexanes/acetone (14 L), then 7:3 hexanes/acetone as the eluant to afford 108.4 g (69%) of the title compound: $^1$H NMR (400 MHz) δ2.38–2.46 (m, 2H), 2.78 . 2.88 (3H), 3.20–3.26 (2H), 3.65 (dd, J=12.0, 4.0, 1H), 3.66 (app s, 2H), 3.74 (dd, J=12.0, 4.0, 1H), 7.18–7.34 (10H); ESI-MS 268 (M+H); HPLC A: 2.35 min.

Step D: 1-Benzyl-3-(R)-(t-butyldimethylsilyloxymethyl)-4-(S)-phenyl pyrrolidine

A solution of 82.0 g (0.31 mol) of 1-benzyl-3-(R)-hydroxymethyl-4(S)-phenyl pyrrolidine (from Step C) and 46.5 g (0.36 mol) of N,N-diisopropylethylamine in 1 L of CH$_2$Cl$_2$ was treated with 54.2 g (0.36 mol) of t-butyldimethylsilyl chloride and the resulting mixture was stirred at rt for 20 h. The reaction was quenched with 750 mL of sat'd NaHCO$_3$ and the layers were separated. The organic layer was combined with 150 g of silica gel and aged for 45 min. The mixture was filtered and the filtrate was concentrated to afford 117 g (100%) of the title compound.

Step E: 3-(R)-(t-Butyldimethylsilyloxymethyl)-4-(S)-phenylpyrrolidine

A mixture of 117 g (0.31 mol) of 1-benzyl-3-(R)-(t-butyldimethylsilyloxymethyl)-4-(S)-phenyl pyrrolidine (from Step D), 31.5 g (0.50 mol) ammonium formate, 20.0 g of 20% palladium hydroxide on carbon in 1.5 L of MeOH was heated at 55° C. for 2.5 h. The mixture was cooled and filtered through a pad of Celite. The filtrate was concentrated. The residue was dissolved in 1 L of CH$_2$Cl$_2$, washed with 300 mL of 10% NH$_4$OH solution, 200 mL of sat'd NaCl, dried over MgSO4 and concentrated to afford 89.2 g (99%) of the title compound: $^1$H NMR (400 MHz) δ−0.09 (s, 3H), −0.08 (s, 3H), 0.77 (s, 9H), 2.25–2.30 (m, 1H), 2.84–2.96 (4H), 3.18 (dd, J=11.2, 3.2, 1H), 3.29–3.36 (m, 1H), 3.44 (dd, J=10.0, 6.0), 3.56 (dd, J=10.0, 4.4, 1H); ESI-MS 292 (M+H); HPLC A: 3.44 min.

Pyrrolidine 2

3-(R)-(t-Butyldimethylsilyloxymethyl)-4-(S)-(3-fluoro) phenylpyrrolidine

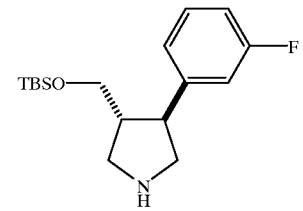

The title compound was prepared using procedures analogous to those described to prepare Pyrrolidine 1, except that trans-(3-fluoro)cinnamic acid was substituted for trans-cinnamic acid in Step A. For the title compound: $^1$H NMR (400 MHz): δ0.013 (s, 3H), 0.016 (s, 3H), 0.87 (s, 9H), 2.09 (br s, 1H), 2.30–2.37 (m, 1H), 2.88–2.90 (3H), 2.23 (dd, J=8.0, 11.2, 1H), 3.39 (dd, J=6.8, 10.0. 1H), 3.56 (dd, J=6.0, 10.0, 1H), 3.64 (dd, J=5.2, 10.0), 6.86–6.91 (m, 1H), 6.95 (dt, J=12.0, 2.4, 1H), 7.01 (d, J=7.6, 1H), 7.22–7.27 (m, 1H); ESI-MS 310 (M+H); HPLC A: 3.05 min.

Pyrrolidine 3
(3-(R)-((t-Butyldimethylsilyloxy)methyl)-4-(S)-(3-thienyl) pyrrolidine

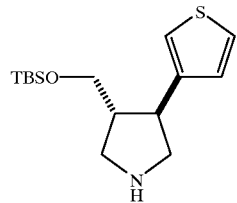

Step A: 1-(Prop-2-enyl)-3-(R)-(hydroxymethyl)-4-(S)-(3-thienyl) pyrrolidine

The title compound was prepared using procedures analogous to those used to prepare 1-benzyl-3-(R)-(hydroxymethyl)-4-(S)-phenylpyrroldine (Pyrrolidine 1, Step C), except that trans-3-(3-thienyl)acrylic was substituted for trans-cinnamic acid in Step A and N-methoxymethyl-N-trimethylsilylmethyl(prop-2-enyl) amine was substituted for N-methoxymethyl-N-trimethylsilylmethyl benzyl amine in Step B. For the title compound: $^1$H NMR (500 MHz) δ2.30–2.34 (m, 1H), 2.44 (t, J=8.5, 1H), 2.67 (t, J=9.0, 1H), 2.77 (dd, J=5.0, 9.0, 1H), 3.02–3.15 (4H), 3.53 (dd, J=7.5, 10.0, 1H), 3.64 (dd, J=5.0, 10.0, 1H), 5.07 (d, J=10.0, 1H), 5.17 (d, J=17.5, 1H), 5.83–5.91 (m, 1H), 6.97–6.99 (2H), 7.20–7.22 (m, 1H); ESI-MS 224 (M+H).

Step B: 1-(Prop-2-enyl)-3-(R)-(t-butyldimethylsilyloxymethyl)-4-(S)-(3-thienyl) pyrrolidine A solution of 1.06 g (4.75 mmol) of 1-(prop-2-enyl)-(3-(R)(hydroxymethyl))-4-(S)-(3-thienyl)pyrrolidine (from Step A) in 12.0 mL of CH$_2$Cl$_2$ at 0° C. was treated with 0.99 mL (5.7 mmol) of N,N-diisopropylethylamine and 855 mg (5.6 mmol) of t-butyldimethylsilyl chloride. After warming to rt and stirring for 20 h, the solution was partitioned between 100 mL of ether and 100 mL of H$_2$O. After separating the phases, the aqueous layer was extracted with 100 mL of ether. The combined organic phases were dried over MgSO$_4$ and concentrated. The residue was purified by flash chromatography eluting with 3:1 v/v hexanes/EtOAc to yield 1.24 g (77%) of the title compound: R$_F$: 0.54 (3:2 v/v hexanes/EtOAc); $^1$H NMR (300 Mhz) δ0.0 (s, 6H), 0.86 (s, 9H), 2.35 (m, 1H), 2.52–2.71 (m, 3H), 2.97–3.20 (m, 4H), 3.54–3.66 (m, 2H), 5.06–5.21 (m, 2H), 5.89 (m, 1H). 6.98–7.02 (m, 2H), 7.22 (m, 1H).

Step C: 3-(R)-(t-Butyldimethylsilyloxymethyl)-4-(S)-(3-thienyl)pyrrolidine

A solution of 3.7 g (11.0 mmol) of 1-(prop-2-enyl)-3-(R)-(t-butyldimethylsilyloxymethyl)-4-(S)-(3-thienyl) pyrrolidine (from Step B) in 16% aqueous acetonitrile (degassed with nitrogen) was treated with 540 mg (0.58 mmol) of chlorotris(triphenylphosphine)rhodium. The reaction was warmed to reflux and the propanal that formed was removed via azeotropic distillation with the solvents. Additional solvent was added periodically to maintain a constant reaction volume. After 6 h, TLC indicated the absence of starting material. The reaction was cooled to rt and concentrated. The residue was purified by flash chromatography eluting with a gradient of 97:2:1 v/v/v CH$_2$Cl$_2$/MeOH/NH$_4$OH, then 94:5:1 v/v/v CH$_2$Cl$_2$/MeOH/NH$_4$OH, then 89:10:1 v/v/v CH$_2$Cl$_2$/MeOH/NH$_4$OH to yield 2.76 g (84%) of the title compound: R$_F$: 0.26 (97:2:1 v/v/v CH$_2$Cl$_2$/MeOH/NH$_4$OH); $^1$H NMR (300 MHz) δ0.0 (s, 6H), 0.86 (s, 9H), 2.36 (m, 1H), 2.93–3.70 (m, 7H), 6.99–7.06 (m, 2H), 7.28 (m, 1H).

Hydroxy Ester 1
2-(S)-Hydroxy-3-(cyclopropyl)propanoic acid, (4-methoxy) benzyl ester

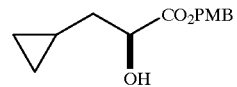

Step A: 2-(S)-Hydroxy-3-cyclopropyl propanoic acid

A 1 L, 3-neck flask was equipped with two dropping funnels, one containing 21.3 mL of 2.0 N H$_2$SO$_4$ and the other containing 21.3 mL of 2.0 N NaNO$_2$. A mixture of 5.00 g (38.7 mmol) of 2-(S)-amino-3-cyclopropyl propanoic acid in 28 mL of H$_2$O at 0° C. was treated with a sufficient amount of the acid solution to dissolve the solids. The remaining H$_2$SO$_4$ solution and the NaNO$_2$ solution were added maintaing the internal temperature at less than 5° C. The resulting mixture was stirred cold for 3 h, then warmed to rt and stirred for 20 h. The reaction mixture was saturated with NaCl and extracted with 4×100 mL of EtOAc. The extracts were dried over MgSO$_4$ and concentrated to afford 4.30 g (85%) of the title compound: $^1$H NMR (300 MHz): δ0.13–0.18 (m, 2H), 0.48–0.54 (m, 2H), 0.89 (m, 1H), 1.67 . 1.76 (m, 2H), 4.37 (dd, J=6.4, 4.7 Hz, 1H).

Step B: 2-(S)-Hydroxy-3-(cyclopropyl)propanoic acid, 4-(methoxy)benzyl ester

A solution of 4.30 g (33 mmol) of 2-(S)-hydroxy-3 (cyclopropyl)propanoic acid (from Step A), 6.40 mL (46 mmol) of TEA and 5.90 mL (44 mmol) of 4-(methoxy) benzyl chloride in 40 mL of DMF was stirred at rt for 2 h. The mixture was partitioned between 500 mL of ether and 300 mL of H$_2$O and the layers were separated. The organic layer was washed with 300 mL of 2.0 N HCl, 300 mL of sat'd NaHCO$_3$, 2×300 mL of H$_2$O, 300 mL of sat'd NaCl, dried over MgSO$_4$ and concentrated. Flash chromatography on 500 g of silica gel using 5:1 v/v hexanes/EtOAc as the eluant afforded 4.30 g (52%, 97.5% ee) of the title compound: R$_F$: 0.20 (4:1 v/v hexanes/EtOAc); $^1$H NMR (300 MHz): δ−0.01–0.09 (m, 2H), 0.40–0.45 (m, 2H), 0.84 (m, 1H), 1.55–1.67 (m, 2H), 2.82 (br m, 1H), 3.81 (s, 3H), 4.25 (br m, 1H), 5.14 (ABq, J=11.8, 2H), 6.90 (d, J=8.7, 2H), 7.29 (d, J=8.7, 2H). HPLC: Chiracel OB 4.6×250 mm column, 65:35 v/v hexanes/EtOH, 0.5 mL/min, 220 nm. Retention times: (S)-enantiomer, 20.4 min; (R)-enantiomer, 17.3 min.

Hydroxy Ester 2
2-(S)-Hydroxy-3-(cyclobutyl)propanoic acid, benzyl ester

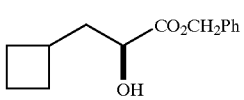

Step A: N,N'-Dimethyl-N,N'-dimethoxy oxamide

A mixture of 48.0 g (0.49 mol) of N,O-dimethylhydroxylamine.HCl in 250 mL of 3:2 v/v CH$_2$Cl$_2$pyridine was cooled to −78° C. and was treated with 17.4 mL (0.2 mol) of oxalyl chloride maintaining the internal temperature at less than −70° C. The resulting mixture was allowed to warm to rt and stirred for 20 h. The reaction was quenched with 250 mL of sat'd NaCl and the quenched mixture was extracted with 3×400 mL of CH$_2$Cl$_2$. The extracts were combined, dried over MgSO$_4$ and concentrated. Recrystallization from 250 mL of MTBE afforded 24.28 g (69%) of the title compound: $^1$H NMR (500 MHz) δ3.25 (s, 6H), 3.75 (s, 6H).

Step B: N-Methyl-N-methoxy 2-oxo-3-cyclobutyl propanamide

A suspension of 4.86 g (0.20 mol) of magnesium turnings in 250 mL of THF was treated with 2.0 mL (0.022 mol) of 1,2-dibromoethane and then was warmed until gas evolution from the surface of the Mg was visible. 15.2 mL (0.178 mol) of 1,2-dibromoethane was added at rate to maintain a gentle reflux. After the addition, the resulting mixture was heated at reflux for 30 min, then cooled to rt. Potassium (15.6 g, 0.40 mol) was added in ~1 g portions; the mixture was warmed until the potassium started to react and a fine black precipitate formed. This was repeated until all of the potassium was added to the reaction mixture. The resulting suspension of Mg was cooled to 0° C.

The finely divided Mg was treated with 22.5 mL (0.20 mol) of bromomethylcyclobutane maintaining the internal temperature at <5° C. The resulting mixture was stirred cold for 1 h, then was treated with 26.40 g (0.15 mol) of N,N'-dimethyl-N,N'-dimethoxy oxamide (from Step A) in portions as a solid. The resulting mixture was stirred at 0° C. for 16 h. The reaction was poured onto a mixture of 100 mL conc. HCl and 500 g of ice under $N_2$ atmosphere. The quenched mixture was extracted with 1.5 L of EtOAc. The extract was washed with 500 mL of sat'd NaCl, dried over $MgSO_4$ and concentrated. Flash chromatography on 500 g of silica gel using 3:1 v/v hexanes/EtOAc as the eluant afforded 22.3 g (80%) of the title compound: $^1$H NMR (500 MHz) δ1.66–1.76 (m, 2H), 1.82–1.98 (m, 2H), 2.12–2.22 (m, 2H), 2.74–2.84 (3H), 3.20 (s, 3H), 3.66 (s, 3H).

Step C: N-Methyl-N-methoxy 2-(S)-hydroxy-3-cyclobutyl propanamide

A mixture of 11.40 g (61.5 mmol) of N-methyl-N-methoxy 2-oxo-3-cyclobutyl propanamide (from Step B) and 250 mL 0.5 N (R)-Alpine Borane® solution in THF was concentrated and stirred at rt for 5 days. The mixture was cooled to 0° C. and quenched with 6.8 mL (75.0 mmol) of isobutyraldehyde. The resulting mixture was diluted with 200 mL of ether and treated with 7.5 mL (125 mmol) of ethanolamine. The precipitate that formed was filtered and the filtrate was concentrated. Flash chromatography on 500 g of silica gel using 9:1 v/v $CH_2Cl_2$ as the eluant afforded 11.48 g (99%, 91% ee) of the title compound: $^1$H NMR (500 MHz) δ1.59–1.70 (m, 2H), 1.67 (s, 1H), 1.77–1.83 (m, 2H), 1.82–1.92 (m, 1H), 2.03–2.13 (m, 2H), 2.53–2.60 (m, 1H), 3.23 (s, 3H), 3.72 (s, 3H), 4.31 (app d, J=5.5, 1H); HPLC: Chiralpak AS 4.6×250 mm column, 75/25 hexanes/iPrOH, 0.5 mL/min, 210 nm. Retention Times: (S)-Enantiomer, 13.3 min; (R)-enantiomer, 17.2 min.

Step D: 2-(S)-Hydroxy-3-(cyclobutyl)propanoic acid

A suspension of 33.66 g (0.3 mol) of potassium t-butoxide in 50 mL of THF was treated with 5.40 mL (0.3 mol) of $H_2O$. The resulting mixture was treated with a solution of 11.48 g (0.061 mol) of N-methyl-N-methoxy 2-(S)-hydroxy-3-cyclobutyl propanamide (from Step C) in 20 mL of THF and stirred at rt for 20 h. The mixture was concentrated and the residue was partitioned between 300 mL of ether and 200 mL of $H_2O$ and the layers were separated. The pH of the aqueous layer was adjusted to 2 with concentrated HCl and extracted with 300 mL of EtOAc. The extract was washed with 100 mL of sat'd NaCl, dried over $MgSO_4$ and concentrated to afford 7.50 g (85%) of the title compound: $^1$H NMR (500 MHz) δ1.66–1.76 (m, 2H), 1.78–1.98 (4H), 2.06–2.16 (m, 2H), 2.51–2.61 (m, 1H), 4.20 (dd, J=8.0,4.0, 1H).

Step E: 2-(S)-Hydroxy-3-(cyclobutyl)propanoic acid, benzyl ester

A mixture of 1.05 g (7.3 mmol) of 2-(S)-hydroxy-3-(cyclobutyl)propanoic acid (from Step D), 40 mL (10.0 mmol) of TEA and 1.20 mL (10.0 mmol) of benzyl bromide in 8 mL of DMF was stirred at rt for 2 h. The mixture was partitioned between 200 mL of ether and 100 mL of $H_2O$ and the layers were separated. The organic layer was washed with 100 mL of 2.0 N HCl, 100 mL of sat'd $NaHCO_3$, 2×100 mL of $H_2O$, 100 mL of sat'd NaCl, dried over $MgSO_4$ and concentrated. Flash chromatography on 60 g of silica gel using 4:1 v/v hexanes/ether as the eluant afforded 1.20 g (70%) of the title compound: $^1$H NMR (500 MHz) δ1.58–1.70 (m, 2H), 1.72–1.82 (m, 2H), 1.84–1.92 (m, 2H), 1.98–2.10 (m, 2H), 2.46–2.58 (m, 1H), 2.63 (br s, 1H), 4.15 (dd, J=7.5, 3.0), 7.33–7.40 (m, 5H).

Hydroxy Ester 3
2-(S)-Hydroxy-3-(cyclopentyl)propanoic acid, benzyl ester

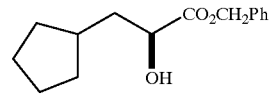

Step A: N-Methoxy-N-methyl-cyclopentylacetamide

A solution of 2.0 mL (15.9 mmol) of cyclopentylacetic acid in 80 mL of $CH_2Cl_2$ at 0° C. was treated with 3.7 mL (33.6 mmol) of N-methyl-morpholine and 2.2 mL (16.9 mmol) of isobutyl chloroformate. After stirring for 20 min, 1.61 g (16.5 mmol) of N,O-dimethyl-hydroxylamine.HCl was added. The reaction was warmed to rt and stirred for 3 h. The reaction was partitioned between 200 mL of EtOAc and 200 mL 2.0 N HCl. After separating the phases, the organic layer was washed with 200 mL of 1.0 N $NaHCO_3$, dried over $Na_2SO_4$ and concentrated. Flash chromatography on silica gel using 4:1 v/v hexanes/EtOAc afforded 2.28 g (83%) of the title compound as a colorless oil. $R_F$: 0.27 (4:1 v/v hexanes/ EtOAc). $^1$H NMR (300 MHz): δ1.12–1.23 (m, 2H), 1.51–1.89 (m, 6H), 2.28 (m, 1H), 2.44 (d, J=7.5, 2H), 3.18 (s, 3H), 3.67 (s, 3H).

Step B: Cyclopentylmethylene phenyl ketone

A solution of 1.98 g (11.5 mmol) of N-methoxy-N-methyl-cyclopentylacetamide (from Step A) in 115 mL of THF at 0° C. was treated with 13.0 mL of 1.8 M phenyllithium in cyclohexane/diethylether over 40 min. After stirring for 1 h, the reaction was quenched with 2.0 N HCl and warmed to rt. The quenched reaction was partitioned between 200 mL of ether and 200 mL 2.0 N HCl and the layers were separated. The organic layer was washed with 200 mL of 1.0 N $NaHCO_3$, dried over $Na_2SO_4$ and concentrated. Flash chromatography on silica gel using 9:1 v/v hexanes/EtOAc afforded 1.57 g (72%) of the title compound: $R_F$: 0.66 (4:1 v/v hexanes/EtOAc); $^1$H NMR (300 MHz): δ1.14–1.22 (m, 2H), 1.52–1.67 (m, 4H), 1.82–1.92 (m, 2H), 2.37 (m, 1H), 2.98 (d, J=7.1, 2H), 7.26–7.61 (m, 5H).

Step C: (S)-2-Cyclopentyl-1-phenylethanol

A solution of 2.7 mL of 1.0 M (R)-2-methyl-CBS-oxazaborolidine solution in toluene in 4 mL of $CH_2Cl_2$ at −25 °C. was treated with 1.4 mL of 2.0 M borane methyl sulfide complex in THF and stirred cold for 10 min. A solution of 501 mg (2.66 mmol) of cyclopentylmethylene phenyl ketone (from Step B) in 2 mL of $CH_2Cl_2$ was added over 25 min and the resulting mixture was stirred cold for an additional 45 min. The reaction was quenched by pouring it into cold (−25° C.) MeOH. The quenched reaction was warmed to rt and stirred for 45 min until gas evolution ceased. The mixture was concentrated and the residue dissolved in 20 mL of MeOH and concentrated again. Flash chromatography on silica gel using 17:3 v/v hexanes/EtOAc afforded 413 mg (81%) of the title compound: $R_F$: 0.53 (4:1 v/v hexanes/ EtOAc); $^1$H NMR (300 MHz): δ1.10–1.17 (m, 2H), 1.47–1.89 (m, 9H), 4.69 (m, 1H), 7.25–7.35 (m, 5H).

Step D: Acetic acid, (S)-2-cyclopentyl-1-phenylethyl ester

A solution of 406 mg (2.13 mmol) of (S)-2-cyclopentyl-1-phenylethanol (from Step C) in 9 mL of pyridine was treated with 1 mL of acetic anhydride. After stirring for 6 h, the reaction was concentrated. Flash chromatography on silica gel using 93:7 v/v hexanes/EtOAc afforded 495 mg (100%) of the title compound: $R_F$: 0.75 (4:1 v/v hexanes/EtOAc); $^1$H NMR (300 MHz): δ1.10–1.21 (m, 2H), 1.44–2.04 (m, 9H), 2.05(s, 3H), 5.75 (dd, J=8.0, 6.1, 1H), 7.25–7.34 (m, 5H).

Step E: (S)-2-Acetoxy-3-(cyclopentyl)propanoic acid

A solution of 479 mg (2.0 mmol) of acetic acid, (S)-2-cyclopentyl-1-phenylethyl ester (from Step D) in 14 mL of 2:2:3 v/v/v $CCl_4/CH_3CN/H_2O$ was treated with 6.59 g (28.9 mmol) of periodic acid and 7.8 mg (0.037 mmol) of $RuCl_3.H_2O$. The reaction was warmed to 33° C. and stirred for 4 h. After cooling to 0° C., 100 mL of ether was added. After stirring for 10 min and separating the phases, the aqueous layer was extracted with 2×100 mL of ether. The combined organic layers were dried over $Na_2SO_4$ and concentrated to give 395 mg (95%) of the title compound: $R_F$: 0.62 (90:10:1 v/v/v $CH_2Cl_2$/MeOH/HOAc); $^1$H NMR (300 MHz): δ1.09–1.98 (m, 11H), 2.14 (s, 3H), 5.03 (dd, J=8.8, 4.3, 1H), 8.9 (br, 1H).

Step F: 2-(S)-Hydroxy-3-(cyclopentyl)propanoic acid

A solution of 395 mg (1.97 mmol) of 2-(S)-acetoxy-3-(cyclopentyl)propanoic acid (from Step E) in 10 mL MeOH and 1 mL of $H_2O$ was treated with 1.29 g (9.33 mmol) of $K_2CO_3$ and stirred at rt for 30 h. The volatiles were removed under reduced pressure. The crude product was partitioned between 100 mL of ether and 100 mL of $H_2O$ and the layers were separated. The aqueous layer was acidified to pH 1–2 using 2.0 N HCl and extracted with 3×150 mL of EtOAc. The combined organic layers were dried over $Na_2So_4$ and concentrated to give 287 mg (92%) of the title compound: $^1$H NMR (300 MHz) δ1.11–2.15 (m, 11H), 4.27 (dd, J=8.1, 4.7, 1H), 6.5 (br, 1H).

Step G: 2-(S)-Hydroxy-3-(cyclopentyl)propanoic acid, benzyl ester

A solution of 287 mg (1.81 mmol) of 2-(S)-hydroxy-3-(cyclopentyl)propanoic acid (from Step F) in 8 mL of DMF was treated with 0.38 mL (2.72 mmol) of TEA and 0.33 mL (2.77 mmol) of benzyl bromide and stirred at rt for 22 h. The reaction was diluted with 200 ml of ether and washed with 200 mL of $H_2O$ , 200 mL of 2.0 N HCl, 200 mL of 1.0 N NaHCO3, 200 mL of $H_2O$ and 200 mL of sat'd NaCl. The organic layer was dried over $MgSO_4$ and concentrated. Flash chromatography on silica gel using 17:3 v/v hexanes/EtOAc afforded 102 mg (22%, 95.5% ee) of the title compound: $R_F$: 0.40 (4:1 v/v hexanes/EtOAc); $^1$H NMR (300 MHz): δ1.04–1.17 (m, 2H), 1.46–1.87 (m, 8H), 1.99 (m, 1H), 2.65 (m, 1H), 4.22 (dd, J=7.8, 4.8, 1H), 5.23 (ABq, J=12.3, 2H), 7.32–7.41 (m, 5H). HPLC: Chirapak AS 4.6×250 mm column, 17:3 v/v hexanes/iPrOH, 0.5 mL/min, 220 nm. Retention times: (S)-Enantiomer, 12.2 min; (R)-enantiomer, 15.3 min.

The following α-hydroxy benzyl and (4-methoxy)benzyl esters were prepared from the corresponding α-hydroxy acids (obtained from commercial sources or prepared as above) using esterification conditions analogous to those described above:

Hydroxy Ester 4
2-(S)-Hydroxy-3-(cyclobutyl)propanoic acid, (4-methoxy)benzyl ester

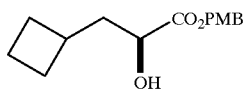

$^1$H NMR (500 MHz) δ1.56–1.94 (6H), 1.98–2.12 (m, 2H), 2.44–2.56 (m, 1H), 2.64 (br s, 1H), 3.82 (s, 3H), 4.11–4.13 (m, 1H), 5.19 (ABq, J=25.0, 2H), 6.90 (d, J=9.0, 2H), 7.30 (d, J=9.0, 2H).

Hydroxy Ester 5
2-(S)-Hydroxy-2-(cyclohexyl)acetic acid, benzyl ester

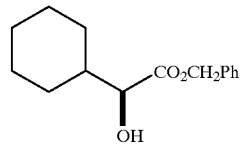

$R_F$: 0.37 (4:1 v/v hexanes/EtOAc); $^1$H NMR (300 MHz) δ1.11–1.38 (m, 11H), 2.65 (d, J=6.3 Hz, 1H), 4.06 (dd, J=6.3, 3.5 Hz, 1H), 5.22 (s, 2H), 7.30–7.39 (m, 5H).

Hydroxy Ester 6
2-(S)-Hydroxy-2-(cyclohexyl)acetic acid, (4-methoxy)benzyl ester

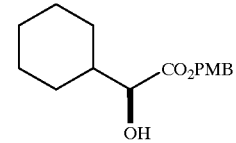

$^1$H NMR (500 MHz) δ1.10–1.80 (11H), 2.68 (t, J=5.7 Hz, 1H), 3.83 (s, 3H), 4.06 (dd, J=6.1, 3.6 Hz, 1H), 5.17 (s, 2H), 6.91 (d, J=8.6 Hz, 1H), 7.31 (d, J=8.6 Hz, 1H).

Hydroxy Ester 7
2-(S)-Hydroxy-3-methylbutanoic acid, benzyl ester

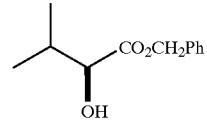

$R_F$: 0.39 (4:1 v/v hexanes/EtOAc); $^1$H NMR (300 MHz) δ0.83 (d, J=7.0, 3H), 1.01 (d, J=7.0, 3H), 2.08 (m, 1H), 2.67 (d, J=6.3, 1H), 4.08 (dd, J=6.0, 3.6, 1H), 5.22 (ABq, J=12.1, 2H), 7.34–7.39 (m, 5H).

Hydroxy Ester 8
2-(S)-Hydroxy-3-methylbutanoic acid, (4-methoxy)benzyl ester

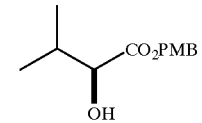

$^1$H NMR (500 MHz, $CDCl_3$): δ7.30~7.33 (m, 2H), 6.90~6.93 (m, 2H), 5.20 (AB d, 11.9 Hz, 1H), 5.15 (AB d, 11.9 Hz, 1H), 4.07 (d, 3.4 Hz, 1H), 3.83 (s, 3H), 2.68 (br s, 1H), 2.04~2.13 (m, 1H), 1.01 (d, 7.0 Hz, 3H), 0.83 (d, 6.9 Hz, 3H).

Hydroxy Ester 9
2-(S)-Hydroxy-3-(S)-methylpentanoic acid, benzyl ester

R$_F$: 0.67 (2:1 v/v hexanes/EtOAc); $^1$H NMR (500 MHz) δ7.35~7.42 (m, 5H), 5.26 (AB d, J=12.1 Hz, 1H), 5.22 (AB d, J=12.2 Hz, 1H), 4.14 (br s, 1H), 2.71 (br s, 1H), 1.81~1.89 (m, 1H), 1.30~1.38 (m, 1H), 1.20~1.29 (m, 1H), 0.99 (d, J=7.1 Hz, 3H), 0.88 (t, J=7.5 Hz, 3H).

Hydroxy Ester 10
2-(S)-Hydroxy-3-(R)-methylpentanoic acid, benzyl ester

R$_F$: 0.64 (2:1 v/v hexanes/EtOAc); $^1$H NMR (500 MHz) δ7.35~7.42 (m, 5H), 5.26 (AB d, J=12.2 Hz, 1H), 5.23 (AB d, J=12.2 Hz, 1H), 4.25 (dd, J=2.8 & 5.6 Hz, 1H), 2.70 (br d, J=~3.8 Hz, 1H), 1.82~1.89 (m, 1H), 1.51~1.60 (m, 1H), 1.29~1.38 (m, 1H), 0.96 (t, J=7.5 Hz, 3H), 0.80 (d, J=6.9 Hz, 3H).

Hydroxy Ester 11
2-(S)-Hydroxy-3-(S)-methylpentanoic acid, (4-methoxy)benzyl ester R$_F$: 0.38 (4:1 v/v hexanes/EtOAc); $^1$H NMR (500 MHz) δ7.30~7.33 (m, 2H), 6.89~6.92 (m, 2H), 5.19 (AB d, J=11.9 Hz, 1H), 5.15 (AB d, J=11.9 Hz, 1H), 4.10 (dd, J=3.7 & 6.0 Hz, 1H), 3.83 (s, 3H), 2.71 (d, J=5.9 Hz, 1H), 1.78~1.86 (m, 1H), 1.18~1.36 (m, 2H), 0.97 (d, J=7.1 Hz, 3H), 0.87 (t, J=7.3 Hz, 3H).

Hydroxy Ester 12
2-(S)-Hydroxy-3-(cyclopropyl)propanoic acid, benzyl ester

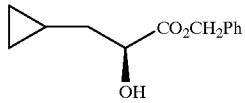

$^1$H NMR (300 MHz, CDCl$_3$): δ7.33~7.47 (m, 5H), 5.21 (s, 2H), 4.28~4.37 (m, 1H), 2.80~2.90 (m, 1H), 1.60~1.72 (m, 2H), 0.79~0.0.91 (m, 1H), 0.40~0.53 (m, 2H), 0.00~0.14 (m, 2H),

Aldehyde 1
2-(R)-(3-(R)-Formyl-4-(S)-phenylpyrrolidin-1-yl)-3-(cyclobutyl)propionic acid, benzyl ester

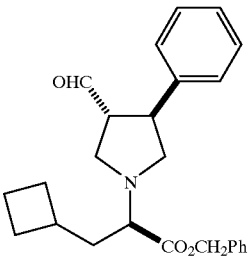

Step A: 2-(R)-(3-(R)-(t-Butyldimethylsilyloxymethyl)-4-(S)-phenyl-pyrrolidin1-yl)-3-(cyclobutyl)propionic acid, benzyl ester A solution of 1.84 g (7.8 mmol) of 2-(S)-hydroxy-3-(cyclobutyl)propionic acid, benzyl ester (Hydroxy Ester 2) in 30 mL of CH$_2$Cl$_2$ at −5° C. was treated with 1.40 mL (8.4 mmol) of trifluoromethanesulfonic anhydride maintaining the internal temperature at less than 0° C. The resulting mixture was stirred cold for 2 min, then treated with 1.10 mL (9.6 mmol) of 2,6-lutidene, maintaining the internal temperature at less than 0° C. The resulting mixture was stirred cold for 30 min, then treated with a solution of 2.65 g (9.5 mmol) of 3-(R)-(t-butyldimethylsilyloxymethyl)4-(S)-phenylpyrrolidine (Pyrroldine 1) in 10 mL of CH$_2$Cl$_2$ and 3.00 mL (31.2 mmol) of DIEA. The resulting mixture was warmed to rt and stirred for 20 h. The reaction was quenched with 50 mL of sat'd NaHCO$_3$ and the quenched mixture was extracted with 200 mL of ether. The ether extract was dried over MgSO$_4$ and concentrated. Flash chromtography on 150 g of silica gel using 20:1 v/v hexanes/ether as the eluant afforded 3.23 g (81% based on Hydroxy Ester 2) of the title compound: $^1$H NMR (300 MHz) δ−0.25 (s, 3H), −0.21 (s, 3H), 0.84 (s, 9H), 1.57–2.07 (8H), 2.29–2.39 (2H), 2.66–2.77 (m, 2H), 2.93 (q, J=7.8, 1H), 3.06 (t, J=8.4, 1H), 3.19 (t, J=8.4, 1H), 3.26 (dd, J=2.1, 6.3, 1H), 3.45–3.60 (m, 2H), 5.15 (s, 2H), 7.17–7.38 (10H).

Step B: 2-(R)-(3-(R)-Hydroxymethyl-4-(S)-phenylpyrrolidin-1-yl)-3(cyclobutyl)propionic acid, benzyl ester A solution of 3.20 g (6.3 mmol) of 2-(R)-(3-(R)-(t-butyldimethylsilyloxymethyl)-4-(S)-phenylpyrrolidin-1-yl)-3-(cyclobutyl) propionic acid, benzyl ester (from Step A) in 40 mL of THF at 0° C. was treated with 10 mL of 1.0 M tetrabutylammonium fluoride solution in THF. The resulting mixture was warmed to rt and stirred for 2.5 h. The reaction mixture was partitioned between 200 mL of ether and 100 mL of 50% sat'd NaHCO$_3$ and the layers were separated. The organic layer was dried over MgSO$_4$ and concentrated. Flash chromatography on 100 g of silica gel using 2:1 v/v hexanes/ether as the eluant afforded 2.34 g (94%) of the title compound: $^1$H NMR (500 MHz) δ1.56–2.07 (8H), 2.15 (br s, 1H), 2.27–2.37 (2H), 2.64 (t, J=11.0, 1H), 2.80 (dd, J=6.5, 11.0), 3.04–3.11 (2H), 3.23–3.30 (2H), 3.56 (dd, J=7.5, 13.0, 1H), 3.68 (dd, J=5.5, 13.0, 1H), 5.15 (ABq, J=20.0, 2H), 7.17–7.40 (10H).

Step C: 2-(R)-(3-(R)-Formyl4-(S)-phenylpyrrolidin-1-yl)-3-(cyclobutyl)propionic acid, benzyl ester A solution of 1.29 mL (14.8 mmol) of oxalyl chloride in 15 mL of CH$_2$Cl$_2$ at −78° C. was treated with 2.10 mL (29.7 mmol) of DMSO maintaining the temperature at less than −60° C. The resulting mixture was stirred cold for 5 min. A solution of 2.33 g (5.9 mmol) of 2-(R)-(3-(R)-(hydroxymethyl)-4 -(S)-phenylpyrrolidin-1-yl)-3-(cyclobutyl)propionic acid, benzyl ester (from Step B) in 10 mL of CH$_2$Cl$_2$ was added maintaining the temperature at less than −60° C. The resulting mixture was stirred cold for 30 min. The mixture was treated with 10.3 mL (59.3 mmol) of DIEA maintaining the temperature at less than −60° C. The reaction was warmed to 0° C., stirred for 20 min and quenched with H$_2$O . The mixture was partitioned between 250 mL of CH$_2$Cl$_2$ and 100 mL of H$_2$O and the layers were separated. The aqueous layer was extracted with 250 mL of CH$_2$Cl$_2$. The combined organic phases were dried over Na$_2$SO$_4$ and concentrated. Flash chromatography on 100 g of silica gel using 4:1 v/v hexanes/ether as the eluant afforded 2.30 g (97%) of the title compound: $^1$H NMR (300 MHz) δ1.54–2.08 (m, 8H), 2.31 (m, 1H), 2.75 (t, J=8.6 Hz, 1H), 2.96 (m, 1H), 3.11–3.35 (m, 4H), 3.56 (q, J=7.9 Hz, 1H), 5.16 (s, 2H), 7.19–7.39 (m, 10H), 9.63 (d, J=2.2 Hz, 1H).

The following 1,3,4-trisubstituted pyrrolidine aldehydes were prepared from the appropriate a-hydroxy ester and 3,4-disubstituted pyrroldine using procedures analogous to those described for the preparation of Aldehyde 1.

Aldehyde 2
2-(R)-(3-(R)-Formyl-4-(S)-(3-fluorophenyl)pyrrolidin-1-yl)-3-(cyclobutyl)propionic acid, benzyl ester

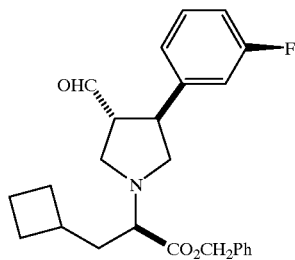

The title compound was prepared from α-Hydroxy Ester 2 and Pyrrolidine 2: $R_F$: 0.60 (7:3 v/v hexane/EtOAc); $^1$H NMR (300 MHz) δ1.57–2.08 (m, 8H), 2.29 (m, 1H), 2.73 (br t, 1H), 2.92 (m, 1H), 3.14–3.34 (m, 4H), 3.56 (br q, 1H), 5.16 (s, 2H), 6.88–6.99 (m, 3H), 7.20–7.39 (m, 6H), 9.62 (d, J=2.0, 1H).

Aldehyde 3
2-(R)-(3-(R)-Formyl-4-(S)-phenylpyrrolidin-1-yl)-3-(cyclobutyl)propionic acid, (4-methoxy)benzyl ester

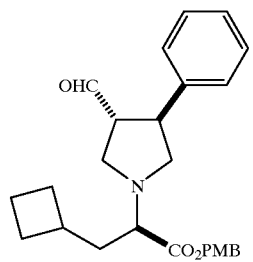

The title compound was prepared from α-Hydroxy Ester 4 and Pyrrolidine 1.

Aldehyde 4
2-(R)-(3-(R)-Formyl-4-(S)-phenylpyrrolidin-1-yl)-2-(cyclohexyl) acetic acid, benzyl ester

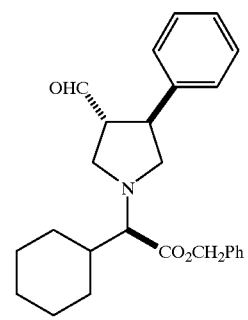

The title compound was prepared from α-Hydroxy Ester 5 and Pyrrolidine 1: $R_F$: 0.50 (4:1 v/v hexanes/EtOAc); $^1$H NMR (500 MHz) δ0.94–1.03 (m, 2H), 1.05–1.29 (4H), 1.59 (app d, J=12.5, 1H), 1.67–1.84 (3H), 1.96 (app d, J=12.5, 1H), 2,71 (t, J=8.5, 1H), 2.93–2.96 (m, 1H), 3.17–3.22 (3H), 3.32 (t, J=8.5, 1H), 3.55 (q, J=8.0, 1H), 5.19 (app s, 2H), 7.19–7.41 (10H), 9.64 (d, J=2.0, 1H).

Aldehyde 5
2-(R)-(3-(R)-Formyl-4-(S)-phenylpyrrolidin-1-yl)-2-(cyclohexyl) acetic acid, (4-methoxy)benzyl ester

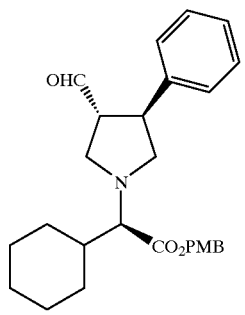

The title compound was prepared from α-Hydroxy Ester 6 and Pyrrolidine 1: $^1$H NMR (500 MHz) δ0.95–1.98 (10H), 2.68 (t, J=8.6, 1H), 2.91–2.95 (m, 1H), 3.16–3.23 (3H), 3.29 (t, J=8.3, 1H), 3.48–3.56 (2H), 3.83 (s, 3H), 5.12 (s, 2H), 6.88–6.91 (2H), 7.17–7.35 (7H), 9.63 (d, J=2.3, 1H).

Aldehyde 6
2-(R)-(3-(R)-Formyl-4-(S)-(3-fluorophenyl)pyrrolidin-1-yl)-2-(cyclohexyl) acetic acid, benzyl ester

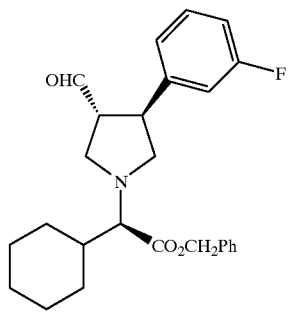

The title compound was prepared from α-Hydroxy Ester 5 and Pyrrolidine 2.

Aldehyde 7
2-(R)-(3-(R)-Formyl-4-(S)-(3-fluorophenyl)pyrrolidin-1-yl)-2-(cyclohexyl) acetic acid, (4-methoxy)benzyl ester

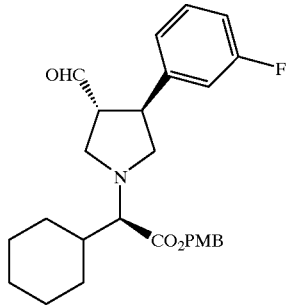

The title compound was prepared from α-Hydroxy Ester 6 and Pyrrolidine 2.

Aldehyde 8
2-(R)-(3-(R)-Formyl-4-(S)-phenylpyrrolidin-1-yl)-3-methyl butanonic acid, benzyl ester

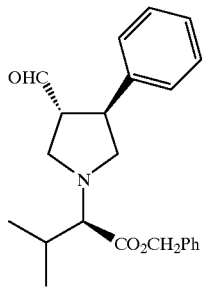

The title compound was prepared from a-Hydroxy Ester 7 and Pyrrolidine 1: $R_F$: 0.77 (3:2 v/v hexanes/EtOAc); $^1$H NMR (300 MHz) δ0.89 (d, J=6.8, 3H), 1.00 (d, J=6.8, 3H), 2.08 (m, 1H), 2.66 (dd, J=8.9, 8.0, 1H), 2.92 (m, 1H), 3.08 (d, J=10.0, 1H), 3.17 (d, J=6.6, 1H), 3.28 (t, J=8.4, 1H), 3.53 (m, 1H), 5.17 (s, 2H), 7.16–7.38 (m, 10H), 9.63 (d, J=2.1, 1H).

Aldehyde 9
2-(R)-(3-(R)-Formyl-4-(S)-phenylpyrrolidin-1-yl)-3-methyl butanonic acid, (4-methoxy)benzyl ester

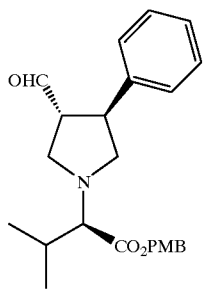

The title compound was prepared from α-Hydroxy Ester 8 and Pyrrolidine 1.

Aldehyde 10
2-(R)-(3-(R)-Formyl-4-(S)-(3-fluorophenyl)pyrrolidin-1-yl)-3-methyl butanonic acid, benzyl ester

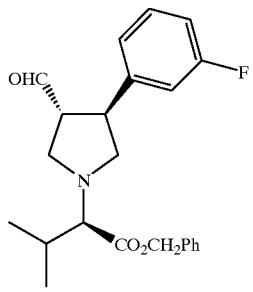

The title compound was prepared from α-Hydroxy Ester 7 and Pyrrolidine 2.

Aldehyde 11
2-(R)-(3-(R)-Formyl-4-(S)-(3-fluorophenyl)pyrrolidin-1-yl)-3-methyl butanonic acid, (4-methoxy)benzyl ester

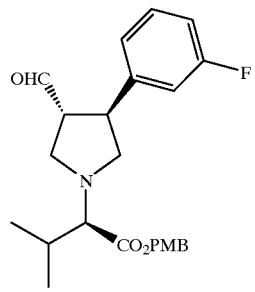

The title compound was prepared from α-Hydroxy Ester 8 and Pyrrolidine 2: $^1$H NMR (500 MHz) δ0.91 (d, J=6.5, 3H), 1.00 (d, J=6.5, 3H), 2.04–2.09 (m, 1H), 2.68 (t, J=8.5, 1H), 2.88–2.92 (m, 1H), 3.06 (d, J=10.0, 1H), 3.14–3.19 (2H), 3.26 (t, J=8.5, 1H), 3.55 (q, J=7.5, 1H), 3.82 (s, 3H), 5.13 (app s, 2H), 6.88–6.97 (4H), 7.18–7.34 (5H), 9.64 (d, J=1.5, 1H).

Aldehyde 12
2-(R)-(3-(R)-Formyl-4-(S)-(3-fluorophenyl)pyrrolidin-1-yl)-3-(cyclopropyl)propionic acid, (4-methoxy)benzyl ester

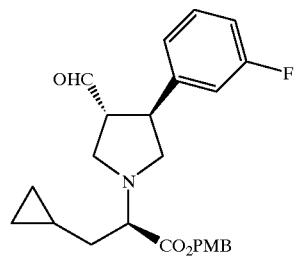

The title compound was prepared from α-Hydroxy Ester 1 and Pyrrolidine 2: $R_F$: 0.40 (7:3 v/v hexanes/EtOAc); $^1$H NMR (300 MHz) ι0.01–0.10 (m, 2H), 0.36–0.49 (m, 2H), 0.69 (m, 1H), 1.54–1.76 (m, 2H), 2.64–3.61 (m, 7H), 3.80 (s, 3H), 5.12 (s, 2H), 6.84–7.04 (m, 5H), 7.21–7.34 (m, 3H) 9.63 (d, J=1.9, 1H).

Aldehyde 13
2-(R)-(3-(R)-Formyl-4-(S)-(3-thienyl)pyrrolidin-1-yl)-3-(cyclobutyl)propionic acid, (4-methoxy)benzyl ester

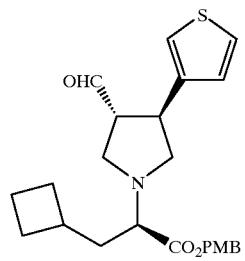

The title compound was prepared from α-Hydroxy Ester 2 and Pyrrolidine 3: $R_F$: 0.56 (4:1 v/v hexanes/EtOAc); $^1$H NMR (300 Mhz) δ1.56–2.05 (m, 8H), 2.27 (m, 1H), 2.69 (br t, 1H), 2.89 (m, 1H), 3.06–3.31 (m, 4H), 3.63 (br q, 1H), 3.81 (s, 3H), 5.09 (s, 2H), 6.86–6.96 (m, 4H), 7.25–7.33 (m, 3H), 9.63 (d, J=2.2, 1H).

Aldehyde 14
2-(R)-(3-(R)-Formyl-4-(S)-(3-fluorophenyl)pyrrolidin-1-yl)-3-(S)-methylpentanoic acid, benzyl ester Step A: 2-(S)-Trifluoromethanesulfonyl-3-(S)-methylpentanoic acid, benzyl ester A solution of 1.887 g triflic anhydride (6.69 mmole) in 5 mL DCM was cooled in a ice acetone bath at about −13° C. To this was added a solution of 1.416 g (6.37 mmole) 2-(S)-hydroxy-3-(S)-methylpentanoic acid, benzyl ester (Hydroxy acid 9), 0.751 g 2,6-lutidine in 10 mL DCM dropwise with stirring under nitrogen over 10 minutes. After stirring in the cold bath for one hour, the reaction mixture was transferred into a separatory funnel with 150 mL ether. It was washed with 60 mL water (3×) and brine (1×), dried over sodium sulfate, and concentrated to give the crude product (2.248 g). FC (0~35% ethyl acetate in hexanes) gave the title compound (1.764 g) as a colorless oil. $R_f$: 0.77 (30% ethyl acetate in hexanes). $^1$H NMR (500 MHz) δ7.36~7.42 (m, 5H), 5.30 (AB d, J=11.9 Hz, 1H), 5.26 (AB d, J=12.1 Hz, 1H), 5.06 (d, 3.9 Hz, 1H), 2.12~2.19 (m, 1H), 1.41~1.49 (m, 1H), 1.26~1.35 (m, 1H), 1.05 (d, J=6.8 Hz, 3H), 0.90 (t, J=7.6 Hz, 3H).

Step B: 2-(R)-(3-(R)-(t-Butyldimethylsilyloxymethyl)-4-(S)-(3 fluorophenyl)pyrrolidin-1-yl)-3-(S)-methylpentanoic acid, benzyl ester A solution of 1.02 g DIEA (7.891 mmole) and 1.437 g (4.642 mmole) 3-(R)-(t-butyldimethylsilyloxymethyl)-4-(S)-(3-fluorophenyl)pyrrolidine (Pyrrolidine 2) in 5 mL DCM. was treated with a solution of 1.645 g (4.642 mmole) 2-(S)-trifluoromethane-sulfonyl-3-(S)-methylpentanoic acid, benzyl ester (from Step A above) in 10 mL DCM. After stirring over night at room temperature, the reaction mixture was transferred into a separatory funnel with 125 mL ether. It was washed with 75 mL 2% sodium bicarbonate, water (2×) and brine, dried over sodium sulfate, and concentrated to give the crude product (2.59 g). FC (5∥105% ethyl acetate in hexanes with 1% triethylamine) gave the title compound (2.378 g) as a colorless oil. $R_f$: 0.70 (5% ethyl acetate in hexanes with 1% triethylamine). $^1$H NMR (500 MHz) δ7.33~7.41 (m, 5H), 7.20~7.24 (m, 1H), 6.98 (d, J=7.5 Hz, 1H), 6.94 (d, J=10.3 Hz, 1H), 6.87~6.90 (m, 1H), 5.18 (s, 2H), 3.55 (dd, J=5.5 & 9.8 Hz, 1H), 3.50 (dd, J=7.1 & ~9.9 Hz, 1H), 3.14~3.20 (m, 2H), 3.08~3.12 (m, 1H), 2.91~2.96 (m, 1H), 2.70~2.73 (m, 1H), 2.62~2.65 (m, 1H), 2.28~2.34 (m, 1H), 1.83~1.90 (m, 1H), 1.41~1.48 (m, 1H), 1.06~1.12 (m, 1H), 1.01 (d, J=6.7 Hz, 3H), 0.90 (t, J=7.4 Hz, 3H), 0.87 (s, 9H), 0.01 (s, 6H).

Step C: 2-(R)-(3-(R)-(Hydroxymethyl)-4-(S)-(3-fluorophenyl)pyrrolidin-1-yl)-3-(S)-methylpentanoic acid, benzyl ester The product from Step B above in 20 mL THF was treated with 10 mL 1 N tetrabutylammonium fluoride in THF overnight. The reaction mixture was partitioned between 300 mL of ether and 150 mL icy water. The organic layer was washed with 75 mL 5% NaHCO$_3$ (3×) and saturated brine. The organic layer was dried over Na$_2$SO$_4$ and concentrated. Flash chromatography on 100 g of silica gel using 15~50% ethyl acetate in hexanes with 1% triethylamine afforded 1.587 g of the title compound as a colorless oil: $^1$H NMR (500 MHz) δ7.33~7.42 (m, 5H), 7.22~7.26 (m, 1H), 6.98 (d, J=7.8 Hz, 1H), 6.88~6.94 (m, 2H), 5.19 (s, 2H), 3.67 (dd, J=4.8 & 10.5 Hz, 1H), 3.55~3.58 (m, 1H), 3.06~3.30 (m, 4H), 2.75~2.79 (m, 1H), 2.63~2.67 (m, 1H), 2.31~2.36 (m, 1H), 1.97 (br s, ~1H, OH?), 1.87~1.91 (m, 1H), 1.43~1.51 (m, 1H), 1.05~1.14 (m, 1H), 1.02 (d, J=6.6 Hz, 3H), 0.90 (t, J=7.3 Hz, 3H).

Step D: 2-(R)-(3-(R)-Formyl-4-(S)-(3-fluorophenyl) pyrrolidin-1-yl)-3-(S)-methylpentanoic acid, benzyl ester After cooling 0.605 g (4.767 mmole) oxalyl chloride in 30 mL DCM in a dry ice acetone bath under nitrogen, 0.748 g (9.569 mmole) DMSO in 5 mL DCM was added over 5 minutes. After stirring for 15 minutes, a solution of the alcohol (1.587 g, 3.987 mmole) from Step C above in 30 mL DCM was added over 20 minutes. After an additional 20 minutes, a solution of 2.017 g (19.935 mmole) triethylamine in 5 mL DCM was added over 5 minutes. The cooling bath was allowed to warm up overnight. The reaction mixture was transferred into a separatory funnel with ether and was washed with 1 N NaOH, water, and saturated brine. The organic layer was dried over sodium sulfate and concentrated to give 1.63 g crude product. FC on silica gel (5~40% ethyl acetate in hexanes) gave 1.257 g title compound as a colorless oil. $R_f$: 0.44 (20% ethyl acetate in hexanes). $^1$H NMR (500 MHz) δ9.64 (d, J=2.1 Hz, 1H), 7.33~7.41 (m, 5H), 7.24~7.27 (m, 1H), 6.90~6.98 (m, 3H), 5.21 (AB d, J=12.2 Hz, 1H), 5.18 (AB d, J=12.2 Hz, 1H), 3.54~3.58 (m, 1H), 3.26~3.29 (m, 1H), 3.14~3.22 (m, 3H), 2.89~2.93 (m, 1H), 2.68~2.71 (m, 1H), 1.86~1.93 (m, 1H), 1.39~1.47 (m, 1H), 1.04~1.15 (m, 1H), 0.99 (d, J=6.7 Hz, 3H), 0.91 (t, J=7.5 Hz, 3H). Some starting material was also recovered (0.298 g). $R_f$: 0.13 (20% ethyl acetate in hexanes).

Aldehyde 15

2-(R)-(3-(R)-Formyl-4-(S)-(3-fluorophenyl)pyrrolidin-1-yl)-3-(R)-methylpentanoic acid, benzyl ester Step A: 2-(S)-Trifluoromethanesulfonyl-3-(R)-methylpentanoic acid, benzyl ester A solution of 1.334 g triflic anhydride (6.00 mmole) in 5 mL DCM was cooled in a ice acetone bath at about −13° C. A solution of 1.777 g (6.3 mmole) 2-(S)-hydroxy-3-(R)-methylpentanoic acid, benzyl ester (Hydroxy acid 10), 0.707 g 2,6-lutidine in 50 mL DCM was added dropwise with stirring under nitrogen over 15 minutes. After stirring in the cold bath for half an hour and without cooling for another half an hour, the reaction mixture was transferred into a separatory funnel with 150 mL ether. It was washed with 60 mL water (3×) and brine (1×), dried over sodium sulfate, and concentrated to give the crude product (2.187 g). FC (0~25% ethyl acetate in hexanes) gave the title compound (1.29 g) as a colorless oil. $R_f$: 0.83 (30% ethyl acetate in hexanes). $^1$H NMR (500 MHz) δ7.35~7.43 (m, 5H), 5.30 (AB d, J=11.9 Hz, 1H), 5.28 (AB d, J=11.9 Hz, 1H), 5.14 (d, J=3.0 Hz, 1H), 2.09~2.17 (m, 1H), 1.48~1.57 (m, 1H), 1.32~1.41 (m, 1H), 0.98 (t, J=7.4 Hz, 3H), 0.945 (d, J=6.8 Hz, 3H).

Step B: 2-(R)-(3-(R)-(t-Butyldimethylsilyloxymethyl)4-(S)-(3-fluorophenyl)pyrrolidin-1-yl)-3-(R)-methylpentanoic acid, benzyl ester A solution of 0.708 g DIEA (5.476 mmole) and 0.997 g (3.221 mmole) 3-(R)-(t-butyldimethylsilyloxymethyl)-4-(S)-(3-fluorophenyl)pyrrolidine (Pyrrolidine 2) in 5 mL DCM. was treated with a solution of 1.141 g (3.221 mmole) 2-(S)-trifluoromethane-sulfonyl-3-(R)-methylpentanoic acid, benzyl ester (from Step A above) in 5 mL DCM. After stirring over night at room temperature, the reaction mixture was transferred into a separatory funnel with 125 mL ether. It was washed with 75 mL 2% sodium bicarbonate, water (2×) and brine, dried over sodium sulfate, and concentrated to give the crude product (1.813 g). FC (5~105% ethyl acetate in hexanes with 1% triethylamine) gave the title compound (1.666 g) as a colorless oil. $R_f$: 0.70 (5% ethyl acetate in hexanes with 1% triethylamine). $^1$H NMR (500 MHz) 7.33~7.42 (m, 5H), 7.20~7.24 (m, 1H), 6.98 (d, J=7.5 Hz, 1H), 6.95 (d, J=10.0 Hz, 1H), 6.87~6.90 (m, 1H), 5.19 (s, 2H), 3.56 (dd, J=5.5 & 9.8 Hz, 1H), 3.50 (dd, J=7.1 & ~10.8 Hz, 1H), 3.14~3.20 (m, 2H), 3.08~3.11 (m, 1H), 2.91~2.96 (m, 1H), 2.68~2.72 (m, 1H), 2.61~2.65 (m, 1H), 2.29~2.33 (m, 1H), 1.84~1.90 (m, 1H), 1.68~1.76 (m, 1H), 1.16~1.23 (m, 1H), 0.89~0.94 (t & d, 6H), 0.87 (s, 9H), 0.01 (s, 6H).

Step C: 2-(R)-(3-(R)-(Hydroxymethyl)-4-(S)-(3-fluorophenyl)pyrrolidin-1-yl)-3-(R)-methylpentanoic acid, benzyl ester The product from Step B above in 15 mL THF was treated with 7 mL 1 N tetrabutylammonium fluoride in THF overnight. The reaction mixture was partitioned between 300 mL of ether and 150 mL icy water. The organic layer was washed with 75 mL 5% NaHCO₃ (3x) and saturated brine. The organic layer was dried over Na₂SO₄ and concentrated. Flash chromatography on 100 g of silica gel using 20~40% ethyl acetate in hexanes with 1% triethylamine afforded 1.24 g of the title compound as a colorless oil: ¹H NMR (500 MHz) δ7.33~7.42 (m, 5H), 7.21~7.26 (m, 1H), 6.98 (d, J=7.6 Hz, 1H), 6.88~6.95 (m, 2H), 5.19 (s, 2H), 3.66~3.69 (m, 1H), 3.55~3.60 (m, 1H), 3.24~3.28 (m, 1H), 3.18 (d, J=9.2 Hz, 1H), 3.05~3.12 (m, 2H), 2.72 (dd, J=5.0 & 9.1 Hz, 1H), 2.60 (dd, J=7.7 & 9.0 Hz, 1H), 2.28~2.34 (m, 1H), 1.99~2.02 (m, 1H, OH?), 1.84~1.91 (m, 1H), 1.61~1.69 (m, 1H), 1.16~1.25 (m, 1H), 0.92 (t, J=7.6 Hz, 3H), 0.91 (d, J=7.6 Hz, 3H).

Step D: 2-(R)-(3-(R)-Formyl-4-(S)-(3-fluorophenyl)pyrrolidin-1-yl)-3-(R)-methylpentanoic acid, benzyl ester The title compound (1.031 g) was obtained from the alcohol in Step C above using the same procedure as described in Aldehyde 14 Step D. R$_f$: 0.47 (20% ethyl acetate in hexanes). ¹H NMR (500 MHz) δ9.64 (s, 1H), 7.34~7.42 (m, 5H), 7.24~7.28 (m, 1H), 6.91~6.99 (m, 3H), 5.20 (s, 2H), 3.53~3.58 (m, 1H), 3.12~3.29 (m, 4H), 2.89~2.94 (m, 1H), 2.66~2.71 (m, 1H), 1.88~1.93 (m, 1H), 1.63~1.70 (m, 1H), 1.15~1.21 (m, 1H), 0.89~0.93 (m, 6H).

Aldehyde 16
2-(R)-(3-(R)-Formyl-4-(S)-(3-fluorophenyl)pyrrolidin-1-yl)-3-(S)-methylpentanoic acid, (4-methoxy)benzyl ester Step A: 2-(S)-Trifluoromethanesulfonyl-3-(S)-methylpentanoic acid, (4-methoxy)benzyl ester The title compound was obtained from Hydroxyester 11 using the same procedure as described in Aldehyde 14 Step A for its benzyl analog. ¹H NMR (500 MHz) δ7.31~7.34 (m, 2H), 6.89~6.93 (m, 2H), 5.24 (AB d, J=11.7 Hz, 1H), 5.19 (AB d, J=11.9 Hz, 1H), 5.03 (d, 4.2 Hz, 1H), 3.83 (s, 3H), 2.09~2.17 (m, 1H), 1.41~1.49 (m, 1H), 1.39~1.47 (m, 1H), 1.24~1.33 (m, 1H), 1.03 (d, J=6.9 Hz, 3H), 0.89 (t, J=7.5 Hz, 3H).

Step B: 2-(R)-(3-(R)-(t-Butyldimethylsilyloxymethyl)-4-(S)-(3-fluorophenyl)pyrrolidin-1-yl)-3-(S)-methylpentanoic acid, (4-methoxy)benzyl ester The title compound was obtained from triflate (Step A above) using the same procedure as described in Aldehyde 14 Step B for its benzyl analogue. R$_f$: 0.26 (1:15 ethyl acetate and hexanes). ¹H NMR (500 MHz) δ7.31~7.34 (m, 2H), 7.19~7.24 (m, 1H), 6.86~6.97 (m, 5H), 5.11 (s, 2H), 3.83 (s, 3H), 3.55 (dd, J=5.6 & 10.0 Hz, 1H), 3.495 (dd, J=7.0 & 9.9 Hz, 1H), 3.12~3.16 (m, 2H), 3.06~3.10 (m, 1H), 2.90~2.94 (m, 1H), 2.695 (dd, J=7.2 & 9.0 Hz, 1H), 2.62~2.65 (dd, J=6.6 & 9.0 Hz, 1H), 2.27~2.33 (m, 1H), 1.82~1.88 (m, 1H), 1.41~1.46 (m, 1H), 1.04~1.10 (m, 1H), 1.00 (d, J=6.7 Hz, 3H), 0.89 (t, J=7.3 Hz, 3H), 0.86 (s, 9H), 0.00 (s, 6H).

Step C: 2-(R)-(3-(R)-(Hydroxymethyl)-4-(S)-(3-fluorophenyl)pyrrolidin-1-yl)3-(S)-methylpentanoic acid, (4-methoxy)benzyl ester The title compound was obtained from triflate from Step B above using the same procedure as described in Aldehyde 14 Step C for its benzyl analogue. ¹H NMR (500 MHz) δ7.32~7.35 (m, 2H), 7.21~7.26 (m, 1H), 6.88~6.97 (m, 5H), 5.13 (s, 2H), 3.82 (s, 3H), 3.67 (dd, J=4.8 & 10.3 Hz, 1H), 3.57 (dd, J=6.2 & 10.3 Hz, 1H), 3.22~3.26 (m, 1H), 3.15 (d, J=9.3 Hz, 1H), 3.09~3.12 (m, 1H), 3.03~3.08 (m, 1H), 2.73 (dd, J=4.9 & 9.3 Hz, 1H), 2.61 (dd, J=7.7 & 9.1 Hz, 1H), 2.27~2.33 (m, 1H), 1.84~1.89 (m, 1H), 1.41~1.49 (m, 1H), 1.03~1.10 (m, 1H), 1.00 (d, J=6.6 Hz, 3H), 0.89 (t, J=7.3 Hz, 3H).

Step D: 2-(R)-(3-(R)-Formyl-4-(S)-(3-fluorophenyl)pyrrolidin-1-yl)-3-(S)-methylpentanoic acid, (4-methoxy)benzyl ester The title compound was obtained from the alcohol (Step C above) using the same procedure as described in Aldehyde 14 Step D for its benzyl analogue. ¹H NMR (500 MHz) δ9.64 (d, J=2.1 Hz, 1H), 7.32~7.35 (m, 2H), 7.23~7.27 (m, 1H), 6.88~6.96 (m, 5H), 5.14 (AB d, J=11.9 Hz, 1H), 5.11 (AB d, J=11.9 Hz, 1H), 3.82 (s, 3H), 3.52~3.57 (m, 1H), 3.24~3.27 (m, 1H), 3.12~3.20 (m, 3H), 2.88~2.92 (m, 1H), 2.68 (dd, J=7.8 & 8.9 Hz, 1H), 1.84~1.91 (m, 1H), 1.38~1.45, 3H), 2.88~2.92 (m, 1H), 2.68 (dd, J=7.8 & 8.9 Hz, 1H), 1.84~1.91 (m, 1H), 1.38~1.45 (m, 1H), 1.05~1.13 (m, 1H), 0.98 (d, J=6.7 Hz, 3H), 0.90 (t, J=7.3 Hz, 3H).

Aldehyde 17
α-(R)-(3-(R)-Formyl-4-(S)-(3-fluorophenyl)pyrrolidin-1-yl)-tert-butylacetic acid, benzyl ester

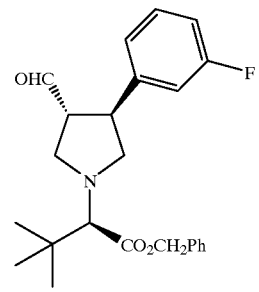

Step A: 3,3-dimethyl-2-(S)-hydroxybutyric acid benzyl ester (S)3,3-dimethyl-2-hydroxybutyric mL, 23.8 mmoL) were dissolved in 15 mL DMF. Benzylbromide (2.8 mL, 23.8 mmol) was added and the mixture was stirred overnight. Ethyl acetate was added and the mixture was washed with water (3x) and sat'd NaCl then dried over sodium sulfate and concentrated. Flash chromatography (150 g silica, 7/1 Hexane/EtOAc) afforded 3.4 grams (96%) of the title compound. ¹H NMR (300 MHz, CDCl₃). δ0.98 (s, 9H), 2.75 (d, 1H), 3.85 (d, 1H), 5.23, (s, 2H), 7.27–7.3 (m, 5H).

Step B: 3,3-dimethyl-2-(S)-trifluoromethanesulfonylbutyric acid benzyl ester

A solution of 3,3-dimethyl-2-(S)-hydroxybutyric acid benzyl ester (3.4 under nitrogen. 2,6-lutidine (2.3 mL, 19.9 mmol) then trifluoromethanesulfonic anhydride (3.1 mL, 18.4 mmol) were added dropwise via syringe. The mixture was warmed to room temperature and stirred for 1 h. Water was added and the mixture was extracted with ethyl acetate. The organic layer was dried over sodium sulfate and concentrated. Flash chromatography (150 g silica, 20/1 Hexane/EtOAc) afforded 3.3 grams (61%) of the desired triflate. ¹H NMR (400 MHz, CDCl₃). δ1.05 (s, 9H), 4.8, (s, 1H), 5.25 (dd, 2H), 7.3–7.4 (m, 5H).

Step C: α-(R)-((3-(R)-(tert butyldimethylsilyloxy)methyl)-4-(S)-(3-fluorophenyl)pyrrolidin-1-yl)-tert-butylacetic acid A dry flask was charged 10 mL DMF and 3,3-dimethyl-2-(S)-trifluoromethanesulfonylbutyric A dry flask was charged 10 mL DMF and 3,3-dimethyl-2-(S)-trifluoromethanesulfonylbutyric was purged with nitrogen and 3-(R)-(t-butyldimethylsilyloxymethyl)-4-(S)-(3-fluoro)

phenyl pyrrolidine (2.7 grams, 8.9 mmol, Pyrrolidine 2) then diisopropylethyl amine (1.8 mL, 10.2 mmol) were added. The mixture was heated to 50° C. overnight. Water (200 mL) was added and the mixture was extracted with ether (2×150 mL). The combined organics were dried over sodium sulfate and concentrated. Flash chromatography (150 g silica, 30/1 Hexane/EtOAc) afforded 2.0 grams (61%) of product. $^1$H NMR (400 MHz, CDCl$_3$). δ0 (s, 6H), 0.84 (s, 9H), 1.05 (s, 9H), 2.25–2.35 (m, 1H), 2.8–2.94 (m, 3H), 3.1–3.22 (m, 3H), 3.45–3.58 (m, 2H), 5.1–5.25 (dd, 2H), 6.83–6.99 (m, 3H), 7.19–7.24 (m, 1H), 7.3–7.42 (m, 5H).

Step D: α-(R)-(3-(R)-Formyl-4-(S)-(3-fluorophenyl) pyrrolidin-1-yl)-tert-butylacetic acid, benzyl ester The title compound was prepared in two steps from α-(R)-(3-(S)-tert butyldimethylsilyloxy)methyl)-4-(S)-(3-fluorophenyl)pyrrolidin-1-yl)-tert-butylacetic acid (Step C) using procedures analogous to those in for Aldehyde 1 Steps B and C. $^1$H NMR (400 MHz, CDCl$_3$). δ1.05 (s, 9H), 2.88–2.96 (m, 2H), 3.2–3.35 (m, 4H), 3.48–4.53 (q, 1H), 5.11–5.25 (dd, 2H), 6.89–6.99 (m, 3H), 7.21–7.26 (m, 1H). 7.35–7.45 (m, 5H), 9.61 (s, 1H).

Aldehyde 18
α-(R)-(3-(R)-Formyl-4-(S)-(3-fluorophenyl)pyrrolidin-1-yl)-tert-butylacetic acid, 4-methoxybenzyl ester

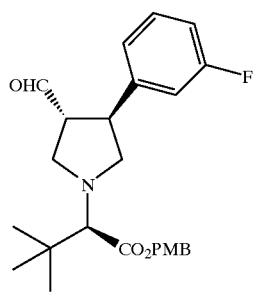

The title compound was prepared in an analagous fashion to aldehyde 17 except that in Step A 4-methyoxybenzyl chloride was used rather than benzyl bromide. $^1$H NMR (400 MHz, CDCl$_3$). δ1.05 (s, 9H), 2.85–2.96 (m, 2H), 3.18–3.36 (m, 4H), 3.45–4.53 (q, 1H), 3.82, (s, 3H), 5.05–5.22 (dd, 2H), 6.89–6.99 (m, 5H), 7.21–7.26 (m, 1H). 7.35–7.45 (m, 2H), 9.61 (s, 1H).

EXAMPLE 1
2-(R)-(3-(S)-(4-(N-(N-(3,4-Difluorobenzyl)carbamoyl)-N-ethylamino)-piperidin-1 yl)methyl-4-(S)-phenyl-pyrrolidin-1-yl)-2-(cyclohexyl)acetic acid Step A: 4-(N-Ethylamino)-1-tert-butoxycarbonylpiperidine Ethylamine (10 mL, 1 M in THF, 10 mmol) and DIEA (2.3 mL, 13.4 mmol) were dissolved in 100 mL of 1,2-dichloroethane under nitrogen. A solution of 1-tert-butoxycarbonyl-4-piperidone (1.3 g, 6.7 mmol) in 100 mL of 1,2-dichloroethane was added, followed by sodium triacetoxyborohydride (4.2 g, 20 mmol). The mixture was stirred at rt under nitrogen for 14 h, then diluted with CH$_2$Cl$_2$. The solution was washed twice with each of 1 N NaOH and brine, dried over Na$_2$So$_4$ and concentrated to afford 1.7 g (97%) of the title compound.

Step B: 4-(N-(N-(3,4-Difluorobenzyl)carbamoyl)-N-ethylamino)-piperidine trifluoroacetate To a solution of 4-(N-ethylamino)-1-tert-butoxycarbonylpiperidine (228 mg, 1 mmol, from Step A) in 5 mL of CH$_2$Cl$_2$ was added 5 mL of a solution of carbonyldiimidazole (170 mg, 1.05 mmol) in CH$_2$Cl$_2$. The mixture was stirred at rt for 1 h, then 3,4-difluorobenzylamine (143 mg, 1 mmol) was added. The resulting mixture was stirred at rt for 16 h, then diluted with CH$_2$Cl$_2$, washed twice with 1 N HCl and dried over Na$_2$So$_4$. The solvent was removed and the residue was redissolved in 2.4 mL of 60% TFA in CH$_2$Cl$_2$. After 1 h, the solution was concentrated to afford 184 mg (45%) of the title compound. ESI-MS: 298.1 (M+H); HPLCA: 1.62 min.

Step C: 2-(R)-(3-(S)-(4-(N-(N-(3,4-Difluorobenzyl) carbamoyl)-N-ethylamino)-piperidin-1-yl)methyl-4-(S)-phenyl-pyrrolidin-1-yl)-2-(cyclohexyl)acetic acid To a solution of DIEA (0.019 mL, 0.11 mmol) in 0.5 mL of 1,2-dichloroethane was added 4-(N-(N-(3,4-difluorobenzyl)carbamoyl)-N-ethylamino)piperidine trifluoroacetate (41 mg, 0.1 mmol, from Step B). To this solution, a solution of 2-(R)-(3-(R)-formyl-4-(S)-phenyl-pyrrolidin-1-yl)-2-(cyclohexyl)acetic acid, (4-methoxy) benzyl ester (26 mg, 0.05 mmol, Aldehyde 5) was added. After mixing well, a slurry of sodium triacetoxyborohydride (35 mg, 0.17 mmol) in 0.5 mL of 1,2-dichloroethane was added. The reaction mixture was stirred well and allowed to stand at rt for 16 h. The solvent was removed and the product was purified by preparative HPLC (column: YMC Combiprep ODS-A 20×50 mm, gradient: 10% acetonitrile/water w/0.1% TFA for 1.5 min then ramp to 90% acetonitrile/water w/0.1% TFA over 7.5 min, flow: 20 mL/min). The isolated material was stirred in 3 mL formic acid for 16 h. After removal of solvent, the residue was purified by ion exchange chromatography (0.5 grams Varian SCX resin, eluting with 100% MeOH, then with 2.0 M NH$_3$/MeOH) to give 16 mg (53%) of the title compound. $^1$H-NMR (400 MHz, CD$_3$OD) δ1.06–1.14 (m, 6H), 1.33 (m, 2H), 1.54 (m, 1H), 1.67–2.05 (m, 10H), 2.57 (m, 1H), 2.87 (br d, J=13, 1H), 2.98 (br t, J=12, 1H), 3.11 (m, 1H), 3.18 (m, 2H), 3.25 (m, 1H), 3.48 (br t, J=11, 2H), 3.65 (m, 2H), 3.71 (d, J=3.1, 1H), 3.79 (dd, J=6.8, 11, 1H), 3.87 (m, 1H), 4.16 (brt, J=12, 1H), 4.29 (s, 2H), 7.04 (m, 1H), 7.10–7.19 (m, 2H), 7.35–7.46 (m, 5H); ESI-MS: 597.4 (M+H); HPLC A: 2.27 min.

Examples 2 through 12 were prepared by the method described in Example 1, Step C, utilizing the appropriate piperidine trifluoroacetate (prepared by a method analogous to that described in Example 1, Steps A and B) and the appropriate aldehyde.

EXAMPLE 2
2-(R)-(3-(S)-(4-(N-(N-(4-Fluorobenzyl)carbamoyl)-N-ethylamino)-piperidin-1-yl)methyl-4-(S)-phenyl-pyrrolidin-1-yl)-2-(cyclohexyl)acetic acid
ESI-MS: 79.5 (M+H); HPLC A: 2.217 min.

EXAMPLE 3
2-(R)-(3-(S)-(4-(N-(N-(4-(Trifluoromethyl)benzyl) carbamoyl)-N-ethylamino)-piperidin 1-yl)methyl-4-(S)-phenyl-pyrrolidin-1-yl)-2-(cyclohexyl)acetic acid
ESI-MS: 629.5 (M+H); HPLC A: 2.50 min.

EXAMPLE 4
2-(R)-(3-(S)-(4-(N-(N-(3-Chlorobenzyl)carbamoyl)-N-ethylamino)-piperidin-1 yl)methyl-4-(S)-phenyl-pyrrolidin-1-yl)-2-(cyclohexyl)acetic acid
ESI-MS: 595.4 (M+H); HPLC A: 2.33 min.

EXAMPLE 5
2-(R)-(3-(S)-(4-(N-(N-(4-Chlorobenzyl)carbamoyl)-N-ethylamino)-piperidin-1 yl)methyl-4-(S)-phenyl-pyrrolidin-1-yl)-2-(cyclohexyl)acetic acid
ESI-MS: 595.4 (M+H); HPLC A: 2.37 min.

EXAMPLE 6
2-(R)-(3-(S)-(4-(N-(N-(3,4-Dichlorobenzyl)carbamoyl)-N-ethylamino)-piperidin-1 yl)methyl-4-(S)-phenyl-pyrrolidin-1-yl)-2-(cyclohexyl)acetic acid ESI-MS: 629.4 (M+H); HPLC A: 2.53 min.

EXAMPLE 7
2-(R)-(3-(S)-(4-(N-(N-(3,4-Dichlorobenzyl)-carbamoyl)-N-prop-1-yl-amino)-piperidin-1 yl)methyl-4-(S)-phenyl-pyrrolidin-1-yl)-2-(cyclohexyl)acetic acid
ESI-MS: 643.5 (M+H); HPLC A: 2.67 min.

EXAMPLE 8
2-(R)-(3-(S)-(4-(N-(N-(3,4-Difluorobenzyl)carbamoyl)-N-ethylamino)-piperidin-1 yl)methyl-4-(S)-(3-fluorophenyl)-pyrrolidin-1-yl)-2-(cyclohexyl)acetic acid
$^1$H-NMR (400 MHz, CD$_3$OD) δ1.11 (t, J=7.1, 3H), 1.16–1.35 (m, 4H), 1.49–1.70 (m, 6H), 1.80–1.93 (m, 5H), 2.04 (m, 1H), 2.34 (dd, J=5.2, 12, 1H), 2.49 (t, J=11, 1H), 2.78 (m, 2H), 2.95 (m, 1H), 3.13–3.24 (m, 4H), 3.45–3.49 (m, 2H), 3.53 (d, J=3.7, 1H), 3.57–3.68 (m, 2H), 3.90 (m, 1H), 4.30 (d, J=5.6, 2H), 6.82 (t, J=5.7, 1H), 7.01–7.06 (m, 2H), 7.10–7.20 (m, 3H), 7.39 (m, 1H); ESI-MS: 615.4 (M+H); HPLC A: 2.34 min.

EXAMPLE 9
2-(R)-(3-(S)-(4-(N-(N-(4-Fluorobenzyl)carbamoyl)-N-ethylamino)-piperidin-1 yl)methyl-4-(S)-(3-fluorophenyl)-pyrrolidin-1-yl)-2-(cyclohexyl)acetic acid
ESI-MS: 597.5 (M+H); HPLC A: 2.28 min.

EXAMPLE 10
2-(R)-(3-(S)-(4-(N-(N-(4-(Trifluoromethyl)benzyl)carbamoyl)-N-ethylamino)-piperidin-1-yl)methyl-4-(S)-(3-fluorophenyl)-pyrrolidin-1-yl)-2-(cyclohexyl)acid
ESI-MS: 647.5 (M+H); HPLC A: 2.56 min.

EXAMPLE 11
2-(R)-(3-(S)-(4-(N-(N-(3-Chlorobenzyl)carbamoyl)-N-ethylamino)-piperidin-1 yl)methyl-4-(S)-(3-fluorophenyl)-pyrrolidin-1-yl)-2-(cyclohexyl)acetic acid
ESI-MS: 613.4 (M+H); HPLC A: 2.42 min.

EXAMPLE 12
2-(R)-(3-(S)-(4-(N-(N-(3,4-Difluorobenzyl)carbamoyl)-N-ethylamino)-piperidin-1yl)methyl-4-(S)-phenyl-pyrrolidin-1-yl)-3-methylbutyric acid
ESI-MS: 557.5 (M+H); HPLC A: 2.04 min.

EXAMPLE 13
2-(R)-(3-(S)-(4-((N-Benzylcarbamoyl)oxy)-piperidin-1-yl)methyl-4-(S)-phenyl pyrrolidin-1-yl)-2-(cyclohexyl)acetic acid
Step A: 4-Hydroxy-1-tert-butoxycarbonylpiperidine
4-Hydroxypiperidine (5.0 g, 49 mmol) and sodium bicarbonate (10.3 g, 123 mmol) were dissolved in 250 mL of 33% water in THF. Di-tert-butyl dicarbonate (10.6 g, 49 mmol) was then added and the reaction mixture was stirred at rt overnight. The mixture was diluted with EtOAc and washed with 1 N HCl, 1 N NaOH and brine. The organic layer was then dried over MgSO$_4$ and concentrated to afford 6.8 g (69%) of the title compound. ESI-MS: 201.8 (M+H); HPLC A: 1.94 min.
Step B: 4-((N-Benzylcarbamoyl)oxy)-piperidine trifluoroacetate
Carbonyldiimidazole (324 mg, 2.0 mmol) was added to a solution of 4-hydroxy-1-tert-butoxycarbonylpiperidine (400 mg, 2.0 mmol, from Step A) in 2mL of CH$_2$Cl$_2$. After stirring at rt for 1 h, benzylamine (0.22 mL, 2.0 mmol) was added and the reaction mixture was stirred at rt for 16 h. The reaction was diluted with CH$_2$Cl$_2$ and washed twice with 1 N HCl and brine. The solvent was removed and the residue was redissolved in 50% TFA in CH$_2$Cl$_2$. After 1 h, the solution was concentrated to afford the title compound. ESI-MS: 234.9 (M+H); HPLC A: 1.22 min.
Step C: 2-(R)-(3-(S)-(4-((N-Benzylcarbamoyl)oxy)-piperidin-1-yl)methyl-4-(S)-phenyl-pyrrolidin-1-yl)-2-(cyclohexyl)acetic acid
The title compound was prepared from 4-((N-benzylcarbamoyl)oxy)-piperidine trifluoroacetate (35 mg, 0.1 mmol, from Step B) and (R)-(3-(R)-formyl-4-(S)-phenylpyrrolidin-1-yl)-2-(cyclohexyl)acetic acid, 4-(methoxy)benzyl ester (25 mg, 0.05 mmol, Aldehyde 5) according to the method described in Example 1, Step C to give 17 mg (64%) of the title compound. ESI-MS: 534.5 (M+H); HPLC A: 2.16 min.

EXAMPLE 14
2-(R)-(3-(S)-(4-(N-((2-Chloro-4-fluorobenzyl)carbonyl)-N-ethylamino)-piperidin-1 yl)methyl-4-(S)-(3-fluorophenyl)-pyrrolidin-1-yl)-3-(cyclobutyl)propionic acid
Step A: 4-(N-((2-Chloro-4-fluorobenzyl)carbonyl)-N-ethylamino)piperidine trifluoroacetate
To a solution of (2-chloro-4-fluorophenyl)acetic acid (189 mg, 1.0 mmol) in CH$_2$Cl$_2$ at −2° C. was added methanesulfonyl chloride (0.093 mL, 1.2 mmol) and 2,6-lutidine (0.186 mL, 1.6 mmol). The solution was stirred at −2° C. for 1.5 h and at rt for 10 min, followed by addition of 4-(N-ethylamino)-1-tert-butoxycarbonylpiperidine (208 mg, 0.9 mmol, from Example 1, Step A) and additional 2,6-lutidine (0.093 mL, 0.8 mmol). The reaction mixture was stirred at rt for 48 h and then diluted with 5% aq. sodium bicarbonate. The aqueous layer was extracted with CH$_2$Cl$_2$. The combined organic extracts were dried over Na$_2$So$_4$. The solvent was removed and the residue was redissolved in 50% TFA in CH$_2$Cl$_2$ for 1 h. The solution was then concentrated to afford the title compound. ESI-MS: 299.2 (M+H); HPLC A: 1.76 min.
Step B: 2-(R)-(3-(S)-(4-(N-((2-Chloro-4-fluorobenzyl)carbonyl)-N-ethylamino)-piperidin-1-yl)methyl-4-(S)-(3-fluorophenyl)-pyrrolidin-1-yl)-3-(cyclobutyl)propionic acid
2-(R)-(3-(R)-Formyl-4-(S)-(3-fluorophenyl)-pyrrolidin-1-yl)-3(cyclobutyl)propionic acid, benzyl ester (25 mg, 0.06 mmol, Aldehyde 2) was dissolved in 3 mL of methanol. 10% palladium on carbon (20 mg, 0.019 mmol) was added and the mixture was placed under 1 atm of hydrogen using a balloon. After vigorous stirring for 3 h, the reaction mixture was filtered through Celite, concentrated and redissolved in 0.5 mL of 1,2-dichloroethane. A solution of DIEA (0.019 mL, 0.11 mmol) and 4-(N-((2-chloro-4-fluorobenzyl)carbonyl)-Nethylamino)-piperidine trifluoroacetate (41 mg, 0.1 mmol, from Step A) in 0.5 mL of 1,2-dichloroethane was added, followed by a slurry of sodium triacetoxyborohydride (35 mg, 0.17 mmol) in 0.5 mL of 1,2-dichloroethane. The mixture was shook well and then left to stand at rt for 4 h. The solvent was removed and the product was purified by preparative HPLC (column: YMC Combiprep ODS-A 20×50 mm, gradient: 10% acetonitrile/water w/0.1% TFA for 1.5 min then ramp to 90% acetonitrile/water w/0.1% TFA over 7.5 min, flow: 20 mL/min). After removal of solvent, the residue was further purified by ion exchange chromatography (0.5 grams Varian SCX resin, eluting with 100% MeOH, then with 2.0 M NH$_3$/MeOH) to give 12 mg (33%) of the title compound. ESI-MS: 602.2 (M+H); HPLC A: 2.75 min.

EXAMPLE 15
2-(R)-(3-(S)-(4-(N-((2-Chloro-4-fluorobenzyl)carbonyl)-N-ethylamino)-piperidin-1 yl)methyl-4-(S)-phenyl-pyrrolidin-1-yl)-3-(cyclobutyl)propionic acid The title compound was prepared from 2-(R)-(3-(R)-formyl-4-(S)-phenyl-pyrrolidin-1-yl)-3-(cyclobutyl) propionic acid, benzyl ester (25 mg, 0.07 mmol, Aldehyde 1) and 4-(N-((2-chloro-4-fluorobenzyl)carbonyl)-N-ethylamino)piperidine trifluoroacetate (41 mg, 0.1 mmol, from Example 14, Step A) according to the method described in Example 14, Step B to give 6.0 mg (15%) of the title compound. ESI-MS: 584.3 (M+H); HPLC A: 2.70 min.

EXAMPLE 16

2-(R)-(3-(S)-(4-(N-(N-(4-Nitrobenzyl)carbamoyl)-N-methylamino)-piperidin-1 yl)methyl-4-(S)-phenyl-pyrrolidin-1-yl)-2-(cyclohexyl)acetic acid Step A: 4-(N-(N-(4-Nitrobenzyl)carbamoyl)-N-methylamino)-piperidine trifluoroacetate The title compound was prepared by the reaction of 4-(N-methylamino)-1-tert-butoxycarbonylpiperidine (prepared by the method described in Example 1, Step A, using methylamine in place of ethylamine) with (4-nitrobenzyl)isocyanate (prepared from phosgene and (4-nitrobenzyl)amine), followed by treatment of the product with 50% TFA in $CH_2Cl_2$ to remove the tert-butoxycarbonyl group, affording the title compound. ESI-MS: 293.1 (M+H).

Step B: 2-(R)-(3-(S)-(4-(N-(N-(4-Nitrobenzyl)carbamoyl)-N-methylamino)piperidin-1-yl)methyl-4-(S)-phenyl-pyrrolidin-1-yl)-2-cyclohexyl)acetic acid The title compound was prepared from 4-(N-(N-(4-nitrobenzyl)carbamoyl)-N-methylamino)-piperidine trifluoroacetate (41 mg, 0.1 mmol, from Step A) and 2-(R)-(3-(R)-formyl-4-(S)-phenyl-pyrrolidin-1-yl)-2(cyclohexyl)acetic acid, 4-(methoxy)benzyl ester (26 mg, 0.05 mmol, Aldehyde 5) according to the method described in Example 1, Step C to give 18 mg (61%) of the title compound. ESI-MS: 592.4 (M+H); BPLC A: 2.12 min.

EXAMPLE 17

2-(R)-(3-(S)-(4-(N-(N-(4-Nitrobenzyl)carbamoyl)-N-(prop-1-yl)amino)-piperidin-1-yl)methyl-4-(S)-phenyl-pyrrolidin-1-yl)-2-(cyclohexyl)acetic acid Step A: 4-(N-(N-(4-Nitrobenzyl)carbamoyl)-N-(prop-1-yl)amino)-piperidinetrifluoroacetate The title compound was prepared by the reaction of 4-(N-(prop-1-yl)amino)-1-tert-butoxycarbonylpiperidine (prepared by the method described in Example 1, Step A, using 1-propylamine in place of methylamine) with (4-nitrobenzyl)isocyanate (prepared from phosgene and (4-nitrobenzyl)amine), followed by treatment of the product with 50% TFA in $CH_2Cl_2$ to remove the tert-butoxycarbonyl group, affording the title compound. ESI-MS: 321.2 (M+H).

Step B: 2-(R)-(3-(S)-(4-(N-(N-(4-Nitrobenzyl)carbamoyl)-N-(prop-1-yl)amino)-piperidin-1-yl)methyl-4-(S)-phenyl-pyrrolidin-1-yl)-2-cyclohexyl)acetic acid The title compound was prepared from 4-(N-(N-(4-nitrobenzyl)carbamoyl)-N-(prop-1-yl)amino)-piperidine trifluoroacetate (21 mg, 0.048 mmol, from Step A) and 2-(R)-(3-(R)-formyl-4-(S)-phenyl-pyrrolidin-1-yl)-2-(cyclohexyl)acetic acid, (4-methoxy)benzyl ester (14 mg, 0.028 mmol, Aldehyde 5) according to the method described in Example 1, Step C to give 11 mg (63%) of the title compound. ESI-MS: 620.4 (M+H); HPLC A: 2.33 min.

EXAMPLE 18

2-(R)-(3-(S)-(4-(N-(N-Benzylcarbamoyl)-N-(prop-1-yl)amino)-piperidin-1-yl)methyl-4-(S)-phenyl-pyrrolidin-1-yl)-2-(cyclohexyl)acetic acid Step A: 4-(N-(N-Benzylcarbamoyl)-N-(prop-1-yl)amino)-piperidine trifluoroacetate The title compound was prepared by the reaction of 4-(N-(prop-1-yl)amino)-1-tert-butoxycarbonylpiperidine (from Example 17, Step A) with benzyl isocyanate, followed by treatment of the product with 50% TFA in $CH_2Cl_2$ to remove the tert-butoxycarbonyl group, affording the title compound. ESI-MS: 276.1 (M+H).

Step B: 2-(R)-(3-(S)-(4-(N-(N-Benzylcarbamoyl)-N-(prop-1-yl)amino)piperidin-1-yl)methyl-4-(S)-phenyl-pyrrolidin-1-yl)-2(cyclohexyl)acetic acid The title compound was prepared from 4-(N-(N-benzylcarbamoyl)-N(prop-1-yl)amino)-piperidine trifluoroacetate (19 mg, 0.048 mmol, from Step A) and 2-(R)-(3-(R)-formyl-4-(S)-phenyl-pyrrolidin-1-yl)-2-(cyclohexyl) acetic acid, 4-(methoxy)benzyl ester (14 mg, 0.028 mmol, Aldehyde 5) according to the method described in Example 1, Step C to give 6.4 mg (40%) of the title compound. ESI-MS: 575.4 (M+H); HPLC A: 2.32 min.

EXAMPLE 19

2-(R)-(3-(S)-(4-(N-((4-Nitrobenzyl)oxycarbonyl)-N-(prop-1-yl)amino)-piperidin-1 yl)methyl-4-(S)-phenyl-pyrrolidin-1-yl)-2-(cyclohexyl)acetic acid Step A: 4-(N-((4-Nitrobenzyl)oxycarbonyl)-N-(prop-1-yl)amino)-piperidine trifluoroacetate The title compound was prepared by the reaction of 4-(N-(prop-1-yl)amino)-1-tert-butoxycarbonylpiperidine (from Example 17, Step A) with (4 -nitrobenzyl) chloroformate, followed by treatment of the product with 50% TFA in $CH_2Cl_2$ to remove the tert-butoxycarbonyl group, affording the title compound. ESI-MS: 322.2 (M+H).

Step B: 2-(R)-(3-(S)-(4-(N-((4-Nitrobenzyl)oxycarbonyl)-N-(prop-1-yl)amino)-piperidin-1-yl)methyl-4-(S)-phenyl-pyrrolidin-1-yl)-2-(cyclohexyl)acetic acid The title compound was prepared from 4-(N-((4-nitrobenzyl)oxycarbonyl)-N-(prop-1-yl)amino)-piperidine trifluoroacetate (21 mg, 0.048 mmol, from Step A) and 2-(R)-(3-(R)-formyl-4-(S)-phenyl-pyrrolidin-1-yl)-2-(cyclohexyl)acetic acid, 4-(methoxy)benzyl ester (14 mg, 0.028 mmol, Aldehyde 5) according to the method described in Example 1, Step C to give 15 mg (89%) of the title compound. ESI-MS: 621.4 (M+H); HPLC A: 2.61 min.

EXAMPLE 20

2-(R)-(3-(S)-(4-((N-(4(Trifluoromethyl)benzyl)carbamoyl) methyl)-piperidin-1-yl)methyl-4-(S)-(3-fluorophenyl)-pyrrolidin-1-yl)-2-(cyclohexyl)acetic acid Step A: 4-((N-(4-(trifluoromethyl)benzyl)carbamoyl) methyl)-piperidine hydrochloride 4-Carboxymethyl-1-tert-butoxycarbonylpiperidine (207 mg, 0.85 mmol, commercially available from Neosystem), 1-(3-(N,N-dimethylamino)-prop-1-yl)-3-ethylcarbodiimide hydrochloride (EDC) (177 mg, 0.92 mmol) and 4-(N,N-dimethylamino)pyridine (2 mg, 0.02 mmol) were dissolved in 4 mL of $CH_2Cl_2$. (4-(Trifluoromethyl)benzyl)amine (0.114 mL, 0.8 mmol) was added and the reaction was stirred at rt for 14 h. The mixture was diluted with $CH_2Cl_2$, washed with 1 N NaOH, 1 N HCl and brine and dried over $MgSO_4$. The solvent was removed, the residue was redissolved in 1% HCl/methanol and the solution was heated to 50° C. for 24 h. The solution was then concentrated to afford 208 mg (77%) of the title compound. ESI-MS: 301.1 (M+H); HPLC A: 1.66 min.

Step B: 2-(R)-(3-(S)-(4-((N-(4-(trifluoromethyl)benzyl) carbamoyl)methyl)piperidin-1-yl)methyl-4-(S)-(3-fluorophenyl)-pyrrolidin-1-yl)-2-(cyclohexyl)acetic acid The title compound was prepared from 4-((N-(4-(trifluoromethyl)benzyl)carbamoyl)methyl)-piperidine hydrochloride (34 mg, 0.1 mmol, from Step A) and 2-(R)-

(3-(R)-formyl-4-(S)-(3-fluorophenyl)-pyrrolidin-1-yl)-2-(cyclohexyl)acetic acid, 4-(methoxy)benzyl ester (25 mg, 0.06 mmol, Aldehyde 6) according to the method described in Example 1, Step C to give 14 mg (38%) of the title compound. ESI-MS: 618.4 (M+H); HPLC A: 2.30 min.

EXAMPLE 21
2-(R)-(3-(S)-(4-((N-(4-Cyanobenzyl)carbamoyl)oxy)-piperidin-1-yl)methyl-4-(S) phenyl-pyrrolidin-1-yl)-2-(cyclohexyl)acetic acid Step A: 4-Cyanobenzylamine hydrochloride 4-Cyanobenzyl bromide (5.0 g, 26 mmol) was dissolved in dimethylformamide. Sodium azide (3.3 g, 50 mmol) was added and the reaction mixture was stirred at 60° C. for 1 h. The mixture was diluted with ether and washed with 1 N sodium bicarbonate, water and brine. The solution was then dried over $MgSO_4$ and concentrated. This azide intermediate was dissolved in methanol and added to a slurry of $SnCl_2$ (7.4 g, 39 mmol) in methanol at 0° C. After warming to rt and stirring for 0.5 h, the reaction mixture was concentrated. Cold 1 N NaOH was added and the mixture was extracted with $CH_2Cl_2$. The combined organic layers were dried over $Na_2SO_4$ and concentrated to afford the title compound. $^1$H-NMR (300 MHz, $CD_3OD$) δ4.11 (s, 2 H), 7.63 (d, J=8, 2 H), 7.82 (d, J=8, 2 H).

Step B: 4-((N-(4-Cyanobenzyl)carbamoyl)oxy)-piperidine trifluoroacetate Carbonyldiimidazole (164 mg, 1.0 mmol) was added to a solution of 4-hydroxy-1-tert-butoxycarbonylpiperidine (271 mg, 0.96 mmol, from Example 13, Step A) in 1 mL of $CH_2Cl_2$. After stirring for 1 h at rt, 4-cyanobenzylamine hydrochloride (162 mg, 0.96 mmol, from Step A) was added and the reaction mixture was stirred at rt overnight. The mixture was diluted with $CH_2Cl_2$, washed twice with 1 N HCl and brine and concentrated. The residue was redissolved in 50% TFA in $CH_2Cl_2$ for 1 h and then concentrated to afford the title compound.

Step C: 2-(R)-(3-(S)-(4-((N-(4-Cyanobenzyl)carbamoyl)oxy)-piperidin-1yl)methyl-4-(S)-phenyl-pyrrolidin-1-yl)-2-(cyclohexyl)acetic acid The title compound was prepared from 4-((N-(4-cyanobenzyl)carbamoyl)oxy)piperidine trifluoroacetate (37 mg, 0.1 mmol, from Step B) and 2-(R)-(3-(R)-formyl-4-(S)-phenyl-pyrrolidin-1-yl)-2-(cyclohexyl)acetic acid, 4-(methoxy)benzyl ester (25 mg, 0.06 mmol, Aldehyde 5) according to the method described in Example 1, Step C to give 13 mg (39%) of the title compound. ESI-MS: 559.5 (M+H); HPLC A: 2.12 min.

EXAMPLE 22
2-(R)-(3-(S)-(4-(N-((3,4-Difluorobenzyl)carbonyl)-N-ethylamino)-piperidin-1-yl)methyl-4-(S)-phenyl-pyrrolidin-1-yl)-2-(cyclohexyl)acetic acid Step A: 4-(N-((3,4-Difluorobenzyl)carbonyl)-N-ethylamino)piperidine trifluoroacetate 3,4-difluorophenylacetic acid (158 mg, 0.92 mmol), 4-(N-ethylamino)-1-tert-butoxycarbonylpiperidine (231 mg, 0.10 mmol, from Example 1, Step A), benzotriazole-1-yl-oxy-tris-pyrrolidino-phosphonium hexafluorophosphate (PyBOP®) (718 mg, 1.4 mmol) and 1-hydroxybenzotriazole (124 mg, 0.92 mmol) were combined in DMF. DIEA (0.320 mL, 1.8 mmol) was added and the reaction mixture was stirred at rt for 15 h. The mixture was diluted with $CH_2Cl_2$ and washed with cold 1 N HCl, 1 N NaOH, water and brine. The organic layer was dried over $Na_2SO_4$ and concentrated. ESI-MS: 383.2 (M+H); HPLC A: 3.41 min. The residue was dissolved in 50% TFA in $CH_2Cl_2$ for 3 h, then concentrated to provide the title compound.

Step B: 2-(R)-(3-(S)-(4-(N-((3,4-Difluorobenzyl)carbonyl)-N-ethylamino)-piperidin-1-yl)methyl-4-(S)-phenyl-pyrrolidin-1-yl)-2-(cyclohexyl)acetic acid The title compound was prepared from 4-(N-((3,4-difluorobenzyl)carbonyl)-N-ethylamino)piperidine trifluoroacetate (40 mg, 0.1 mmol, from Step A) and 2-(R)-(3-(R)-formyl-4-(S)-phenyl-pyrrolidin-1-yl)-2-(cyclohexyl)acetic acid, 4-(methoxy)benzyl ester (25 mg, 0.06 mmol, Aldehyde 5) according to the method described in Example 1, Step C to give 19 mg (54%) of the title compound. ESI-MS: 582.5 (M+H); HPLC A: 2.35 min.

EXAMPLE 23
2-(R)-(3-(S)-(4-((2-Methylphenyl)oxycarbonylamino)-piperidin-1-yl)methyl-4-(S) phenylpyrrolidin-1-yl)-2-(cyclohexyl)acetic acid The title compound was prepared from 4-((2-methylphenyl)oxycarbonylamino)-piperidine and 2-(R)-(3-(R)-formyl-4-(S)phenylpyrrolidin-1-yl)-2-(cyclohexyl) acetic acid, 4-methoxybenzyl ester (Aldehyde 5) according to the method described in Example 1, Step C. ESI-MS: 534 (M+H); HPLC A: 2.29 min.

EXAMPLE 24
2-(R)-(3-(S)-(4-(3-Oxo-3-phenylpropyl)piperidin-1-yl) methyl-4-(S)-phenylpyrrolidin-1-yl)-2-(cyclohexyl)acetic acid Step A: 1-(tert-Butoxycarbonyl)-4-(hydroxymethyl) piperidine Di-tert-butyl dicarbonate (4.69 g, 21.5 mmol) in $CH_2Cl_2$ (5 mL) was added over 10 min. to a solution of 4-(hydroxymethyl)piperidine (2.47 g, 21.4 mmol) in $CH_2Cl_2$ (16 mL). After stirring at rt for 1 h, the solution was diluted with ether (50 mL) and washed with 2 N aq. HCl, sat'd $NaHCO_3$, and sat'd NaCl (25 mL of each). The organic layer was dried ($Na_2SO_4$), decanted, and evaporated to give 4.57 g of the title compound as a crystalline solid.

Step B: 1-(tert-Butoxycarbonyl)-4-piperidinecarboxaldehyde 1,1,1-Triacetoxy-1,1-dihydro-1,2-benzoiodoxol-3(1H)-one (3.34 g, 7.87 mmol) was added to a solution of 1-(tert-butoxycarbonyl)-4-(hydroxymethyl)piperidine (1.50 g, 6.97 mmol, from Step A) in $CH_2Cl_2$ (45 mL) and the mixture was stirred at rt for 40 min. Ether (100 mL) and 1.3 N aq. NaOH (45 mL) were added and stirring was continued for 15 min. After transfer of the mixture to a separatory funnel, the aqueous layer was extracted with ether (50 mL). The organic layers were washed in succession with 1.3 N aq. NaOH (45 mL) and water (50 mL), dried ($Mg_2SO_4$), filtered, and evaporated to give 1.21 g of the title compound as a colorless oil.

Step C: 1-(tert-Butoxycarbonyl)-4-(3-oxo-3-phenylproyl) piperidine

Diethyl (2-oxo-2-phenylethyl)phosphonate (0.255 mL, 301 mg, 1.17 mmol) was added in one portion to a stirred suspension of sodium hydride (60% oil dispersion, 45 mg, 1.13 mmol) in THF (7 mL) at rt. After 15 min, a portion (1.8 mL) of the clear solution was removed and discarded, and the remainder cooled in an ice bath. 1-(tert-Butoxycarbonyl)-4-piperidinecarboxaldehyde (177 mg, 0.830 mmol, from Step B) was added in THF (1.0 mL) with additional THF (2×1.0 mL) for rinsing. After 16 h at rt, the mixture was then partitioned between ether (40 mL) and 2.5 N aq. NaOH (20 mL). The organic layer was washed with sat'd NaCl (20 mL), dried ($Na_2SO_4$), decanted, and evaporated. The crude product was purified by flash column chromatography on silica gel, eluting with 10% EtOAc in hexane, to give 201 mg of 1-(tert-butoxycarbonyl)-4-(3-oxo- 3-phenylprop-1-enyl)piperidine as a colorless oil. Hydrogenation of this material using 5% Pd/C in 95% ethanol at atmospheric pressure yielded the title compound as a white crystalline solid.

Step D: 4-(3-Oxo-3-phenylpropyl)piperidine trifluoroacetate

TFA (1.0 mL) was added to a solution of 1-(tert-butoxycarbonyl)-4-(3-oxo-3-phenylpropyl)piperidine (50 mg, 0.16 mmol, from Step C) in $CH_2Cl_2$ (1.0 mL) at rt. After stirring for 3 h, the solution was concentrated at reduced pressure. Toluene was added and evaporated at reduced pressure, and this was repeated with two additional portions of toluene. Drying under vacuum yielded the title compound as colorless crystals.

Step E: 2-(R)-(3-(S)-(4-(3-Oxo-3-phenylpropyl)piperidin-1-yl)methyl-4-(S)-phenylpyrrolidin-1-yl)-2-(cyclohexyl) acetic acid, 4-(methoxy)benzyl ester Molecular sieve pellets (3 Å) were added to a solution of 2-(R)-(3-(R)-formyl-4-(S)-phenylpyrrolidin-1-yl)-2-(cyclohexyl)acetic acid, 4-(methoxy)benzyl ester (30 mg, 0.069 mmol, Aldehyde 5), 4-(3-oxo-3-phenylpropyl) piperidine trifluoroacetate (25 mg. 0.075 mmol, from Step D), and DIEA (0.013 mL, 10 mg, 0.075 mmol) in 1,2-dichloroethane (0.70 mL). The mixture was stirred for 15 min at rt before the addition of sodium triacetoxyborohydride (17 mg, 0.080 mmol). After 2.5 h, the mixture was diluted with EtOAc (20 mL) and washed with sat'd $NaHCO_3$ (10 mL) followed by sat'd NaCl (10 mL). The organic layer was dried ($Na_2SO_4$), decanted, and evaporated. Purification by flash column chromatography on silica gel, eluting with 15–20% EtOAc/0.5% $CH_3OH/CH_2Cl_2$ gave 30 mg of the title compound as a colorless viscous oil. ESI-MS: 637 (M+H).

Step F: 2-(R)-(3-(S)-(4-(3-Oxo-3-phenylpropyl)piperidin-1-yl)methyl-4-(S)phenylpyrrolidin-1-yl)-2-(cyclohexyl) acetic acid A solution of 2-(R)-(3-(S)-(4-(3-oxo-3-phenylpropyl) piperidin-1-yl)methyl-4-(S)-phenylpyrrolidin-1-yl)-2-(cyclohexyl)acetic acid 4-(methoxy)benzyl ester (29 mg, 0.046 mmol, from Step E) in 96% formic acid (2.0 mL) was stirred at rt. After 2 h, the formic acid was evaporated at reduced pressure. Toluene was added and evaporated, and this was repeated with two additional portions of toluene. The crude product was purified by flash column chromatography on silica gel packed in $CH_2Cl_2$. Elution with 5% $CH_3OH$/1% conc. aq. $NH_4OH/CH_2Cl_2$ followed by 10% $CH_3OH$/2% conc. aq. $NH_4OH/CH_2Cl_2$ gave 17 mg of the title compound as a colorless glass. ESI-MS: 517 (M+H).

EXAMPLE 25

2-(R)-(3-(S)-(4-(3-(4-Fluorophenyl)-3-oxopropyl)piperidin-1-yl)methyl-4-(S) phenylpyrrolidin-1-yl)-2-( cyclohexyl) acetic acid Step A: 3-(1-(tert-Butoxycarbonyl)piperidin-4-yl)propionic acid Triethyl phosphonoacetate (1.40 g, 6.24 mmol) was added in one portion to a stirred suspension of sodium hydride (60% oil dispersion, 245 mg, 6.13 mmol) in THF (20 mL) cooled in an ice bath. After 15 min, the cooling bath was removed. After an additional 20 min, the clear solution was cooled in an ice bath, and 1-(tert-butoxycarbonyl)-4-piperidinecarboxaldehyde (1.19 g, 5.58 mmol, from Example 24, Step B) was added in THF (1.0 mL) with additional THF (2×1.0 mL) for rinsing. After 5 min, the cooling bath was removed and the reaction was stirred for 2.5 h at rt. The mixture was partitioned between ether (100 mL) and 2.5 N aq. NaOH (50 mL). The organic layer was washed with sat'd NaCl (50 mL), dried ($Na_2SO_4$), decanted, and evaporated. The crude product was purified by flash column chromatography on silica gel, eluting with 8–10% EtOAc in hexane, to give 1.18 g of 3-(1-(tert-butoxycarbonyl)piperidin-4-yl)prop-2-enoic acid ethyl ester as a colorless oil. This material was hydrogenated using 10% Pd/C (20 mg) in 95% ethanol (15 mL) at atmospheric pressure for 2.5 h to give 1.18 g of 3-(1-(tert-butoxycarbonyl)piperidin-4-yl)propionic acid ethyl ester as a colorless oil.

A solution of KOH (86%, 0.42 g, 6.4 mmol) in water (1.5 mL) was added to a solution of 3-(1-(tert-butoxycarbonyl) piperidin-4-yl)propionic acid ethyl ester in 95% EtOH (15 mL) at rt. After 2.5 h, the mixture was partitioned between EtOAc (50 mL) and 2 N aq. HCl (50 mL). After extraction of the aqueous layer with EtOAc (50 mL), the organic layers were washed with sat'd NaCl (25 mL), dried ($Na_2SO_4$), decanted, and evaporated to give 1.06 g of the title compound as a crystalline solid.

Step B: 1-(tert-Butoxycarbonyl)-4-(3-(4-fluorophenyl)-3-oxopropyl)piperidine

Molecular sieve pellets (4 Å), N,O-dimethylhydroxylamine hydrochloride (227 mg, 3.32 mmol), and DIEA (0.41 mL, 0.30 g, 2.4 mmol) were added to a solution of 3-(1-(tert-butoxycarbonyl)piperidin-4-yl) propionic acid (500 mg, 1.94 mmol, from Step A) in 1,4-dioxane (10 mL). 4-(Dimethylamino)pyridine (57 mg, 0.47 mmol) and EDC (483 mg, 2.52 mmol) were added and the mixture was stirred for 16 h at rt. The mixture was partitioned between EtOAc (50 mL) and 1 N aq. HCl (50 mL). The aqueous layer was extracted with EtOAc (50 mL). The organic layers were washed with sat'd NaCl (30 mL), dried ($Na_2SO_4$), decanted, and evaporated to give 583 mg of N-methoxy-N-methyl-3-(1-(tert-butoxycarbonyl)piperidin-4-yl)propionamide.

N-Methoxy-N-methyl-3-(1-(tert-butoxycarbonyl) piperidin-4-yl)propionamide (345 mg, 1.15 mmol), dried by evaporation of a toluene solution at reduced pressure, was dissolved in TBF (5.0 mL) and the solution was cooled in a dry ice/2-PrOH bath. A THF solution of 4-fluorophenylmagnesium bromide (1.0 M, 1.4 miL, 1.4 mmol) was added dropwise over 5 min, and the stirred reaction mixture was allowed to warm to 10° C. over 3 h. The mixture was partitioned between ethyl ether (30 mL) and 1 N aq. HCl (30 mL). The aqueous layer was extracted with ether (30 mL). The organic layers were washed with sat'd NaCl (15 mL), dried ($Na_2SO_4$), and evaporated. The crude product was combined with material similarly obtained from 228 mg of N-methoxy-N-methyl-3-(1-(tert-butoxycarbonyl)piperidin-4-yl)propionamide and purified by flash column chromatography on silica gel, eluting with 10–40% EtOAc in hexane to give 461 mg of the title compound as a white crystalline solid. $R_F$: 0.6 (20% EtOAc in hexane).

Step C: 4-(3-(4-Fluorophenyl)-3-oxopropyl)piperidine trifluoroacetate

The title compound was prepared by a reaction analogous to Example 24, Step D, utilizing 1-(tert-butoxycarbonyl)-4-(3-(4-fluorophenyl)-3-oxopropyl)piperidine (from Step B) in place of 1-(tert-butoxycarbonyl)-4-(3-oxo-3phenylpropyl)piperidine.

Step D: 2-(R)-(3-(S)-(4-(3-(4-Fluorophenyl)-3-oxopropyl) piperidin-1-yl)methyl-4-(S)-phenylpyrrolidin-1-yl)-2-(cyclohexyl)acetic acid, 4-(methoxy)benzyl ester The title compound was prepared by a reaction analogous to Example 24, Step E, utilizing 4-(3-(4-fluorophenyl)-3-oxopropyl)piperidine trifluoroacetate (from Step C) in place of 4-(3-oxo-3-phenylpropyl)piperidine trifluoroacetate. ESI-MS: 655 (M+H).

Step E: 2-(R)-(3-(S)-(4-(3-(4-Fluorophenyl)-3-oxopropyl) piperidin-1-yl)methyl-4-(S)-phenylpyrrolidin-1-yl)-2-(cyclohexyl)acetic acid The title compound was prepared by a reaction analogous to Example 24, Step F, utilizing 2-(R)-(3-(S)-(4-(3-(4-fluorophenyl)-3-oxopropyl)piperidin-1-yl)methyl-4-(S)-phenylpyrrolidin-1-yl)-2-(cyclohexyl)acetic acid, 4-(methoxy)benzyl ester (from Step D) in place of 2-(R)-(3-(S)-(4-(3-oxo-3-phenylpropyl)piperidin-1-yl)methyl-4-(S)-phenylpyrrolidin-1-yl)-2-(cyclohexyl)acetic acid, 4-(methoxy)benzyl ester. ESI-MS: 535 (M+H).

EXAMPLE 26

2-(R)-(3-(S)-(4-(3-(4-Cyanophenyl)-3-oxo-propyl)-piperidin-1-yl)methyl-4-(S) phenylpyrrolidin-1-yl)-2-(cyclohexyl)acetic acid Step A: 3-(1-(tert-Butoxycarbonyl)piperidin-4-yl)propionic acid A mixture of trans-3-(4-pyridyl)acrylic acid (7.4 grams, 50 mmol) and 10% palladium on carbon (3.7 grams, 3.45 mmol) in 50 mL MeOH was placed in a Parr bottle and hydrogenated at 50 psi for 20 hours. The catalyst was filtered off and the solvent was removed. The resulting solid was dissolved in 150 mL 1/1 THF/water and sodium bicarbonate (11.2 grams, 134 mmol) was added. Di-tert-butyl dicarbonate (11.7 grams, 53 mmol) was added and the mixture was stirred for 16 h. The solution was poured into 300 mL EtOAc and 1 M HCl was added until the pH was about 2. The aqueous layer was drawn off and the organic phase was washed with sat'd NaCl, then dried over $Na_2SO_4$ and concentrated. The product (9.5 grams, 74%) was used without further purification.

Step B: N-Methyl-N-methoxy-3-(1-(tert-butoxycarbonyl)piperidin-4-yl)propionamide A solution of 3-(1-(tert-butoxycarbonyl)piperidin-4-yl)propionic acid (2.6 grams, 10 mmol, from Step A) and DIEA (4.4 mL, 25 mmol) in 50 mL $CH_2Cl_2$ was cooled to 0° C. Trimethylacetyl chloride (1.4 mL, 11 mmol) was added and the mixture was stirred for 1 h. Solid N,O-dimethylhydroxylamine hydrochloride (1.4 grams, 15 mmol) was added and the mixture was warmed to rt and stirred for 16 h. The solvent was removed and the product was purified by flash chromatography (125 grams silica, 2/1 hexane/EtOAc eluant) to give 1.5 grams (50%) of the title compound. $^1$H NMR (300 MHz, $CDCl_3$). δ1.05–1.18 (m, 2H), 1.45 (s, 9H), 1.53–1.75 (m, 4H), 2.4–2.5 (t, 2H), 2.6–2.77 (m, 2H), 3.18 (s, 3H), 3.63 (s, 3H), 4.0–4.15 (m, 2H).

Step C: 4-(3-(4-Fluorophenyl)-3-oxo-propyl)-1-tert-butoxycarbonyl-piperidine

N-Methyl-N-methoxy-3-(1-(tert-butoxycarbonyl)piperidin-4-yl)propionamide (550 mg, 1.83 mmol, from Step B) was dissolved in 10 mL dry ether and the solution was cooled to 0° C. A solution of 4-fluorophenyl magnesium bromide (2 mL, 1.0 M in THF, 2.01 mmol) was added dropwise. A solid mass formed upon addition and 1 mL 1,2-dimethoxyethane was added. The mixture was warmed to room temperature and stirred for 45 min then poured into 100 mL EtOAc/10 mL 1 M aqueous HCl. The layers were separated and the organic phase was washed with water, then sat'd NaCl, then dried over $Na_2SO_4$ and concentrated. Flash chromatography (25 grams silica, 5/1 hexane/EtOAc eluant) afforded 423 mg (69%) of the title compound. $^1$H NMR (300 MHz, $CDCl_3$) δ1.0–1.20 (m, 2H), 1.45 (s, 9H), 1.65–1.75 (m 4H), 2.6–2.75 (m 2H), 2.9–3.0 (t, 2H), 4.03–4.08 (m, 2H), 7.1–7.19 (m, 2H), 7.95–8.04 (m, 2H).

Step D: 4-(3-(4-Cyanophenyl)-3-oxo-propyl)-1-tert-butoxycarbonyl-piperidine

A round bottom flask was charged with 4-(3-(4-fluorophenyl)-3-oxopropyl)-1-tert-butoxycarbonyl-piperidine (614 mg, 1.83 mmol, from Step C), LiI, (294 mg, 2.2 mmol), KCN (358 mg, 5.5 mmol), and $K_2CO_3$ (3 grams, 22 mmol) in 30 mL DMSO. The mixture was heated to 135° C. for 72 h. The solution was cooled to room temperature and di-tert-butyl dicarbonate (500 mg, 2.3 mmol) was added. After 1 h the mixture was diluted with 100 mL EtOAc and the organic phase washed with water (50 mL) and sat'd NaCl (2×50 mL), then dried over $Na_2SO_4$ and concentrated. Flash chromatography (3/1 hexane/EtOAc eluant) afforded 75 mg (12%) of the title compound.

Step E: 4-(3-(4-Cyanophenyl)-3-oxo-propyl)piperidine trifluoroacetate

A solution of 4-(3-(4-cyanophenyl)-3-oxo-propyl)-1-tert-butoxycarbonyl-piperidine (75 mg) in 30% $TFA/CH_2Cl_2$ was stirred for 30 min then concentrated and dried under vacuum to provide the title compound.

Step F: 2-(R)-(3-(S)-(4-(3-(4-Cyanophenyl)-3-oxo-propyl)-piperidin-1-yl)methyl-4-(S)-phenylpyrrolidin-1-yl)-2-(cyclohexyl)acetic acid A solution of 2-(R)-(3-(R)-Formyl-4-(S)-phenylpyrrolidin-1-yl)-2-(cyclohexyl)acetic acid, 4-(methoxy)benzyl ester (35 mg, 0.08 mmol, Aldehyde 5), 4-(3-(4-cyanophenyl)-3-oxo-propyl)piperidine trifluoroacetate (37 mg, 0.104 mmol from Step E), triethylamine (0.015 mL, 0.104 mmol) and sodium triacetoxyborohydride, (34 mg 0.16 mmol) in 1 mL of 1,2-dichloroethane was stirred for 4 h. The solvent was removed and the product was passed through a pad of silica eluting with 19/1 $CH_2Cl_2$ /MeOH. The recovered material was stirred in 2 mL of formic acid overnight. After removal of solvent, flash chromatography (3 grams silica, eluting with 19/1 $CH_2Cl_2$/MeOH, then with 19/1/0.2 $CH_2Cl_2$/MeOH/$NH_4OH$) afforded 22 mg (50%) of the title compound. $^1$H NMR (500 MHz, $CD_3OD$) δ1.15–1.5 (m, 9H), 1.58–2.05 (m, 10H), 2.33–2.35 (m, 1H), 2.49–2.52 (m, 1H), 2.7–2.8 (m, 2H), 2.92–2.94 (m, 1H), 3.02–3.05 (t, 2H, J=7), 3.1–3.13 (m, 1H), 3.3–4.8 (m, 6H) 7.26–7.29 (m, 1H), 7.31–7.34 (m, 4H), 7.83–7.85 (d, 2H, J=8.5), 8.08–8.10 (d, 2H, J=8.5). ESI-MS: 542.5 (M+H).

EXAMPLE 27

2-(R)-(3-(S)-(4-(4-(4-Fluorophenyl)-4-oxo-butyl)-piperidin-1-yl)methyl-4-(S)-phenylpyrrolidin-1-yl)-2-(cyclohexyl)acetic acid Step A: 4-(1-(tert-Butoxycarbonyl)piperidin-4-yl)butanoic acid A solution of triethyl-4-phosphonocrotonate (7.2 grams, 28.8 mmol) in 50 mL dry toluene was cooled to 0° C. under nitrogen. A solution of potassium hexamethyldisilazide (48 mL, 28.8 mmol, 0.5 M in toluene) was added via syringe. After stirring for 30 min, solid 1-tert-butoxycarbonyl-4-piperidone was added and the mixture was warmed to rt. After 16 h, the mixture was diluted with 300 mL EtOAc, washed with sat'd NaCl and dried over $Na_2SO_4$. Removal of the solvent and flash chromatography (150 grams silica, 4/1 hexane/EtOAc) afforded 327 mg (5%) of product as a mixture of isomers. The material (327 mg, 1.1 mmol) was dissolved in 10 nmL MeOH along with 200 mg (0.22 mmol) 10% palladium on carbon. The solution was stirred under 1 atm of hydrogen using a balloon for 2 h. The mixture was filtered through celite, concentrated and the residue was dissolved in 8 mL 1/1 THF/water. Lithium hydroxide (96 mg, 4.4 mmol) was added and the mixture was stirred overnight. EtOAc and 1 M HCl were added (50 mL each) and the layers were separated. The organic layer was dried over $MgSO_4$ and concentrated to provide 291 mg (98%) of the title compound.

Step B: N-Methyl-N-methoxy-4-(1-(tert-butoxycarbonyl) piperidin-4-yl)-butanamide A solution of 4-(1-(tert-butoxycarbonyl)piperidin-4-yl)-butanoic acid (291 mg, 1.07 mmol, from Step A), N,O-dimethylhydroxylamine hydrochloride (177 mg, 1.82 mmol), EDC (350 mg, 1.82 mmol), and triethylamine, 0.25 mL, 1.82 mmol) were stirred together in 5 mL $CH_2Cl_2$ for 16 h. The mixture was diluted with 100 mL $CH_2Cl_2$ and washed with 1M HCl. The organic layer was dried over $MgSO_4$ and concentrated. Flash chromatography (1/1 hexane/EtOAc) afforded 237 mg (71%) of the title compound.

Step C: 4-(4-(4-Fluorophenyl)-4-oxo-butyl)-1-tert-butoxycarbonyl-piperidine

The title compound was prepared from N-methyl-N-methoxy-4-(1-(tert-butoxycarbonyl)piperidin-4-yl)-butanamide (237 mg, 0.75 mmol, from Step B) using the procedure described in Example 26, Step C to afford 184 mg (70%) of the title compound. $^1$H NMR (300 MHz, $CDCl_3$) δ1.0–1.20 (m, 2H), 1.25–1.4 (m, 2H), 1.45 (s, 9H), 1.63–1.8 (m 4H), 2.6–2.75 (m 2H), 2.9–3.0 (t, 2H), 4.03–4.08 (m, 2H), 7.1–7.18 (m, 2H), 7.95–8.04 (m, 2H).

Step D: 4-(4-(4-Fluorophenyl)-4-oxo-butyl)piperidine trifluoroacetate

A solution of 4-(4-(4-fluorophenyl)-4-oxo-butyl)-1-tert-butoxycarbonyl-piperidine (184 mg, 0.52 mmol, from Step C) in 30% TFA/$CH_2Cl_2$ was stirred for 30 min, then concentrated and dried under vacuum to provide the title compound.

Step E: 2-(R)-(3-(S)-(4-(4-(4-Fluorophenyl)-4-oxo-butyl)-piperidin-1-yl)methyl-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, 4-(methoxy)benzyl ester (40 mg, 0.092 mmol, Aldehyde 5) and 4-(4-(4-fluorophenyl)-4-oxo-butyl)piperidine trifluoroacetate (43 mg, 0.119 mmol from Step D) using the procedure described in Example 26, Step F to provide 28 mg (56%) of the title compound. $^1$H NMR (500 MHz, $CD_3OD$) δ1.15–1.5 (m, 9H), 1.58–2.05 (m, 10H), 2.33–2.35 (m, 1H), 2.49–2.52 (m, 1H), 2.7–2.8 (m, 2H), 2.92–2.94 (m, 1H), 2.95–2.98 (t, 2H, J=7), 3.1–3.13 (m, 1H), 3.3–4.8 (m, 6H), 7.18–7.21 (m, 2H) 7.26–7.29 (m, 1H), 7.31–7.34 (m, 4H), 8.01–8.5 (m, 2H). ESI-MS: 549 (M+H).

EXAMPLE 28

2-(R)-(3-(S)-((4-(N-(4-Nitro)benzyloxycarbonyl-N-prop-2-enyl)aminopiperidin-1yl)methyl)-4-(S)-phenylpyrrolidin-1-yl)-2-(cyclohexyl)acetic acid Step A: 1-(t-Butoxycarbonyl)-4-(N-(4-nitro)benzyloxycarbonyl-N-prop-2enyl)aminopiperidine Allylamine (0.45 mL, 0.34 g, 6.0 mmol), acetic acid (0.300 mL, 315 mg, 5.24 mmol), and 3 Å molecular sieves (2.00 g) were added to a solution of 1-(t-butyoxycarbonyl)-4-piperidone (1.00 g, 5.01 mmol) in 1,2-dichloroethane (14 mL). The resulting mixture was stirred for 30 min at rt, then treated with sodium triacetoxyborohydride (1.62 g, 7.6 mmol). The reaction was stirred at rt for 3 h, then partitioned between EtOAc (30 mL) and sat'd $NaHCO_3$ (20 mL). The aqueous layer was extracted with EtOAc (30 mL) and the organic layers were washed with 20 mL of sat'd NaCl, combined, dried over $Na_2SO_4$, and evaporated to give 1.20 g of crude 1-(t-butoxycarbonyl)-4-(N-prop-2-enyl) aminopiperidine.

A portion of the crude 1-(t-butoxycarbonyl)-4-(N-prop-2-enyl)aminopiperidine (400 mg, 1.66 mmol) was dissolved in $CH_2Cl_2$ (10 mL) and treated with DIEA (0.70 mL, 4.0 mmol) and 4-nitrobenzyl chloroformate (392 mg, 1.82 mmol). After stirring for 3 h at rt, the mixture was diluted with EtOAc (30 mL) and washed with 15 mL each of 2.0 N HCl, sat'd NaHCO3, and sat'd NaCl. The organic layer was dried over $Na_2SO_4$ and concentrated. Flash chromatography on silica gel using 7:3 v/v hexanes/EtOAc afforded 572 mg (82%) of the title compound: $^1$H NMR (400 MHz) δ8.22 (d, J=8, 2H), 7.50 (d, J=8, 2H), 5.80 (ddt, J=17, 10, 5, 1H), 5.23 (s, 2H), 5.18–5.09 (m, 2H), 4.27–4.08 (m, 3H), 3.89–3.79 (m, 2H), 2.79–2.66 (m, 2H), 1.74–1.52 (m, 4H), 1.46 (s, 9H); ESI-MS: 420 (M+H, 27%), 437 (M+H+NH3, 100%).

Step B: 4-(N-(4-Nitro)benzyloxycarbonyl-N-prop-2-enyl) amino piperidine hydrochloride A solution of 400 mg (0.95 mmol) of 1-(t-butoxycarbonyl)-4-(N-(4-nitro)benzyloxycarbonyl-N-prop-2-enyl)aminopiperidine (from Step A) in 3.5 mL of 1.0 N HCl in MeOH was stirred at rt for 4 h. The mixture was concentrated. The residue was triturated with ether and the resulting solid was filtered and dried to afford 338 mg (100%) of the title compound: $^1$H NMR (400 MHz, $CD_3OD$) δ8.24 (d, J=8, 2H), 7.60 (d, J=8, 2H), 5.87 (ddt, J=17, 10, 5, 1H), 5.27 (s, 2H), 5.23–5.13 (m, 2H), 4.14–3.94 (m, 1H), 3.94 (d, J=5, 2H), 3.45 (d, J=13, 2H), 3.06 (t, J=13, 2H), 2.20–2.03 (m, 2H), 2.02–1.90 (m, 2H); ESI-MS: 320 (M+H).

Step C: 2-(R)-(3-(S)-((4-(N-(4-Nitro)benzyloxycarbonyl-N-prop-2-enyl)aminopiperidin-1-yl)methyl)-4-(S)-phenylpyrrolidin-1-yl)-2-(cyclohexyl)acetic acid, (4-methoxy)benzyl ester A solution of 44 mg (0.10 mmol) of 2-(R)-(3-(R)-formyl-4-(S)-phenylpyrrolidin-1-yl)-2-(cyclohexyl)acetic acid, (4-methoxy)benzyl ester (Aldehyde 5) and 38 mg (0.11 mmol) of 4-(N-(4-nitro)benzyloxycarbonyl-N-prop-2-enyl) amino piperidine hydrochloride (from Step B) in 2 mL of $CH_2Cl_2$ at rt was treated with 0.019 mL (0.011 mmol) of DIEA and 32 mg (0.15 mmol) of sodium triacetoxyborohydride. The resulting mixture was stirred at rt for 1 h. The reaction mixture was partitioned between 25 mL of $CH_2Cl_2$ and 25 mL of sat'd $NaHCO_3$ and the layers were separated. The aqueous layer was extracted with 25 mL of $CH_2Cl_2$. The combined organic extracts were washed with 50 mL of sat'd NaCl, dried over $MgSO_4$ and concentrated. Flash chromatography using 50:1 v/v $CH_2Cl_2$/MeOH as the eluant afforded 71 mg (96%) of the title compound: $^1$H NMR (500 MHz) δ0.89–3.25 (34H), 3.82 (s, 3H), 3.72–3.96 (5H), 5.09–5.22 (6H), 5.77–5.84 (m, 1H), 6.89 (d, J=8.7, 2H), 7.16–7.22 (3H), 7.25–7.28 (2H), 7.34 (d, J=8.5, 2H), 7.49 (d, J=8.5, 2H), 8.21 (d, J=8.7, 2H); CI-MS: 739 (M+H).

Step D: 2-(R)-(3-(S)-((4-(N-(4-Nitro)benzyloxycarbonyl-N-prop-2-enyl)aminopiperidin-1-yl)methyl)-4-(S)-phenylpyrrolidin-1-yl)-2-(cyclohexyl)acetic acid A solution of 71 mg (0.096 mmol) of 2-(R)-(3-(S)-((4-(N-(4-nitro)benzyloxy-carbonyl-N-prop-2-enyl) aminopiperidin-1-yl)methyl)4-(S)-phenylpyrrolidin-1-yl)-2-(cyclohexyl)acetic acid, (4-methoxy)benzyl ester (from Step C) in 4 mL of 96% formic acid was stirred at rt for 2 h. The solution was concentrated. Flash chromatography using 90:10:1 v/v/v $CH_2Cl_2$/MeOH/$NH_4OH$ as the eluant afforded 47 mg (79%) of the title compound: $^1$H NMR (500 MHz) δ1.00–3.95 (31H), 5.09–5.20 (4H), 5.73–5.79 (m, 1H), 7.22–7.31 (5H), 7.47 (d, J=8.6, 2H), 8.20 (d, J=8.6, 2H); ESI-MS: 619 (M+H).

The following compounds were prepared from the appropriate aldehyde and piperidine hydrochloride using procedures analogous to those described in Example 28. Catalytic hydrogenation (40 psi $H_2$, 10% Pd/C, MeOH, 1 h) was used in place of Step D in cases where an intermediate benzyl ester was obtained.

EXAMPLE 29

2-(R)-(3-(S)-((4-(N-(3-Phenyl)propionyl-N-ethyl) aminopiperidin-1-yl)methyl)-4-(S) phenylpyrrolidin-1-yl)-2-(cyclohexyl)acetic acid $^1$H NMR (500 MHz) ε0.91–4.56 (38H), 7.16–7.56 (10H); ESI-MS 560 (M+H).

EXAMPLE 30

2-(R)-(3-(S)-((4-(N-(4-Nitro)benzyloxycarbonyl-N-ethyl) aminopiperidin-1-yl)methyl)-4-(S)-phenylpyrrolidin-1-yl)-3-methylbutanoic acid $^1$H NMR (500 MHz) δ1.03–4.00 (30H), 5.16 (s, 2H), 7.22–7.29 (5H), 7.44 (d, J=7.5, 2H), 8.16 (d, J=8.4, 2H); ESI-MS 567 (M+H).

EXAMPLE 31

2-(R)-(3-(S)-((4-(N-(4-Nitro)benzyloxycarbonyl-N-propyl) aminopiperidin-1-yl)methyl)-4-(S)-phenylpyrrolidin-1-yl)-3-methylbutanoic acid $^1$H NMR (500 MHz, $CD_3OD$) δ0.73–3.63 (32H), 5.09 (s, 2H), 7.16–7.24 (5H), 7.43 (s, 2H), 8.08 (s, 2H), 8.41 (br s, 1H); ESI-MS 581 (M+H).

EXAMPLE 32

2-(R)-(3-(S)-((4-(N-(4-Nitro)benzyloxycarbonyl-N-prop-2-enyl)aminopiperidin-yl)methyl)-4-(S)-(3-fluorophenyl) pyrrolidin-1-yl)-3-methylbutanoic acid $^1$H NMR (500 MHz) δ1.04 (d, J=6.7, 3H), 1.14 (d, J=6.7, 3H), 1.26–4.10 (21H), 5.06–5.10 (2H), 5.20 (s, 2H), 5.71–5.77 (m, 1H), 6.94 (t, J=7.4, 1H), 7.04 (d, J=9.8, 1H), 7.08 (d, J=7.6, 1H), 7.25–7.31 (m, 1H), 7.46 (d, J=8.5, 2H), 8.20 (d, J=8.5, 2H); ESI-MS: 597 (M+H); HPLC A: 2.48 min.

EXAMPLE 33

2-(R)-(3-(S)-((4-((3-Phenyl)propionyl)piperidin-1-yl) methyl)-4-(S)-phenylpyrrolidin-1-yl)-2-(cyclohexyl)acetic acid $^1$H NMR (500 MHz) δ0.77–3.58 (33H), 7.07–7.28 (10H), 8.44 (br s, 1H). ESI-MS: 515 (M+H).

EXAMPLE 34

2-(R)-(3-(S)-((4-(N-(4-Nitro)benzyloxycarbonyl-N-prop-2-enyl)aminopiperidin-1 yl)methyl)-4-(S)-(3-fluorophenyl) pyrrolidin-1-yl)-2-(cyclohexyl)acetic acid ESI-MS: 637 (M+H); HPLC B: 7.34 min.

EXAMPLE 35

2-(R)-(3-(S)-((4-(N-(4-Nitro)benzyloxycarbonyl-N-prop-2-enyl)aminopiperidin-1 yl)methyl)-4-(S)-phenylpyrrolidin-1-yl)-3-methylbutanoic acid ESI-MS: 579 (M+H); HPLC B: 6.83 min.

EXAMPLE 36

2-(R)-(3-(S)-((4-(N-(3,4-Difluoro)benzylcarbamoyl-N-ethyl)aminopiperidin-1 yl)methyl)-4-(S)-phenylpyrrolidin-1-yl)-2-(cyclopentyl)acetic acid ESI-MS: 583 (M+H); HPLC B: 6.56 min.

EXAMPLE 37

2-(R)-(3-(S)-((4-(N-(4-Nitro)benzyloxycarbonyl-N-ethyl) aminopiperidin-1-yl)methyl)-4-(S)-phenylpyrrolidin-1-yl)-2-(cyclopentyl)acetic acid $R_F$: 0.31 (89:10:1 v/v/v $CH_2Cl_2$/MeOH/$NH_4OH$); $^1$H NMR (300 MHz, $CD_3OD$) δ0.78–3.73 (m, 32H), 5.12 (s, 2H), 7.16–7.62 (m, 7H), 8.12 (d, J=8.5, 2H); ESI-MS: 593.8 (M+H).

EXAMPLE 38

2-(R)-(3-(S)-((4-(N-(4-Nitro)benzyloxycarbonyl-N-prop-2-enyl)aminopiperidin-1 yl)methyl)-4-(S)-(3-fluorophenyl) pyrrolidin-1-yl)-3-(cyclobutyl)propionic acid $^1$H NMR (300 MHz, $CD_3OD$) δ1.38–3.72 (m, 29H), 4.96–5.11 (m, 4H), 5.69 (m, 1H), 6.86–7.07 (m, 3H), 7.24 (m, 1H), 7.45 (br d, 2H), 8.10 (br, d, 2H); ESI-MS: 623 (M+H); HPLC A: 2.91 min.

EXAMPLE 39

2-(S)-(3-(S)-((4-(N-(4-Nitro)benzyloxycarbonyl-N-prop-2-enyl)aminopiperidin-1-yl)methyl)-4-(S)-phenylpyrrolidin-1-yl)-3-(cyclobutyl)propionic acid $^1$H NMR (300 MHz, $CD_3OD$) δ1.45–3.74 (m, 29H), 4.97–5.12 (m, 4H), 5.71 (m, 1H), 7.16–7.30 (m, 5H), 7.46 (d, J=8.8, 2H), 8.12 (d, J=8.8, 2H); ESI-MS: 605 (M+H); HPLC A: 2.56 min.

EXAMPLES 40–92

Examples 40–92 in Table 1 were prepared according to the general procedures given in Examples 1, 13 and 19.

TABLE 1

| EX # | Z | R | MS m/Z (M + H) | HPLC A (min) |
|---|---|---|---|---|
| 40 | ethyl-N (piperidine link) | 4-NC-C6H4-CH2-NH- | 586.5 | 2.07 |
| 41 | ethyl-N (piperidine link) | 1-(4-Cl-phenyl)cyclopropyl-NH- | 621.4 | 2.42 |
| 42 | methyl-N | 4-Cl-C6H4-CH2-NH- | 581.5 | 2.12 |
| 43 | methyl-N | 4-NC-C6H4-CH2-NH- | 572.5 | 1.90 |
| 44 | methyl-N | 4-F3C-C6H4-CH2-NH- | 615.5 | 2.25 |
| 45 | ethyl-N | 3,5-(CF3)2-C6H3-CH2-NH- | 397.4 | 2.25 |
| 46 | propyl-N | C6H5-NH- | 561.6 | 1.82 |
| 47 | HN | 4-NC-C6H4-CH2-NH- | 558.4 | 2.00 |

TABLE 1-continued

| EX # | Z | R | MS m/Z (M + H) | HPLC A (min) |
|---|---|---|---|---|
| 48 | phenethyl-N | 3,4-difluorobenzyl-NH | 673.4 | 2.72 |
| 49 | 3-phenylpropyl | 3,4-difluorobenzyl-NH | 687.5 | 2.83 |
| 50 | O | 3,4-difluorobenzyl-NH | 570.5 | 2.28 |
| 51 | O | 4-(CF$_3$)benzyl-NH | 602.4 | 2.52 |
| 52 | HN | 3,5-bis(CF$_3$)benzyl-NH | 683.4 | 2.68 |
| 53 | N-Me | benzyl-NH | 547.6 | |
| 54 | N-Me | 4-nitrophenethyl-O | 607.6 | |
| 55 | N-Me | phenethyl-O | 562.7 | |
| 56 | N-Me | 4-nitrobenzyl-O | 593.6 | |

TABLE 1-continued
| EX # | Z | R | MS m/Z (M + H) | HPLC A (min) |
|---|---|---|---|---|
| 57 | 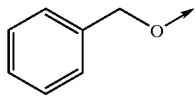 |  | 548.7 | |
| 58 | 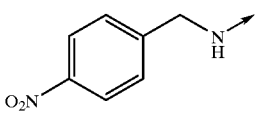 | 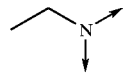 | 606.7 | |
| 59 | 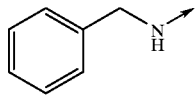 |  | 561.8 | |
| 60 | 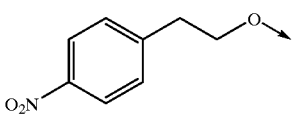 | 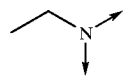 | 621.6 | |
| 61 | 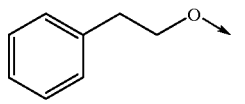 | 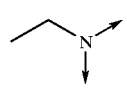 | 576.7 | |
| 62 | 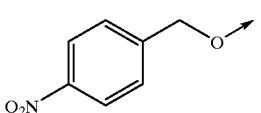 | 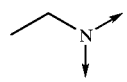 | 607.6 | |
| 63 | 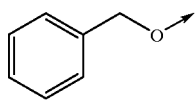 | 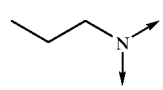 | 562.6 | |
| 64 | 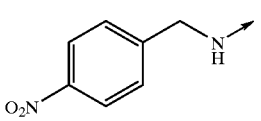 | 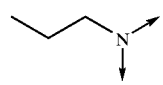 | 620.8 | |
| 65 | 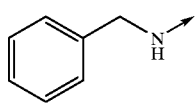 | | 575.8 | |

TABLE 1-continued

| EX # | Z | R | MS m/Z (M + H) | HPLC A (min) |
|---|---|---|---|---|
| 66 | propyl-N | 4-O2N-C6H4-CH2CH2-O- | 635.8 | |
| 67 | propyl-N | C6H5-CH2CH2-O- | 590.8 | |
| 68 | propyl-N | 4-O2N-C6H4-CH2-O- | 621.5 | |
| 69 | propyl-N | C6H5-CH2-O- | 576.8 | |
| 70 | butyl-N | 4-O2N-C6H4-CH2-NH- | 634.6 | |
| 71 | butyl-N | C6H5-CH2-NH- | 589.8 | |
| 72 | butyl-N | 4-O2N-C6H4-CH2CH2-O- | 649.6 | |
| 73 | butyl-N | C6H5-CH2CH2-O- | 604.8 | |
| 74 | butyl-N | 4-O2N-C6H4-CH2-O- | 635.7 | |

TABLE 1-continued

| EX # | Z | R | MS m/Z (M + H) | HPLC A (min) |
|---|---|---|---|---|
| 75 | butyl-N | benzyl-O | 590.7 | |
| 76 | allyl-N | 4-nitrobenzyl-NH | 618.7 | |
| 77 | allyl-N | benzyl-NH | 573.7 | |
| 78 | allyl-N | 4-nitrophenethyl-O | 633.7 | |
| 79 | allyl-N | phenethyl-O | 588.6 | |
| 80 | allyl-N | benzyl-O | 574.8 | |
| 81 | cyclopropylmethyl-N | 4-nitrobenzyl-NH | 632.6 | |
| 82 | cyclopropylmethyl-N | benzyl-NH | 587.6 | |
| 83 | cyclopropylmethyl-N | 4-nitrophenethyl-O | 647.7 | |

TABLE 1-continued
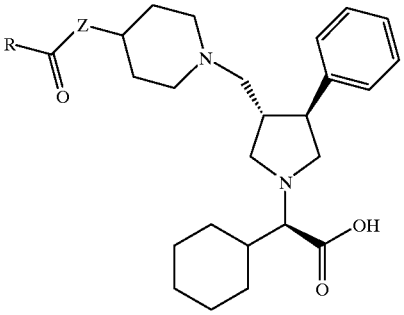
| EX # | Z | R | MS m/Z (M + H) | HPLC A (min) |
|---|---|---|---|---|
| 84 | 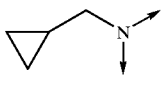 | 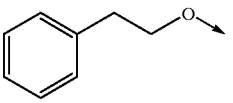 | 602.7 | |
| 85 | 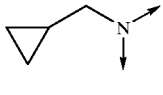 | 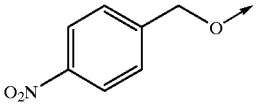 | 633.7 | |
| 86 | 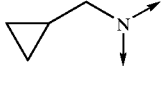 | 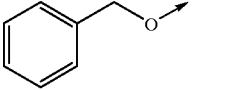 | 588.7 | |
| 87 | 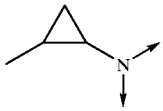 | 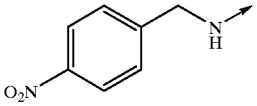 | 632.7 | |
| 88 | 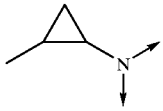 | 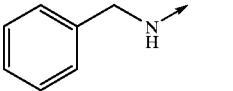 | 587.7 | |
| 89 | 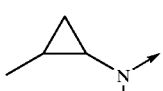 | 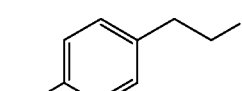 | 647.7 | |
| 90 | 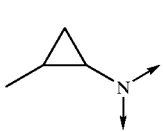 | 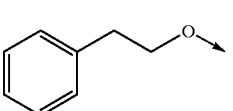 | 602.7 | |
| 91 |  | 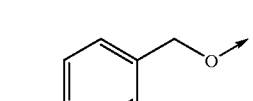 | 633.6 | |
| 92 |  | 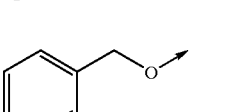 | 588.7 | |

EXAMPLES 93–109

Examples 93–109 in Table 2 were prepared according to the general procedure given in Examples 1, 13 and 19.

TABLE 2

| EX # | Z | R | MS m/Z (M + H) | HPLC A (min) |
|---|---|---|---|---|
| 93 | ethyl-N | 4-Cl-benzyl-NH | 613.4 | 2.43 |
| 94 | ethyl-N | 3,4-diCl-benzyl-NH | 647.4 | 2.58 |
| 95 | propyl-N | 3,4-diCl-benzyl-NH | 661.3 | 2.72 |
| 96 | methyl-N | 4-NO₂-benzyl-NH | 610.4 | 2.21 |
| 97 | ethyl-N | 4-CN-benzyl-NH | 604.5 | 2.14 |
| 98 | O | benzyl-NH | 552.5 | 2.23 |
| 99 | ethyl-N | 1-(4-Cl-phenyl)cyclopropyl-NH | 639.4 | 2.49 |

TABLE 2-continued

| EX # | Z | R | MS m/Z (M + H) | HPLC A (min) |
|---|---|---|---|---|
| 100 | ethyl-N (piperidine-like) | 4-Cl-C6H4-C(CH3)2-NH- | 641.5 | 2.72 |
| 101 | HN | 4-Cl-benzyl-NH- | 585.4 | 2.31 |
| 102 | CH3-N | 4-CN-benzyl-NH- | 590.5 | 2.00 |
| 103 | CH3-N | 4-CF3-benzyl-NH- | 633.5 | 2.32 |
| 104 | O | 4-CN-benzyl-NH- | 577.4 | 2.22 |
| 105 | O | 3,4-diF-benzyl-NH- | 588.4 | 2.40 |
| 106 | O | 4-CF3-benzyl-NH- | 620.4 | 2.59 |
| 107 | HN | 4-CN-benzyl-NH- | 576.4 | 2.08 |
| 108 | HN | 3,4-diF-benzyl-NH- | 587.4 | 2.25 |

TABLE 2-continued

[Structure: R-C(=O)-Z-piperidine-N-CH2-pyrrolidine with 3-fluorophenyl, N-substituted with cyclohexyl-CH-COOH]

| EX # | Z | R | MS m/Z (M + H) | HPLC A (min) |
|---|---|---|---|---|
| 109 | ethyl-N (up/down) | benzyl-NH | 579 | |

EXAMPLES 110–112

Examples 110–112 in Table 3 were prepared according to the general procedure given in Example 1.

TABLE 3

[Structure: Ra-C(=O)-Z-piperidine-N-CH2-pyrrolidine with 3-Rb-phenyl, N-substituted with isopropyl-CH-COOH]

| EX # | Z | Ra | Rb | MS m/z (M + H) | HPLC A (min) |
|---|---|---|---|---|---|
| 110 | ethyl-N (up/down) | 4-chlorobenzyl-NH | H→ | 555.5 | 2.10 |
| 111 | ethyl-N (up/down) | 3,4-difluorobenzyl-NH | F→ | 575.2 | 2.1 |
| 112 | O | 4-(trifluoromethyl)benzyl-NH | F→ | 580.4 | 2.39 |

EXAMPLES 113–126

Examples 113–126 in Table 4 were prepared according to the general procedure given in Example 1.

TABLE 4
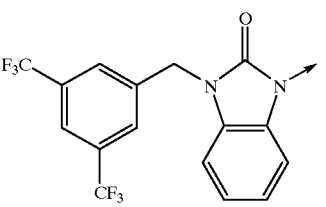
| EX # | Ra | Rb | MS m/Z (M + H) | HPLC A (min) |
|---|---|---|---|---|
| 113 | F→ | 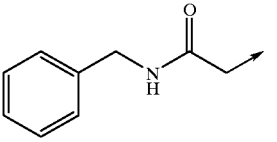 | 761 | |
| 114 | H→ | 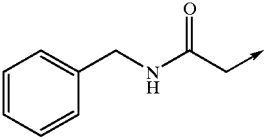 | 532.4 | 2.04 |
| 115 | F→ | 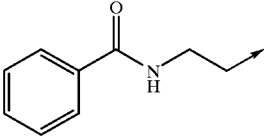 | 550.5 | 2.12 |
| 116 | H→ | 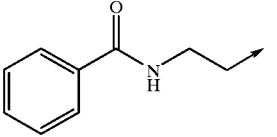 | 532.5 | 2.03 |
| 117 | F→ | 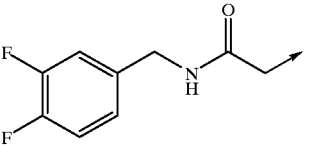 | 550.5 | 2.08 |
| 118 | F→ | | 586.4 | 2.11 |

TABLE 4-continued
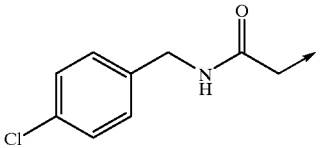
| EX # | Rₐ | R_b | MS m/Z (M + H) | HPLC A (min) |
|---|---|---|---|---|
| 119 | F→ | 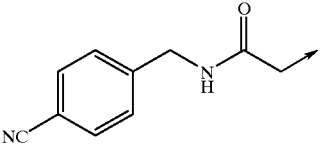 | 584.4 | 2.16 |
| 120 | F→ | 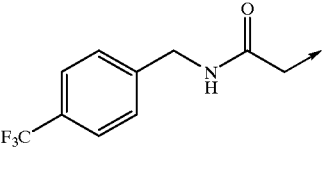 | 575.5 | 1.95 |
| 121 | H→ | 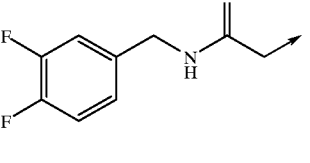 | 600.2 | 2.4 |
| 122 | H→ | 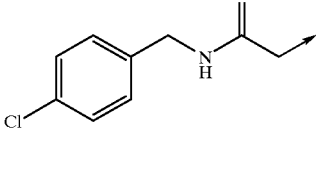 | 568.2 | 2.2 |
| 123 | H→ | 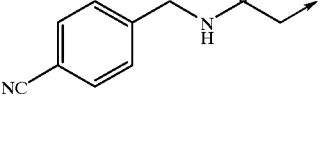 | 566.2 | 2.3 |
| 124 | F→ |  | 557.2 | 2.0 |

TABLE 4-continued
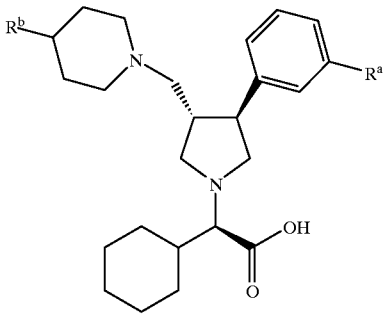
| EX # | Rₐ | R_b | MS m/Z (M + H) | HPLC A (min) |
|---|---|---|---|---|
| 125 | F→ | 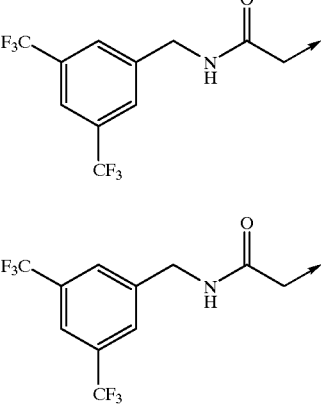 | 686.4 | 2.73 |
| 126 | H→ | 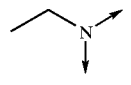 | 668.4 | 2.66 |
EXAMPLES 127–163
Examples 127–163 in Table 5 were prepared according to the general procedure given in Example 14.
TABLE 5
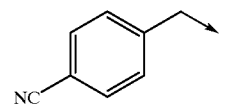
| EX # | Z | R | MS m/Z (M + H) | HPLC A (min) |
|---|---|---|---|---|
| 127 | | | 572.7 | 2.05 |

TABLE 5-continued
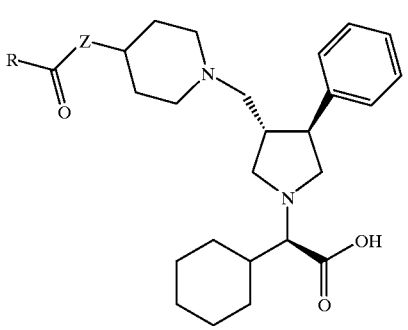
| EX # | Z | R | MS m/Z (M + H) | HPLC A (min) |
|---|---|---|---|---|
| 128 | 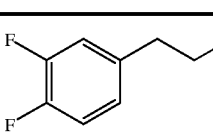 | 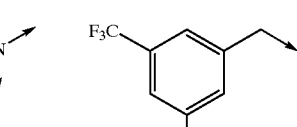 | 596.5 | 2.35 |
| 129 | 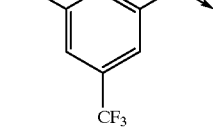 | 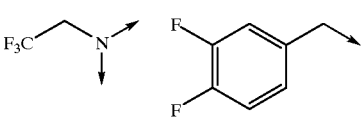 | 682.4 | 2.83 |
| 130 | 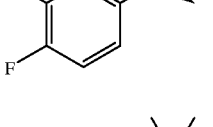 | 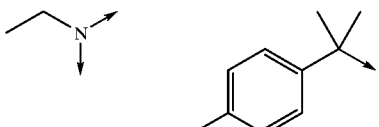 | 636.2 | 2.61 |
| 131 | 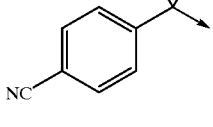 | 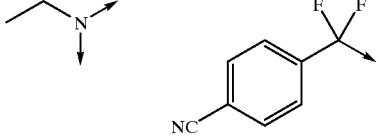 | 599.3 | 2.38 |
| 132 | 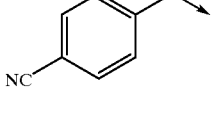 |  | 607.2 | 2.42 |
| 133 | 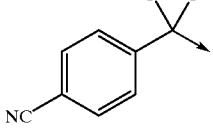 | 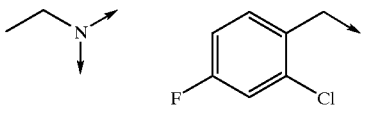 | 661.3 | 2.66 |
| 134 | 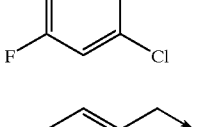 | 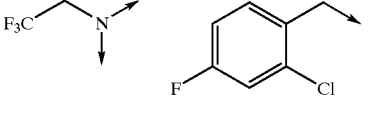 | 598.3 | 2.45 |
| 135 | 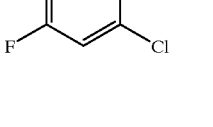 | | 652.3 | 2.68 |

TABLE 5-continued
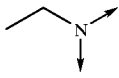
| EX # | Z | R | MS m/Z (M + H) | HPLC A (min) |
|---|---|---|---|---|
| 136 | 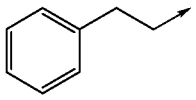 |  | 560.7 | |
| 137 | 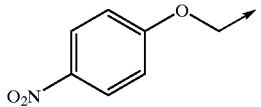 |  | 593.6 | |
| 138 | 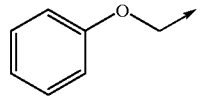 |  | 548.7 | |
| 139 | 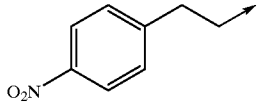 |  | 591.6 | |
| 140 | 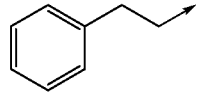 | 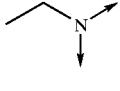 | 546.7 | |
| 141 | 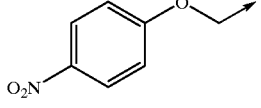 | 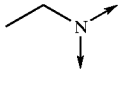 | 607.5 | |
| 142 | 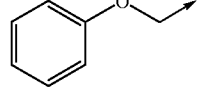 | 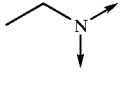 | 562.8 | |
| 143 | 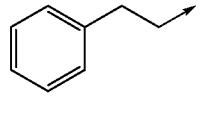 | 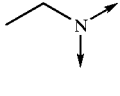 | 560.7 | |
| 144 | 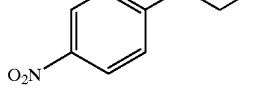 | | 621.6 | |

TABLE 5-continued

| EX # | Z | R | MS m/Z (M + H) | HPLC A (min) |
|---|---|---|---|---|
| 145 | propyl-N(N) | phenoxymethyl | 576.5 | |
| 146 | propyl-N(N) | 4-nitrophenethyl | 619.8 | |
| 147 | propyl-N(N) | phenethyl | 574.7 | |
| 148 | butyl-N(N) | 4-nitrophenoxymethyl | 635.7 | |
| 149 | butyl-N(N) | phenoxymethyl | 590.7 | |
| 150 | butyl-N(N) | 4-nitrophenethyl | 633.7 | |
| 151 | butyl-N(N) | phenethyl | 588.7 | |
| 152 | allyl-N(N) | 4-nitrophenoxymethyl | 619.7 | |
| 153 | allyl-N(N) | phenoxymethyl | 574.7 | |

TABLE 5-continued

| EX # | Z | R | MS m/Z (M + H) | HPLC A (min) |
|---|---|---|---|---|
| 154 | allyl-N-N | 4-O₂N-C₆H₄-CH₂CH₂- | 617.8 | |
| 155 | allyl-N-N | C₆H₅-CH₂CH₂- | 572.7 | |
| 156 | cyclopropyl-CH₂-N-N | 4-O₂N-C₆H₄-O-CH₂- | 633.7 | |
| 157 | cyclopropyl-CH₂-N-N | C₆H₅-O-CH₂- | 588.7 | |
| 158 | cyclopropyl-CH₂-N-N | 4-O₂N-C₆H₄-CH₂CH₂- | 631.7 | |
| 159 | cyclopropyl-CH₂-N-N | C₆H₅-CH₂CH₂- | 586.7 | |
| 160 | 2-methylcyclopropyl-N-N | 4-O₂N-C₆H₄-O-CH₂- | 633.6 | |
| 161 | 2-methylcyclopropyl-N-N | C₆H₅-O-CH₂- | 588.7 | |
| 162 | 2-methylcyclopropyl-N-N | 4-O₂N-C₆H₄-CH₂CH₂- | 631.8 | |

TABLE 5-continued

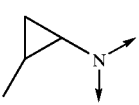

| EX # | Z | R | MS m/Z (M + H) | HPLC A (min) |
|---|---|---|---|---|
| 163 | 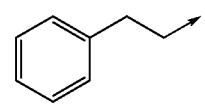 | 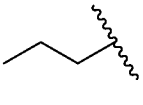 | 586.8 | |

EXAMPLES 164–168

Examples 164–168 in Table 6 were prepared according to the general procedure given in Example 14. Aldehydes were prepared in according to the procedure described for Aldehyde 7, but without resolution of the two diastereomers.

TABLE 6

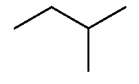

| EXAMPLE # | R | MS m/Z (M + 1) |
|---|---|---|
| 164 | 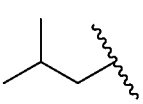 | 560 |
| 165 | 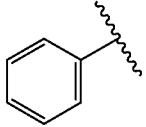 | 534 |
| 166 | 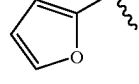 | 534 |

TABLE 6-continued

| EXAMPLE # | R | MS m/Z (M + 1) |
|---|---|---|
| 167 | | 554 |
| 168 | | 544 |

EXAMPLE 169

2-(R)-(3-(S)-(4-(N-(N-(3,4-Difluorobenzyl)carbamoyl)-N-ethylamino)-piperidin-1 yl)methyl-4-(S)-phenyl-pyrrolidin-1-yl)-tert-butylacetic acid The title compound was prepared from Aldehyde 17 (25 mg, 0.063 mmol) and 4-(N-(N-(3,4-Difluorobenzyl) carbamoyl)-N-ethylamino)-piperidine trifluoroacetate (33 mg, 0.08 mmol, from Example 1, Step B) by a method analogous to that described for Example 14, Step B to provide 31.3 mg (84% yield) of the title compound. ESI-MS: 589.5 (M+H); HPLC A: 2.19 min.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

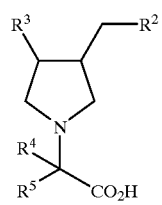

I wherein:

$R^2$ is

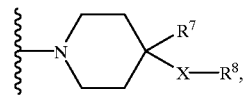

wherein $R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo, wherein X is —($C_{0-6}$ alkyl)-Y—($C_{0-6}$ alkyl)-,
where the alkyl is unsubstituted or substituted with 1–7 substituents where the substituents are independently selected from:
(a) halo,
(b) hydroxy,
(c) —O—$C_{1-3}$ alkyl, and
(d) trifluoromethyl, and where Y is selected from:
—(CO)—, —(CO)O—, —O(CO)—, —(CO)$NR^{10}$—, —$NR^{10}$(CO)—, —O(CO)$NR^{10}$—, —$NR^{10}$(CO)O—, and —$NR^{10}$(CO)$NR^9$—, and where $R^{10}$ is independently selected from: hydrogen, $C_{1-6}$ alkyl, $C_{2-6}$ alkenyl, $C_{2-6}$ alkynyl, benzyl, phenyl, and $C_{1-6}$ alkyl-$C_{3-6}$ cycloalkyl,
which is unsubstituted or substituted with 1–3 substituents where the substituents are independently selected from: halo, $C_{1-3}$ alkyl, $C_{1-3}$ alkoxy and trifluoromethyl, and wherein $R^8$ is selected from:

phenyl, naphthyl, biphenyl, and heterocycle,
which is unsubstituted or substituted with 1–7 of $R^{11}$
where $R^{11}$ is independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), phenyl, trifluoromethyl, and —$NR^9R^{10}$,
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$;

$R^3$ is selected from the group consisting of:

phenyl and thienyl,
which is unsubstituted or substituted with 1–5 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$ is selected from:

$C_{1-10}$ alkyl, $C_{3-8}$ cycloalkyl, —($C_{1-3}$ alkyl)-$C_{3-8}$ cycloalkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl,
which is unsubstituted or substituted with 1–7 of $R^{11}$ where $R^{11}$ is independently as defined above;

$R^5$ is selected from:

hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$, (g) —NR$^9$R$^{10}$, and
(h) —CONR$^9$R$^{10}$,
or where R$^4$ and R$^5$ may be joined together to form a C$_{3-8}$ cycloalkyl ring which may be unsubstituted or substituted with 1–7 of R$^{11}$;
and pharmaceutically acceptable salts thereof and individual diastereomers thereof.

2. The compound of claim 1 wherein R$^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) C$_{1-3}$ alkyl, and
(e) —O—C$_{1-3}$ alkyl.

3. The compound of claim 1 wherein R$^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) C$_{1-3}$ alkyl.

4. The compound of claim 1 wherein R$^3$ is selected from the group consisting of:
phenyl, which may be unsubstituted or substituted with 1–5 substituents where the substituents are independently selected from:
(a) fluoro, and
(b) chloro; and
unsubstituted thienyl.

5. The compound of claim 1 wherein R$^3$ is unsubstituted phenyl, (3-fluoro)phenyl or 3-thienyl.

6. The compound of claim 1 wherein R$^4$ is C$_{1-10}$ alkyl, C$_{3-8}$ cycloalkyl, or —(C$_{1-3}$ alkyl)-C$_{3-8}$ cycloalkyl,
which is unsubstituted or substituted with 1–5 substituents where the substituents are independently selected from:
(a) halo,
(b) hydroxy,
(c) —C$_{1-6}$ alkyl, which is unsubstituted or substituted with halo, cyano, —CO$_2$H, hydroxy or trifluoromethyl,
(d) —O—C$_{1-6}$ alkyl, which is unsubstituted or substituted halo, cyano, —CO$_2$H, hydroxy or trifluoromethyl,
(e) —CF$_3$,
(f) —CHF$_2$,
(g) —CH$_2$F, and
(h) —CO$_2$H.

7. The compound of claim 1 wherein R$^4$ is selected from: isopropyl, isobutyl, sec-butyl, t-butyl, cyclohexyl, cyclopentyl, cyclobutyl, cyclopropyl, —CH$_2$-cyclohexyl, —CH$_2$-cyclopentyl, —CH$_2$-cyclobutyl, and —CH$_2$-cyclopropyl.

8. The compound of claim 1 wherein R$^4$ is selected from: isopropyl, sec-butyl, t-butyl, cyclohexyl, cyclopentyl, cyclobutyl, cyclopropyl, —CH$_2$-cyclobutyl, and —CH$_2$-cyclopropyl.

9. The compound of claim 1 wherein R$^4$ is selected from: cyclohexyl, isopropyl, sec-butyl, t-butyl, —CH$_2$-cyclobutyl and —CH$_2$-cyclopropyl.

10. The compound of claim 1 wherein R$^5$ is hydrogen.

11. The compound of claim 1 wherein R$^7$ is hydrogen, fluoro, hydroxy or C$_{1-6}$ alkyl.

12. The compound of claim 1 wherein R$^7$ is hydrogen or fluoro.

13. The compound of claim 1 wherein R$^7$ is hydrogen.

14. The compound of claim 1 wherein X is:
—(C$_{0-4}$ alkyl)-Y—(C$_{0-4}$ alkyl)-,
where the alkyl is unsubstituted or substituted with 1–4 substituents where the substituents are independently selected from:
(a) halo,
(b) hydroxy,
(c) —O—C$_{1-3}$ alkyl, and
(d) trifluoromethyl,
and where Y is selected from:
—(CO)NR$^{10}$—, —NR$^{10}$(CO)—, —O(CO)NR$^{10}$—, —NR$^{10}$(CO)O—, and —NR$^{10}$O(CO)NR$^9$—,
and where R$^{10}$ is independently selected from: hydrogen, C$_{1-6}$ alkyl, C$_{2-6}$ alkenyl, C$_{2-6}$ alkynyl, benzyl, phenyl, and C$_{1-6}$ alkyl—C$_{3-6}$ cycloalkyl,
which is unsubstituted or substituted with 1–3 substituents where the substituents are independently selected from: halo, C$_{1-3}$ alkyl, C$_{1-3}$ alkoxy and trifluoromethyl.

15. The compound of claim 1 wherein X is:
—(C$_{0-2}$ alkyl)-Y—(C$_{0-2}$ alkyl)-,
where the alkyl is unsubstituted or substituted with 1–4 substituents where the substituents are independently selected from:
(a) halo,
(b) hydroxy,
(c) —O—C$_{1-3}$ alkyl, and
(d) trifluoromethyl,
and where Y is selected from:
—(CO)NR$^{10}$—, —NR$^{10}$(CO)—, —O(CO)NR$^{10}$—, —NR$^{10}$(CO)O—, and —NR$^{10}$(CO)NR$^9$—,
where R$^9$ is independently selected from: hydrogen and C$_{1-6}$ alkyl, and
R$^{10}$ is independently selected from: hydrogen, C$_{1-6}$ alkyl, C$_{2-6}$ alkenyl, C$_{2-6}$ alkynyl, benzyl, phenyl, and C$_{1-6}$ alkyl-C$_{3-6}$ cycloalkyl,
which is unsubstituted or substituted with 1–3 substituents where the substituents are independently selected from: halo, C$_{1-3}$ alkyl, C$_{1-3}$ alkoxy and trifluoromethyl.

16. The compound of claim 1 wherein X is selected from:
—(C$_{0-2}$ alkyl)-Y—(C$_{0-2}$ alkyl)-, where the alkyl is unsubstituted,
and where Y is selected from:
—(CO)NR$^{10}$—, —NR$^{10}$(CO)—, —O(CO)NR$^{10}$—, —NR$^{10}$(CO)O—, and —NR$^{10}$(CO)NH—,
where R$^{10}$ is independently selected from: hydrogen, C$_{1-3}$ alkyl, C$_{2-3}$ alkenyl, and C$_{2-3}$ alkynyl.

17. The compound of claim 1 wherein X is selected from:
(1) —N(C$_{1-4}$ alkyl)(CO)O—CH$_2$—,
(2) —N(allyl)(CO)O—CH$_2$—,
(3) —N(C$_{1-4}$ alkyl)(CO)NH—CH$_2$—, (4) —N(allyl)(CO)NH—CH$_2$—, and
(5) —N(CH$_2$CH$_3$)(CO)NH—CH$_2$CH$_2$—.

18. The compound of claim 1 wherein R$^8$ is selected from:
phenyl, naphthyl, benzoimidazolyl, benzofurazanyl, isoxazolyl, pyrazinyl, pyridazinyl, pyridyl, pyrimidyl, and tetrazolopyridyl,
  which is unsubstituted or substituted with 1–7 substituents where the substituents are independently selected from:
  (a) halo,
  (b) cyano,
  (c) hydroxy,
  (d) C$_{1-6}$ alkyl, which is unsubstituted or substituted with 1–5 of R$^{12}$ where R$^{12}$ is independently selected from: halo, cyano, hydroxy, C$_{1-6}$ alkoxy, —CO$_2$H, phenyl, —CO$_2$(C$_{1-6}$ alkyl), trifluoromethyl, and —NR$^9$R$^{10}$, wherein R$^9$ and R$^{10}$ are independently selected from: hydrogen, C$_{1-6}$ alkyl, C$_{5-6}$ cycloalkyl, benzyl or phenyl, which is unsubstituted or substituted with 1–3 substituents where the substituents are independently selected from: halo, C$_{1-3}$ alkyl, C$_{1-3}$ alkoxy and trifluoromethyl;
  (e) —O—C$_{1-6}$ alkyl, which is unsubstituted or substituted with 1–5 of R$^{12}$,
  (f) —CF$_3$,
  (g) —CHF$_2$,
  (h) —CH$_2$F,
  (i) —NO$_2$,
  (j) phenyl,
  (k) —CO$_2$R$^9$,
  (l) tetrazolyl,
  (m) —NR$^9$R$^{10}$,
  (n) —NR$^9$—COR$^{10}$,
  (o) —NR$^9$—CO$_2$R$^{10}$,
  (p) —CO—NR$^9$R$^{10}$,
  (q) —OCO—NR$^9$R$^{10}$,
  (r) —NR$^9$CO—NR$^9$R$^{10}$,
  (s) —S(O)$_m$—R$^9$, wherein m is an integer selected from 0, 1 and 2,
  (t) —S(O)$_2$—NR$^9$R$^{10}$,
  (u) —NR$^9$S(O)$_2$—R$^{10}$, and
  (v) —NR$^9$S(O)$_2$—NR$^9$R$^{10}$.

19. The compound of claim 1 wherein R$^8$ is selected from: phenyl, benzofurazanyl, benzoimidazolyl, isoxazole, and pyridyl;
  which is unsubstituted or substituted with 1–5 substituents where the substituents are independently selected from:
  (a) halo,
  (b) cyano,
  (c) —NO$_2$,
  (d) —CF$_3$,
  (e) —CHF$_2$,
  (f) —CH$_2$F,
  (g) tetrazolyl,
  (h) C$_{1-6}$ alkyl, which is unsubstituted or substituted with phenyl, and
  (i) —O—C$_{1-6}$ alkyl.

20. The compound of claim 1 wherein R$^8$ is phenyl, which is unsubstituted or substituted with 1–3 substituents where the substituents are independently selected from:
  (a) fluoro,
  (b) chloro,
  (c) cyano,
  (d) —NO$_2$, and
  (e) —CF$_3$.

21. The compound of claim 1 wherein R$^8$ is selected from: phenyl, 2-cyanophenyl, 3-cyanophenyl, 4-cyanophenyl, 4-fluorophenyl, 3,4-difluorophenyl, 3,5-difluorophenyl, 2,6-difluorophenyl, 2,4,6-trifluorophenyl, 3-nitrophenyl, 4-nitrophenyl, 4-chlorophenyl, 3-chlorophenyl, 4-trifluoromethylphenyl, and 3,5-bis(trifluoromethyl) phenyl.

22. The compound of claim 1 which is of the stereochemical configuration:

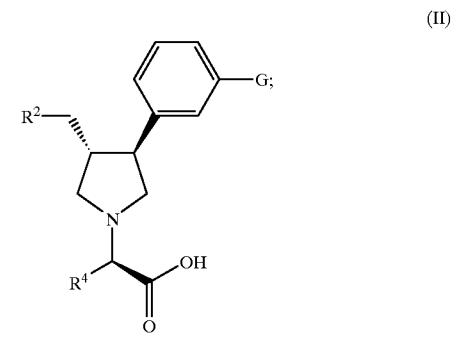

23. The compound of claim 1, which is a compound of formula (II):

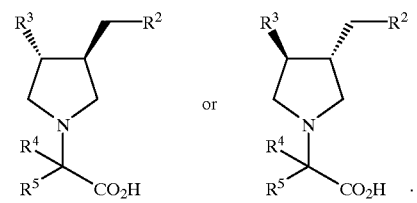

(II)

wherein

R$^2$ is selected from the group consisting of

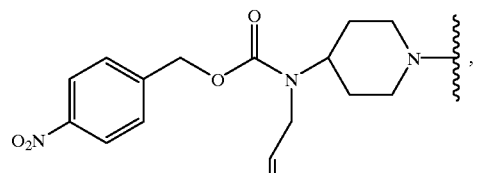

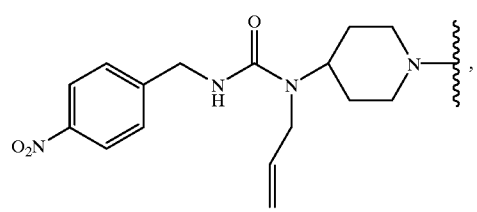

-continued

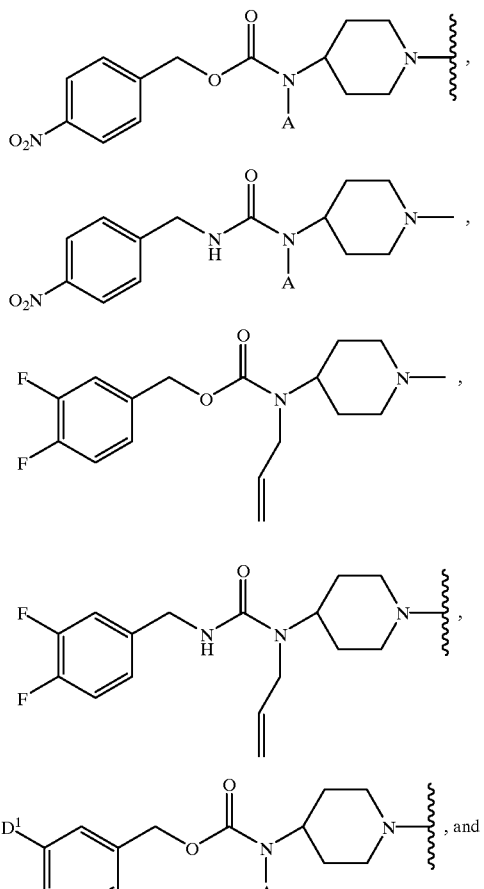

R⁴ is selected from the group consisting of

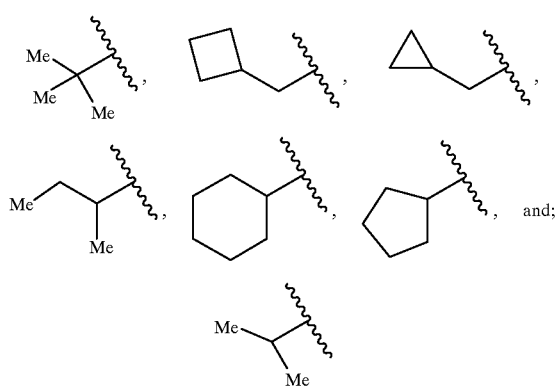

A is methyl, ethyl, propyl, butyl, or cyclopropylmethyl-; and

D¹ and D² are both fluoro; or one of D¹ and D² is hydrogen and the other of D¹ and D² is fluoro, chloro, CN, CF₃, or SO₂CH₃; and G is hydrogen or fluoro;

and pharmaceutically acceptable salts thereof and individual diastereomers thereof.

24. The compound according to claim 1, which is a compound selected from the group consisting of

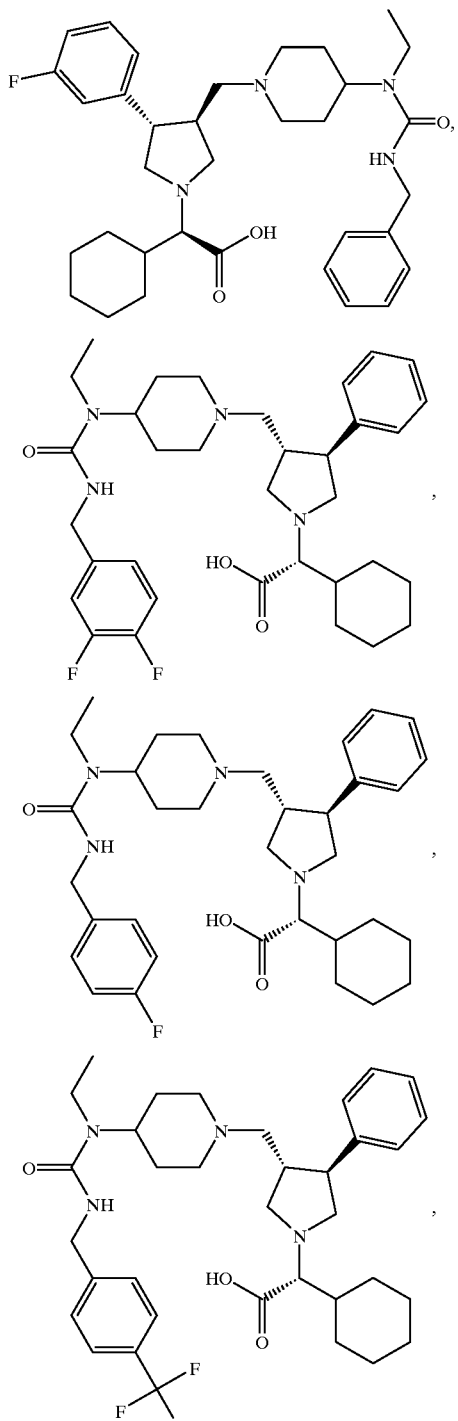

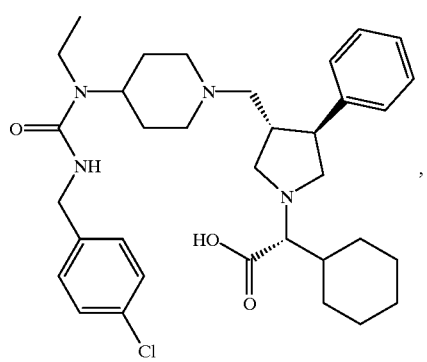
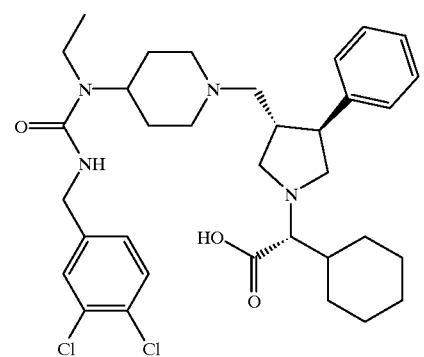
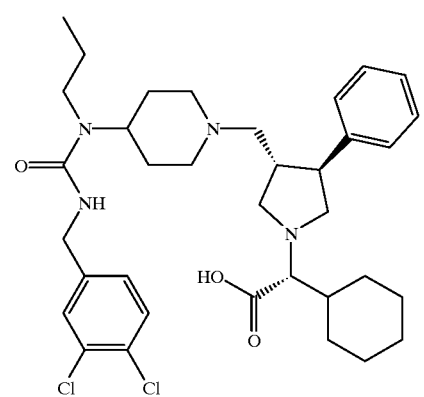
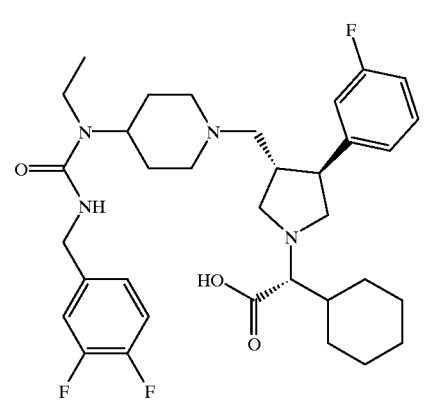
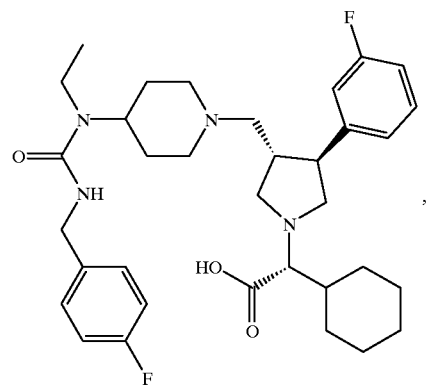
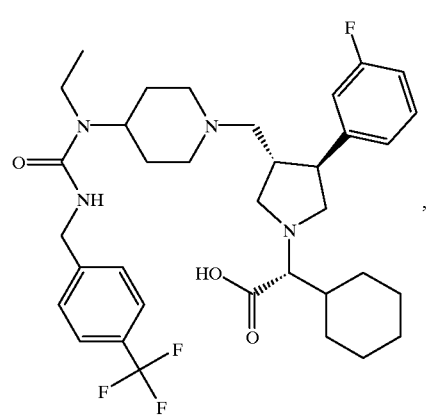
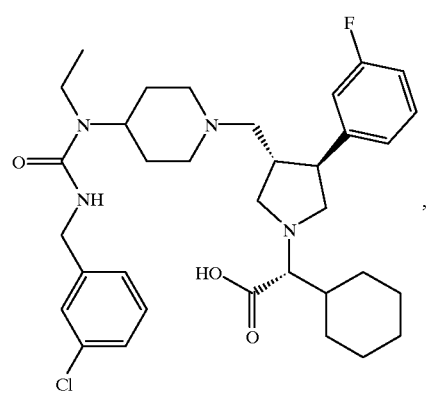
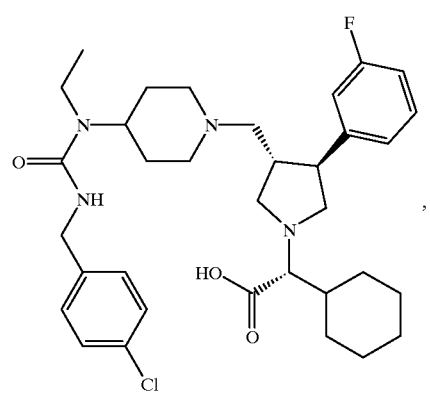

167
-continued
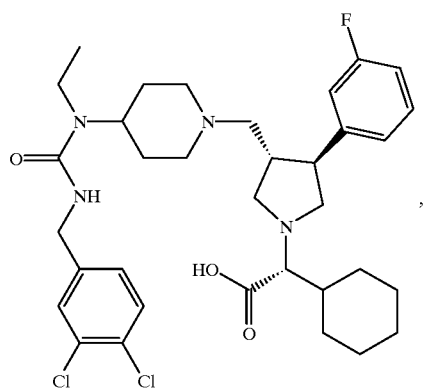
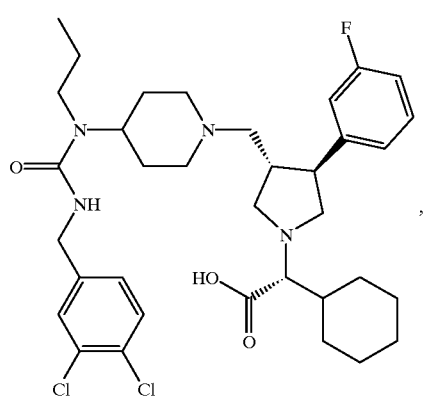
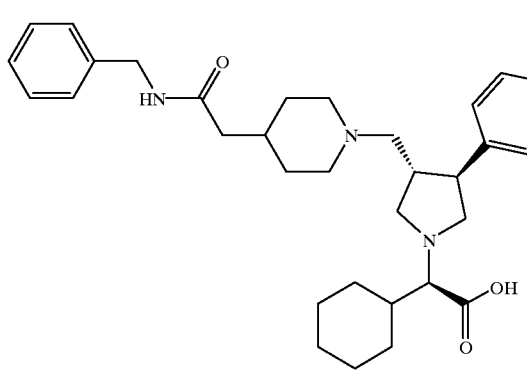
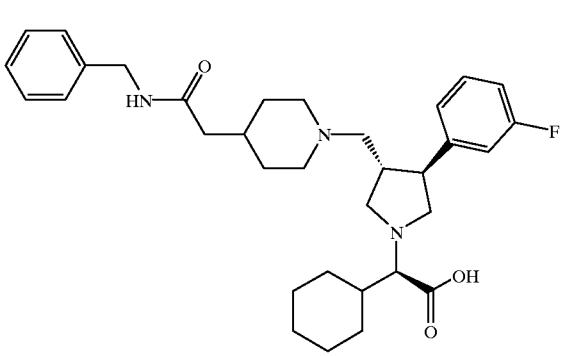
168
-continued
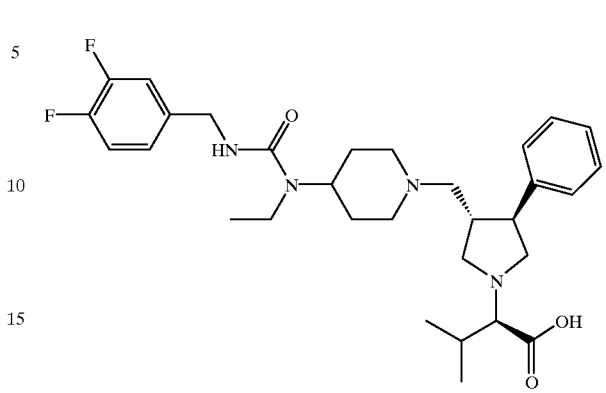
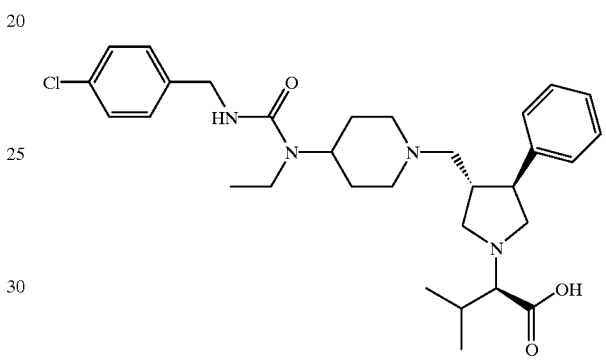
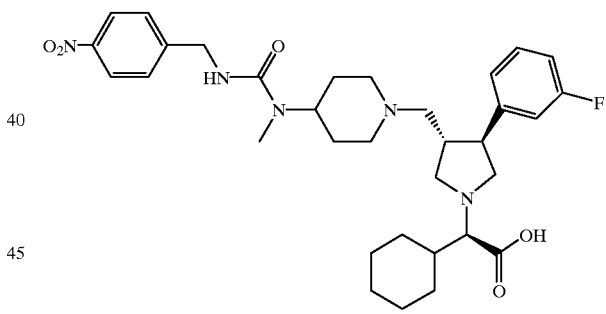
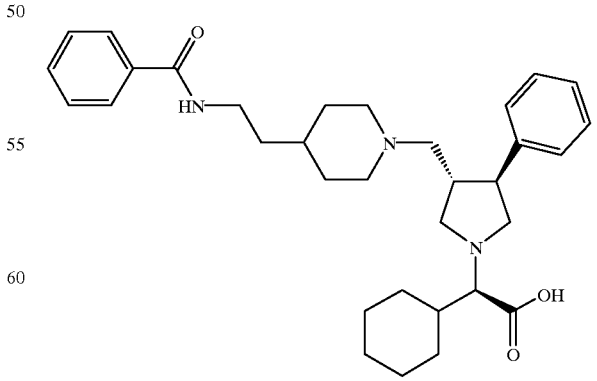

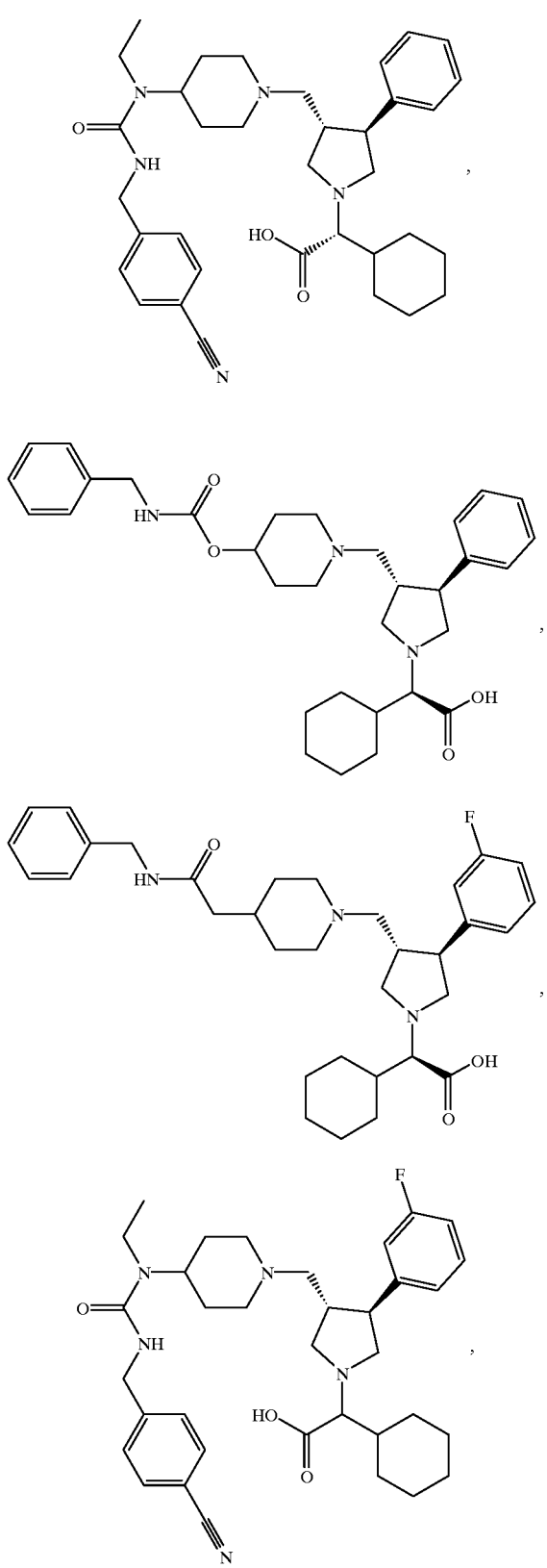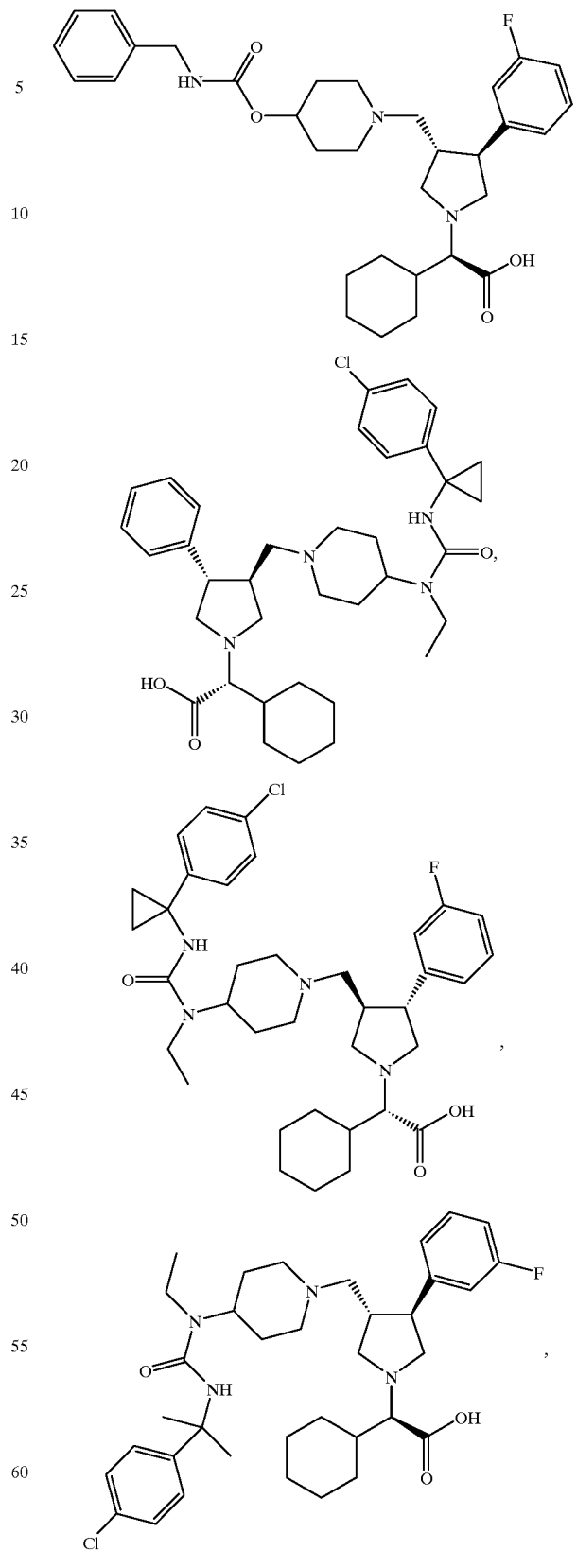

171
-continued
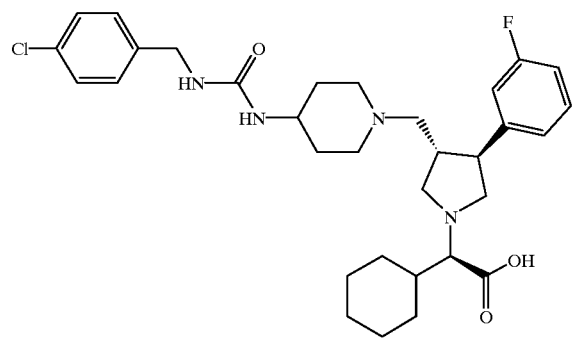
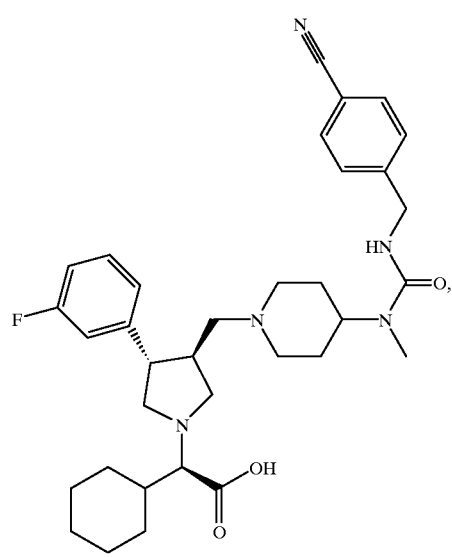
172
-continued
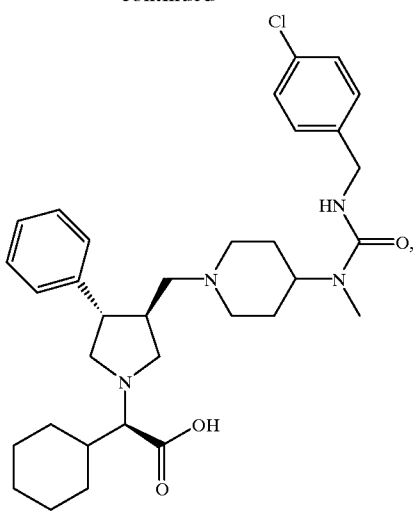
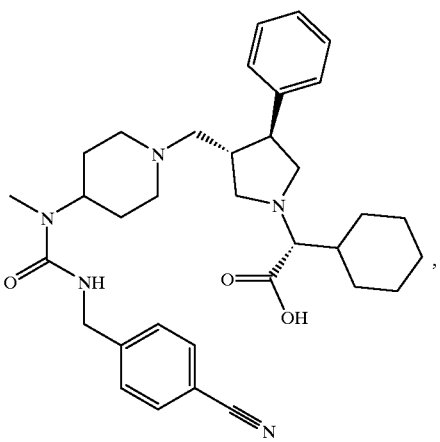
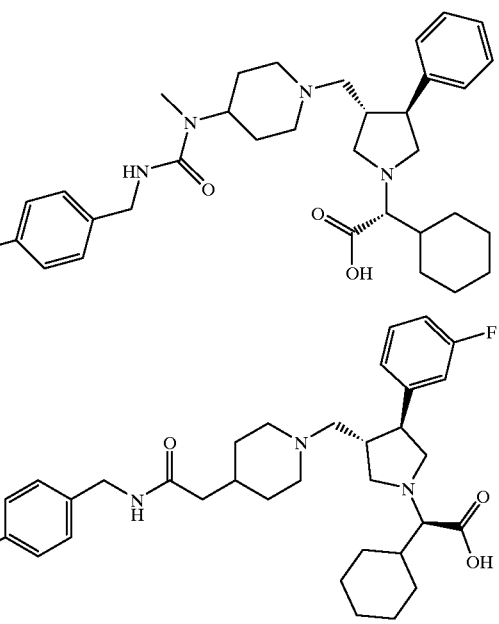

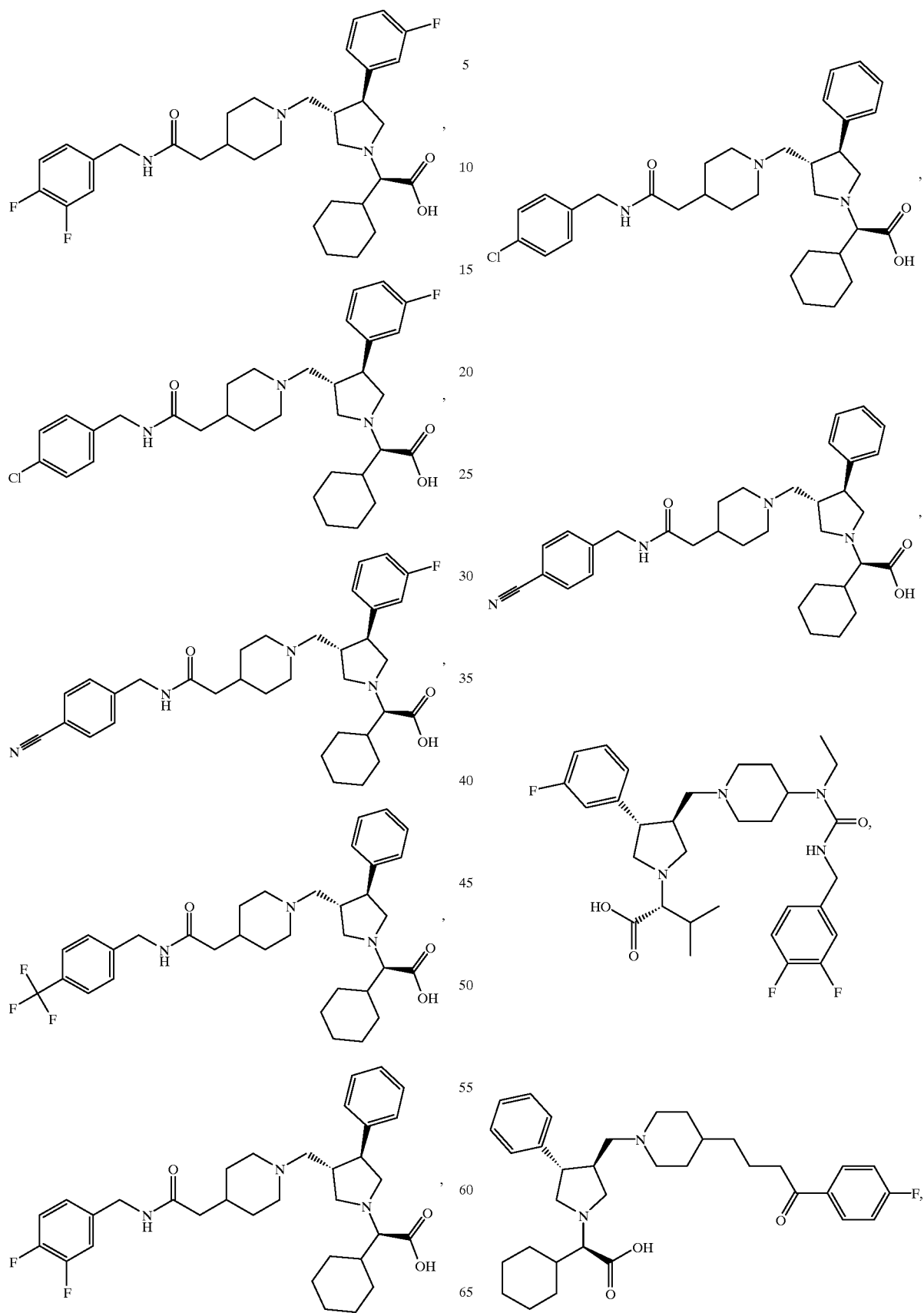

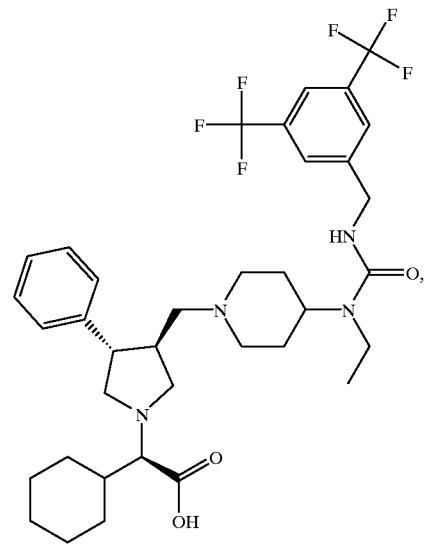
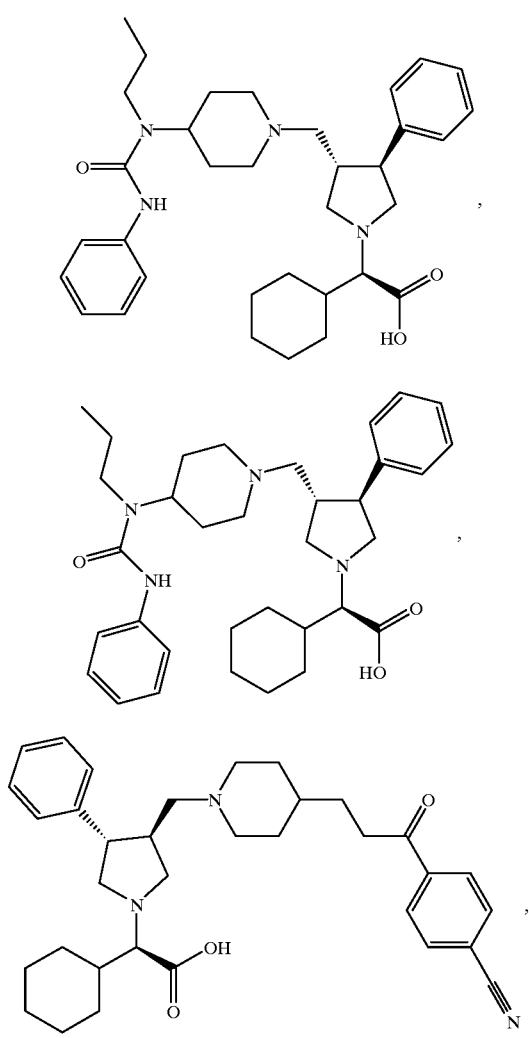

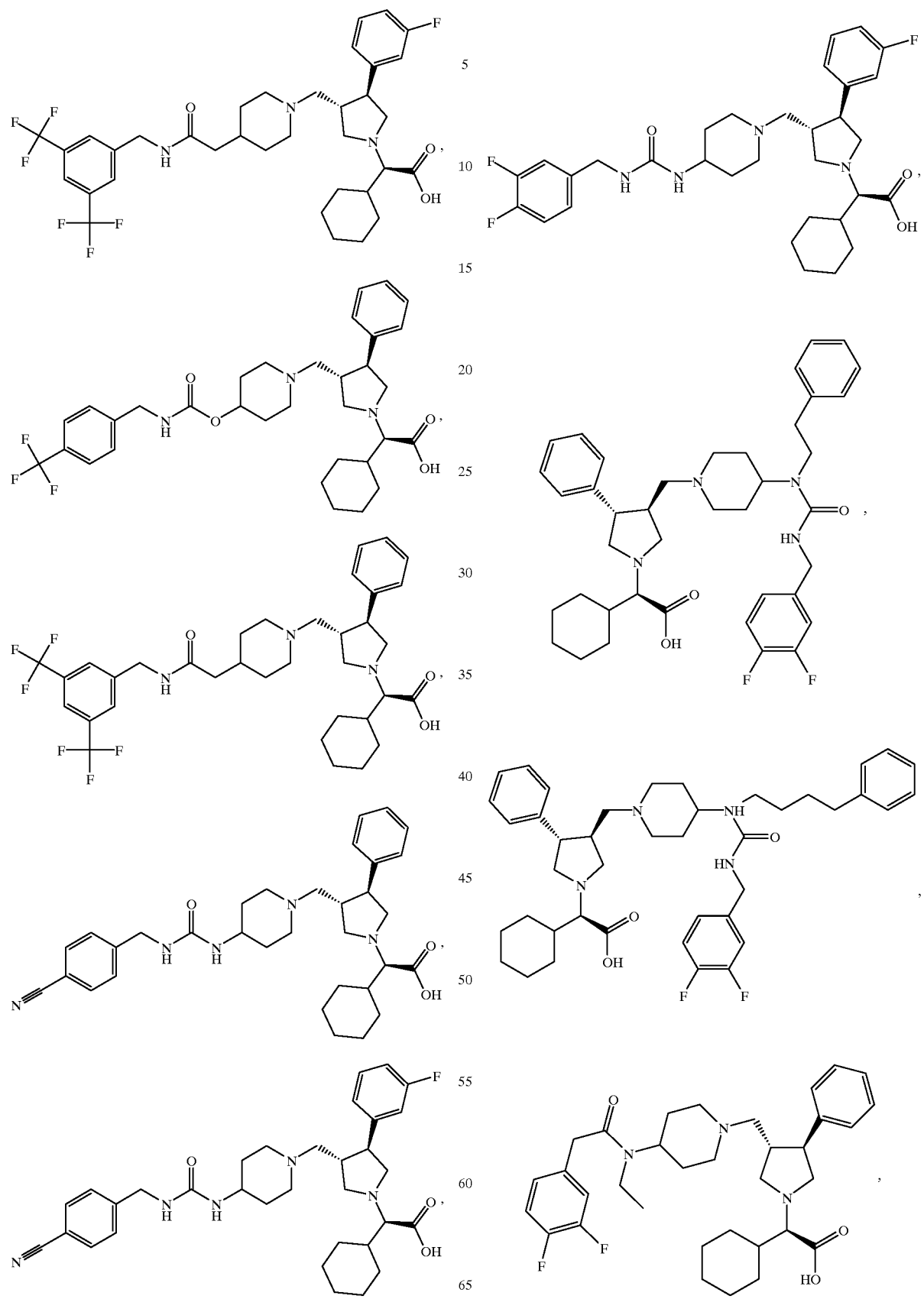

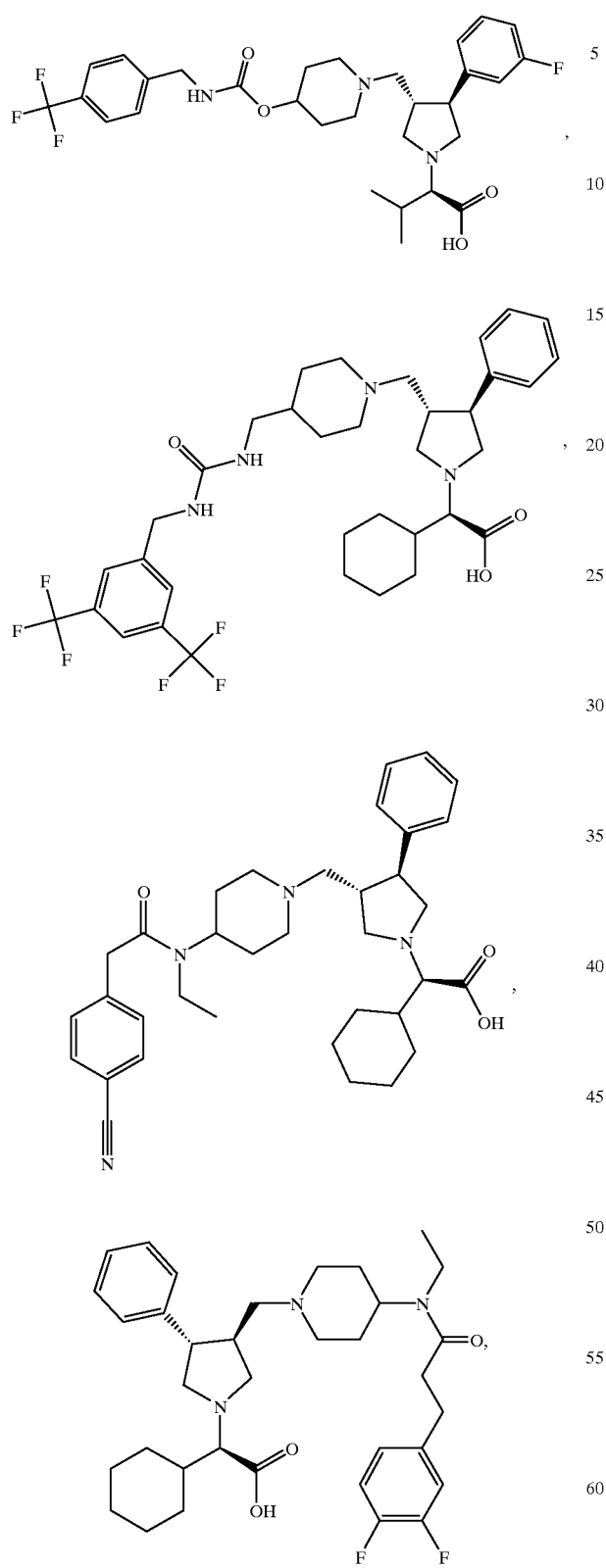
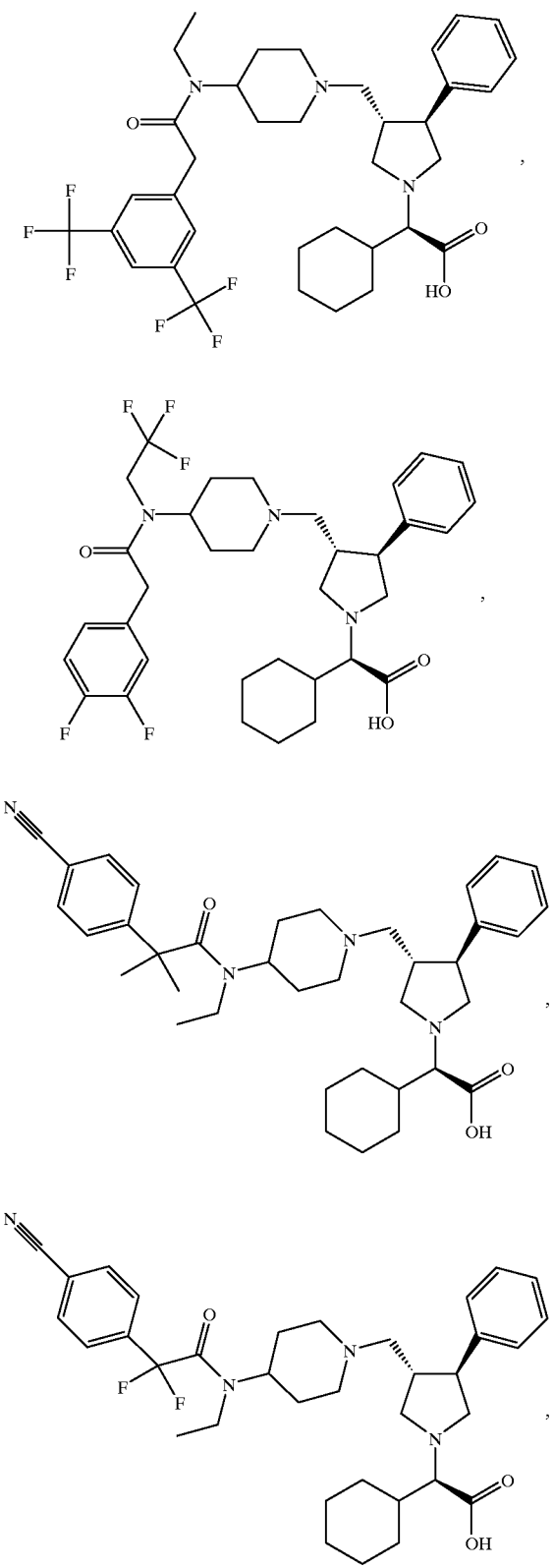

181
-continued
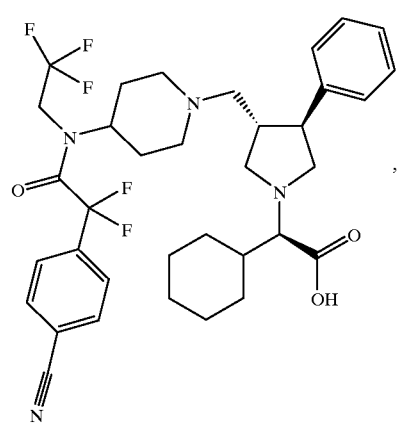
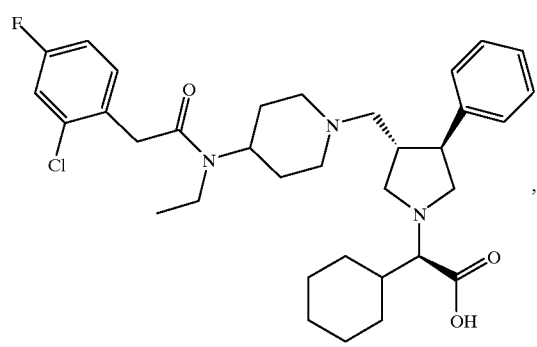
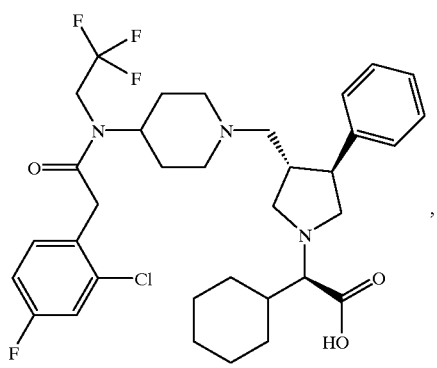
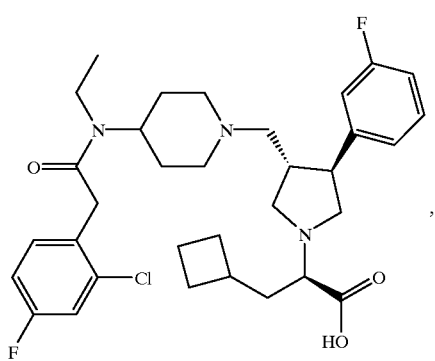
182
-continued
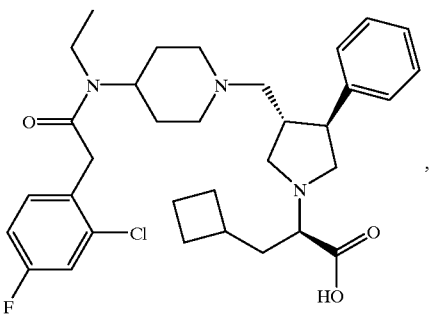
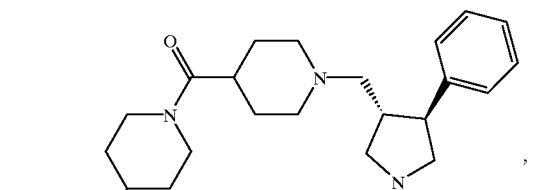
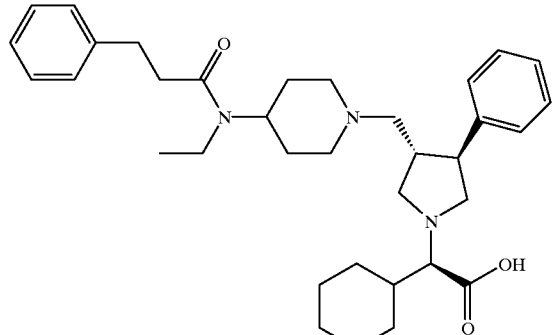
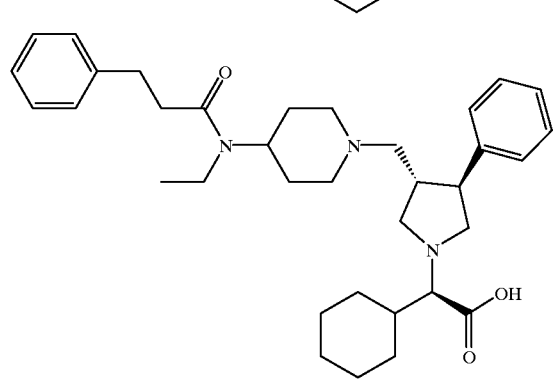
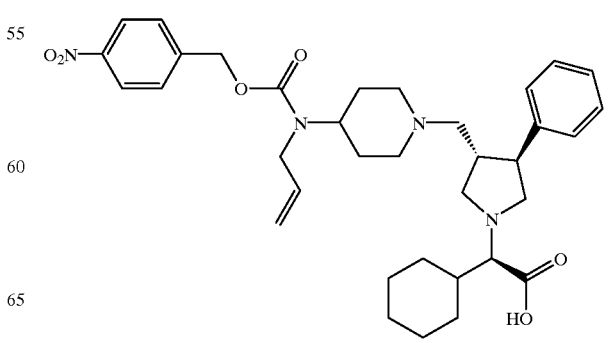

183
-continued
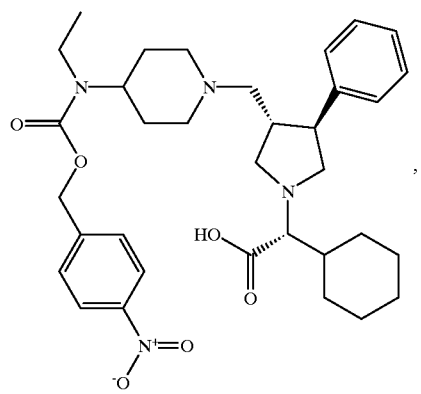
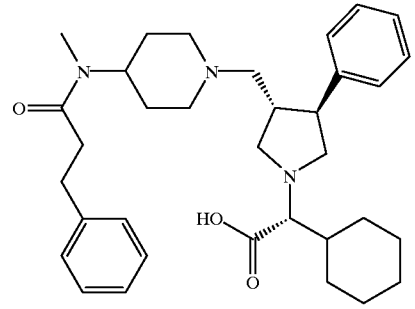
184
-continued
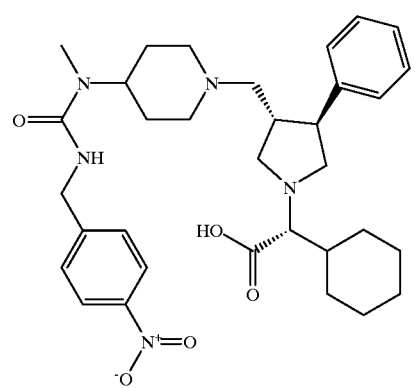
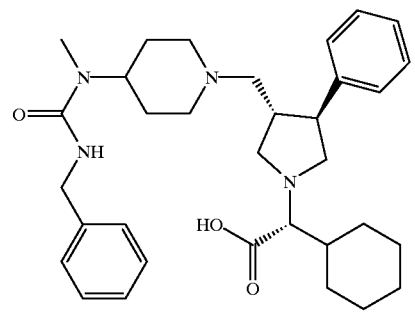
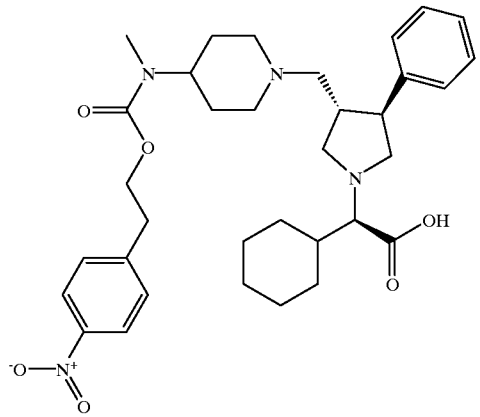

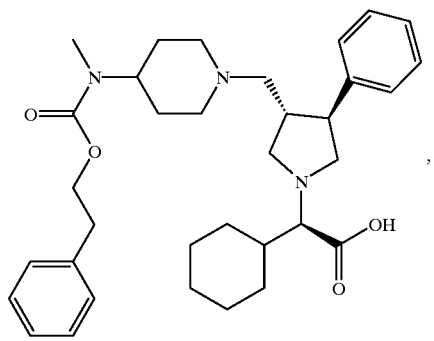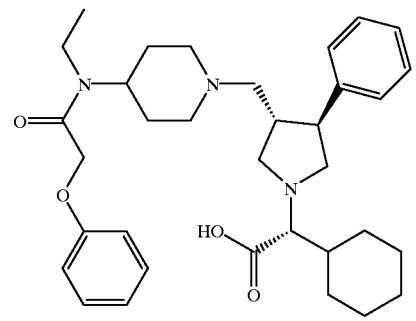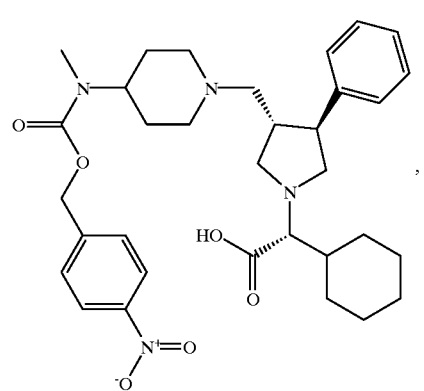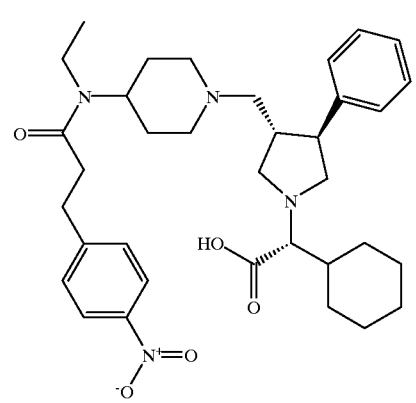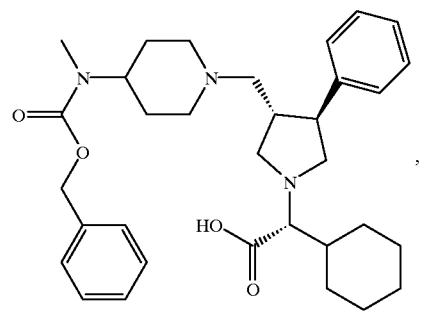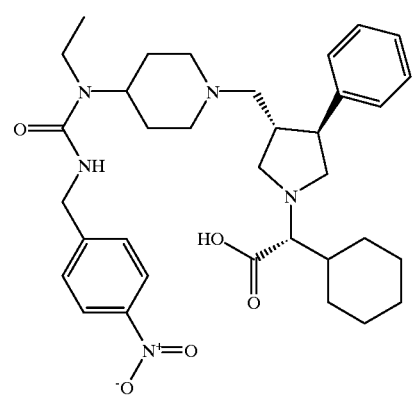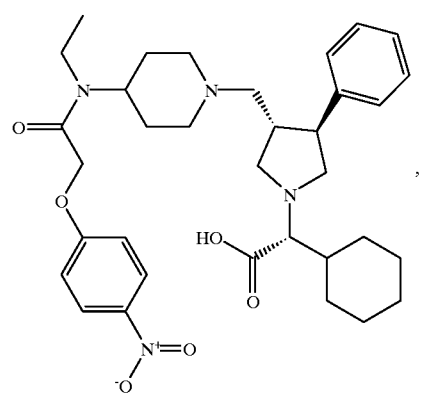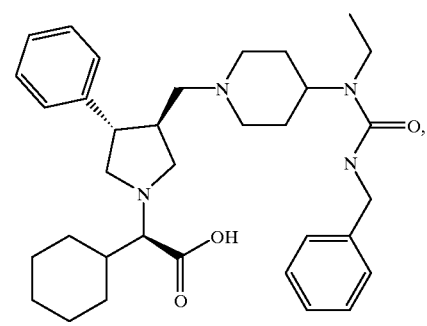

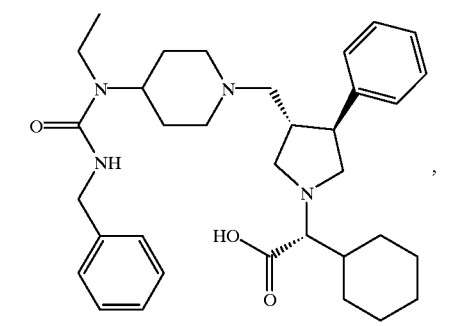
,
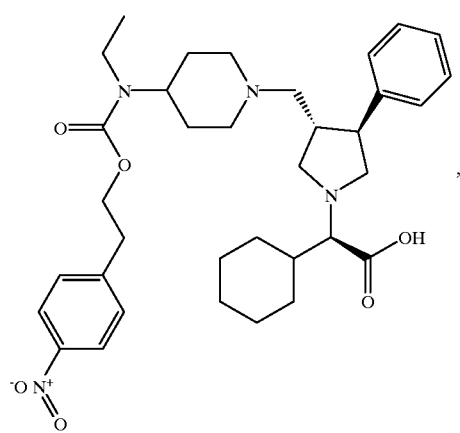
,
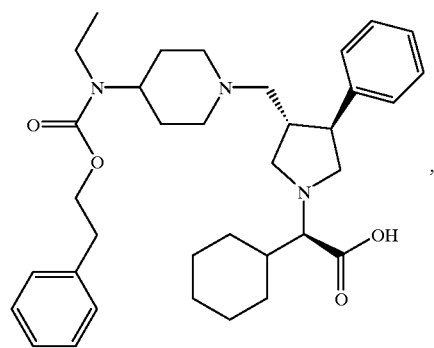
,
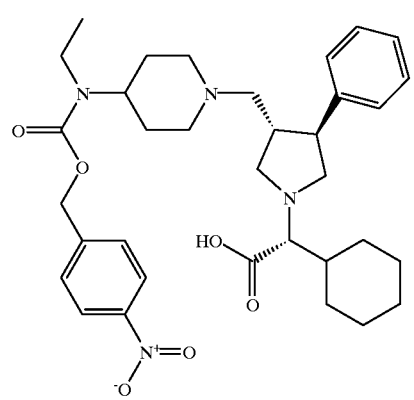
,
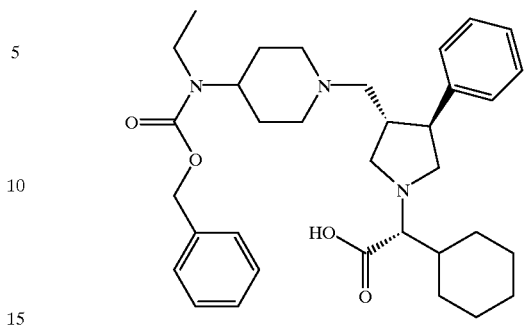
,
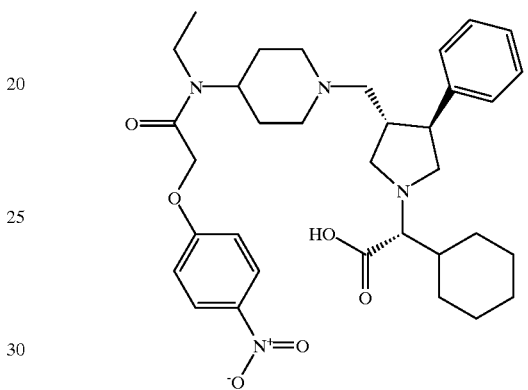
,
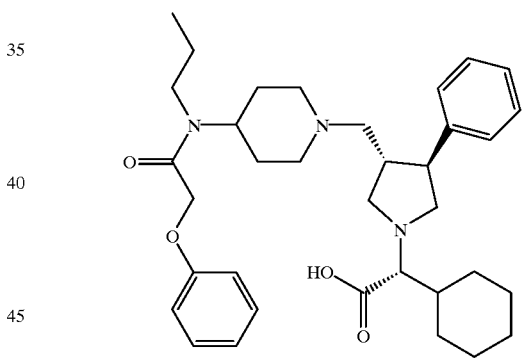
,
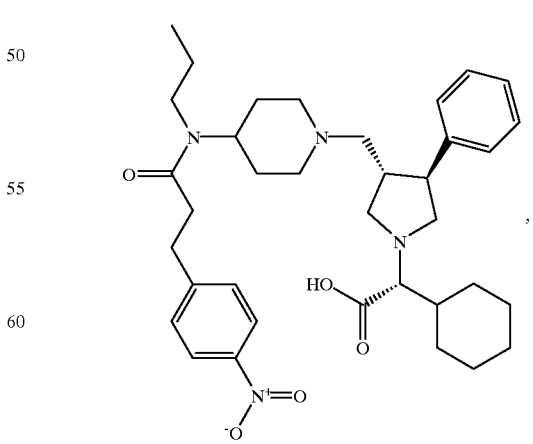
,

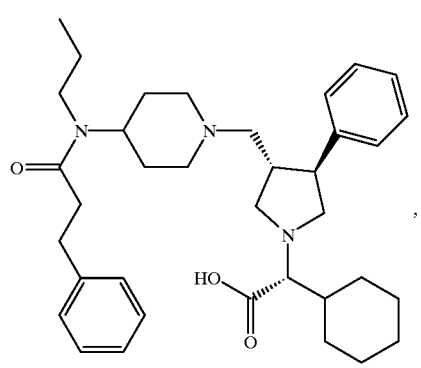
,
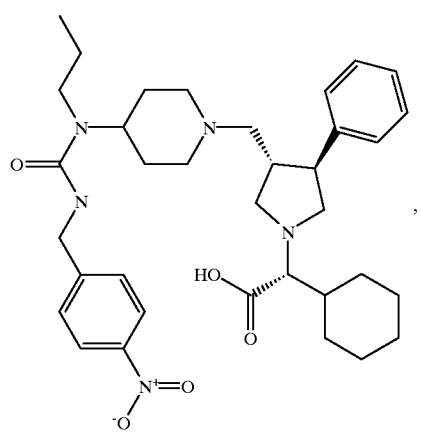
,
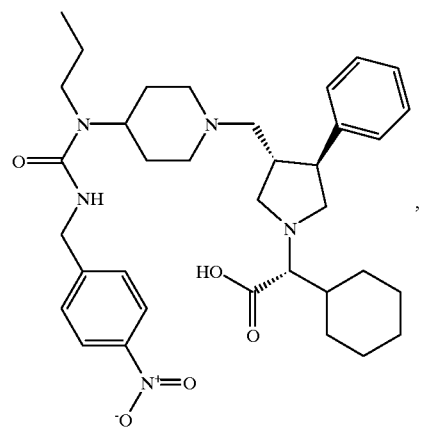
,
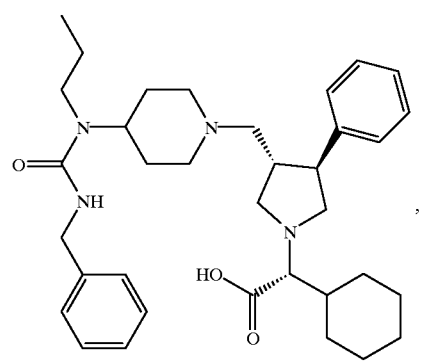
,
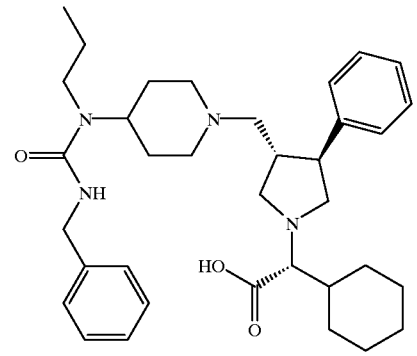
,
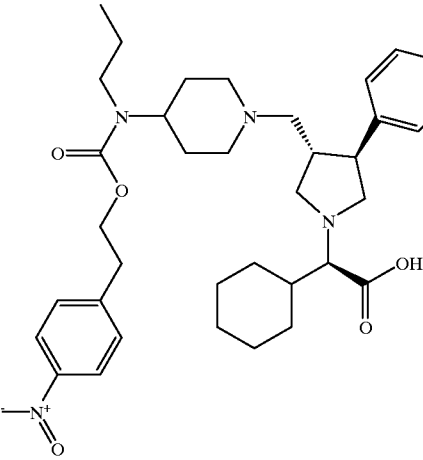
,
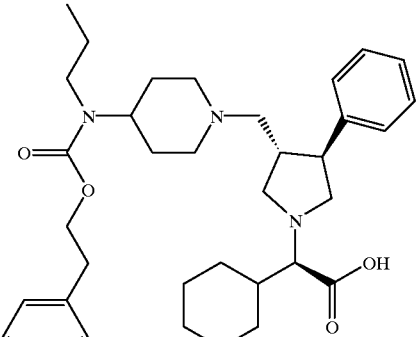
,
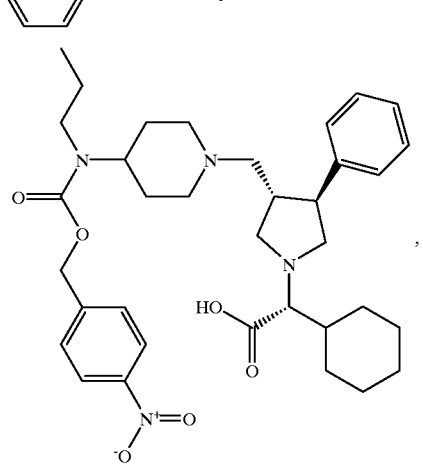
, 191
-continued
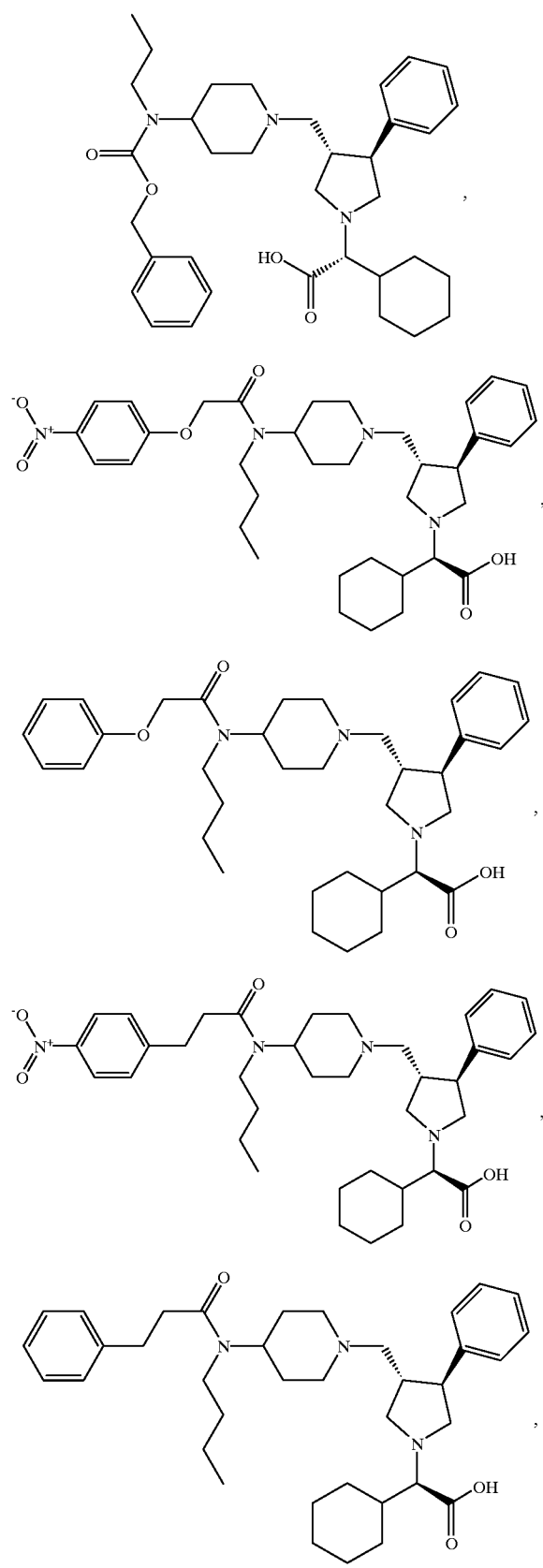
192
-continued
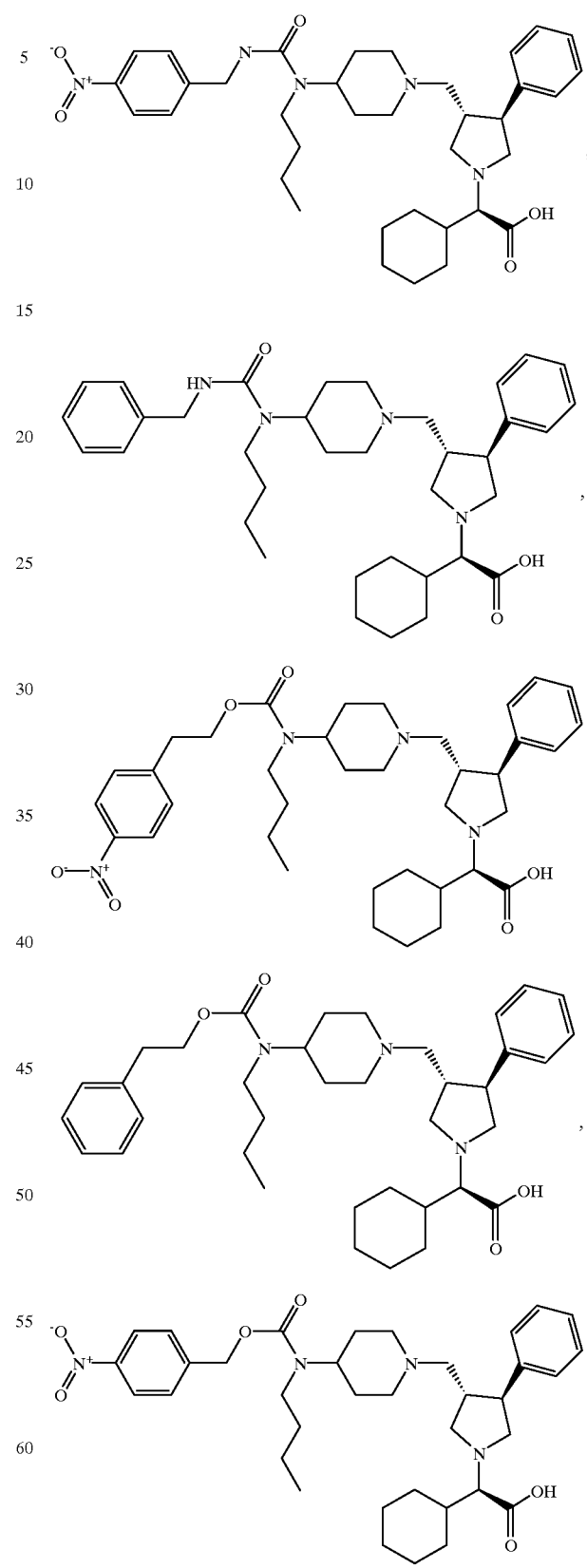

193
-continued
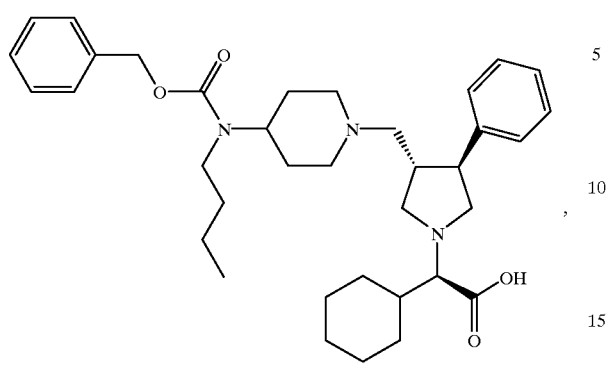
,
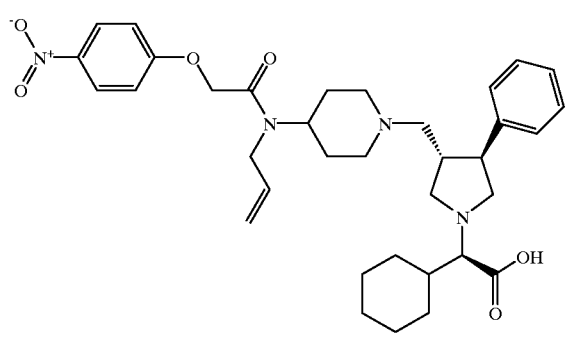
,
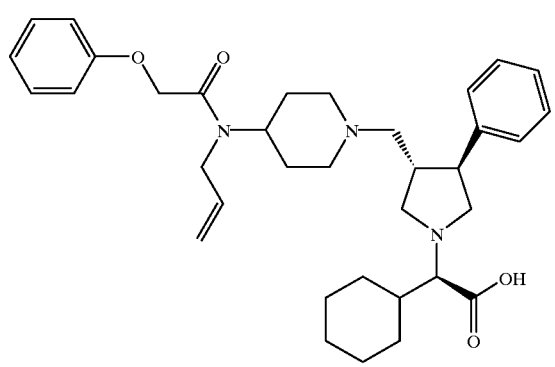
,
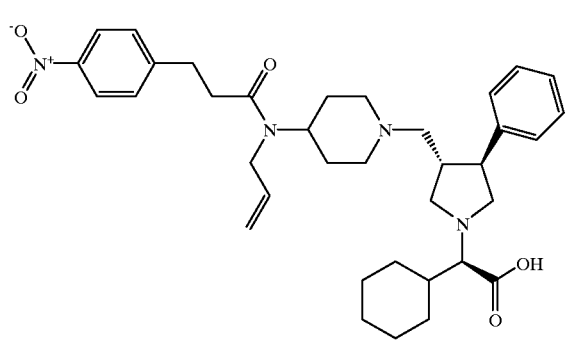
,
194
-continued
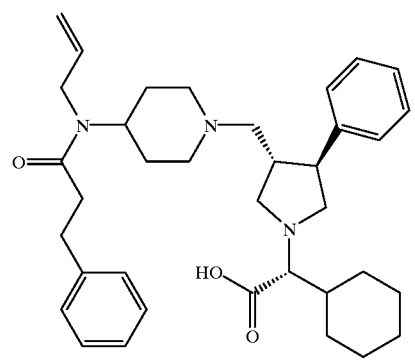
,
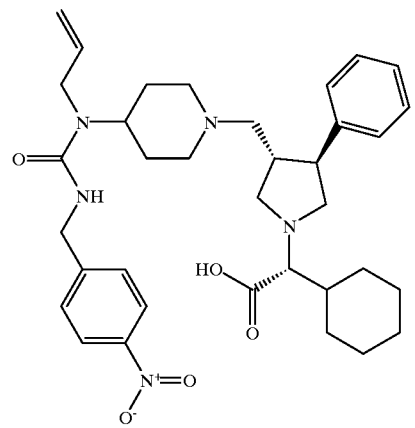
,
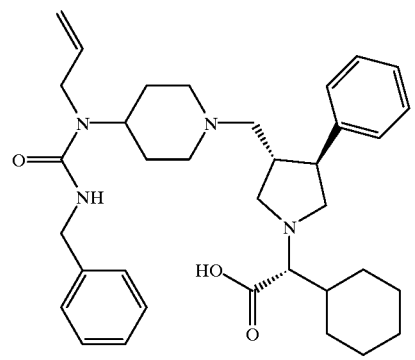
,
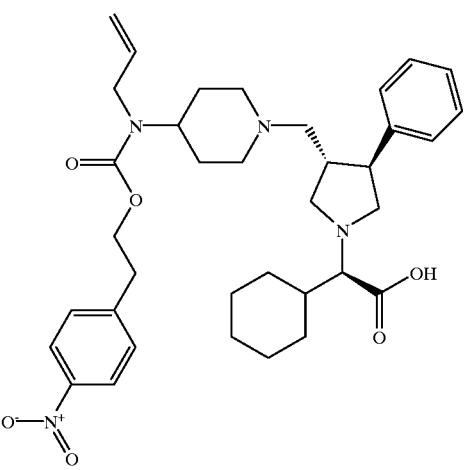
,

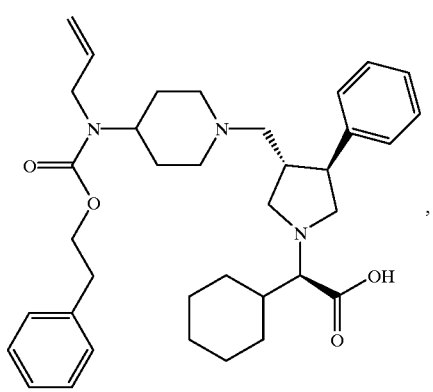,
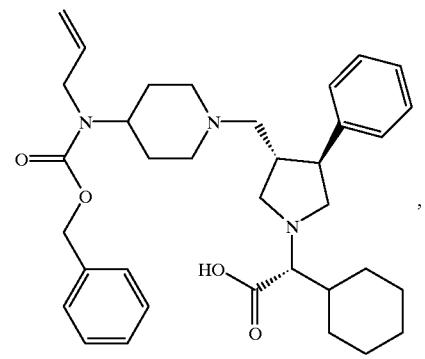,
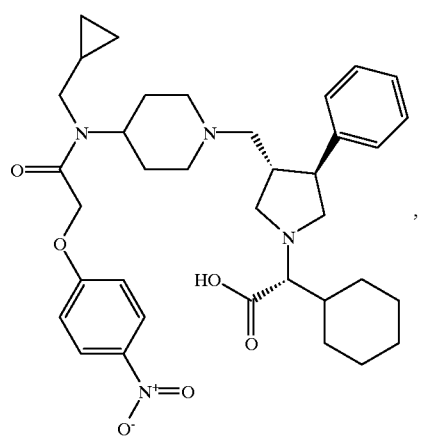,
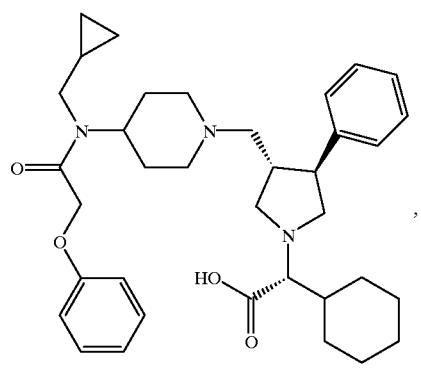,
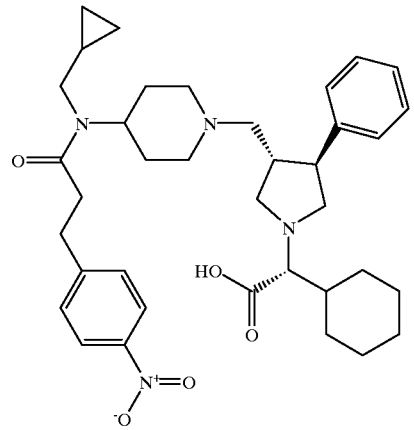,
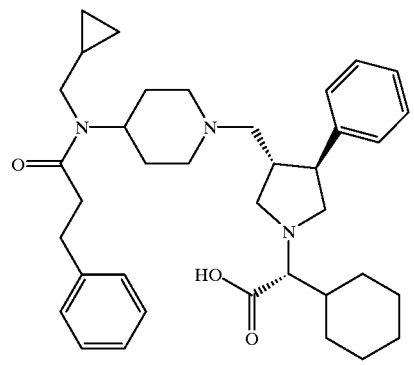,
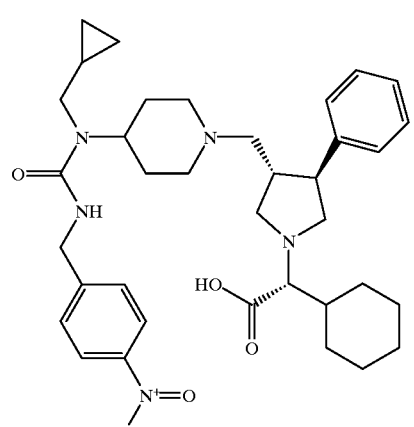,
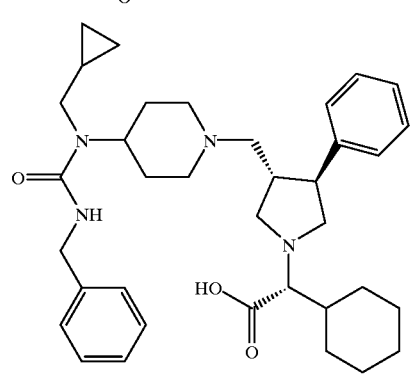, 197
-continued
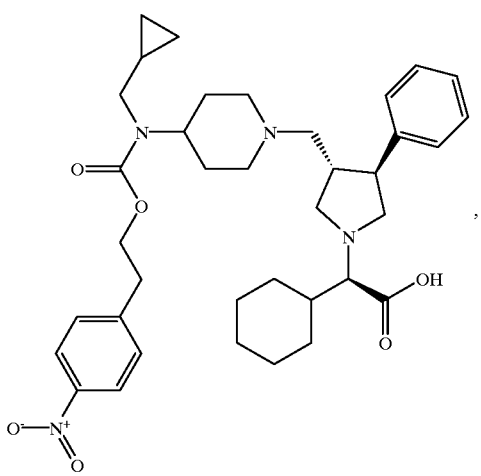
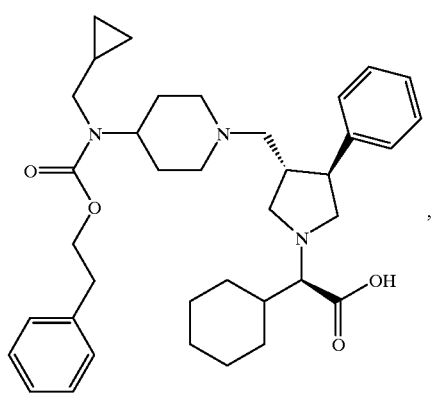
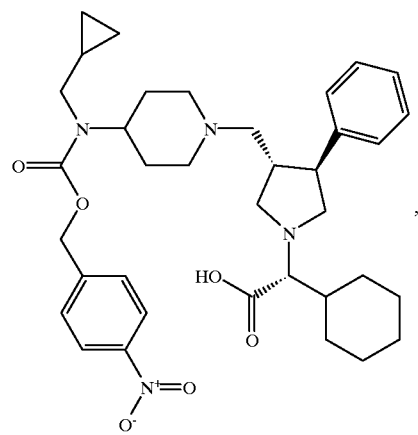
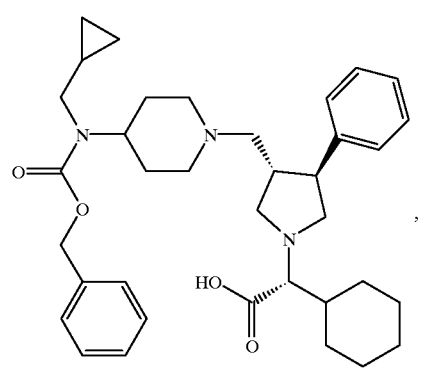
198
-continued
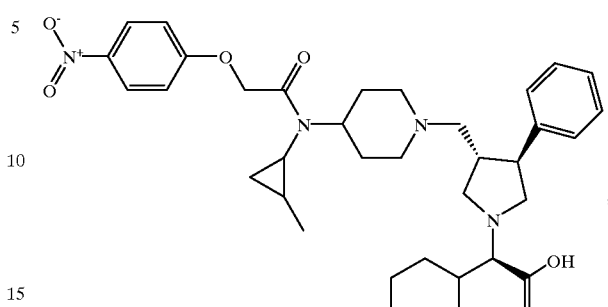
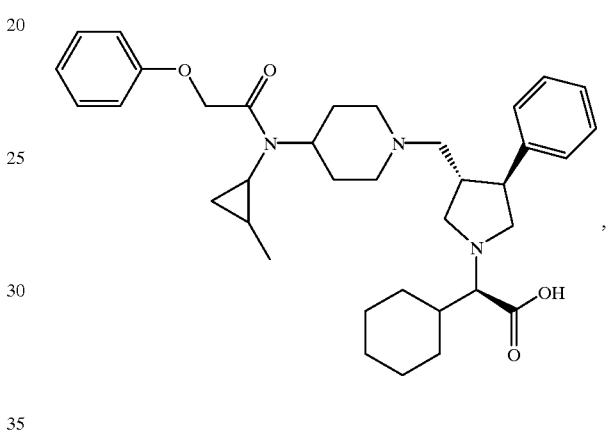
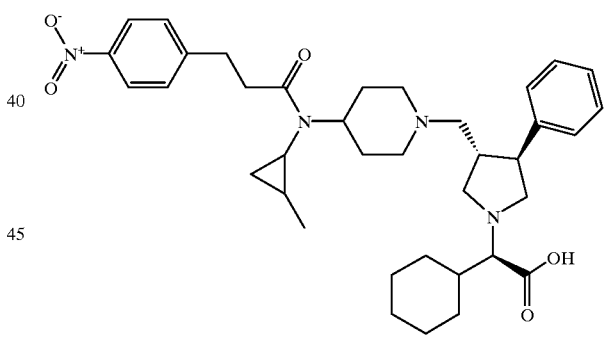
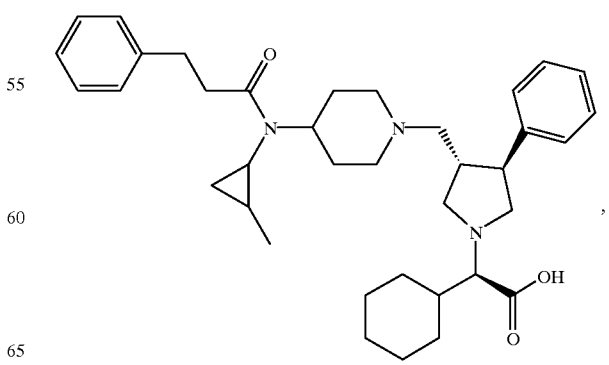

-continued
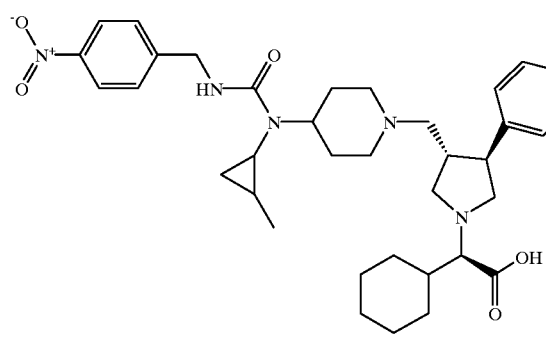
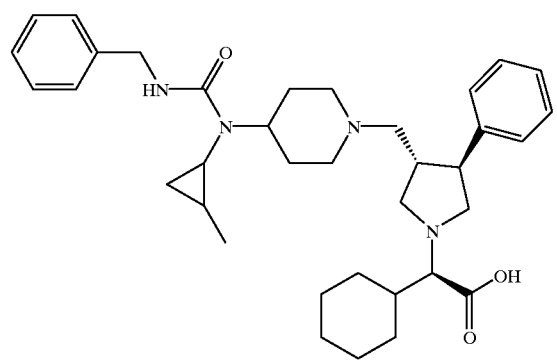
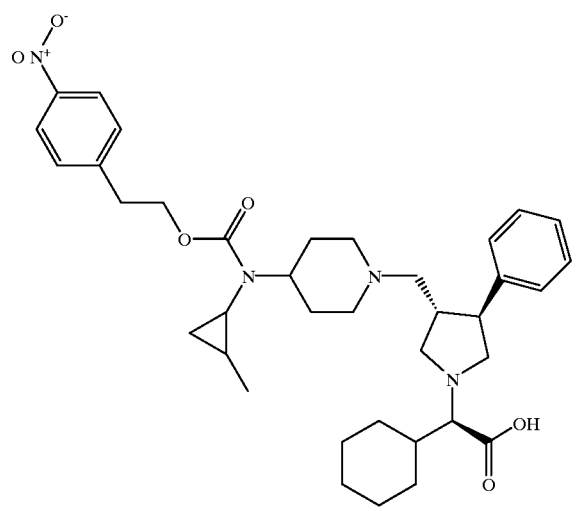
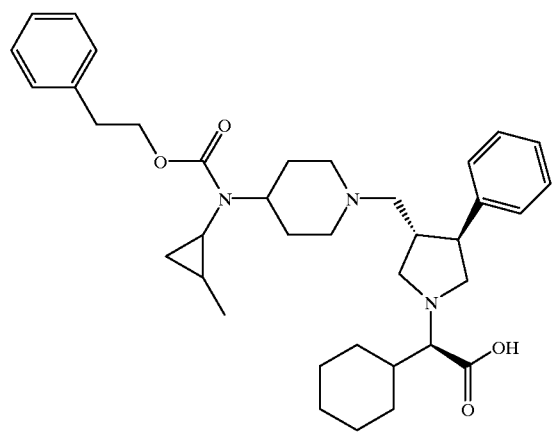
-continued
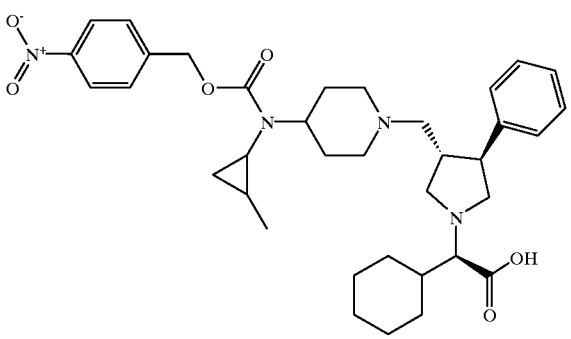
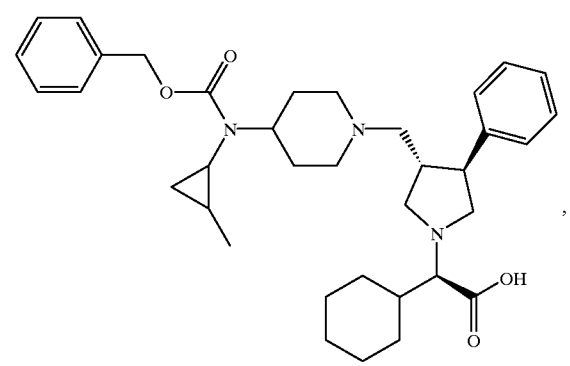
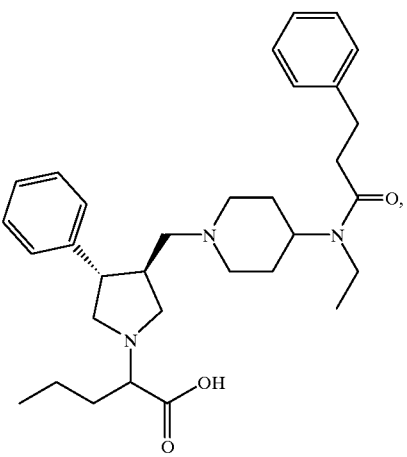
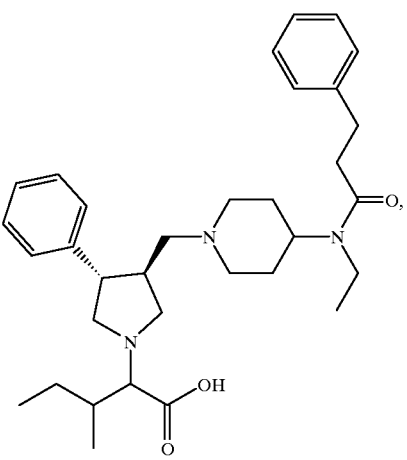

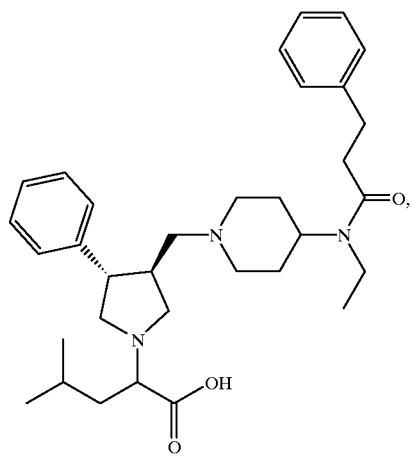
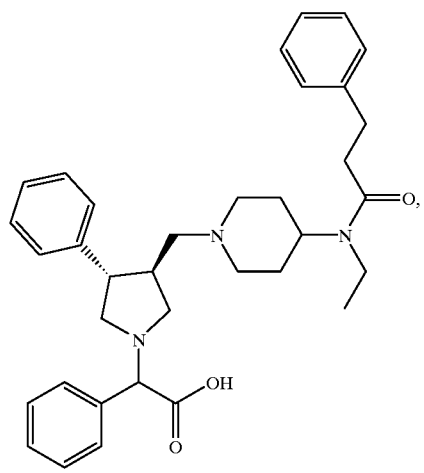
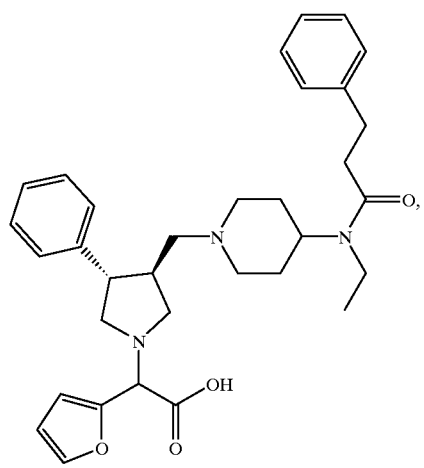
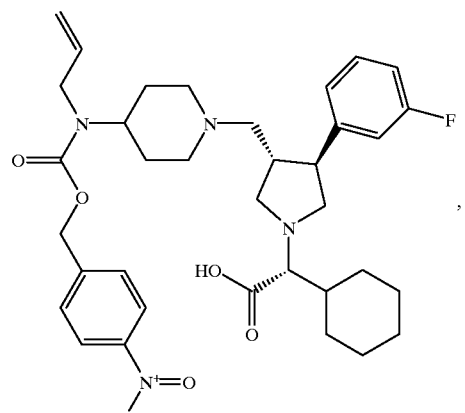
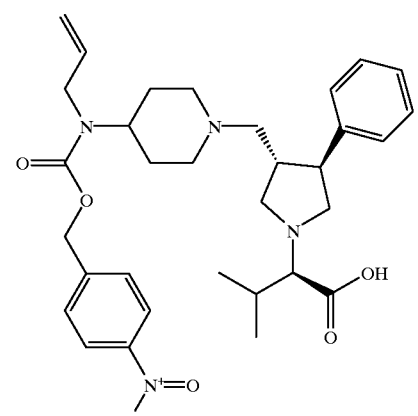
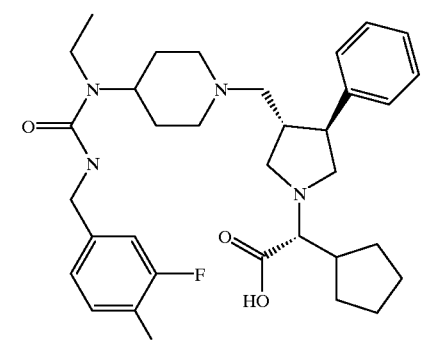
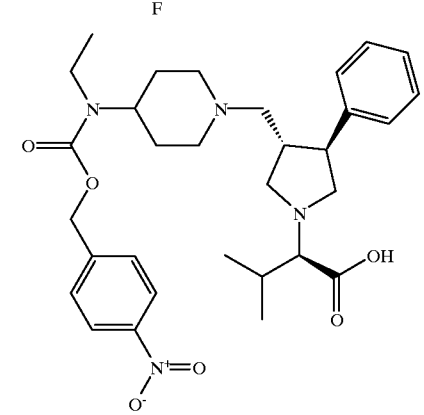

203
-continued
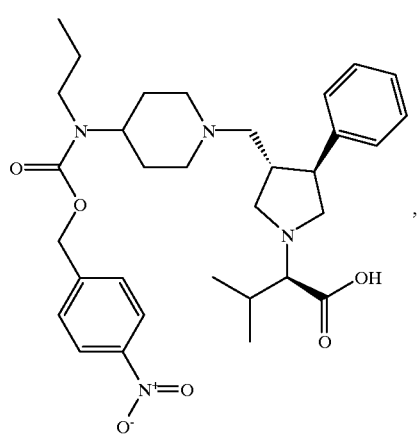
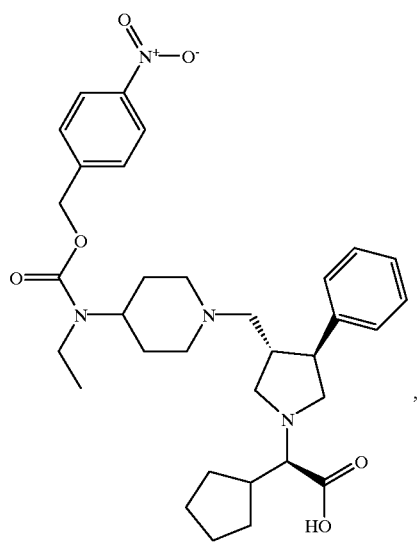
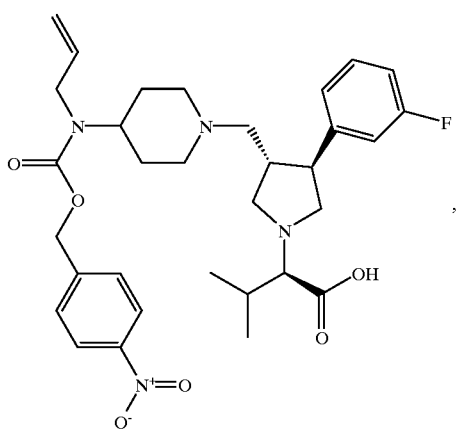
204
-continued
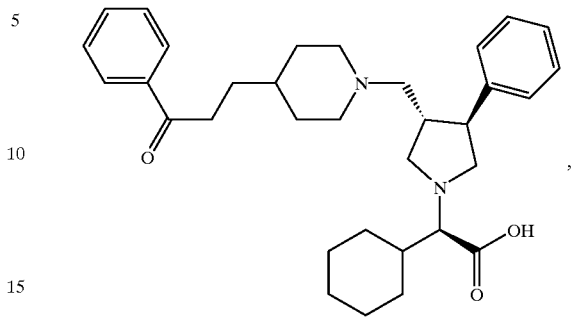
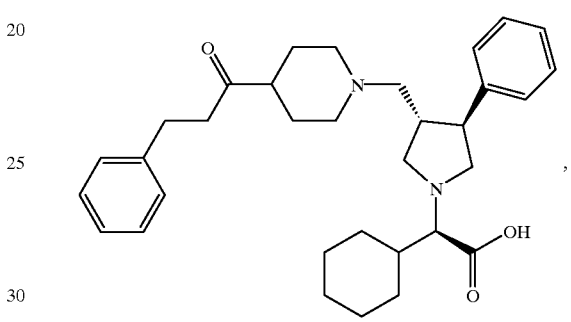
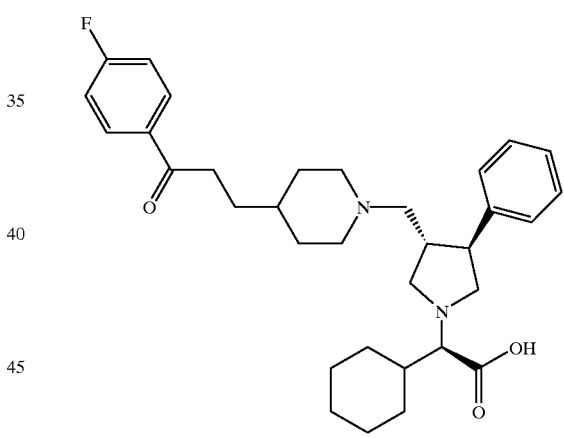
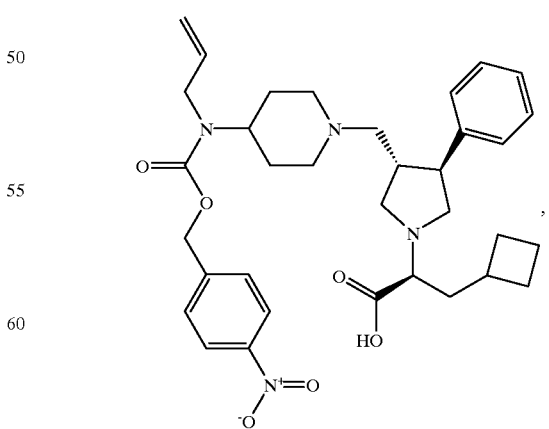

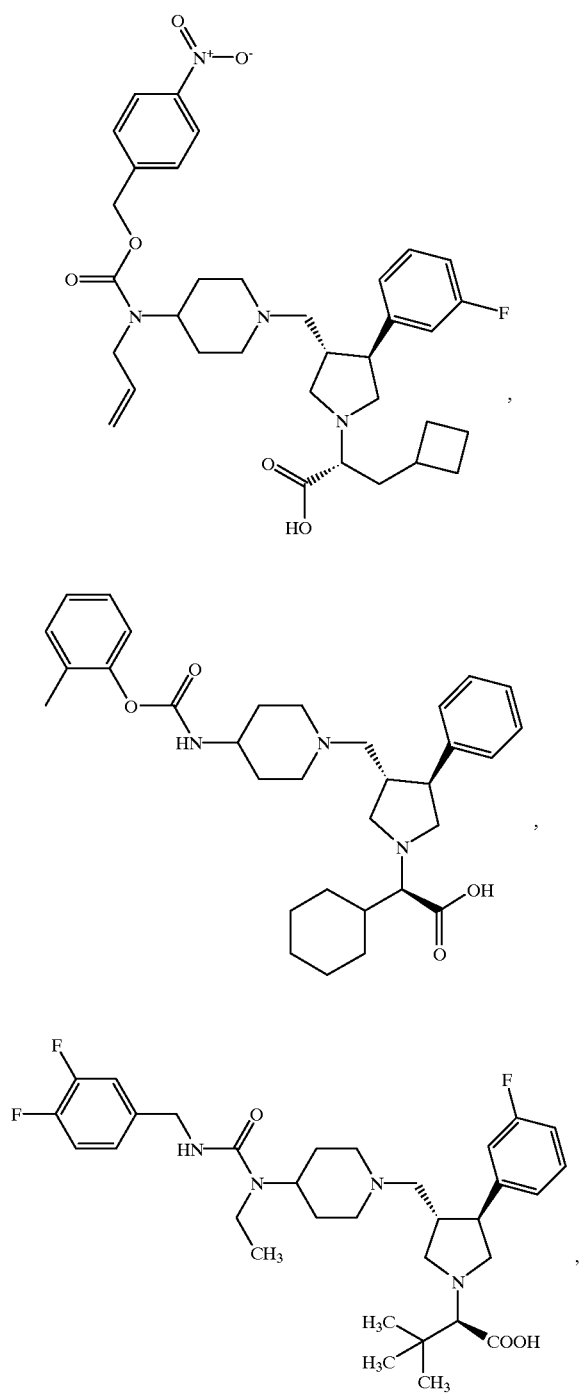
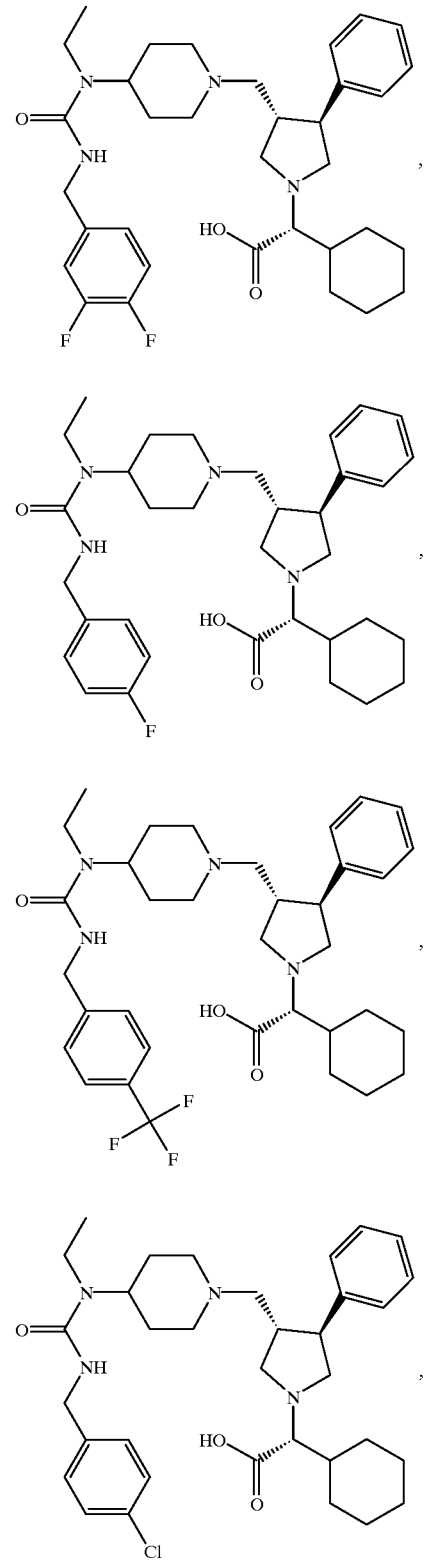
and pharmaceutically acceptable salts thereof.
25. A compound according to claim 24, which is a compound selected from the group consisting of

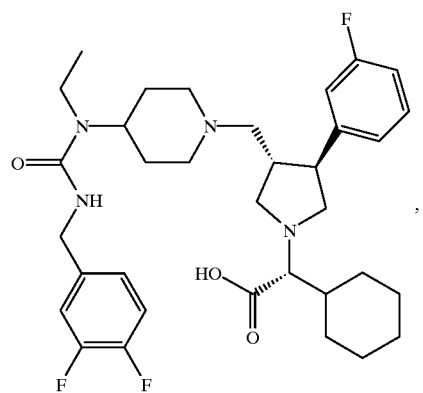
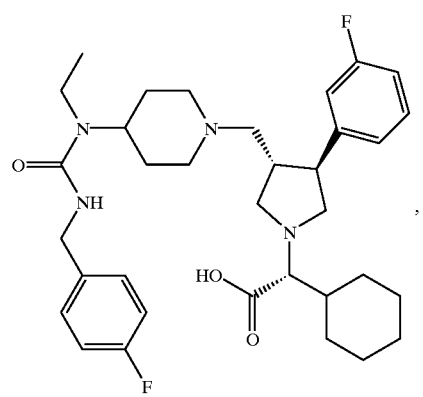
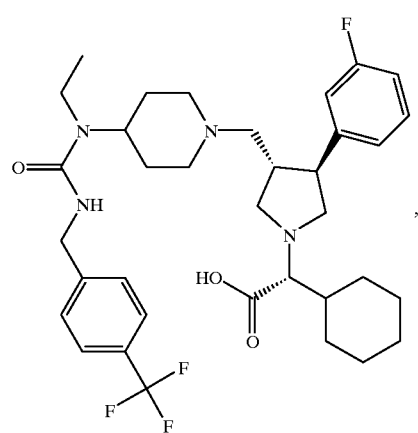
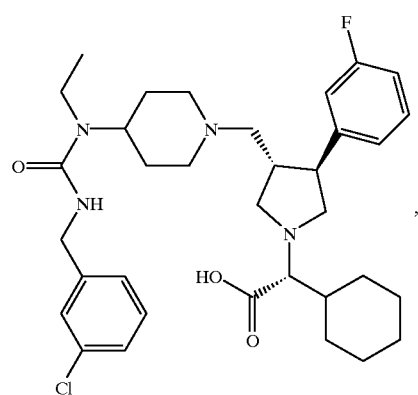
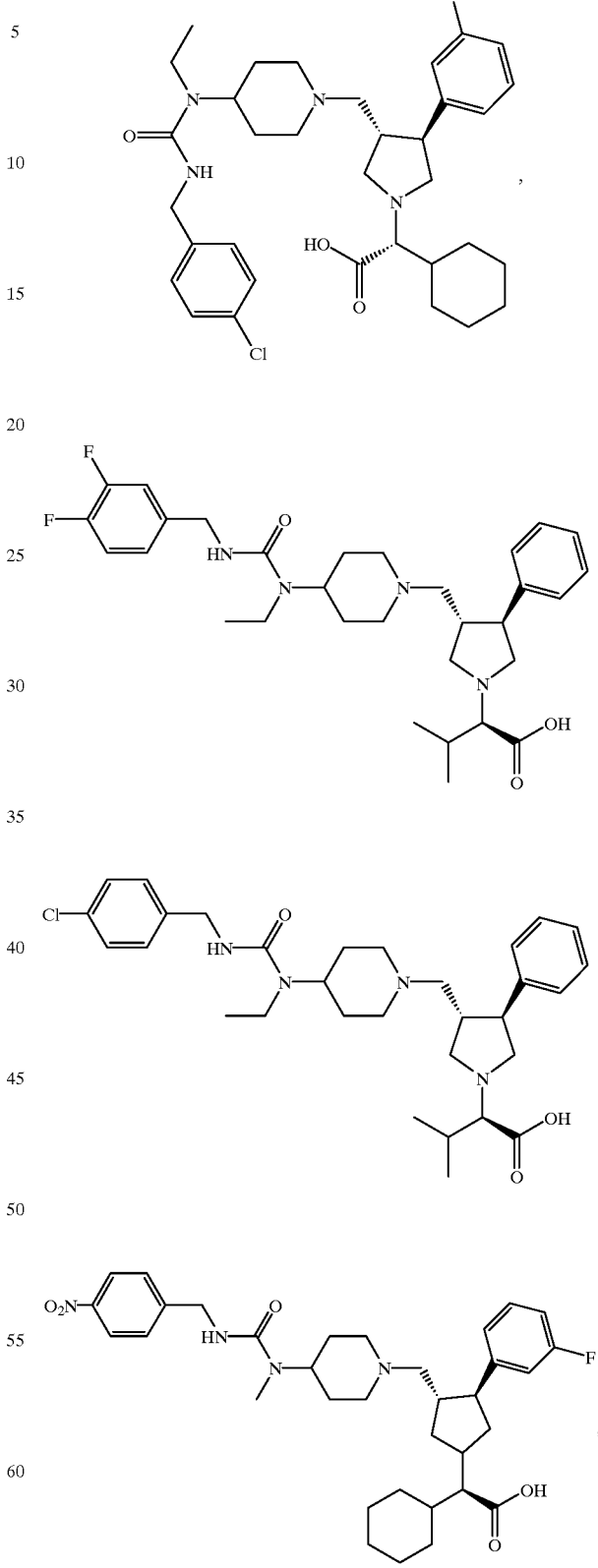

-continued
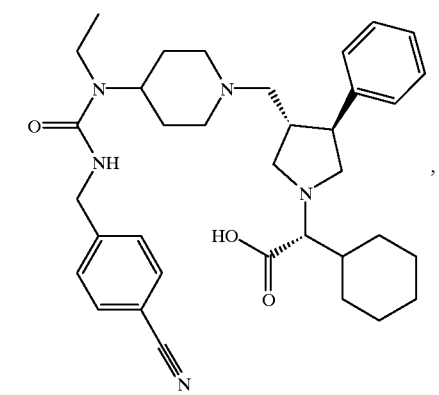
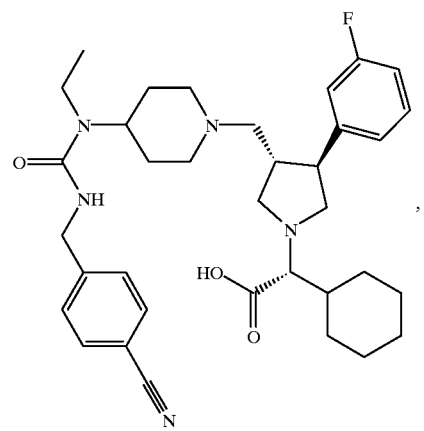
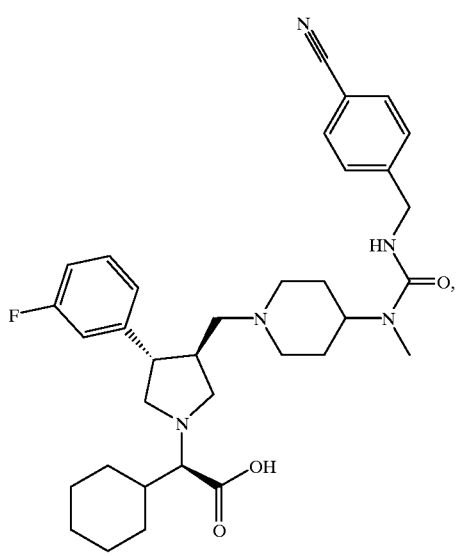
-continued
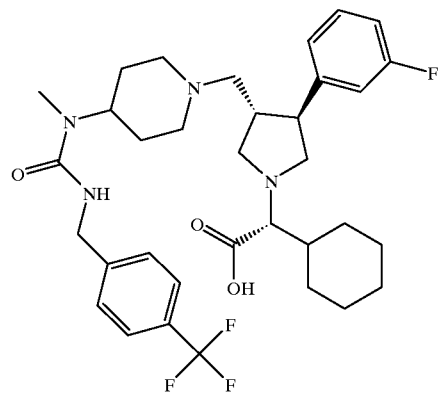
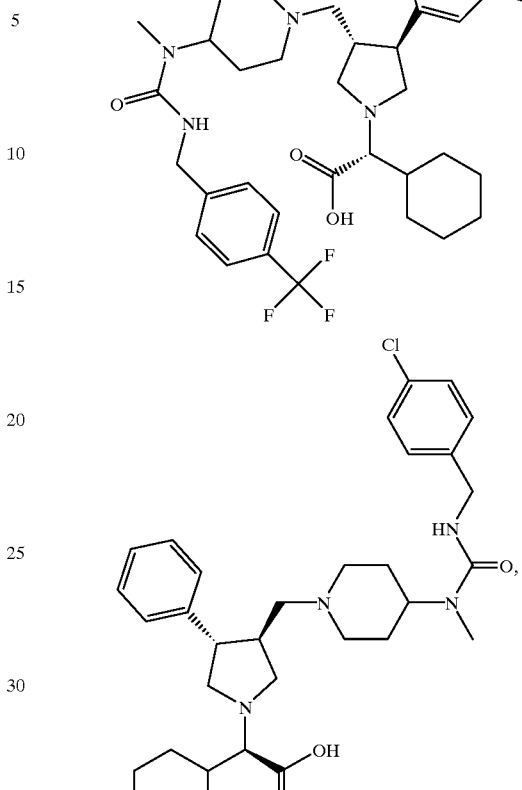
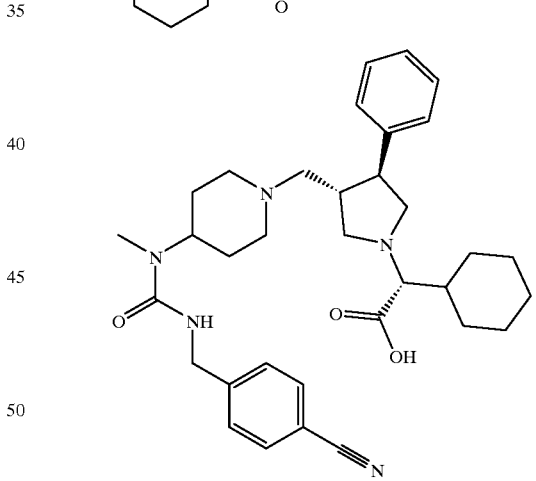
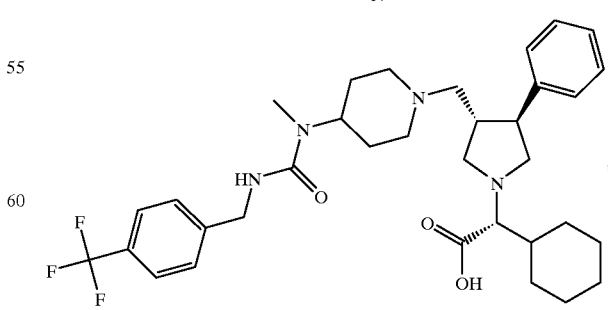

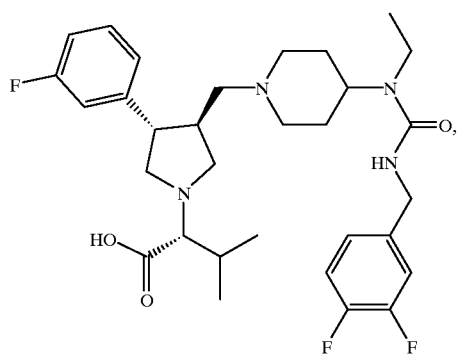
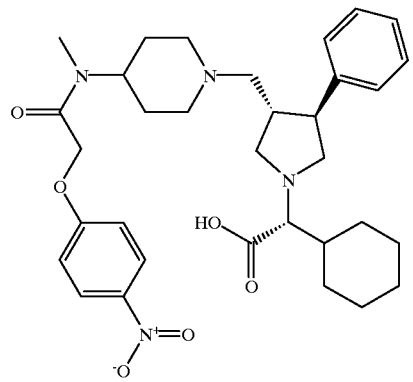
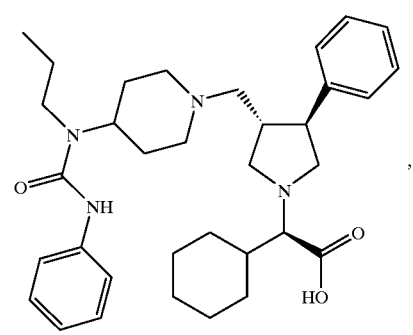
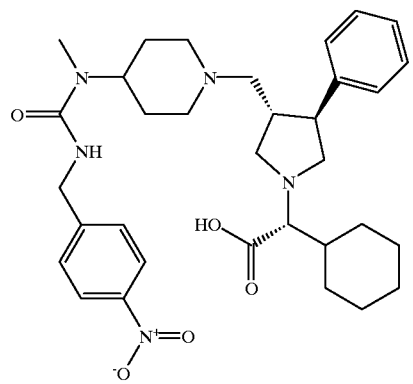
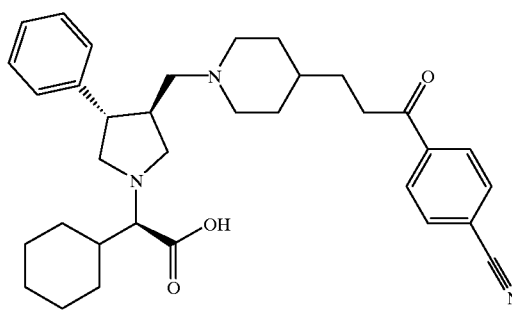
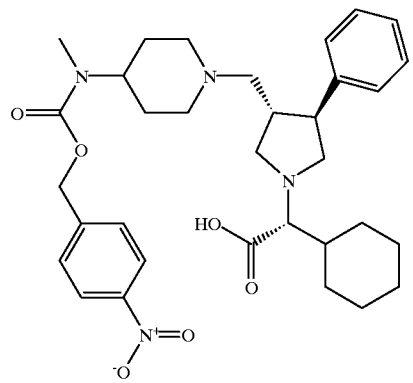
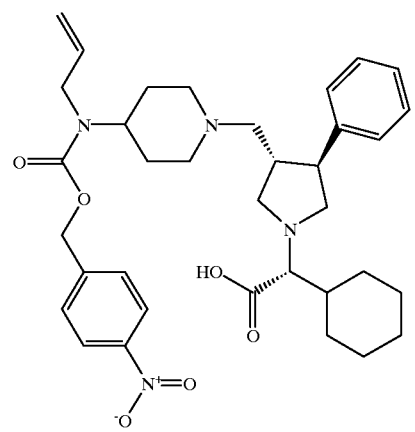
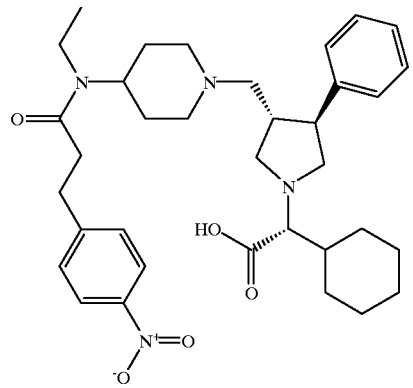

213
-continued
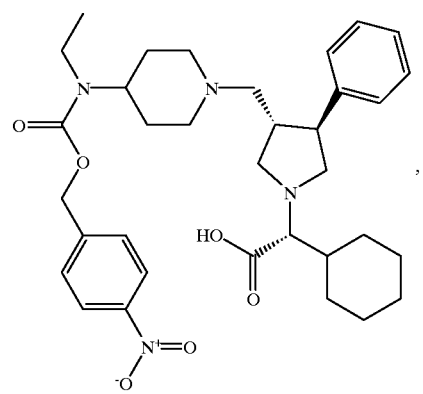
,
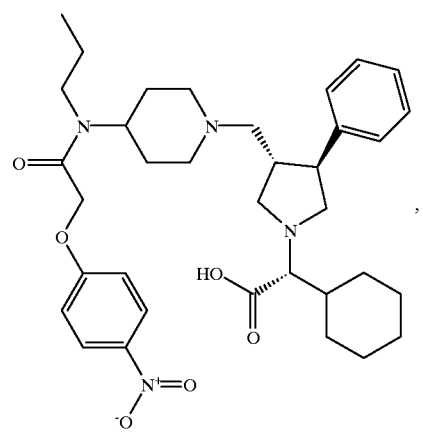
,
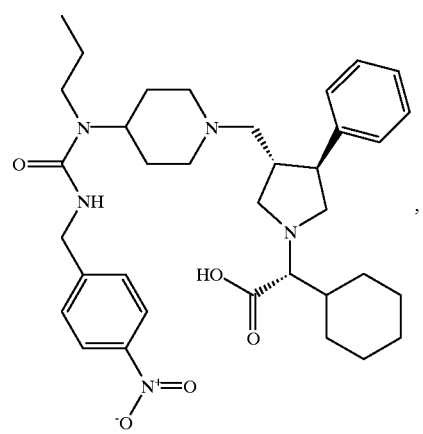
,
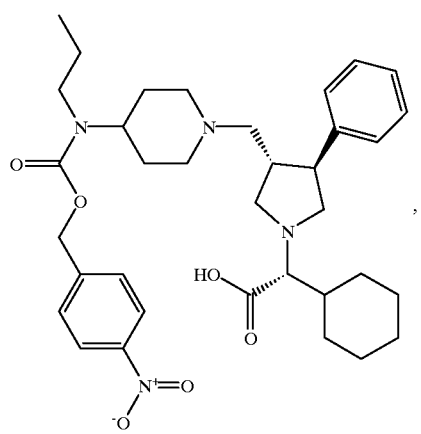
,
214
-continued
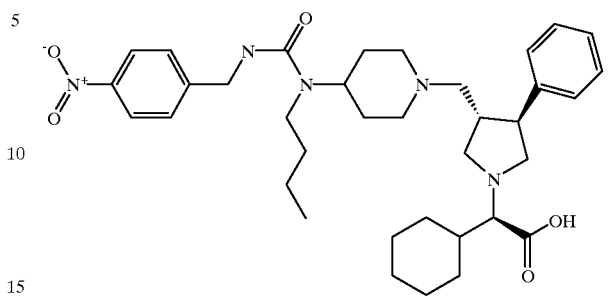
,
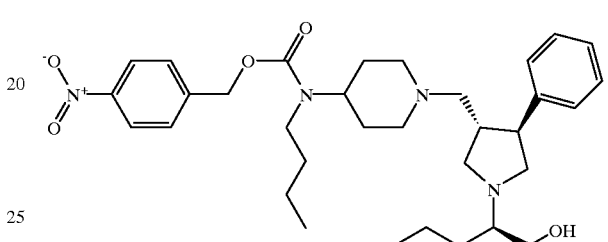
,
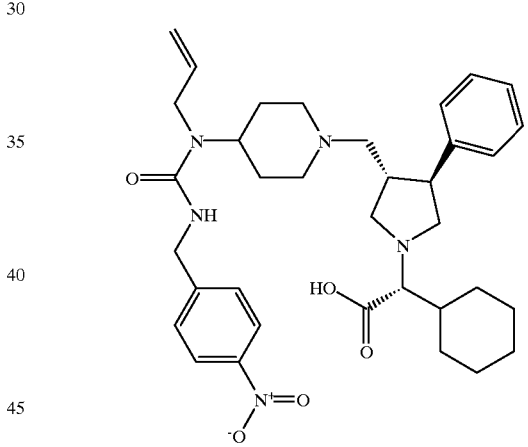
,
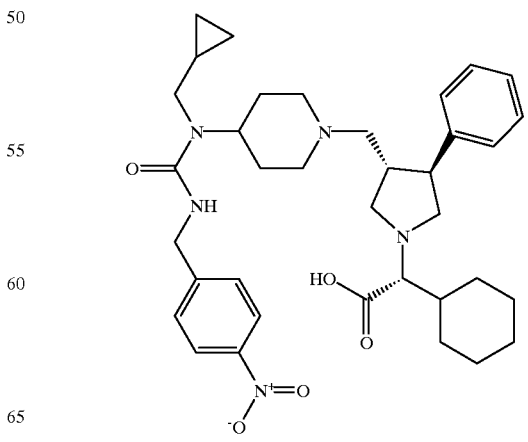
, 215
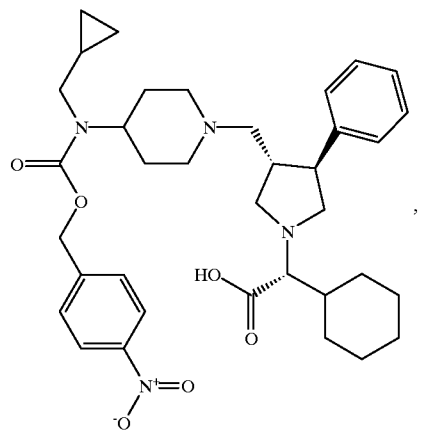
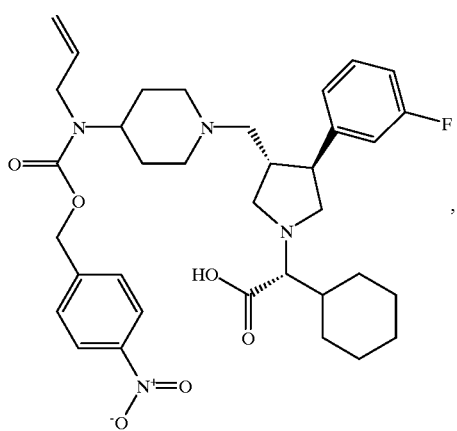
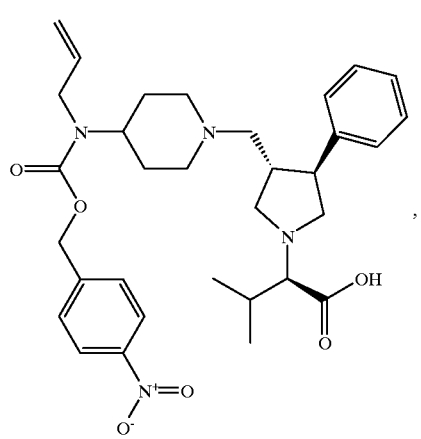
216
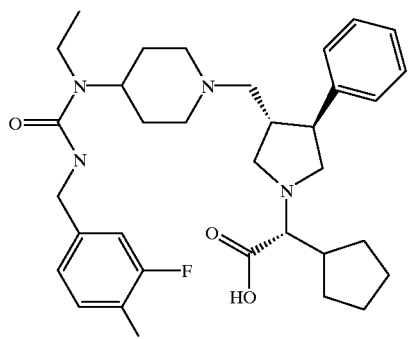
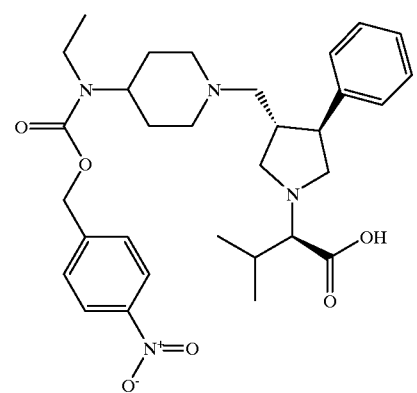
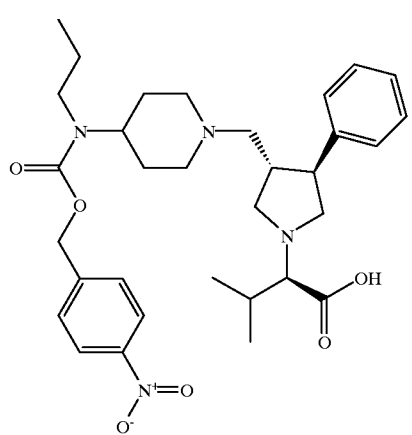

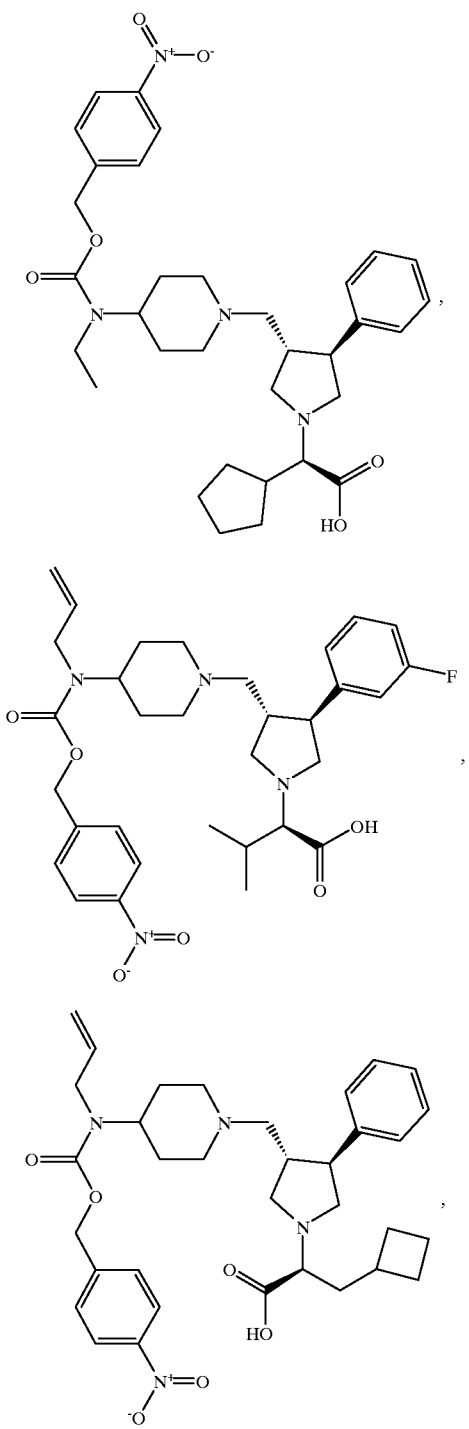

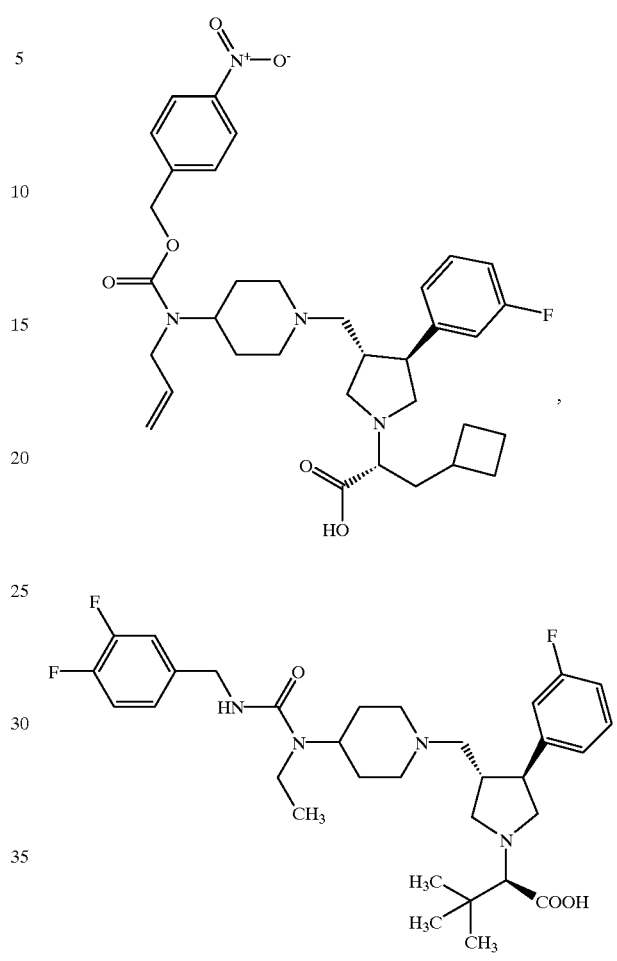

and pharmaceutically acceptable salt thereof.

26. A pharmaceutical composition which comprises an inert carrier and a compound of claim 1.

27. A method for preventing infection by HIV, treating infection by HIV, delaying of the onset of AIDS, or treating AIDS comprising the administration to a patient of an effective amount of the compound of claim 1.

28. A method for the prevention or treatment of asthma or rheumatoid athritis which comprises tie administration to a patient of an effective amount of the compound of claim 1.

* * * * *